United States Patent
Ito et al.

(10) Patent No.: US 9,884,882 B2
(45) Date of Patent: Feb. 6, 2018

(54) METHOD FOR PRODUCING THIOLANE SKELETON-TYPE GLYCOCONJUGATE, AND THIOLANE SKELETON-TYPE GLYCOCONJUGATE

(71) Applicant: FUJIFILM Corporation, Tokyo (JP)

(72) Inventors: Takayuki Ito, Kanagawa (JP); Toru Watanabe, Kanagawa (JP); Hideki Okada, Kanagawa (JP); Hidenobu Kuniyoshi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/238,232

(22) Filed: Aug. 16, 2016

(65) Prior Publication Data

US 2016/0355536 A1    Dec. 8, 2016

Related U.S. Application Data

(63) Continuation of application No. PCT/JP2015/054305, filed on Feb. 17, 2015.

(30) Foreign Application Priority Data

Feb. 18, 2014  (JP) ................. 2014-029020
Oct. 29, 2014  (JP) ................. 2014-220368

(51) Int. Cl.
| C07H 13/08 | (2006.01) |
| C07D 333/32 | (2006.01) |
| C07H 15/04 | (2006.01) |
| C07H 15/18 | (2006.01) |

(52) U.S. Cl.
CPC ......... C07H 13/08 (2013.01); C07D 333/32 (2013.01); C07H 15/04 (2013.01); C07H 15/18 (2013.01)

(58) Field of Classification Search
CPC .................................... C07H 13/08
USPC ............................................. 549/66
See application file for complete search history.

(56) References Cited

U.S. PATENT DOCUMENTS

| 3,116,282 A | 12/1963 | Hunter |
| 3,243,425 A | 3/1966 | Whistler et al. |
| 4,211,773 A | 7/1980 | Lopez et al. |
| 4,220,774 A | 9/1980 | Kuehne |
| 4,803,272 A | 2/1989 | Anton et al. |
| 5,811,408 A | 9/1998 | Yoshimura et al. |
| 6,103,707 A | 8/2000 | Yamada et al. |
| 6,147,058 A | 11/2000 | Yoshimura et al. |
| 6,448,415 B1 | 9/2002 | Lee et al. |
| 7,148,223 B2 | 12/2006 | Secrist, III et al. |
| 7,285,572 B2 | 10/2007 | Shinagawa et al. |
| 7,858,788 B2 | 12/2010 | Yoshida et al. |
| 8,329,925 B2 | 12/2012 | Voigtlander et al. |
| 8,420,831 B2 | 4/2013 | Voigtlander et al. |
| 9,221,865 B2 | 12/2015 | Nakamura et al. |
| 9,475,835 B2 | 10/2016 | Nakamura et al. |
| 2006/0142238 A1 | 6/2006 | McGuigan |
| 2009/0069263 A1 | 3/2009 | Damha et al. |
| 2013/0252918 A1 | 9/2013 | McGuigan |

(Continued)

FOREIGN PATENT DOCUMENTS

| CN | 101058557 A | 10/2007 |
| CN | 101200463 | * 6/2008 |

(Continued)

OTHER PUBLICATIONS

Vorbruggen et al., Org. Reactions (2000), pp. 55.*
Watts et al., Nuclei. Acids Res. (2007) vol. 35(5), pp. 1441-1451.*
Karrer, Org Chem. 2nd Ed. (1996). pp. 92-102.*
Communication dated Jan. 31, 2017, from the European Patent Office in counterpart European Application No. 15751503.2.
Kamal N. Tiwari et al. "Synthesis and Biological Activity of 4'-Thio-L-Xylofuranosyl Nucleosides" Nucleosides, Nucleotides & Nucleic Acids, 20(4-7), 2001, pp. 743-746 (4 pages total).
Kamal N. Tiwari et al. "The Synthesis and Biological Activity of 1-(2-Deoxy-4-Thio-a-L-Threo-Pentofuranosyl) Thymine" Nucleosides & Nucleotides, 12(8), pp. 841-846 (1993).

(Continued)

*Primary Examiner* — Taofiq A Solola
(74) *Attorney, Agent, or Firm* — Sughrue Mion, PLLC

(57) ABSTRACT

There is provided a production method of a compound represented by the following formula (II) through a step of reacting a compound represented by the following General Formula (I) with a sulfur compound.

General Formula (I)

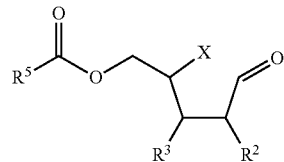

General Formula (II)

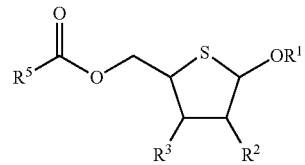

In General Formulas (I) and (II), $R^1$ represents a hydrogen atom or an acyl group, $R^2$ represents a hydrogen atom, a fluorine atom, an acyloxy group, an arylmethyloxy group, an allyloxy group, an arylmethyloxycarbonyloxy group, or an allyloxycarbonyloxy group, $R^3$ represents a hydrogen atom or an acyloxy group, $R^5$ represents an alkyl group or an aryl group, and X represents a leaving group. Here, in a case where $R^2$ is a fluorine atom, an acyloxy group, an arylmethyloxy group, an allyloxy group, an arylmethyloxycarbonyloxy group, or an allyloxycarbonyloxy group, $R^3$ is an acyloxy group.

12 Claims, No Drawings

(56) References Cited

U.S. PATENT DOCUMENTS

| | | |
|---|---|---|
| 2015/0011499 A1 | 1/2015 | Baba et al. |
| 2016/0355497 A1 | 12/2016 | Takeda et al. |
| 2016/0362389 A1 | 12/2016 | Nakamura et al. |

FOREIGN PATENT DOCUMENTS

| | | | |
|---|---|---|---|
| CN | 101200463 A | | 6/2008 |
| EP | 0 841 344 A1 | | 5/1998 |
| EP | 2 883 866 A1 | | 6/2015 |
| JP | 53-119810 A | | 10/1978 |
| JP | 55-49395 A | | 4/1980 |
| JP | 56-92239 A | | 7/1981 |
| JP | 5-178875 A | | 7/1993 |
| JP | 6-501261 A | | 2/1994 |
| JP | 8-53490 A | | 2/1996 |
| JP | 8-504753 A | | 5/1996 |
| JP | 10-282039 A | | 10/1998 |
| JP | 2003-172990 A | | 6/2003 |
| JP | 2005-503358 A | | 2/2005 |
| JP | 2006-335737 A | | 12/2006 |
| JP | 2006-528162 A | | 12/2006 |
| JP | 2007-514643 A | | 6/2007 |
| JP | 4202327 B2 | | 12/2008 |
| JP | 2009-538829 A | | 11/2009 |
| JP | 2010-59173 A | | 3/2010 |
| JP | 4719356 B2 | | 7/2011 |
| JP | 2011-526242 A | | 10/2011 |
| JP | 2013-514260 A | | 4/2013 |
| JP | 2013-540129 A | | 10/2013 |
| WO | 91/04982 A1 | | 4/1991 |
| WO | 94/05687 A1 | | 3/1994 |
| WO | 96/01834 A1 | | 1/1996 |
| WO | 97/37993 A1 | | 10/1997 |
| WO | 1997/38001 A1 | | 10/1997 |
| WO | 97/49716 A1 | | 12/1997 |
| WO | 99/28312 A2 | | 6/1999 |
| WO | 1999/43690 A1 | | 9/1999 |
| WO | 03/000200 A2 | | 1/2003 |
| WO | 2004/014930 A1 | | 2/2004 |
| WO | 2004/014931 A1 | | 2/2004 |
| WO | 2004/100891 A2 | | 11/2004 |
| WO | 2004/106352 A1 | | 12/2004 |
| WO | 2006/073197 A1 | | 7/2006 |
| WO | 2007/068113 A1 | | 6/2007 |
| WO | 2007/130783 A2 | | 11/2007 |
| WO | 2011/074484 A1 | | 6/2011 |
| WO | 2013/146833 A1 | | 10/2013 |
| WO | 2014/027658 A1 | | 2/2014 |

OTHER PUBLICATIONS

Hiroshi Satoh et al. "Synthesis of L-Enantiomers of 4'—Thioarabinofuranosyl Pyrimidine Nucleosides" Bioorganic & Medicinal Chemistry Letters 8 (1998) pp. 989-992.

Yuichi Yoshimura et al. "A Facile, Alternative Synthesis of 4'-Thioarabinonucleosides and their Biological Activities" J. Med. Chem. 1997, 40(14); pp. 2177-2183.

Yun-Lung Fu et al. "An Alternative Synthesis of Anomeric Methyl 2-Deoxy-4-thio-D-erythro-pentofuranosides" J. Org. Chem., vol. 41 No. 24; 1976, pp. 3831-3834 (4 pages total).

John A. Secrist III et al. "Synthesis and Biological Activity of 2'—Deoxy-4'—thio Pryimidine Nucleosides" J. Med. Chem. 1991, 34, No. 8 (pp. 2361-2366).

International Search Report, issued by International Searching Authority in corresponding International Application No. PCT/JP2015/054305, dated May 19, 2015.

Martin W. Bredenkamp et al. "Stannylene Directed Selective Acylation of Some Open-Chain L-Arabinose Derivatives" Tetrahedron Letters, 1990, 31(19) pp. 2759-2762.

Elmer J. Reist et al. "Thio Sugars, Synthesis of the Adenine Nucleosides of 4-Thio-D-Xylose and 4-Thio-D-Arabinose" Journal of Organic Chemistry, 1968, 33(1) pp. 189-192.

Elmer J. Reist et al. "Synthesis the 4-Thio-D-and-L-Ribofuranose and the Corresponding Adenine Nucleosides" Journal of the American Chemical Society, 1964, 86(24), pp. 5658-5663.

Stephanie A. Hartsel et al. "Synthesis of 9-(4-Thioxylofuranosyl) adenine via a Novel Glycosylation Reaction" Tetrahedron Letters 39 (1998) pp. 205-208.

Vjera Pejanovic et al. "Synthesis and Biological Evaluation of Some Novel 4'-Thio-L-ribonucleosides with Modified Nucleobase Moieties" Bioorganic & Medicinal Chemistry Letters, 2003, 13(11) pp. 1849-1852.

Kamal N. Tiwari et al. "Synthesis and Anti-cancer Activity of Some Novel 5-Azacytosine Nucleosides" Nucleosides, Nucleotides & Nucleic Acids, 2003, 22(12), pp. 2161-2170.

International Preliminary Report on Patentability issued from the International Bureau in counterpart International Application No. PCT/JP2015/054305, dated Jan. 4, 2016.

Wu-Bao Wang et al. "A Practical Synthesis of Sugar-Derived Cyclic Nitrones: Powerful Synthons for the Synthesis of Iminosugars" Synlett 2010, No. 3; pp. 488-492.

Peter Haeberli et al. "Syntheses of 4'-thioribonucleosides and thermodynamic stability and crystal structure of RNA oligomers with incorporated 4'-thiocytosine" Nucleic Acids Research, 2005, vol. 33 No. 13; pp. 3965-3975.

Yuichi Yoshimura et al. "An Alternative Synthesis of the Antineoplastic Nucleoside 4'-ThioFAC and Its Application to the Synthesis of 4'-ThioFAG and 4'-Thiocytarazid" Journal of Organic Chemistry, 1999, vol. 64 No. 21; pp. 7912-7920.

G. Inguaggiato et al. "Novel Triazole 2'-Deoxy-4'—Thionucleosides: Stereoselective Synthesis and Biological Evaluation" Nucleosides & Nucleotides, 1999; vol. 18 No. 3; pp. 457-467.

Houssine Ait-sir et al;. "Synthesis and configurational assignments of 3-substituted 2-deoxy-4-thio-D-erythro-pentofuranose derivatives" Journal of the Chemical Society, Perkin transactions 1, 1996; No. 14; pp. 1665-1671.

Johan Fanton et al. "Enzymatic and Organocatalyzed Asymmetric Aldolization Reactions for the Synthesis of Thiosugar Scaffolds" European Journal of Organic Chemistry 2012, No. 1; pp. 203-210.

Office Action dated Jun. 23, 2017, in co-pending U.S. Appl. No. 15/581,834.

Joseph V. Simone, Part XIV, Oncology: Introduction, Cecil Textbook of Medicine, 20th Edition, vol. 1, 1995, pp. 1004-1010 (8 pages total).

Homer L. Pearce et al., "Failure modes in anticancer drug discovery and development", Cancer Drug Design and Discovery, edited by Stephen Neidle, Chapter 18, 2008 (pp. 424-435).

Ji Johnson et al., "Relationships between drug activity in NCI preclinical in vitro and in vivo models and early clinical trials", British Journal of Cancer, 84 (10), 2001 (pp. 1424-1431).

Trisha Gura et al., "Cancer Models: Systems for Identifying New Drugs Are Often Faulty", Science, vol. 278, No. 5340, Nov. 7, 1997 (5 pages total).

Office Action dated Mar. 13, 2017, in co-pending U.S. Appl. No. 15/238,784.

Communication dated Mar. 1, 2016, from the Japanese Patent Office in counterpart application No. 2014-530560.

Communication dated Apr. 4, 2017 from the Japanese Patent Office in Japanese Application No. 2014-029978.

Communication dated Mar. 28, 2017 from the European Patent Office in European Application No. 15751531.3.

Communication dated Apr. 18, 2017 from the Japanese Patent Office in Japanese Application No. 2016-504110.

Communication dated Jul. 2, 2015 from the U.S. Patent and Trademark Office in U.S. Appl. No. 14/621,119.

Communication dated Nov. 30, 2015 from the U.S. Patent and Trademark Office in U.S. Appl. No. 14/621,119.

Communication dated Sep. 12, 2016 from the U.S. Patent and Trademark Office in U.S. Appl. No. 14/873,966.

Miura et al., "Suppression of Peritoneal Dissemination by 4'-thio-FAC," Oncology Reports, vol. 9, No. 6, Nov.-Dec. 2002, pp. 1319-1322 (9 pages total).

(56) References Cited

OTHER PUBLICATIONS

King, "Bioisosteres, Conformational Restriction, and Pro-drugs—Case History: An Example of a Conformational Restriction Approach," Med. Chem., Principle and Practice (1994), pp. 206-208.
Jeong, et al., The Stereochemical Outcome of the DAST Fluorination of 4'-Thiopyrimidine Nucleosides with "Up" Hydroxyl Groups is Controlled by the Oxidation State of the Sulfur Atom, Chemistry Letters, pp. 301-302, 1995. (2 pages total).
Jeong, et al., Unanticipated Retention of Configuration in the DAST Fluorination of Deoxy-4'-thiopyrimidine Nucleosides with "Up" Hydroxyl Groups, Tetrahedron Letters, vol. 35, No. 41, pp. 7569-7572, 1994. (4 pages total).
Jeong, et al., Facile Fluorination of Deoxy-4'-thiopyrimidine Nucleosides with "Down" Hydroxyl Groups. Retention of Configuration After Fluoride Opening of the Quartenized N3-MEM Anhydronucleosides, Tetrahedron Letters, vol. 35, No. 41, pp. 7573-7576,1994. (4 pages total).
Yoshimura, et al., Synthesis of 2'-deoxy-2'-fluoro-4'-thioarabinonucleosides as potential antitumor and antiviral agents from D-glucose, Nucleic Acids Symposium Series, No. 35, pp. 15-16, 1996. (2 pages total).
Yoshimura, et al., A Novel Synthesis of New Antineoplastic 2'-Deoxy-2'-substituted -4'-thiocytidines, Journal of Organic Chemistry, vol. 61, No. 3, pp. 822-823, 1996. (2 pages total).
Tann, et al., Fluorocarbohydrates in Synthesis. An Efficient Synthesis of 1-(2-Deoxy-2-fluoro-13-D-arabino-furanosyl)-5-iodouracil (13-FIAU) and 1-(2-Deoxy-2-fluoro-p-D-arabinofuranosyl) thymine (13-FMAU),Journal of Organic Chemistry, American Chemical Society, vol. 50, No. 19, 1985. pp. 3644-3647 (4 pages total).
Jeong, et al., Participation of sulfur occurred during the Mitsunobu reaction: synthesis of novel isodideoxythionucleosides, J. Chem. Soc., Perkin Trans. 1, pp. 3325-3326, 1998. (2 pages total).
Office Action dated May 12, 1999, which issued during the prosecution of U.S. Appl. No. 08/973,529 (now U.S. Pat. No. 6,147,058).
Office Action dated Apr. 26, 2017, issued from the Mexican Patent Office in counterpart Mexican Patent Application No. MX/a/2014/011182.
Office Action dated May 19, 2017, issued from the European Patent Office in counterpart European Patent Application No. 13770090.2.
International Preliminary Report on Patentability with a Translation of Written Opinion issued from the International Bureau in International Application No. PCT/JP2015/080885, dated May 11, 2017.
Notices of Allowance and Allowability dated Nov. 8, 1999, which issued during the prosecution of U.S. Appl. No. 08/973,529 (now U.S. Pat. No. 6,147,058).
Office Action in European Patent Application No. 13879640.4 dated May 8, 2017.
Giorgio Attardo et al, Efficient Synthesis of 5,8-Disubstituted-1,4-Dihydrobenzoxathiin-3-Oxides and Their Isomeric Structures, 4,7-Disubstituted-1,3-Dihydrobenzob Thiophene-2,2-Dioxides, Tetrahedron Letters, vol. 35, No. 27, pp. 4743-4746, 1994.
William Plunkett et al., "Preclinical characteristics of gemcitabine", Anti-Cancer Drugs, 1995, pp. 7-13, vol. 6, Suppl. 6.
Larry W. Hertel et al., "Evaluation of the Antitumor Activity of Gemcitabine (2',2'-Difluoro-2'-deoxycytidine)", Cancer Research, Jul. 15, 1990, pp. 4417-4422, vol. 50.
Communication dated Dec. 22, 2016, from the European Patent Office in European Application No. 15751531.3.
Cox, J.M., et al., "Cyclic Hemithioacetals: Analogues of Thiosugars with Sulphur in the Ring", J. Chem. Soc., Section C. 1967, pp. 1130-1134.
International Search Report, issued by International Searching Authority in International Application No. PCT/JP2015/052304, dated Mar. 10, 2015.

Hua Lin et al., "Highly Efficient Asymmetric Synthesis of Enantiopure Dihydro-1, 2-oxazines: Dual-Organocatalyst-Promoted Asymmetric Cascade Reaction", Organic Letters (2012), vol. 14, No. 15; pp. 3818-3821.
David A. Berges et al., "Bicyclic diazasugars. Part 3: B-D-Mannose and 6-deoxy-B-L-gulose analogues", Tetrahedron, 2001, vol. 57; pp. 9915-9924.
Ronald C. Horton Jr. et al, "Aldehyde-Terminated Self-Assembled Monolayers on Gold: Immobilization of Amines onto Gold Surfaces", J. Am. Chem. Soc., 1997, vol. 119; pp. 12980-12981.
H. Driguez et al., "A Novel Synthesis of 5-Thio-D-Glucose" Tetrahedron Letters, 1981, vol. 22, No. 50, pp. 5061-5062.
R. M. Rowell et al., "Derivatives of a-D-Glucothiopyranose", J. Org. Chem., 1996, vol. 31; pp. 1514-1516.
Eva Bozo et al., "Synthesis of 4-cyanophenyl and 4-nitrophenyl 1,5-dithio-L-and -D- arabinopyranosides possessing antithrombotic activity1,2", Carbohydrate Research 1998, vol. 311; pp. 191-202.
International Preliminary Report on Patentability issued from the International Bureau in International Application No. PCT/JP2015/052304, dated Feb. 16, 2016.
Junji Fujita et al., "Synthesis of thiosaccharides employing the Pummerer rearrangement of tetrahydrothiopyran oxides", Tetrahedron 2004, vol. 60, No. 32, pp. 6829-6851.
Dusan Miljkovic et al., "An improved synthesis of methyl 5-thio-D-arabino-pyranosides", Journal of the Serbian Chemical Society, vol. 55, 1990; pp. 359-361.
Hironobu Hashimoto et al., "Novel conversion of aldopyranosides into 5-thioaldopyranosides via acyclic monothioacetals with inversion and retention of configuration at C-5", Carbohydrate Research, vol. 282, Issue 2 (Feb. 23, 1996) pp. 207-221.
Communication dated Jun. 14, 2017 from the State of Israel Patent Office in Israeli Application No. 237086.
Office Action dated May 19, 2017, issued from the Canadian Patent Office in corresponding Canadian Patent Application No. 2,880,794.
Zheng, F., et al., "Synthesis of L-β-3'-Deoxy-3',3'-difluoro-4'-thionucleosides", Organic Letters, vol. 8, No. 26, pp. 6083-6086, 2006 (4 pages total).
Communication dated Mar. 30, 2016 from the U.S. Patent and Trademark Office in counterpart U.S. Appl. No. 14/498,334.
Communication dated Aug. 11, 2016 from the U.S. Patent and Trademark Office in counterpart U.S. Appl. No. 14/498,334.
Communication dated Feb. 15, 2017 from the U.S. Patent and Trademark Office in counterpart U.S. Appl. No. 14/498,334.
Communication dated Jun. 27, 2017 from the U.S. Patent and Trademark Office in counterpart U.S. Appl. No. 14/498,334.
Communication dated Aug. 11, 2017 from the U.S. Patent and Trademark Office in counterpart U.S. Appl. No. 14/498,334.
Hayato Fujita et al., "Gene Expression Levels as Predictive Markers of Outcome in Pancreatic Cancer after Gemcitabine-Based Adjuvant Chemotherapy1,2", NEO PLASIA, Oct. 2010, pp. 807-817, vol. 12, No. 10.
Magdalena Slusarczyk et al., "Application of ProTide Technology to Gemcitabine: A Successful Approach to Overcome the Key Cancer Resistance Mechanisms Leads to a New Agent (NUC-1031) in Clinical Development", J. Med. Chem, 2014, pp. 1531-1542, vol. 57, No. 4.
Hyunah Choo et al., "Synthesis, Anti-HIV Activity, and Molecular Mechanism of Drug Resistance of L-2',3'-Didehydro-2',3'-dideoxy-2'-fluoro-4'-thionucleosides", J. Med. Chem., 2003, pp. 389-398, vol. 46, No. 3.
A. G. Cottrell et al., "Reaction of Sugar Chlorosulfates VII. Some Conformational Aspects", Canadian Journal of chemistry, Jul. 1, 1966, pp. 1483-1491, vol. 44, No. 13.
International Preliminary Report on Patentability and Written Opinion of the international Searching Authority (forms PCT/IB388, PCT/373, PCT/ISA 237 and PCT/IB/326), dated Feb. 26, 2015, for International Application No. PCT/JP2013/071871.
International Search Report for PCT/JP2013/071871, dated Nov. 26, 2013.
Laetitia Jean-Baptise et al., "Synthesis of 2',3'-Dideoxy-2'-Fluoro-4'-Thionucleosides from a Fluoroxanthate", Synlett, 2008, pp. 817-820, No. 6.

(56) References Cited

OTHER PUBLICATIONS

Masajiro Kawana et al., The Synthesis of 2',3'-Diodexycytidene and Its 2'-Azido Analogue Applications of the Deoxygenative 1,2-Hydride Shift of Sulfonates with $Mg(OMe)_2$-$NaBH_4$, Chemistry Letters, 1987, pp. 2419-2422.

Naveen K. Khare et al., "Synthesis of 4-deoxy-4-thioarabinofuranosyl disaccharides, analogs of Mycobactrial arabinoglactan", Indian Journal of Chemistry, Nov. 2008, pp. 1748-1752, vol. 47B.

Office Action issued in U.S. Appl. No. 14/621,119, dated Mar. 24, 2015.

N. Otonani et al., "Preparation and Antitumor Activity of 4'-Thio Analogs of 2,2'-Anhydro-1-11-D-arabinofuranosylcytosine", Journal of Medicinal Chemistry, 1974, pp. 535-537, vol. 17, No. 5.

Australian Office Action for Application No. 2013303534, dated Dec. 1, 2015.

Official Action for Canadian Patent Application No. 2,880,794, dated Nov. 2, 2015.

Chinese Office Action for Application No. 201280042642.1, dated Nov. 2, 2015.

Extended European Search Report for Application No. 13879640.4 dated May 18, 2016.

Japanese Office Action for Application No. 2014-563560 dated Mar. 1, 2016.

Korean Office Action for Application No. 10-2015-7003655, dated May 12, 2016.

Office Action issued in U.S. Appl. No. 14/873,966, dated Feb. 8, 2016.

Notice of Allowance issued in U.S. Appl. No. 14/873,966, dated May 26, 2016.

Partial Supplementary European Search Report issued in European Application No. 13879640.4, dated Feb. 16, 2016.

Supplemental Notice of Allowance issued in U.S. Appl. No. 14/873,966, dated Jul. 6, 2016.

Russian Office Action for Application No. 2015108790, dated Apr. 25, 2016.

Yuichi Yoshimura et al., "Synthetic Studies on 2'-Substituted-4'-Thiocytidine Derivatives As Antineoplastic Agents", Nucleosides & Nucleotides, 1999, pp. 815-820, vol. 18, nos. 4&5.

Official Action issued in the Canadian Patent Application No. 2,880,794, dated Aug. 18, 2016.

Notice of Final Rejection issued in Korean Patent Application No. 10-2015-7003655, dated Nov. 21, 2016.

Official Action issued in Korean Patent Application No. 10-2015-7003655, dated Jan. 11, 2017.

Feng Zheng et al., "Synthesis of L-β-3'Deoxy -3',3'-difluoro-4'-thionucleosides", Organic Letters, 2006, pp. 6083-6086, vol. 8, No. 26.

Takashi Komine et al., "Synthesis and Structure-Activity Relationship Studies of Highly Potent Novel Oxzolidinone Antibacterials", J. Med. Chem., vol. 51, No. 20, pp. 6558-6562, 2008.

Shinji Miura et al., "Antitumor activity of a novel orally effective nucleoside, 1-(2-deoxy-2-fluoro-4-thio-B-D-arabinofuranosyl)cytosine", Cancer Letters, 1998, pp. 103-110, vol. 129.

Koen Vanhessche et al., "L-Ribulose A: Novel Chiral Pool Compound", Tetrahedron Letters, pp. 2337-2340, 1990, vol. 31, No. 16.

Oscar Varela et al., "First Synthesis of Aldopentono-1,4-thiolactones", J. Org. Chem., 1993, pp. 7860-7864, vol. 58, No. 27.

Chia-Lin J. Wang et al., "Synthesis of 2'(S), 3'(R), 5'-Trihydroxypentyladenine1", Tetrahedron Letters, 1988, pp. 1107-1110, vol. 29, No. 10.

Jonathan K. Watts et al., Synthesis and Conformal Analysis of 2'-Fluoro-5-methyl-4'-thioarabinouridine (4'S-FAMAU), J. Org. Chem., 2006, pp. 921-924, vol. 71.

Yuichi Yoshimura et al., A Novel Synthesis of 2'-Modified 2'-Deoxy-4'-thocytidines from D-Glucoser, J. Org. Chem., 1997, pp. 3140-3152, vol. 62, No. 10.

Yuichi Yoshimura e al., "Synthesis and Biological Activities of 2'-Deoxy-2'fluoro-4'thioarabinofuranosylpyrimidine and -Purine Nucleosides", Bioorganic & Medicinal Chemistry, 2000, pp. 1545-1558, vol. 8.

Deborah A. Zajchowski et al., "Anti-tumor efficacy of the nucleoside analog 1-(-deoxy-2-fluoro-4-thio-g-D-arabinofuranosyl) cytosine (4'-thio-FAC) on human pancreatic and ovarian tumor xenograft models", Int. J. Cancer, 2005, pp. 1002-1009, vol. 114.

Partial European Search Report issued in European Patent Application No. 10163406.1, dated Nov. 24, 2010.

PCT International Preliminary Report on Patentability (IPRP), dated Jun. 28, 2012 for PCT International Application No. PCT/JP2010/072182.

International Search Report and Written Opinion for PCT/JP2010/072182, dated Apr. 29, 2011.

Thomas B. Mercer et al., Looking glass inhibitors: both enantiomeric N-benzyl derivatives of 1,4-dideoxy-1,4-imino-D-lyxitol a potent competitive inhibitor of a-D-glactosidase and of 1-4-dideoxy-1,4-imino-L-lyxitol a weak competitive inhibitor of a-D-glactosidase inhibit naringinase, an a-L-rhamnosidase competitively, Tetrahedron: Asymmetry, 2009, pp. 2368-2373, vol. 20, No. 20.

Paul Karrer, "Organic Chemistry", 2nd English Edition, Elsevier Publ. Comp., Inc. NY, pp. 91-93.

International Search Report for PCT/JP2015/080885, dated Feb. 2, 2016.

Written Opinion for PCT/JP2015/080885, dated Feb. 2, 2016.

Official Action issued in Russian Patent Application No. 2015108790, dated Dec. 29, 2016.

Extended European Search Report issued in European Patent Application No. 17150141.4, dated Mar. 16, 2017.

Official Action issued in Chinese Patent Application No. 201380042642.1, dated Jan. 16, 2017.

David Baker et al., "Large-scale preparation of D-allose: observations on the stereoselectivity of the reduction of 1,2:5,6-di-O-isopropylidene-a-D-ribo-hexofuranos-3-ulose hydrate", Carbohydrate Research, 1972, pp. 192-197, vol. 24.

Lak Shin Jeong et al., "$N^6$-Substituted D-4'-Thioadenosine-5'-methyluronamides: Potent and Selective Agonists at the Human A3 Adenosine Receptor", J. Med. Chem., 2003, pp. 3775-3777, vol. 46, No. 18.

Jeong et al., Chemistry Letters, pp. 301-302, 1995.

Jeong et al., Tetrahedron Letters, 35(41):7569-7572, 1994.

Jeong et al., Tetrahedron Letters, 35(41):7573-7576, 1994.

Y. Yoshimura et al., Nucleic Acids Symposium Series, No. 35, pp. 15-16 (1996).

Y. Yoshimura et al., Journal of Organic Chemistry, vol. 61, No. 3, pp. 822-823 (1996).

Office Action dated Nov. 8, 2012 in U.S. Appl. No. 13/606,746 (now U.S. Pat. No. 8,420,831).

Notice of Allowance dated Aug. 30, 2012 in U.S. Appl. No. 12/959,735 (now U.S. Pat. No. 8,329,925).

Office Action dated Apr. 3, 2017 from the Korean Intellectual Property Office in counterpart Korean Application No. 10-2014-7030209.

Office Action dated Oct. 25, 2016, issued by the Korean Intellectual Property Office in corresponding Korean Application No. 10-2014-7030209.

Office Action dated Sep. 13, 2016 from the Israeli Patent Office in counterpart Israeli Application No. 234222.

Office Action dated Sep. 30, 2016 from the Taiwanese Intellectual Property Office in counterpart Taiwanese Application No. 102110915.

Berge et al., J. Pharm. Sci., 1977, 66(1), p. 1-19.

Serajuddin, A.T.M., Adv. Drug Deliv. Rev., 2007, 59(7), p. 603-616.

Office Action dated May 25, 2016 from the Taiwanese Intellectual Property Office in counterpart Taiwanese Application No. 102110915.

Office Action dated Mar. 21, 2016 in corresponding Russian Application No. 2014143277/04.

Office Action dated Mar. 29, 2016, from the Canadian Intellectual Property Office in counterpart Canadian Application No. 2865742.

(56) References Cited

OTHER PUBLICATIONS

Office Action dated Nov. 5, 2015 from the Russian Patent Office in counterpart Russian Application No. 2014143277/04.
Office Action (Patent Examination Report) dated Oct. 5, 2015, issued by the Australian Patent Office in counterpart Australian Application No. 2013241341.
Extended European Search Report (EESR) dated Oct. 12, 2015 from the European Patent Office in counterpart European Application No. 13770090.2.
Office Action dated Aug. 21, 2015, issued by the Intellectual Property Office of New Zealand in corresponding New Zealand Application No. 701245.
Yuichi Yoshimura et al., "An Alternative Synthesis of Antineoplastic 4'—Thiocytidine Analogue 4'-ThioFAC", Pergamon, Tetrahedron Letters, 40, (1999), pp. 1937-1940.
Mayumi Takahashi et al., "Synthesis and crystal structure of 2'-deoxy-2'-fluoro-4'-thioribonucleosides: substrates for the synthesis of novel modified RNAs", Elsevier, Tetrahedron, 64, (2008), pp. 4313-4324.
Office Action dated Jul. 1, 2015 from the State Intellectual Property Office of the People's Republic of China in counterpart Chinese Application No. 201380016308.9.
Office Action dated Apr. 7, 2015 in corresponding Japanese Application No. 2014-507938.
Office Action dated Mar. 19, 2015, issued by the Intellectual Property Office of Singapore in corresponding Singapore Application No. 11201406080V.
Office Action dated Jan. 28, 2015, issued by the Intellectual Property Office of New Zealand in corresponding New Zealand Application No. 701245.
International Preliminary Report on Patentability, dated Oct. 9, 2014, from the International Bureau of WIPO in counterpart Application No. PCT/JP2013/058896.
Shinji Miura et al., "Comparison of 1-(2-deoxy-2-fluoro-4-thio43-D-arabinofuranosyl)cytosine with gemcitabine in its antitumor activity", Cancer Letters 1999, pp. 177-182, vol. 144.
Yuichi Yoshimura et al., "An Alternative Synthesis of the Antineoplastic Nucleoside 4'-ThioFAC and Its Application to the Synthesis of 4'-ThioFAG and 4'-Thiocytarazid", J. Org. Chem. 1999, pp. 7912-7920, vol. 64.
Shinji Miura et al., "Potent antitumor effect of 1-(2-deoxy-2-fluoro-4-thio-(3-D-arabinofuranosyl) cytosine on peritoneal dissemination models of gastrointestinal cancers", Oncology Reports 2002, pp. 1319-1322, vol. 9.
International Search Report for PCT/JP2013/058896 dated Jun. 4, 2013.

* cited by examiner

METHOD FOR PRODUCING THIOLANE SKELETON-TYPE GLYCOCONJUGATE, AND THIOLANE SKELETON-TYPE GLYCOCONJUGATE

CROSS-REFERENCE TO RELATED APPLICATIONS

This application is a Continuation of PCT International Application No. PCT/JP2015/054305 filed on Feb. 17, 2015, which claims priority under 35 U.S.C. § 119 (a) to Japanese Patent Application No. 2014-029020 filed on Feb. 18, 2014, and to Japanese Patent Application No. 2014-220368 filed on Oct. 29, 2014. Each of the above applications is hereby expressly incorporated by reference, in its entirety, into the present application.

BACKGROUND OF THE INVENTION

1. Field of the Invention

The present invention relates to a method for producing a thiolane skeleton-type glycoconjugate and the thiolane skeleton-type glycoconjugate.

2. Description of the Related Art

It is known that thionucleoside obtained by substituting an oxygen atom with a sulfur atom exhibits an antiviral activity or an antitumor activity.

For example, it is known that 1-(2-deoxy-2-fluoro-4-thio-β-D-arabinofuranosyl) cytosine has an excellent antitumor activity and is useful as a tumor therapeutic agent (refer to WO1997/038001A).

Therefore, studies on routes for synthesizing thionucleoside and synthetic intermediates thereof have been actively performed.

Among these, reactions for forming a thiolane ring are also widely studied and proposed (for example, refer to U.S. Pat. Nos. 3,243,425A, 7,148,223B, JP4719356B, WO1999/043690A, JP2007-514643A, JP4202327B, and JP2006-335737A).

On the other hand, although not a glycoconjugate, synthesis of a benzotetrahydrothiophene ring (refer to JP2006-335737A) and a synthesis reaction of iminosugar (refer to CN1010585855A and Synlett, 2010, No 3, p. 488-492) are also known.

SUMMARY OF THE INVENTION

The methods in the related art for synthesizing thiosugar by a reaction for forming a thiolane ring are mainly a dithioketal method and a Pummerer method. In the dithioketal method, a relatively lower mercaptan such as dibenzyl mercaptan is used, and due to this, stench is strong, and the dithioketal method is not preferable in an environmental aspect and for health. On the other hand, in the Pummerer method, in a Pummerer rearrangement step, inevitably positional isomers are generated, and thus, the Pummerer method is not preferable from the viewpoint of a yield and mass production suitability.

An object of the present invention is to provide a simple production method for a thionucleoside synthetic intermediate with a high yield under mild conditions and a production method capable of synthesizing a compound having a thiosugar skeleton, in a small number of steps, in a reaction for forming a thiolane ring.

Another object of the present invention is to provide a thiolane skeleton-type glycoconjugate or a compound of the synthetic intermediate thereof, useful as a thionucleoside synthetic intermediate which exhibits an antiviral activity or an antitumor activity.

As a result of various studies on reactions for forming a thiolane ring, the present inventors have found that by using a sulfur compound in a specific compound, the above-described objects can be achieved.

The above-described objects are achieved by the following means.

<1> A production method of a compound represented by the following General Formula (II) through a step of reacting a compound represented by the following General Formula (I) with a sulfur compound.

General Formula (I)

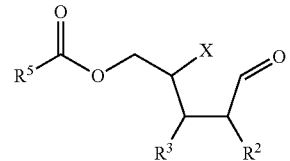

General Formula (II)

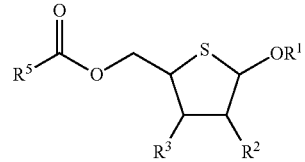

In General Formulas (I) and (II), $R^1$ represents a hydrogen atom or an acyl group, $R^2$ represents a hydrogen atom, a fluorine atom, an acyloxy group, an arylmethyloxy group, an allyloxy group, an arylmethyloxycarbonyloxy group, or an allyloxycarbonyloxy group, $R^3$ represents a hydrogen atom or an acyloxy group, $R^5$ represents an alkyl group or an aryl group, and X represents a leaving group.

Here, in a case where $R^2$ is a fluorine atom, an acyloxy group, an arylmethyloxy group, an allyloxy group, an arylmethyloxycarbonyloxy group, or an allyloxycarbonyloxy group, $R^3$ is an acyloxy group.

<2> The production method according to <1>, in which the compound represented by General Formula (II) is any one of the following General Formulas (II-1) to (II-14).

General Formula (II-1)

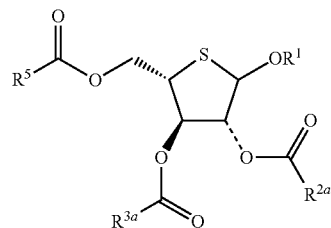

General Formula (II-2)

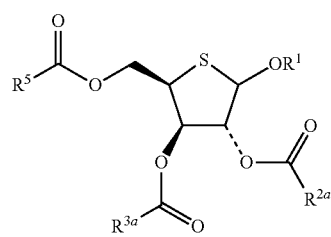

General Formula (II-3)
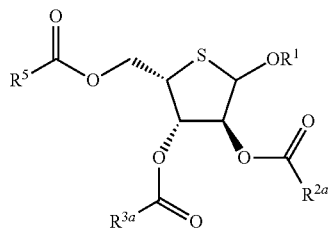

General Formula (II-4)
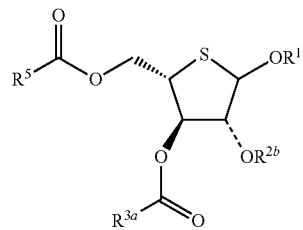

General Formula (II-5)
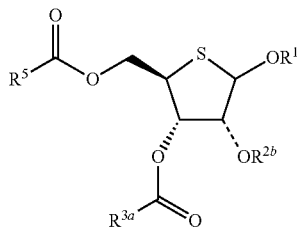

General Formula (II-6)
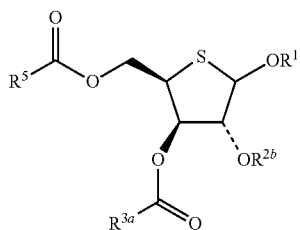

General Formula (II-7)
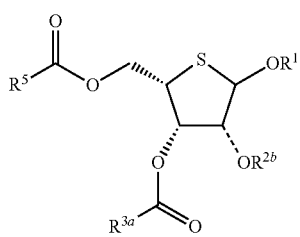

General Formula (II-8)
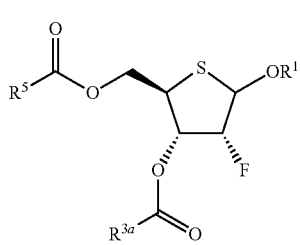

General Formula (II-9)
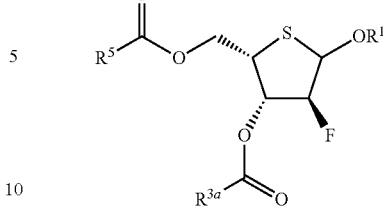

General Formula (II-10)
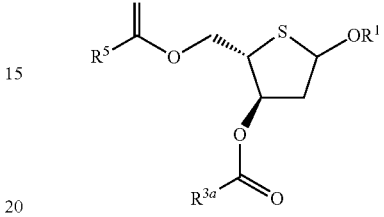

General Formula (II-11)
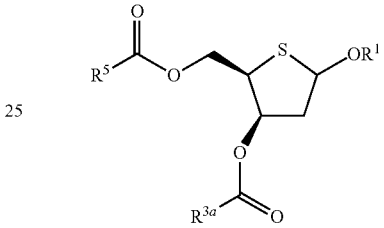

General Formula (II-12)
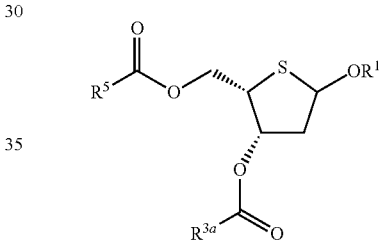

General Formula (II-13)
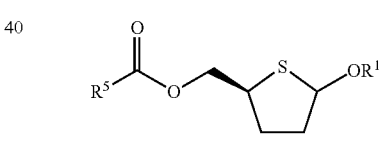

General Formula (II-14)
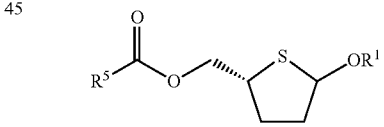

In General Formulas (II-1) to (II-14), $R^1$ and $R^5$ have the same meaning as $R^1$ and $R^5$ in General Formula (II), respectively. Each of $R^{2a}$ and $R^{3a}$ independently represents an alkyl group or an aryl group. $R^{2b}$ represents —$CH_2$—Ar, an allyl group, —C(=O)O$CH_2$—Ar, or an allyloxycarbonyl group. Here, Ar represents an aryl group. Moreover, the direct bond represented by a dashed line having a constant thickness which is bonded to a thiolane ring is positioned at any one of an α-position or a β-position.

<3> The production method according to <1> or <2>, in which $R^5$ is an aryl group, and $R^3$ or —O—C(=O)—$R^{3a}$ is an arylcarbonyloxy group.

<4> The production method according to any one of <1> to <3>, in which $R^5$ is a phenyl group, a 4-methylphenyl group, a 4-phenylphenyl group, or a 2-naphthyl group, and $R^3$ or —O—C(=O)—$R^{3a}$ is a phenylcarbonyloxy group, a 4-methylphenylcarbonyloxy group, a 4-phenylphenylcarbonyloxy group, or a 2-naphthylcarbonyloxy group.

<5> The production method according to any one of <1> to <4>, in which, after a compound represented by the following General Formula (IIA) is synthesized in the step of reacting the compound represented by General Formula (I) with a sulfur compound, a compound represented by the following General Formula (IIB) is synthesized in a step of acylating the compound represented by General Formula (IIA).

General Formula (IIA)

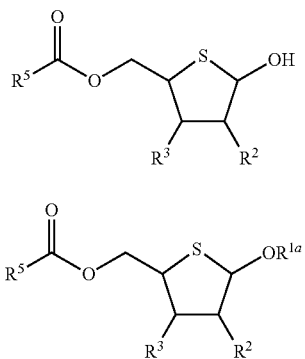

General Formula (IIB)

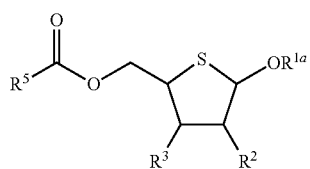

In General Formulas (IIA) and (IIB), $R^2$, $R^3$, and $R^5$ have the same meaning as $R^2$, $R^3$, and $R^5$ in General Formula (II), respectively. $R^{1a}$ represents an acyl group.

<6> The production method according to any one of <1> to <5>, in which $R^1$ or $R^{1a}$ is an acetyl group or an arylcarbonyl group.

<7> The production method according to any one of <1> to <6>, in which X is a halogen atom, an alkylsulfonyloxy group, or an arylsulfonyloxy group.

<8> The production method according to any one of <1> to <7>, in which the sulfur compound is MSH or $M_2S$ in which M is an alkali metal.

<9> A compound represented by any one of the following General Formulas (II-1) to (II-14).

General Formula (II-1)

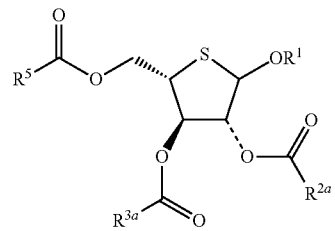

General Formula (II-2)

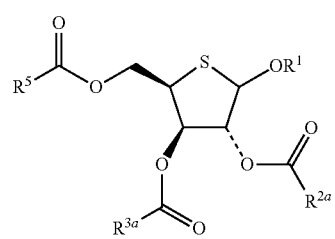

General Formula (II-3)

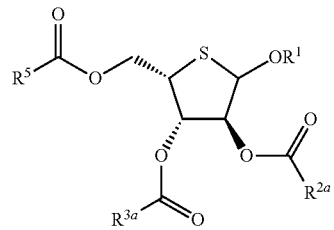

General Formula (II-4)

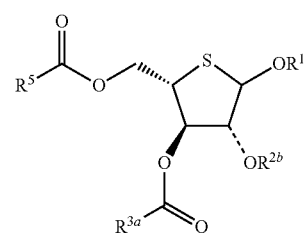

General Formula (II-5)

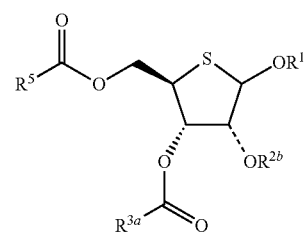

General Formula (II-6)

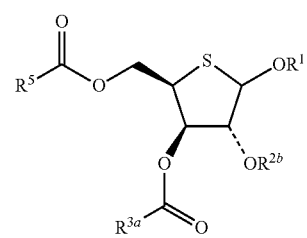

General Formula (II-7)

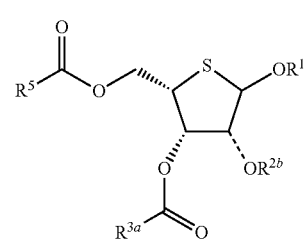

General Formula (II-8)

-continued

General Formula (II-9)

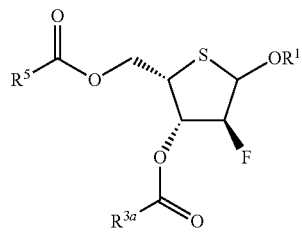

General Formula (II-10)

General Formula (II-11)

General Formula (II-12)

General Formula (II-13)

General Formula (II-14)

In General Formulas (II-1) to (II-14), $R^1$ represents a hydrogen atom or an acyl group, each of $R^{2a}$ and $R^{3a}$ independently represents an alkyl group or an aryl group, and $R^5$ represents an alkyl group or an aryl group. $R^{2b}$ represents —CH$_2$—Ar, an allyl group, —C(=O)OCH$_2$—Ar, or an allyloxycarbonyl group. Here, Ar represents an aryl group. Moreover, the direct bond represented by a dashed line having a constant thickness which is bonded to a thiolane ring is positioned on any one of an α-side or a β-side.

<10> The compound according to <9>, in which $R^1$ is a hydrogen atom, an acetyl group, or an arylcarbonyl group, and each of $R^{2a}$, $R^{3a}$, and $R^5$ is independently an aryl group.

<11> The compound according to <9> or <10>, in which each of $R^{2a}$, $R^{3a}$, and $R^5$ is independently a phenyl group, a 4-methylphenyl group, a 4-phenylphenyl group, or a 2-naphthyl group.

<12> A compound represented by any one of the following General Formula (II-1A'), (II-1B), (II-2A), (II-2B'), (II-3), (II-6B), (II-9), (II-13'), and (II-14').

General Formula (II-1A')

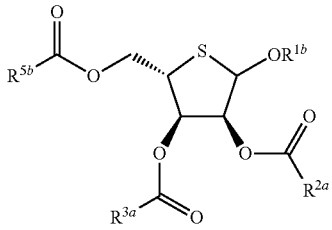

General Formula (II-1B)

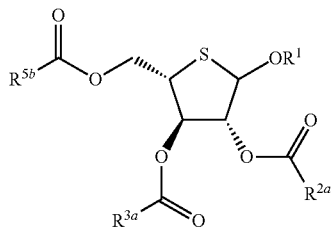

General Formula (II-2A)

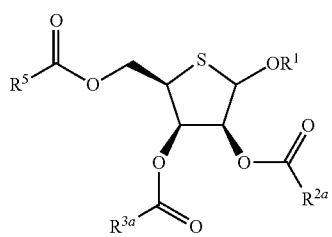

General Formula (II-2B')

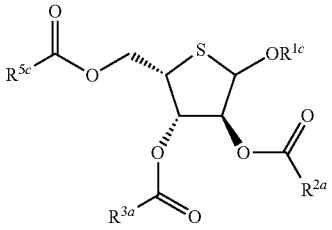

General Formula (II-3)

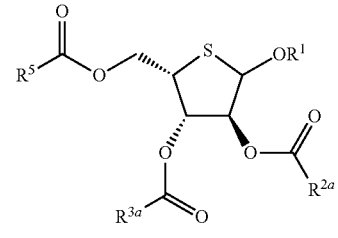

General Formula (II-6B)

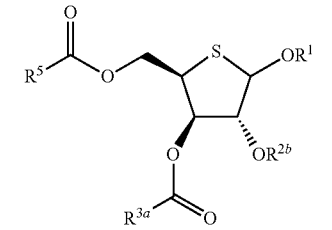

-continued

General Formula (II-9)

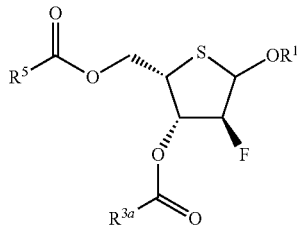

General Formula (II-13')

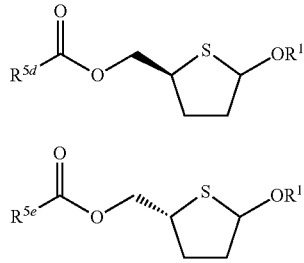

General Formula (II-14')

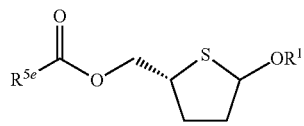

In General Formulas (II-1A'), (II-1B), (II-2A), (II-2B'), (II-3), (II-6B), (II-9), (II-13'), and (II-14'), each of $R^1$, $R^{1b}$, and $R^{1c}$ independently represents a hydrogen atom or an acyl group. Each of $R^{2a}$ and $R^{3a}$ independently represents an alkyl group or an aryl group. $R^{2b}$ represents —CH$_2$—Ar, an allyl group, —C(=O)OCH$_2$—Ar, or an allyloxycarbonyl group. Here, Ar represents an aryl group. Each of $R^5$, $R^{5b}$, $R^{5c}$, $R^{5a}$, and $R^{5e}$ independently represents an alkyl group or an aryl group. Here, in a case where $R^{1b}$ and $R^{1c}$ are acetyl groups, $R^{5b}$ is an aryl group, and $R^{5c}$ is an aryl group substituted with an alkyl group or a substituent.

<13> The compound according to <12>, in which $R^1$ is a hydrogen atom, an acetyl group, a 4-methylbenzoyl group, a 4-phenylbenzoyl group, or a 2-naphthoyl group, each of $R^{1b}$ and $R^{1c}$ is independently a hydrogen atom, a 4-methylbenzoyl group, a 4-phenylbenzoyl group, or a 2-naphthoyl group, each of $R^{2a}$, $R^{3a}$, $R^5$, $R^{5b}$, and $R^{5c}$ is independently a 4-methylphenyl group, a 4-phenylphenyl group, or a 2-naphthyl group, $R^{2b}$ is a phenylmethyl group, and each of $R^{5d}$ and $R^{5e}$ is independently a phenyl group, a 4-methylphenyl group, a 4-phenylphenyl group, or a 2-naphthyl group.

<14> The compound according to any one of <9> to <13>, in which the compound is a thionucleoside synthetic intermediate.

Moreover, "—O—C(=O)—$R^{3a}$ is an arylcarbonyloxy group" means that entire —O—C(=O)—$R^{3a}$ represents an arylcarbonyloxy group. That is, $R^{3a}$ is an aryl group.

In the specification, each substituent may be further substituted with a substituent unless specified otherwise.

According to the present invention, it is possible to provide a simple production method for a thionucleoside synthetic intermediate with a high yield under mild conditions and a production method capable of synthesizing a compound having a thiosugar skeleton, in a small number of steps.

Furthermore, it is possible to provide a thiolane skeleton-type glycoconjugate or a compound of the synthetic intermediate thereof, useful as a thionucleoside synthetic intermediate which exhibits an antiviral activity or an antitumor activity.

The above-described or other features and advantages of the present invention will become apparent from the following description.

DESCRIPTION OF THE PREFERRED EMBODIMENTS

<<Production Method of Thiolane Skeleton-Type Glycoconjugate>>

The production method of a thiolane skeleton-type glycoconjugate of the present invention is a production method of a compound stereocontrolled represented by the following General Formula (II) through a step of reacting a compound represented by the following General Formula (I) with a sulfur compound.

General Formula (I)

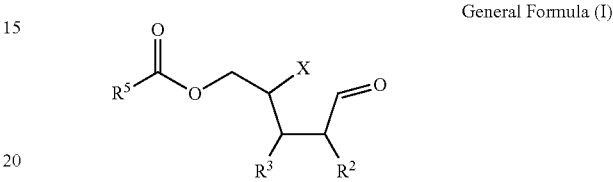

General Formula (II)

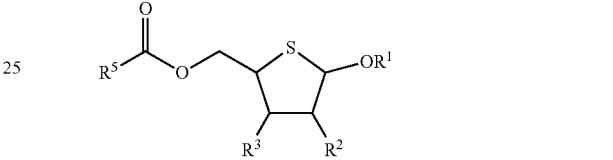

In General Formulas (I) and (II), $R^1$ represents a hydrogen atom or an acyl group, $R^2$ represents a hydrogen atom, a fluorine atom, an acyloxy group, an arylmethyloxy group, an allyloxy group, an arylmethyloxycarbonyloxy group, or an allyloxycarbonyloxy group, $R^3$ represents a hydrogen atom or an acyloxy group, $R^5$ represents an alkyl group or an aryl group, and X represents a leaving group.

Here, in a case where $R^2$ is a fluorine atom, an acyloxy group, an arylmethyloxy group, an allyloxy group, an arylmethyloxycarbonyloxy group, or an allyloxycarbonyloxy group, $R^3$ is an acyloxy group.

Moreover, in a case where the carbon atoms to be substituted with $R^2$, $R^3$, and CH$_2$—O—C(=O)—$R^5$ in General Formulas (I) and (II) are asymmetric carbon atoms, the steric configuration when carbon atoms are substituted with $R^2$, $R^3$, and CH$_2$—O—C(=O)—$R^5$ is substantially any one of R or S on each asymmetric carbon atom. In addition, in General Formula (II), $R^2$ is substantially positioned on any one of the α side or the β side, $R^3$ is substantially positioned on any one of the α side or the β side, and, CH$_2$—O—C(=O)—$R^5$ is substantially positioned on the α side or the β side.

Here, the "passing through" means that even in a case where there is only a step of reacting the compound represented by General Formula (I) with a sulfur compound, a step of acylating the compound synthesized in the step of reacting compound represented by General Formula (I) with a sulfur compound after the step of reacting with a sulfur compound may be included.

In a case where $R^1$ in General Formula (II) is a hydrogen atom, the compound represented by General Formula (I) can be produced by only a step of reacting the compound represented by General Formula (I) with a sulfur compound.

In addition, in a case where $R^1$ is an acyl group, the compound represented by General Formula (II) can be produced by performing a step of acylating after the step of reacting with a sulfur compound.

Moreover, in the present invention, the OH body obtained by a reaction with a sulfur compound is preferably acylated.

That is, in a case where $R^1$ in General Formula (II) is an acyl group, it is preferable that a compound represented by the following General Formula (IIA) is synthesized in the step of reacting the compound represented by General Formula (I) with a sulfur compound, and then, a compound represented by the following General Formula (IIB) is produced in a step of acylating the compound represented by General Formula (IIA).

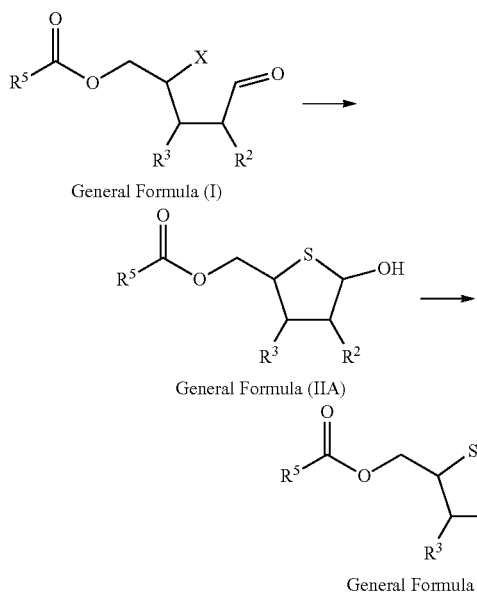

In General Formulas (IIA) and (IIB), $R^2$, $R^3$, and $R^5$ have the same meaning as $R^2$, $R^3$, and $R^5$ in General Formula (II), respectively. $R^{1a}$ represents an acyl group.

The compound represented by General Formula (II) in the present invention has two to four asymmetric carbon atoms as carbon atoms configuring a thiolane ring which is a basic skeleton. Specifically, in a case where $R^2$ and $R^3$ are hydrogen atoms, the compound has two asymmetric carbon atoms, in a case where any one of $R^2$ or $R^3$ is a hydrogen atom, the compound has three asymmetric carbon atoms, and in other cases, the compound has four asymmetric carbon atoms.

In the present invention, the "stereocontrolled" means that the compound represented by General Formula (II) is produced while controlling the steric configuration present in the asymmetric carbon atoms to become a specific configuration.

For example, the case of a compound represented by the following General Formula (II-1A) is as follows.

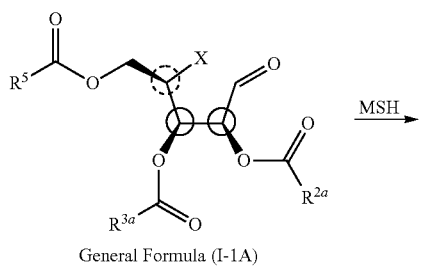

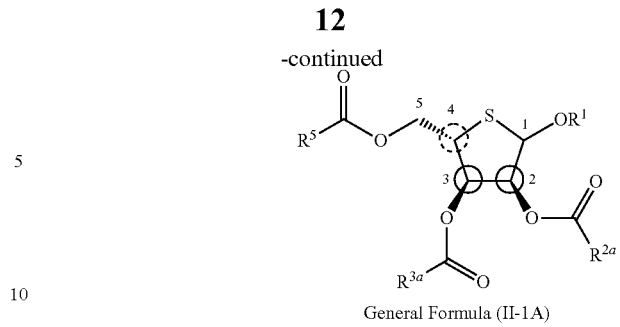

In General Formulas (I-1A) and (II-1A), $R^1$, $R^5$, and X have the same meaning as $R^1$, $R^5$, and X in General Formulas (I) and (II), respectively. Each of $R^{2a}$ and $R^{3a}$ independently represents an alkyl group or an aryl group. M represents an alkali metal.

Here, MSH nucleophilically attacks the carbon atom substituted with X through the following route. Since this nucleophilic substitution reaction is a $S_N2$ reaction, only the configuration on the carbon atom at the 4-position of the thiolan ring is inversed (Walden inversion), and configurations of the asymmetric carbon atoms at other than the 4-position are fixed without change. Moreover, in the following reaction route, the portions shown by a solid line circle portion are configurations fixed.

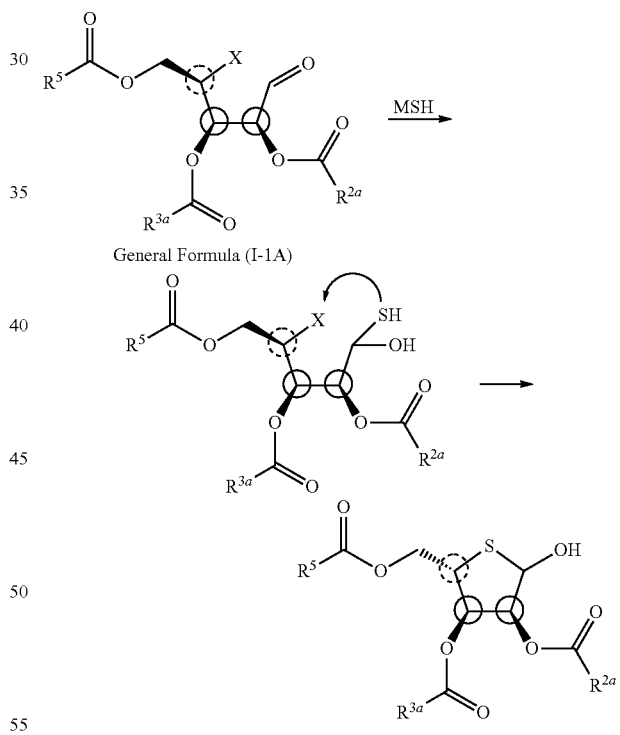

The solvent used in the reaction of the step of reacting the compound represented by General Formula (I) with a sulfur compound is not particularly limited as long as it is a solvent which does not affect the reaction. Examples thereof include aliphatic hydrocarbons, halogenated hydrocarbons, alcohols, ethers, esters, ketones, nitriles, amides, sulfoxides, aromatic hydrocarbons, ureas, and water, and these solvents may be used in combination.

Preferable solvents are solvents having an amide moiety or a sulfonyl group in a partial structure, that is, amides, cyclic amides, ureas, cyclic ureas, or sulfoxides.

Specific examples thereof include N,N-dimethylformamide, N,N-dimethylacetamide, N-methylpyrrolidone, N-ethylpyrrolidone, 1,3-dimethyl-2-imidazolidinone, and dimethylsulfoxide.

Although the amount of solvent used is not particularly limited, the amount used may be 1-fold to 50-fold (v/w), and preferably 1-fold to 15-fold (v/w) with respect to the compound represented by General Formula (I).

Examples of the sulfur compound used in this reaction include hydrogen sulfide and a salt thereof.

Examples of the salt of hydrogen sulfide include an alkali metal salt and an alkali earth metal salt.

The sulfur compound is preferably MSH or $M_2S$ in which M is an alkali metal.

Examples of the sulfur compound include hydrogen sulfide, sodium hydrogen sulfide, sodium sulfide, potassium hydrogen sulfide, calcium hydrogen sulfide, and magnesium sulfide, and sodium hydrogen sulfide is preferable.

The sulfur compound may be hydrate, and can also be used by being dissolved in an aqueous solution.

The amount of sulfur compound used is preferably 0.2-fold by mole to 10-fold by mole, more preferably 0.5-fold by mole to 2.0-fold by mole, and still more preferably 0.7-fold by mole to 1.5-fold by mole, with respect to the compound represented by General Formula (I).

The reaction temperature is preferably −20° C. to 100° C., more preferably −10° C. to 80° C., and still more preferably −5° C. to 60° C.

The reaction time is preferably 5 minutes to 50 hours, more preferably 5 minutes to 24 hours, and still more preferably 5 minutes to 6 hours.

Examples of the acylating agent used in the step of acylating the compound represented by General Formula (IIA) include acyl halide and acid anhydride.

Moreover, each of the acyl moiety of an acylating agent and $R^{1a}$ in the compound represented by General Formula (IIB) has the same meaning as the acyl group in $R^1$ described below, and the preferable range thereof is also the same.

These acylating agents are preferably 0.5-fold by mole to 10-fold by mole, more preferably 0.8-fold by mole to 5-fold by mole, and still more preferably 1-fold by mole to 2-fold by mole, with respect to the compound represented by General Formula (IIA).

As the reaction solvent, aliphatic hydrocarbons, halogenated hydrocarbons, ethers, esters, ketones, nitriles, amides, sulfoxides, aromatic hydrocarbons, or ureas are preferable, and ethers, esters, ketones, nitriles, amides, sulfoxides, or aromatic hydrocarbons are more preferable. These solvents may be used in combination.

In the step of acylating, a base is preferably used, and examples thereof include pyridines, trialkylamines which may have a ring structure, N,N-dialkylanilines, N-alkyl-N-arylanilines, triarylamines, guanidines, alkali metal hydroxides, alkali earth metal hydroxides, alkali metal carbonates, alkali earth metal carbonates, and alkali metal hydrogen carbonates, and pyridines or trialkylamines are preferable.

In addition, the amount of base used is preferably 0.2-fold by mole to 5-fold by mole with respect to the compound represented by General Formula (IIA).

The reaction temperature is preferably −20° C. to 100° C., more preferably −10° C. to 80° C., and still more preferably 0° C. to 50° C.

The reaction time is preferably 5 minutes to 50 hours, more preferably 10 minutes to 24 hours, and still more preferably 30 minutes to 6 hours.

In addition, it is preferable that, in the step of acylating, the compound represented by General Formula (IIA) is synthesized from the compound represented by General Formula (I), and then the compound represented by General Formula (IIB) is preferably synthesized in the same vessel without taking out the compound represented by General Formula (IIA).

<<Thiolane Skeleton-Type Glycoconjugate>>

The thiolane skeleton-type glycoconjugate of the present invention is the compound represented by General Formula (II).

In General Formula (II), $R^1$ represents a hydrogen atom or an acyl group, $R^2$ represents a hydrogen atom, a fluorine atom, an acyloxy group, an arylmethyloxy group, an allyloxy group, an arylmethyloxycarbonyloxy group, or an allyloxycarbonyloxy group, $R^3$ represents a hydrogen atom or an acyloxy group, and $R^5$ represents an alkyl group or an aryl group.

Here, in a case where $R^2$ is a fluorine atom, an acyloxy group, an arylmethyloxy group, an allyloxy group, an arylmethyloxycarbonyloxy group, or an allyloxycarbonyloxy group, $R^3$ is an acyloxy group.

Moreover, in General Formula (II), $R^2$ is substantially positioned on any one of the α side or the β side, $R^3$ is substantially positioned on any one of the α side or the β side, and, $CH_2$—O—C(=O)—$R^5$ is substantially positioned on any one of the α side or the β side.

Here, the term "substalcially" means that, for example, for each asymmetric carbon (other than an anomeric position), the asymmetry purity [in a case where the S body is excessive, (S body/(S body+R body)×100)] is 95% or greater, preferably 97% or greater, and more preferably 99% or greater.

The number of carbon atoms of the acyl group represented by $R^1$ is preferably 1 to 20 carbon atoms, more preferably 2 to 20 carbon atoms, and still more preferably 2 to 16 carbon atoms. In addition, an acyl group, an alkylcarbonyl group, or an arylcarbonyl group is preferable.

Examples of the alkylcarbonyl group include an acetyl group, a propionyl group, a butyryl group, an isobutyryl group, a valeryl group, an isovaleryl group, a pivaloyl group, a lauroyl group, a myristoyl group, a palmitoyl group, and a stearoyl group. Moreover, the acyl group represented by $R^1$ also includes a formyl group.

Examples of the arylcarbonyl group include a benzoyl group, a 4-methylbenzoyl group, a 4-chlorobenzoyl group, a 4-phenylbenzoyl group, and a 2-naphthoyl group, and a 4-methylbenzoyl group, a 4-phenylbenzoyl group, or a 2-naphthoyl group is preferable.

These acyl groups may be substituted with a substituent, and examples of the substituent include a halogen atom, an alkyl group, an aryl group, a heterocyclic group, an alkoxy group, an aryloxy group, an alkylthio group, and an arylthio group.

$R^1$ is preferably a hydrogen atom, an acetyl group, or an arylcarbonyl group.

Examples of the acyl moiety of the acyloxy group represented by $R^2$ or $R^3$ include the acyl moiety exemplified in the acyl group represented by $R^1$.

The number of carbon atoms of the alkyl group represented by $R^5$ is preferably 1 to 19 carbon atoms, and the number of carbon atoms of the aryl group represented by $R^5$ is preferably 6 to 19 carbon atoms, and more preferably 6 to 15 carbon atoms.

Each of the alkyl group and the aryl group may have a substituent, and examples thereof include a halogen atom, an alkyl group, an aryl group, a heterocyclic group, an alkoxy group, an aryloxy group, an alkylthio group, and an arylthio group.

Examples of the alkyl group include a methyl group, an ethyl group, an isopropyl group, an n-propyl group, an n-butyl group, a t-butyl group, an n-hexyl group, a 2-ethylhexyl group, a dodecyl group, and an octadecyl group.

Examples of the aryl group include a phenyl group, a 4-chlorophenyl group, a 4-methylphenyl group, a 4-phenylphenyl group, and a 2-naphthyl group.

Each of the acyloxy group represented by $R^3$ and the acyloxy group represented by 5-position —O—C(=O)—$R^5$ is preferably an benzoyloxy group, a 4-methylbenzoyl group, a 4-chlorobenzoyl group, a 4-phenylbenzoyl group, or a 2-naphthoyl group.

The number of carbon atoms of the arylmethyloxy group represented by $R^2$ is preferably 7 to 20, and more preferably 7 to 16, and examples thereof include a phenylmethyloxy group, a 4-chlorophenylmethyloxy group, a 4-methylphenylmethyloxy group, a 4-phenylphenylmethyloxy group, and a 2-naphthylmethyloxy group.

The number of carbon atoms of the arylmethyloxycarbonyloxy group represented by $R^2$ is preferably 8 to 21, and more preferably 8 to 17, and examples thereof include a phenylmethyloxycarbonyloxy group, a 4-chlorophenylmethyloxycarbonyloxy group, a 4-methylphenylmethyloxycarbonyloxy group, a 4-phenylphenylmethyloxycarbonyloxy group, and a 2-naphthylmethyloxycarbonyloxy group.

$R^2$ is preferably a hydrogen atom, a fluorine atom, an acyloxy group, or an arylmethyloxy group.

In General Formula (II), $R^5$ is preferably an aryl group, and $R^3$ is preferably an arylcarbonyloxy group.

In General Formula (II), a case where $R^5$ is an aryl group and $R^3$ is an arylcarbonyloxy group is more preferable, and a case where $R^5$ is a phenyl group, a 4-methylphenyl group, a 4-phenylphenyl group, or a 2-naphthyl group, and $R^3$ is a phenylcarbonyloxy group, a 4-methylphenylcarbonyloxy group, a 4-phenylphenylcarbonyloxy group, or a 2-naphthylcarbonyloxy group, is still more preferable.

The compound represented by General Formula (II) is preferably a compound represented by any one of the following General Formulas (II-1) to (II-14).

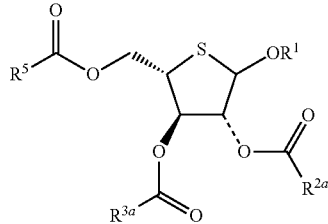

General Formula (II-1)

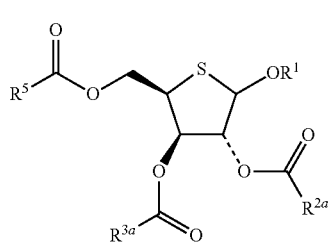

General Formula (II-2)

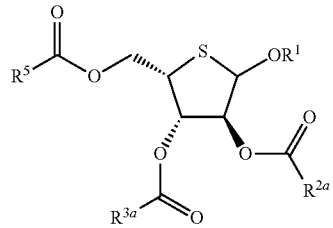

General Formula (II-3)

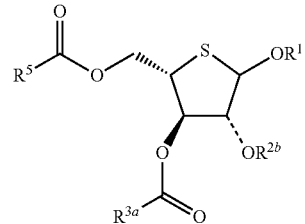

General Formula (II-4)

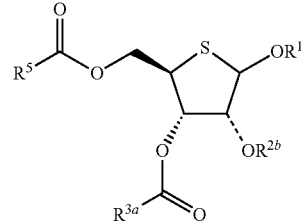

General Formula (II-5)

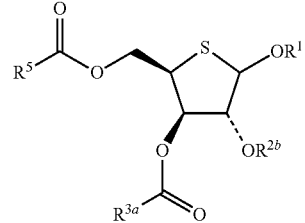

General Formula (II-6)

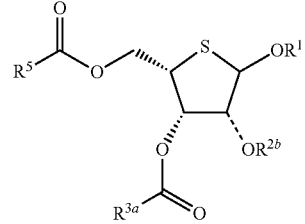

General Formula (II-7)

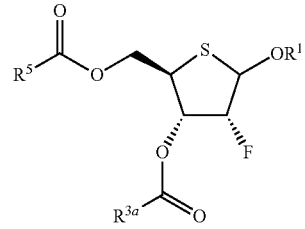

General Formula (II-8)

General Formula (II-9)
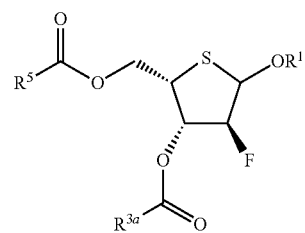

General Formula (II-10)
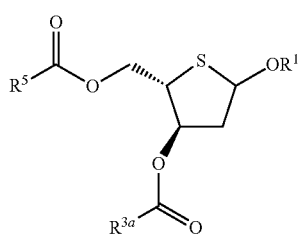

General Formula (II-11)
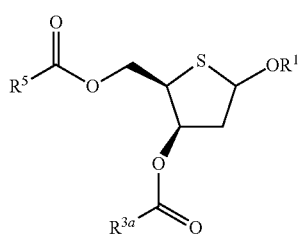

General Formula (II-12)
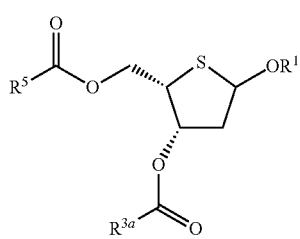

General Formula (II-13)
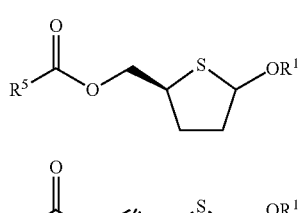

General Formula (II-14)
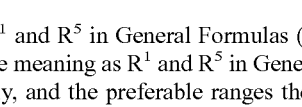

General Formula (II-1A)
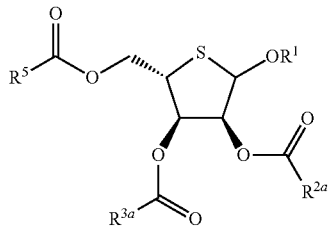

General Formula (II-1B)
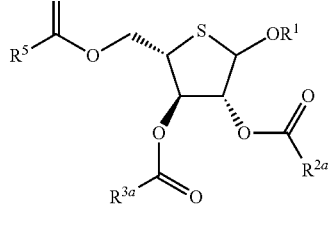

General Formula (II-2A)
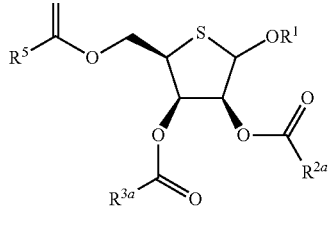

General Formula (II-2B)
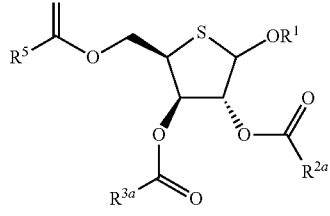

General Formula (II-4A)
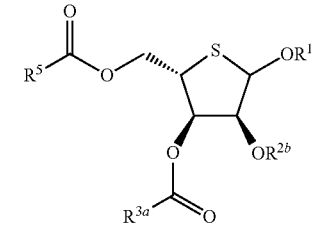

General Formula (II-4B)
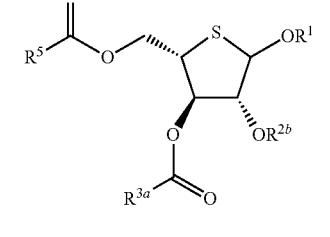

$R^1$ and $R^5$ in General Formulas (II-1) to (II-14) have the same meaning as $R^1$ and $R^5$ in General Formula (II), respectively, and the preferable ranges thereof are also the same. Each of $R^{2a}$ and $R^{1a}$ independently represents an alkyl group or an aryl group. $R^{2b}$ represents —CH$_2$—Ar, an allyl group, —C(=O)OCH$_2$—Ar, or an allyloxycarbonyl group. Here, Ar represents an aryl group. Moreover, the direct bond represented by a dashed line having a constant thickness which is bonded to a thiolane ring is substantially positioned on any one of an α-side or a β-side.

Here, the compounds represented by each of General Formulas (II-1), (II-2), and (II-4) to (II-7) having a direct bond represented by a dashed line having a constant thickness which is bonded to a thiolane ring are represented by each of the following General Formulas (II-1A), (II-1B), (II-2A), (II-2B), (II-4A) to (II-7A), and (II-4B) to (II-7B).

-continued

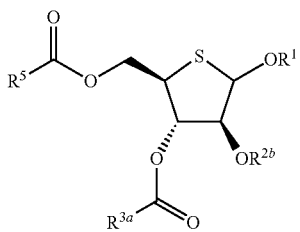
General Formula (II-5A)

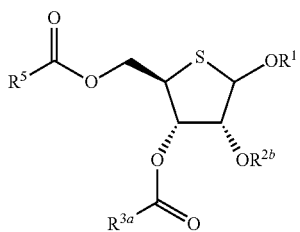
General Formula (II-5B)

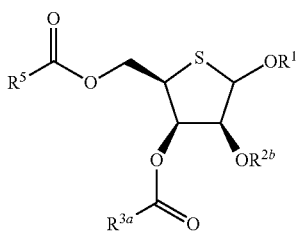
General Formula (II-6A)

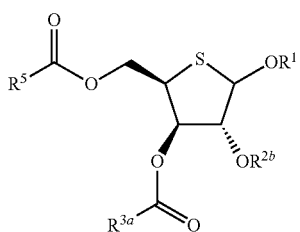
General Formula (II-6B)

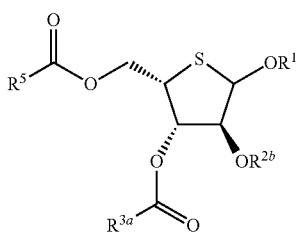
General Formula (II-7A)

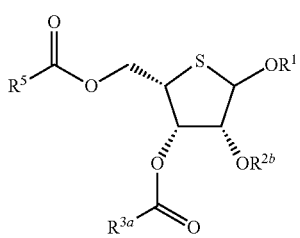
General Formula (II-7B)

The alkyl group and the aryl group represented by each of $R^{2a}$ and $R^{3a}$ have the same meaning as the alkyl group and the aryl group represented by $R^5$, respectively, and the preferable ranges thereof are also the same.

Each of $R^{2a}$ and $R^{3a}$ is independently preferably an aryl group.

The aryl group represented by Ar has the same meaning as the aryl group represented by $R^5$ in General Formula (II), and the preferable range thereof is also the same.

$R^{2b}$ is preferably —CH$_2$—Ar, and more preferably a phenylmethyl group.

In General Formulas (II-1) to (II-12), $R^5$ is preferably an aryl group, and $R^{3a}$ is preferably an aryl group, and a compound in which $R^5$ is an aryl group and $R^{3a}$ is an aryl group is more preferable. A compound in which $R^5$ is a phenyl group, a 4-methylphenyl group, a 4-phenylphenyl group, or a 2-naphthyl group, and $R^{3a}$ is a phenyl group, a 4-methylphenyl group, a 4-phenylphenyl, or a 2-naphthyl group is still more preferable.

Moreover, in General Formulas (II-13) and (II-14), $R^5$ is preferably an aryl group.

In General Formulas (II-1) to (II-14), $R^1$ is preferably a hydrogen atom, an acetyl group, or an arylcarbonyl group, each of $R^{2a}$, $R^{3a}$, and $R^5$ is independently preferably an aryl group, and a compound in which $R^1$ is a hydrogen atom, an acetyl group, or an arylcarbonyl group, and each of $R^{2a}$, $R^{3a}$, and $R^5$ is independently an aryl group is more preferable.

A compound in which each of $R^{2a}$, $R^{3a}$, and $R^5$ is independently a phenyl group, a 4-methylphenyl group, a 4-phenylphenyl group, or a 2-naphthyl group is still more preferable.

The compound represented by any one of General Formulas (II-1) to (II-14) is particularly preferably a compound represented by any one of the following General Formulas (II-1A'), (II-1B), (II-2A), (II-2B'), (II-3), (II-6B), (II-9), (II-13'), and (II-14').

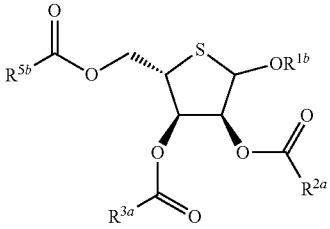
General Formula (II-1A')

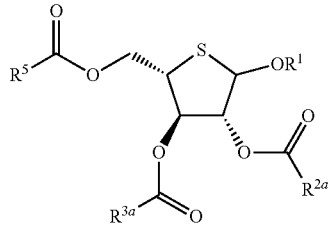
General Formula (II-1B)

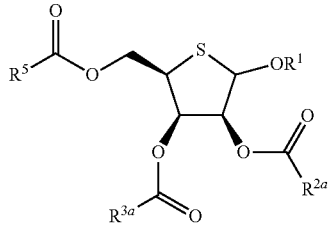
General Formula (II-2A)

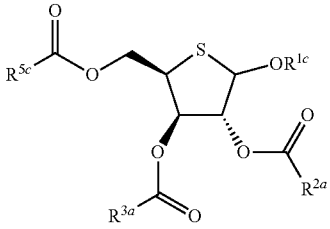
General Formula (II-2B')

-continued

General Formula (II-3)

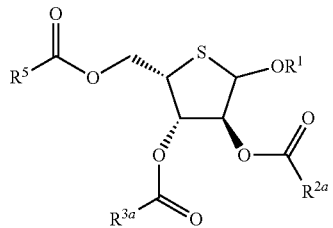

General Formula (II-6B)

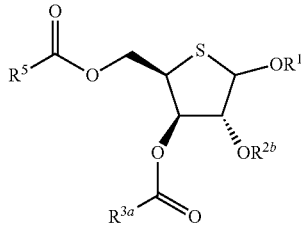

General Formula (II-9)

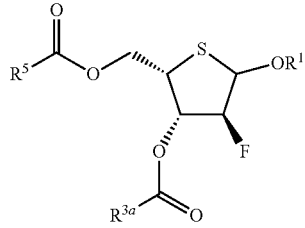

General Formula (II-13')

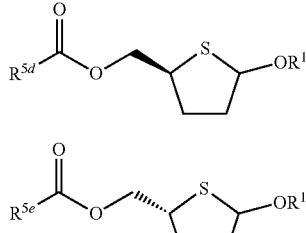

General Formula (II-14')

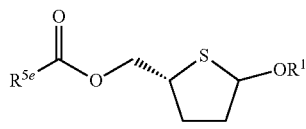

$R^1$, $R^{2a}$, $R^{2b}$, $R^{3a}$, and $R^5$ in General Formulas (II-1A'), (II-1B), (II-2A), (II-2B'), (II-3), (II-6B), (II-9), (II-13'), and (II-14') have the same meaning as $R^1$, $R^{2a}$, $R^{2b}$, $R^{3a}$, and $R^5$ in General Formulas (II-1) to (II-14), respectively, and the preferable ranges thereof are also the same. Each of $R^{1b}$ and $R^{1c}$ represents a hydrogen atom or an acyl group. Each of $R^{5b}$, $R^{5c}$, $R^{4d}$, and $R^{5C}$ represents an alkyl group or an aryl group. Here, in a case where $R^{1b}$ and $R^{1c}$ are acetyl groups, $R^{5b}$ is an aryl group, and $R^{5c}$ is an aryl group substituted with an alkyl group or a substituent.

The acyl group represented by $R^{1b}$ or $R^{1c}$ has the same meaning as the acyl group in General Formula (II), and the preferable range thereof is also the same.

The alkyl group and the aryl group represented by $R^{5b}$, $R^{5c}$, $R^{5d}$, or $R^{5e}$ have the same meaning as those represented by $R^5$ in General Formula (II), respectively, and the preferable ranges thereof are also the same.

Moreover, in $R^{1b}$ and $R^{1c}$, the acyl group is preferably an arylcarbonyl group, and the aryl moiety of the arylcarbonyl group is also preferably an aryl moiety which has been substituted with a substituent.

Examples of the substituent with which the aryl moiety is substituted include a halogen atom, an alkyl group, an aryl group, a heterocyclic group, an alkoxy group, an aryloxy group, an alkylthio group, and an arylthio group described above, and a halogen atom, an alkyl group, or an aryl group is preferable, an alkyl group or an aryl group is more preferable, and a methyl group or a phenyl group is still more preferable.

In addition, each of $R^{1b}$ and $R^{1c}$ is also preferably a 2-naphthylcarbonyl group. The compound represented by any one of General Formulas (II-1A'), (II-1B), (II-2A), (II-2B'), (II-3), (II-6B), (II-9), (II-13') or (II-14') is most preferably a compound in which $R^1$ is a hydrogen atom, an acetyl group, a 4-methylbenzoyl group, a 4-phenylbenzoyl group, or a 2-naphthoyl group, each of $R^{1b}$ and $R^{1c}$ is a hydrogen atom, a 4-methylbenzoyl group, a 4-phenylbenzoyl group, or a 2-naphthoyl group, each of $R^{2a}$, $R^{3a}$, $R^5$, $R^{5b}$, and $R^{5c}$ is independently a 4-methylphenyl group, a 4-phenylphenyl group, or a 2-naphthyl group, $R^{2b}$ is a phenylmethyl group, and each of $R^{5d}$ and $R^{5e}$ is a phenyl group, a 4-methylphenyl group, a 4-phenylphenyl group, or a 2-naphthyl group.

Hereinafter, specific examples of the compound represented by General Formula (II) of the present invention will be shown. Moreover, the present invention is not limited thereto.

Compounds Represented by General Formula (II-1A)

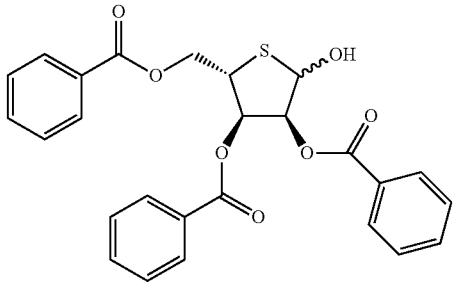

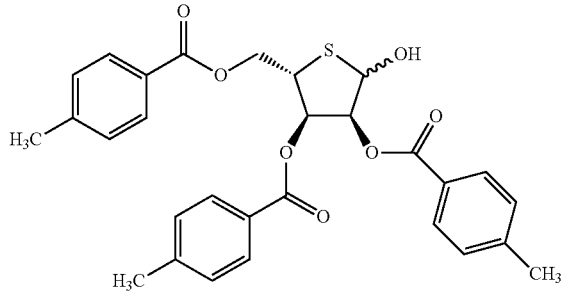

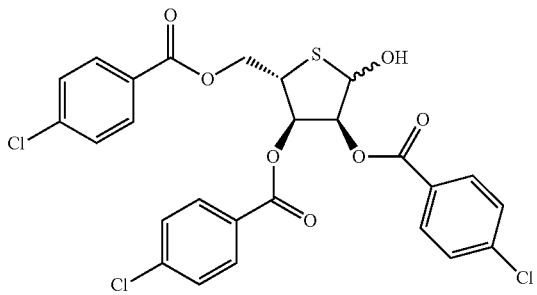

23
-continued
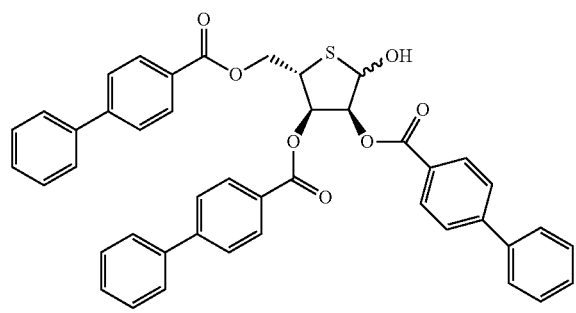
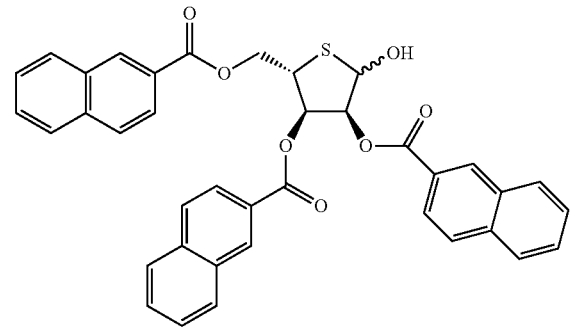
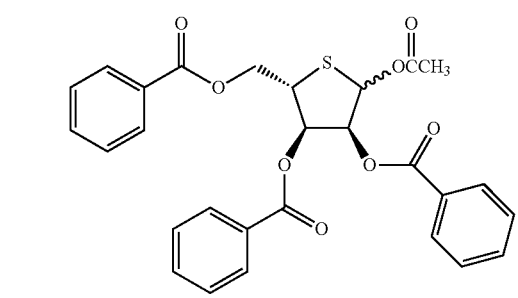
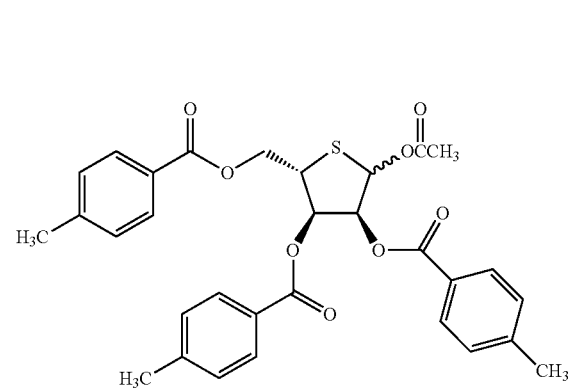
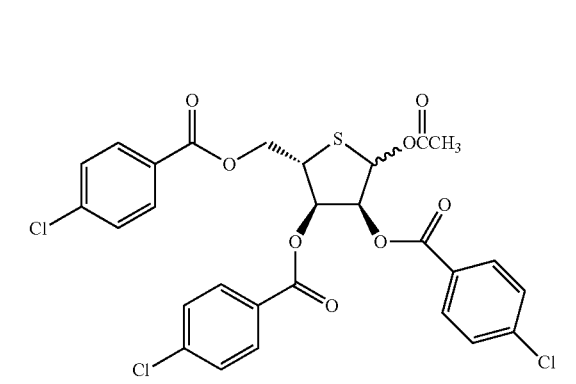
24
-continued
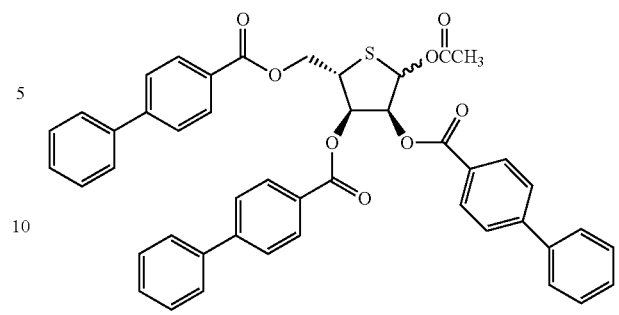
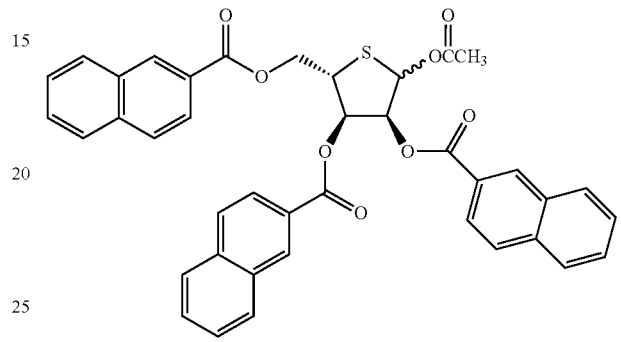
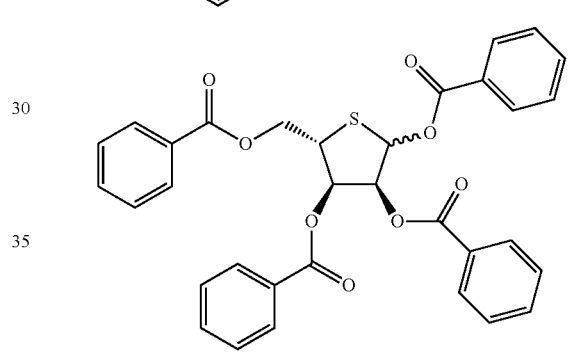
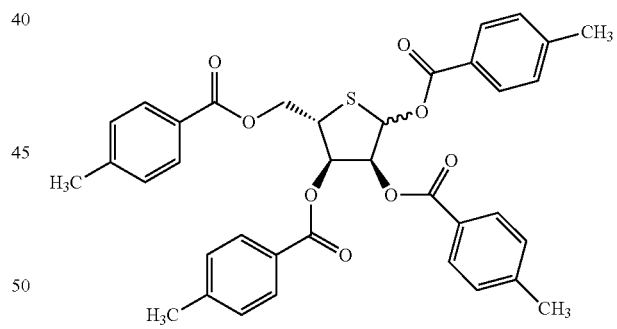
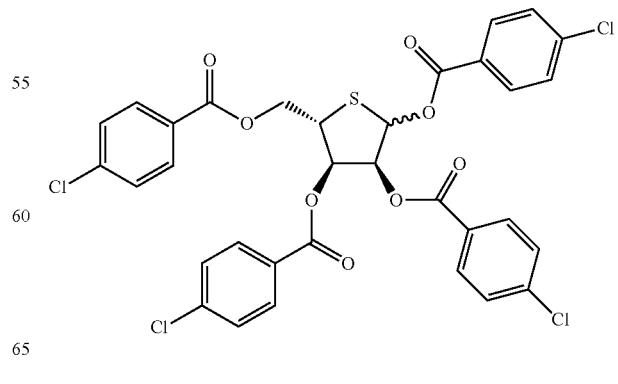

25
-continued
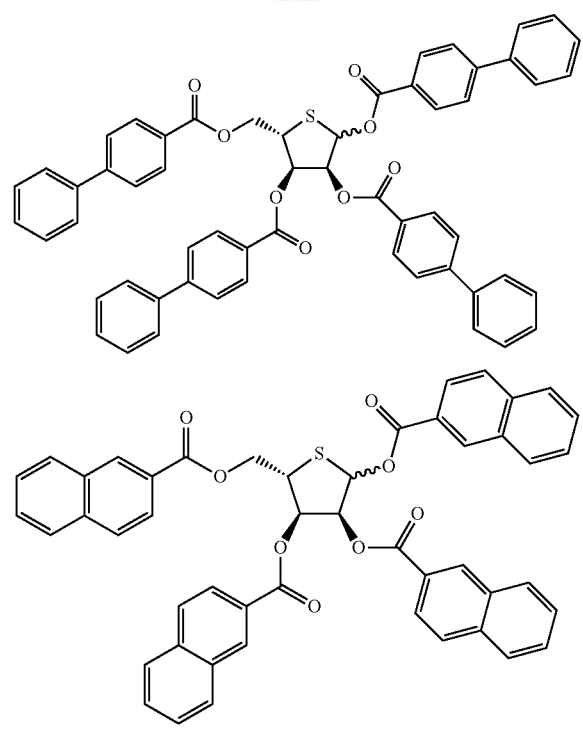
Compounds Represented by General Formula (II-1B)
26
-continued
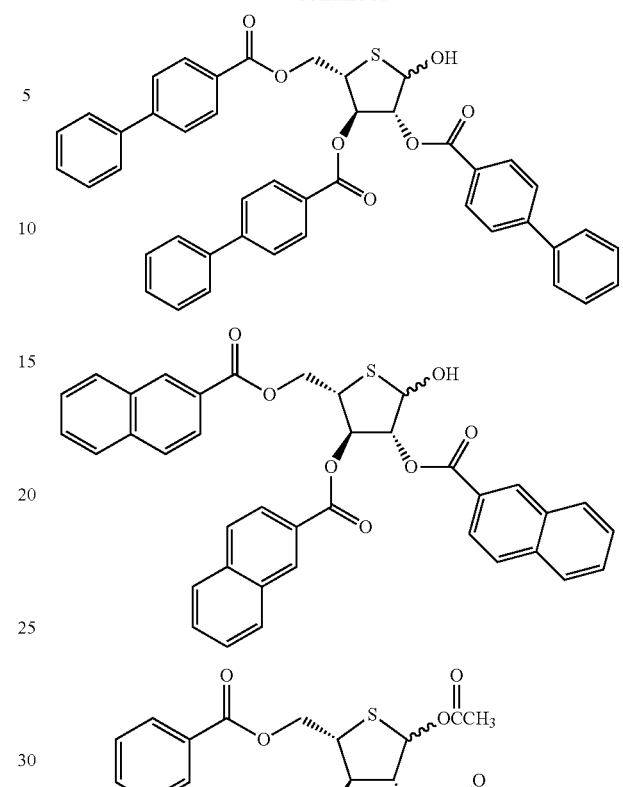
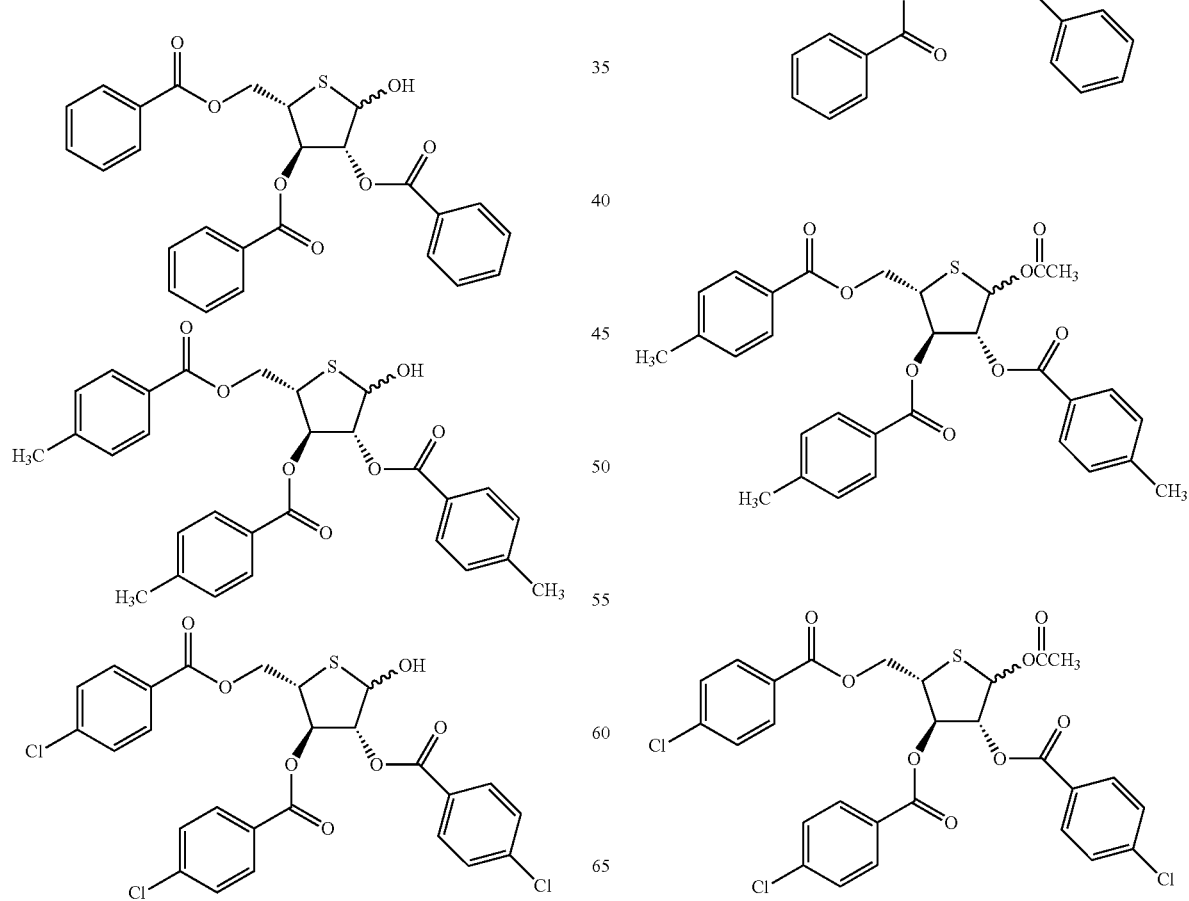

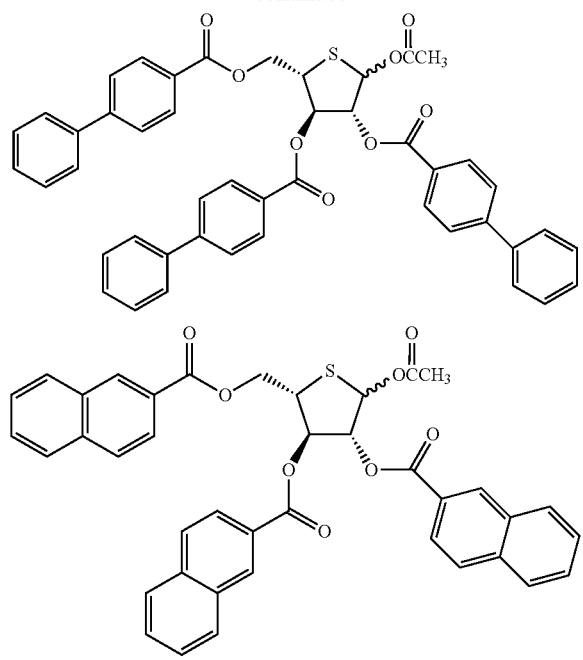
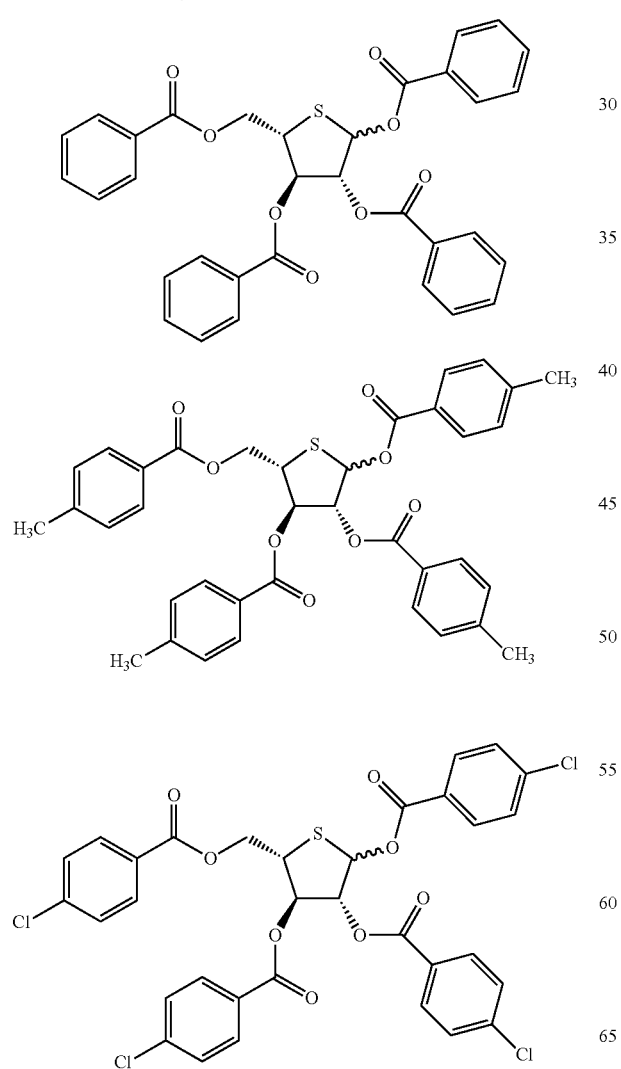
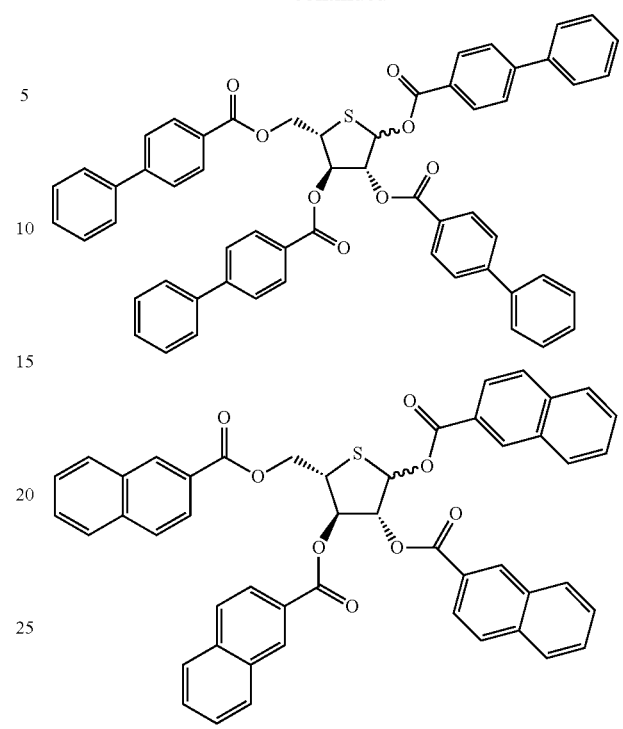
Compounds Represented by General Formula (II-2A)
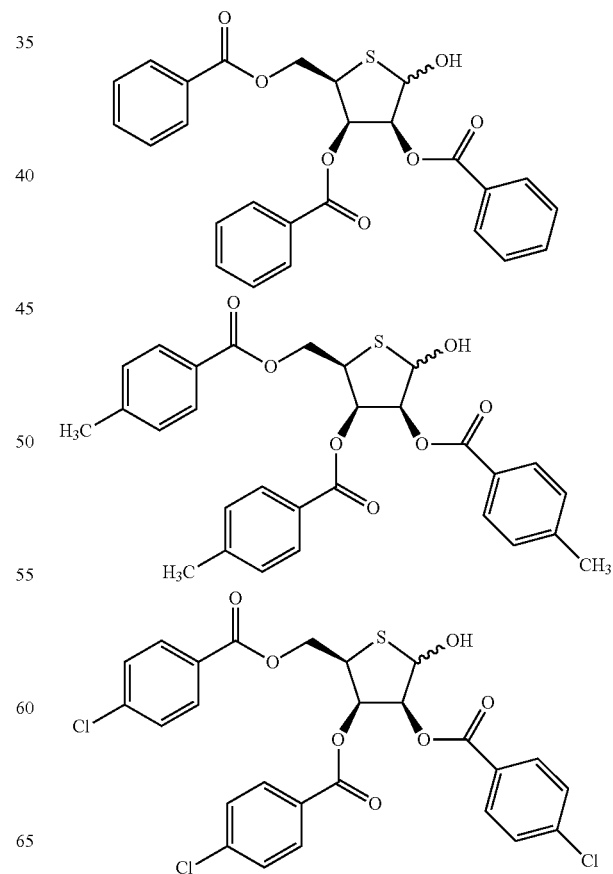

29
-continued
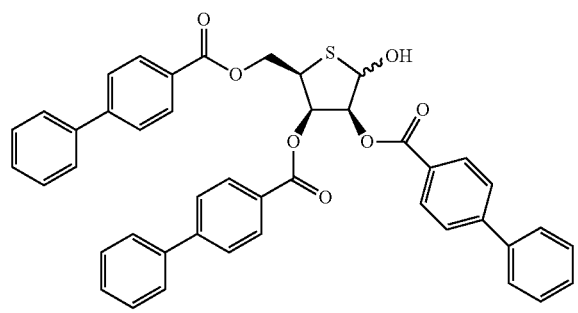
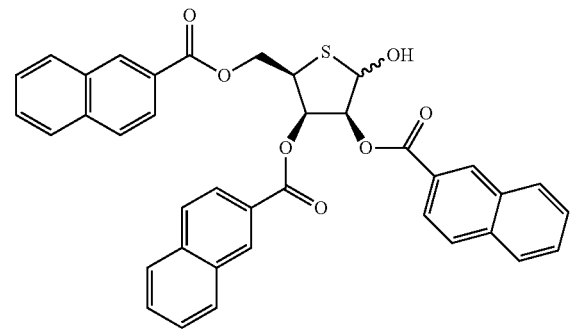
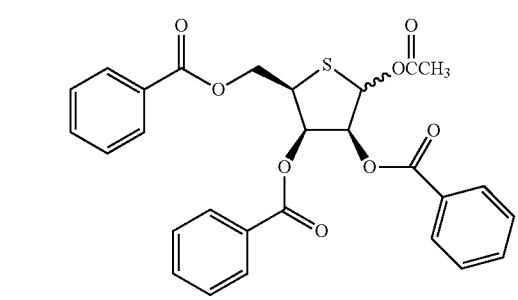
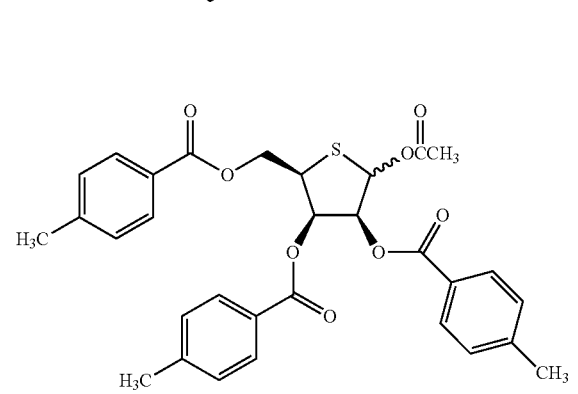
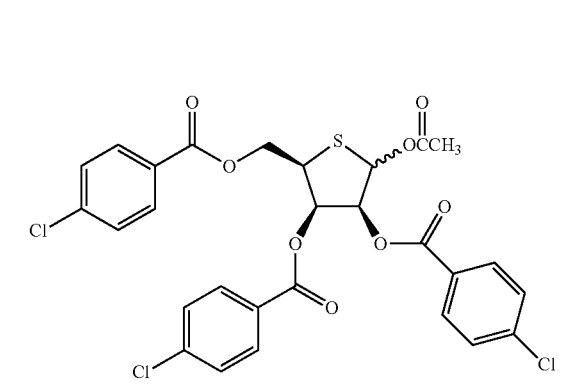
30
-continued
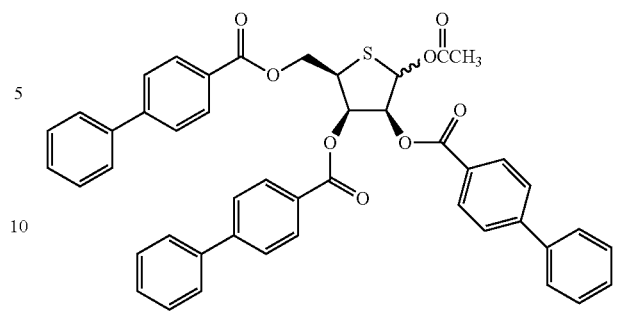
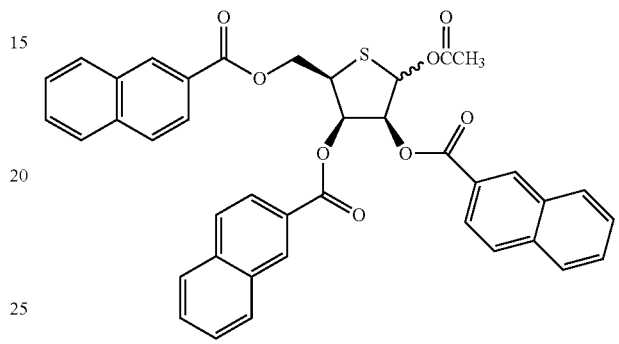
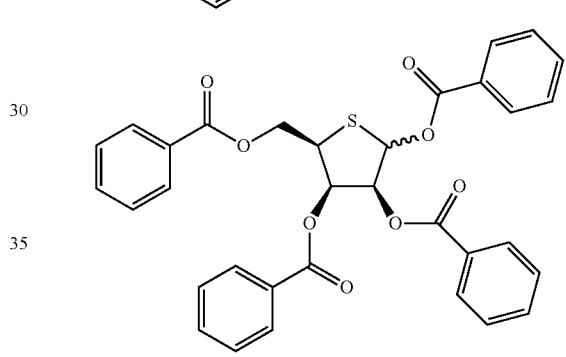
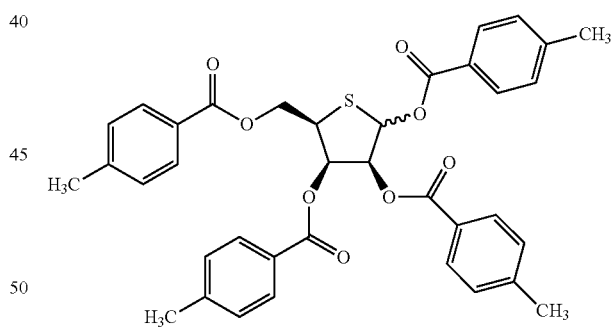
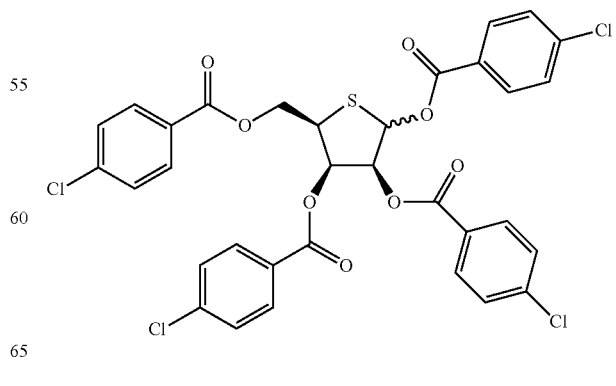

31
-continued
32
-continued
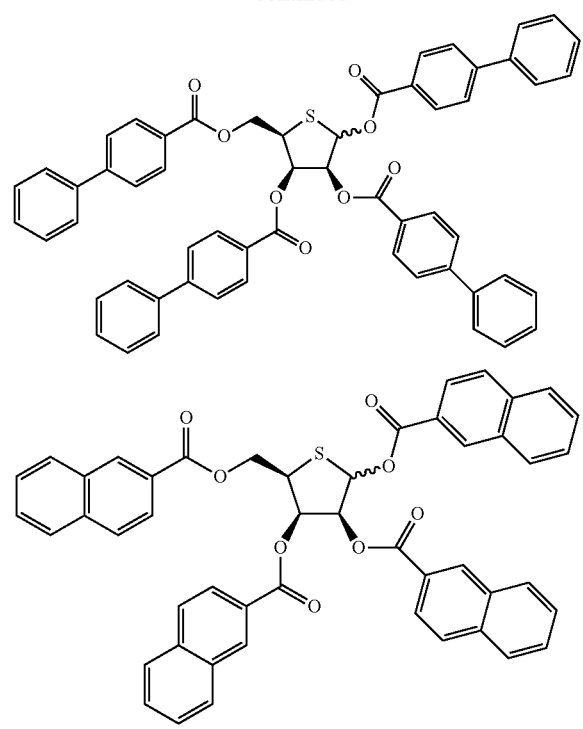
Compounds Represented by General Formula (II-2B)
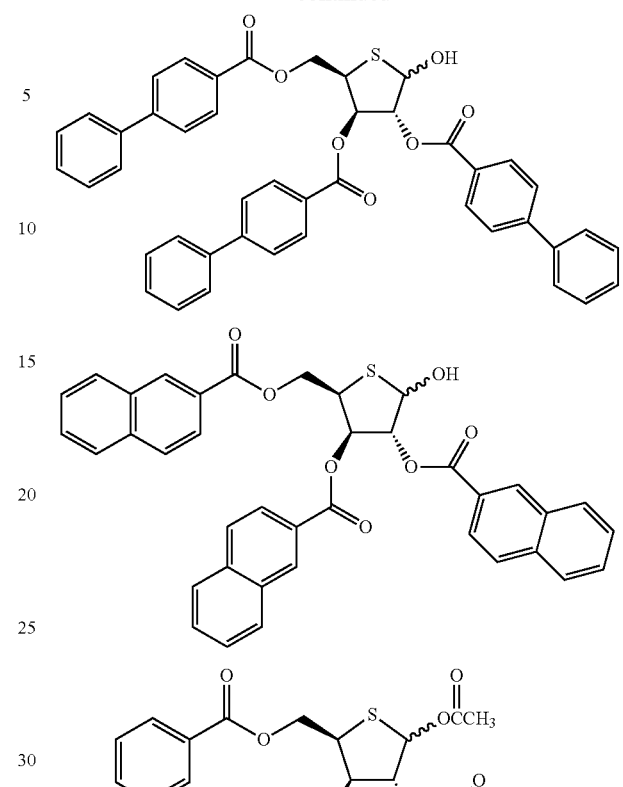
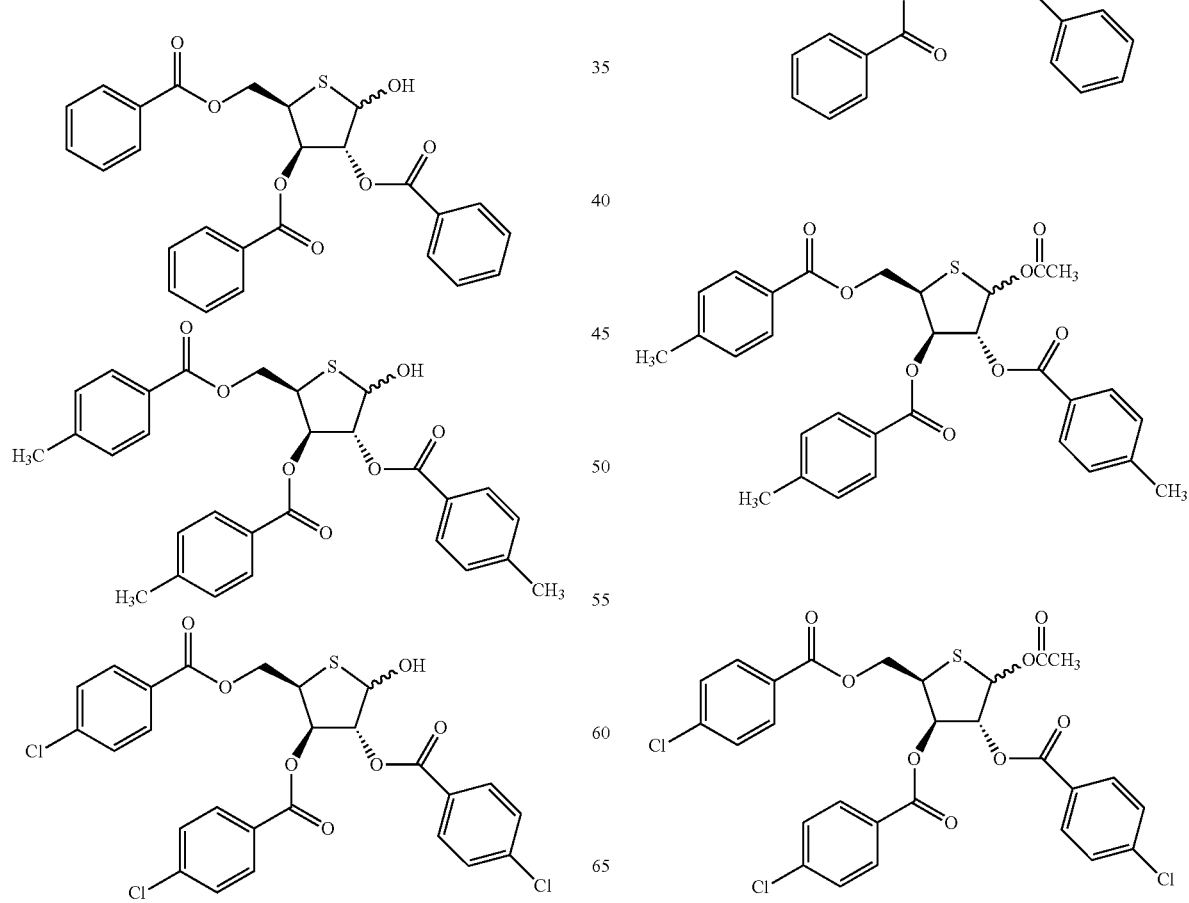

-continued
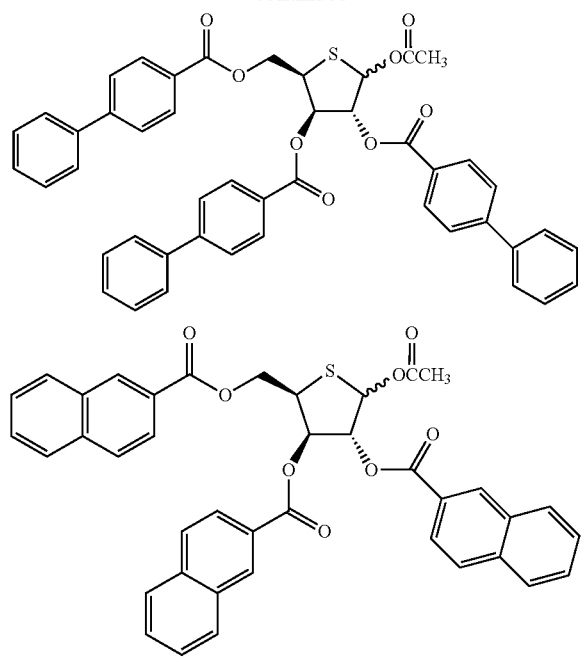
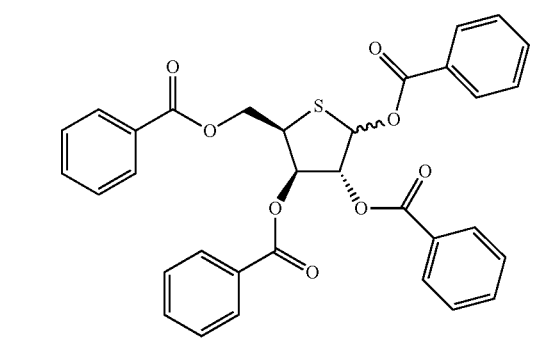
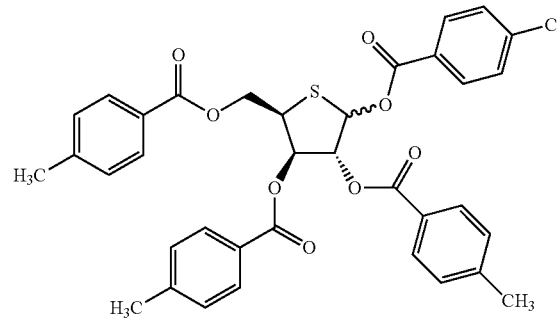
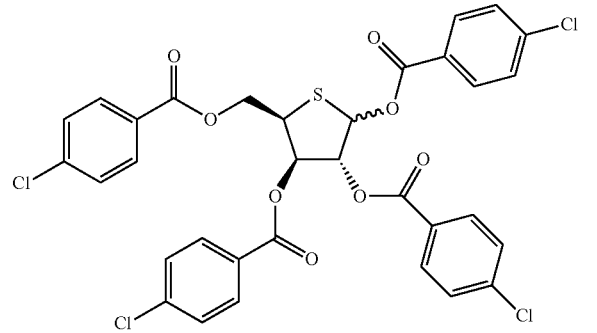
-continued
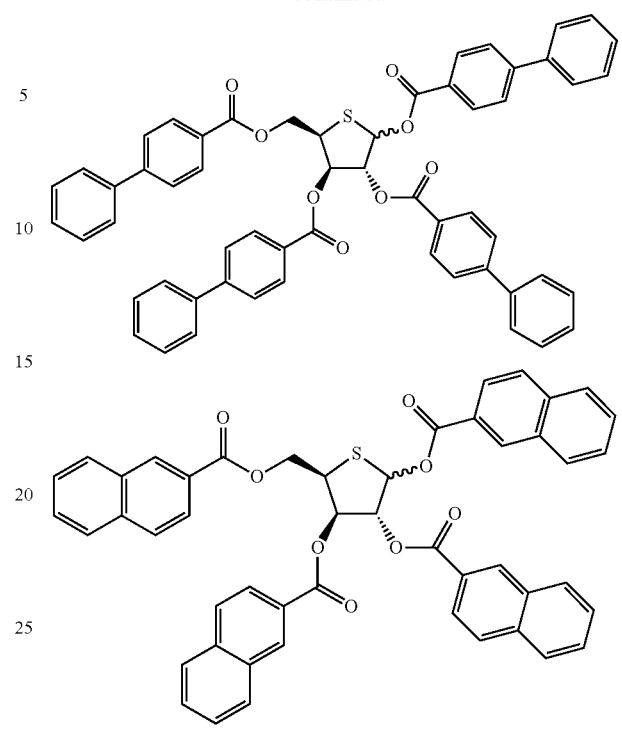
Compounds Represented by General Formula (II-3)
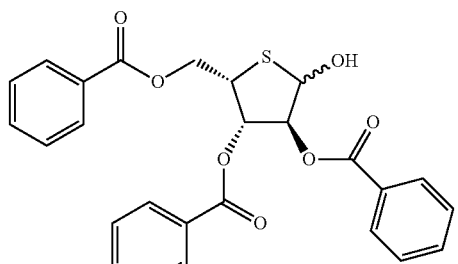
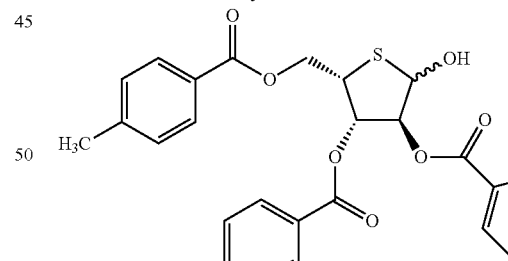
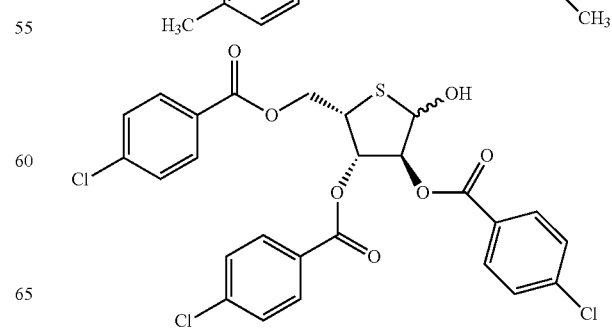

35
-continued
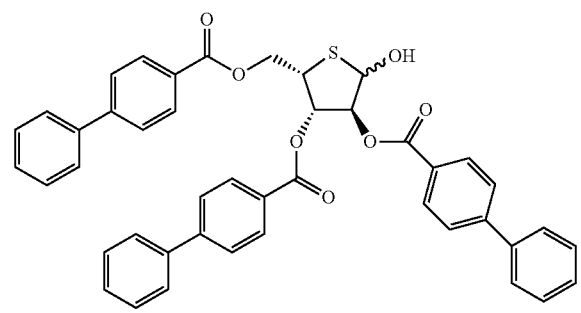
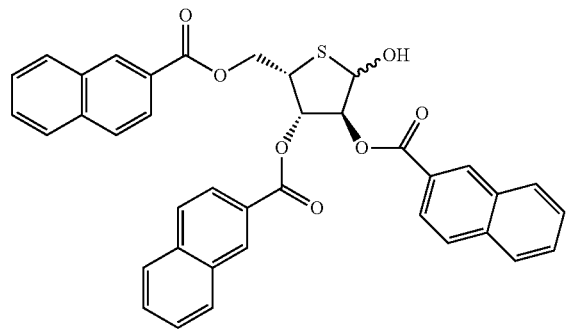
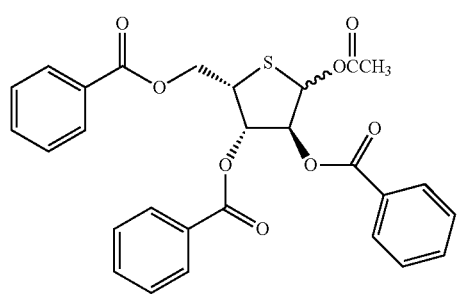
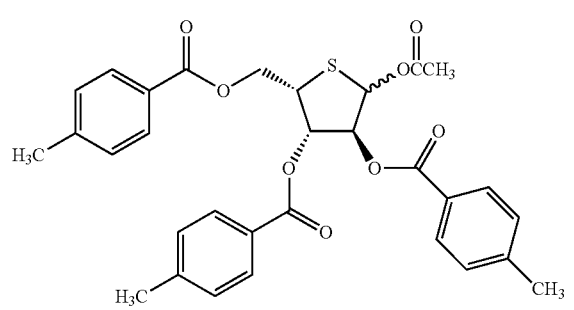
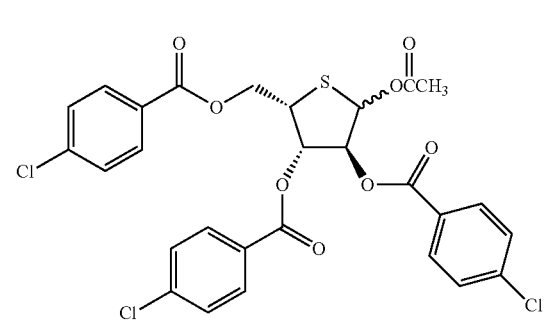
36
-continued
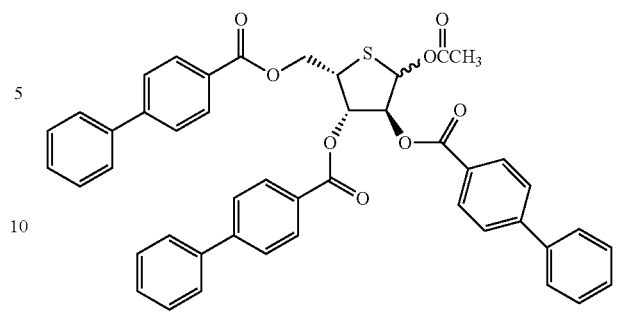
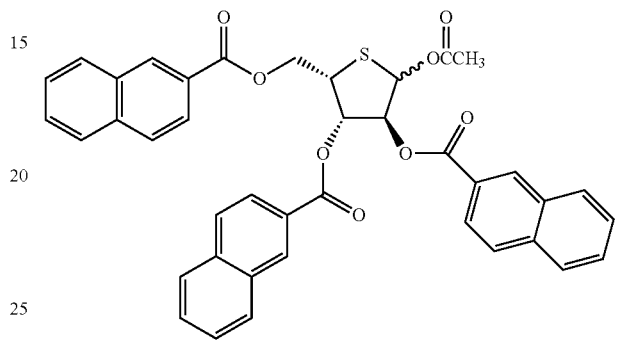
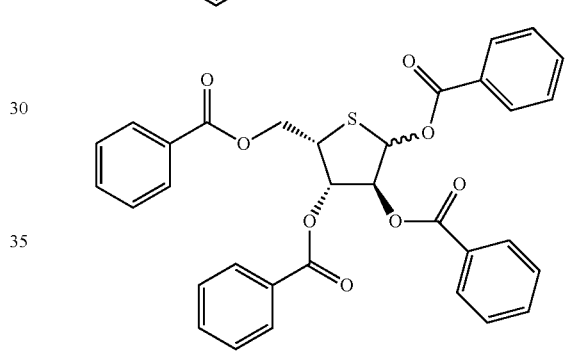
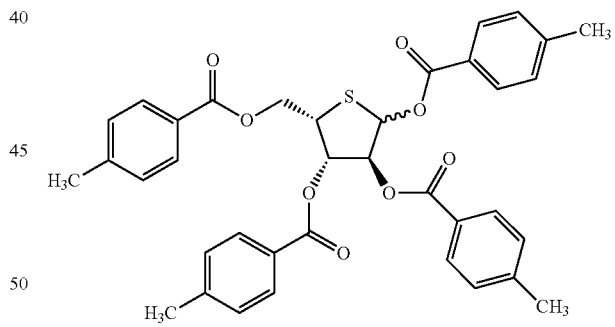
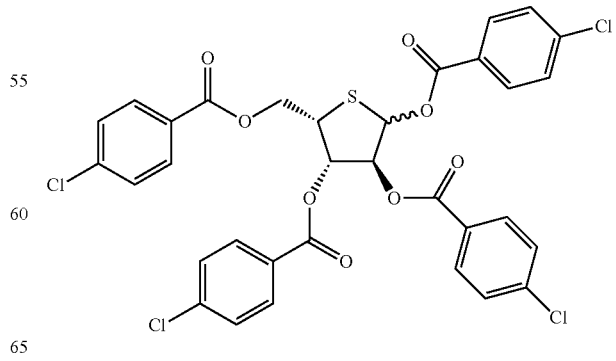

37
-continued
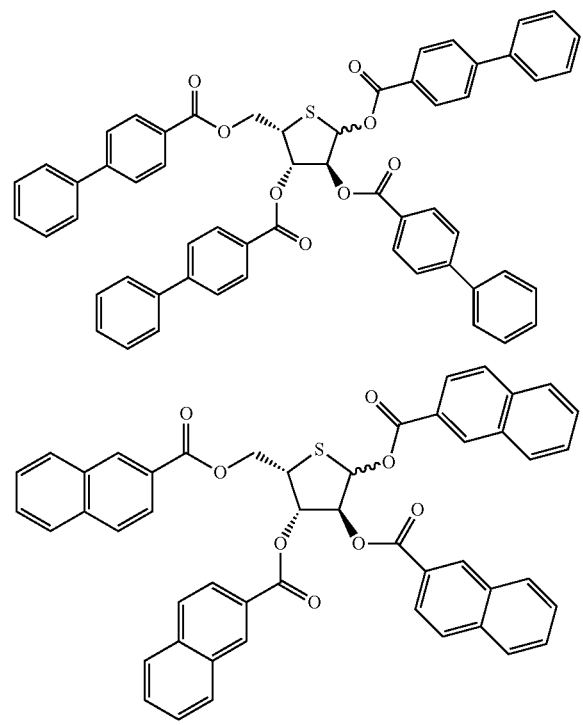
Compounds Represented by General Formula (II-4)
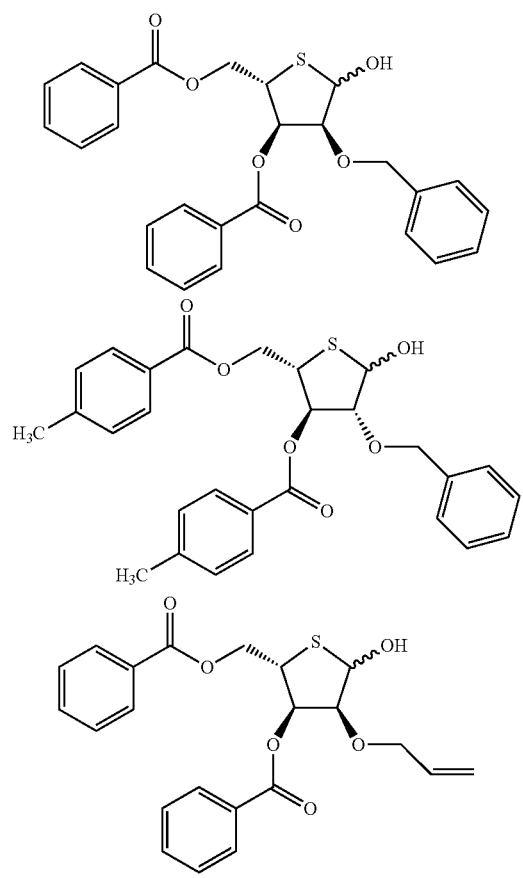
38
-continued
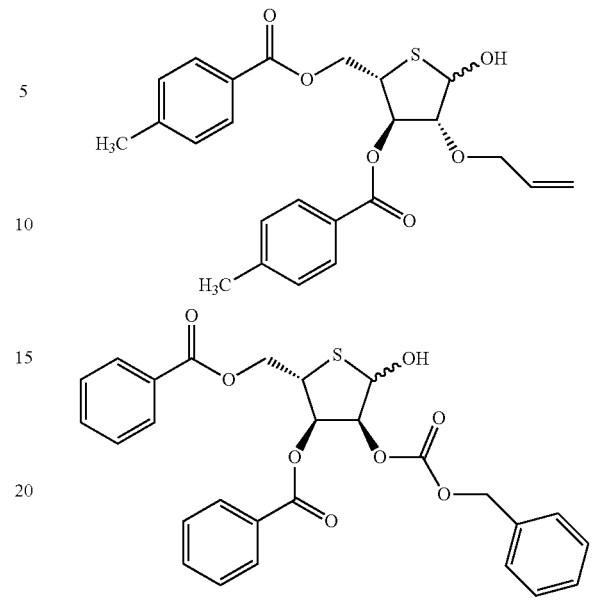
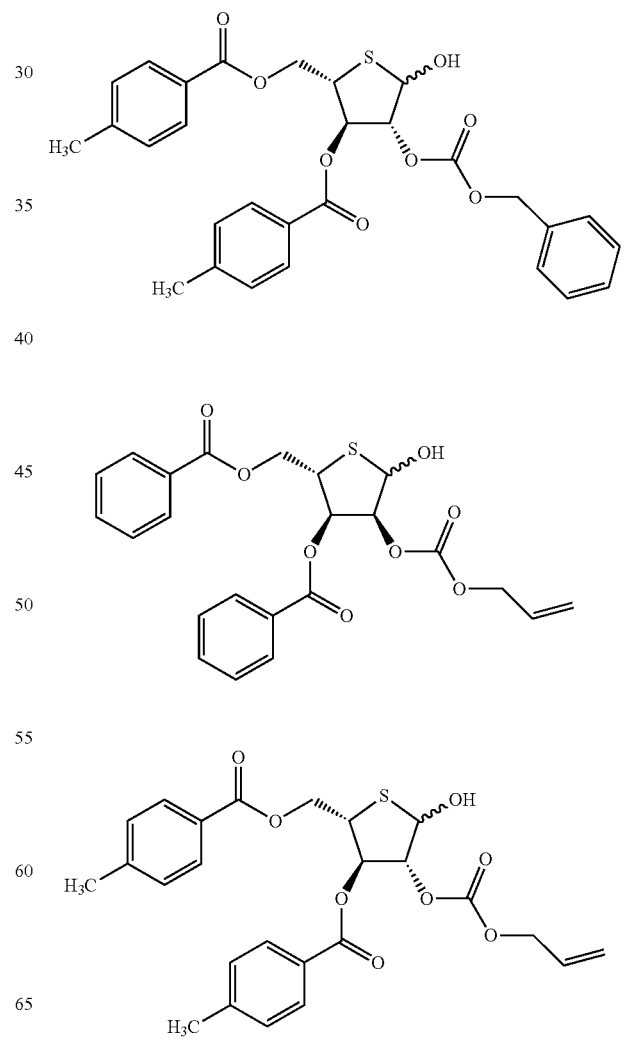

39
-continued
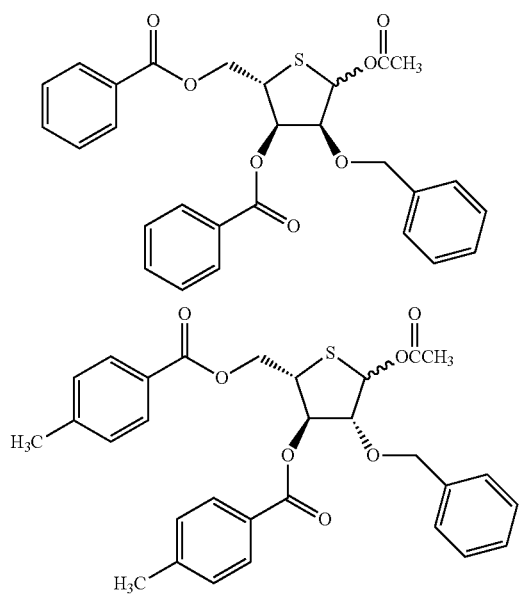
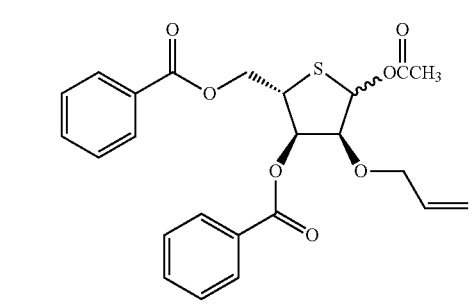
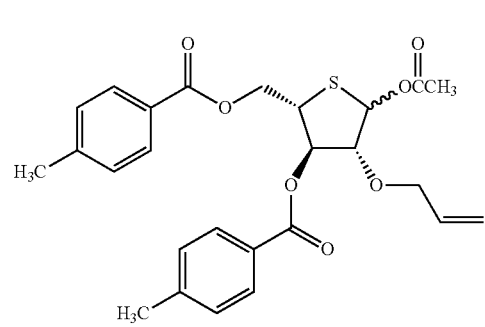
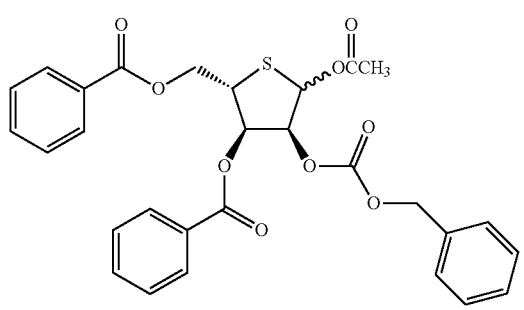
40
-continued
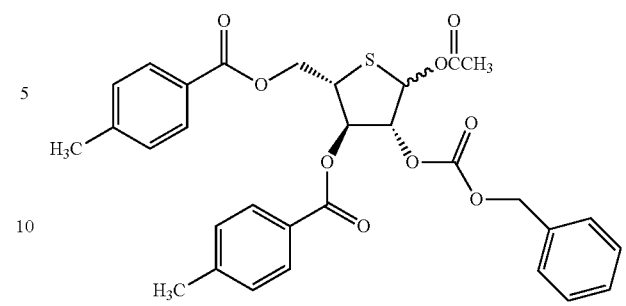
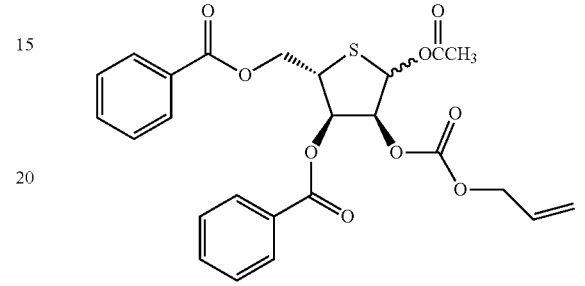
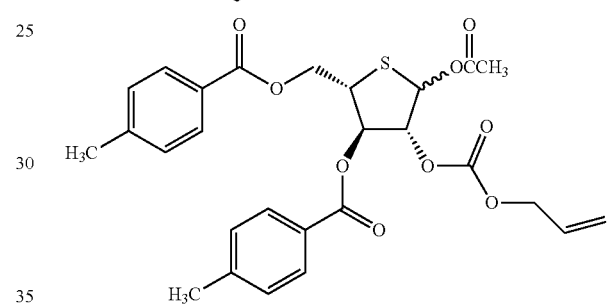
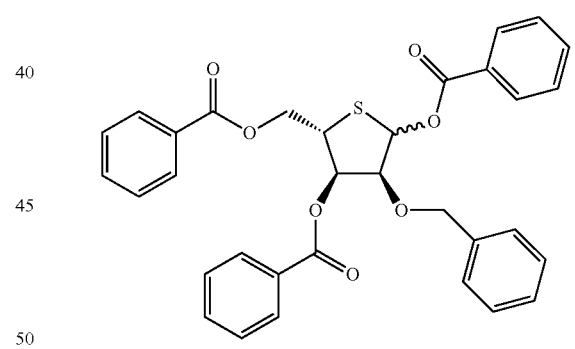
Compounds Represented by General Formula (II-5)
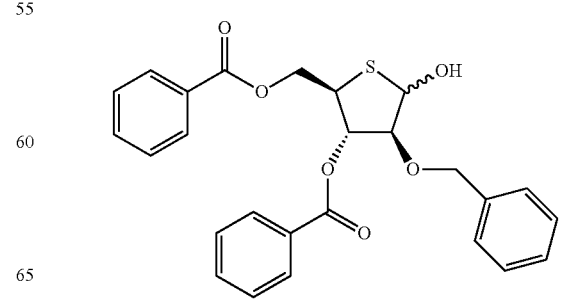

41
-continued
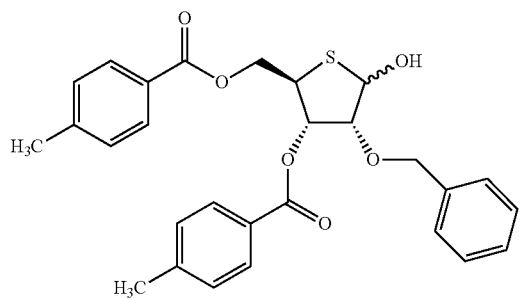
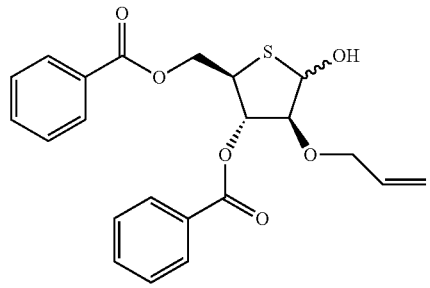
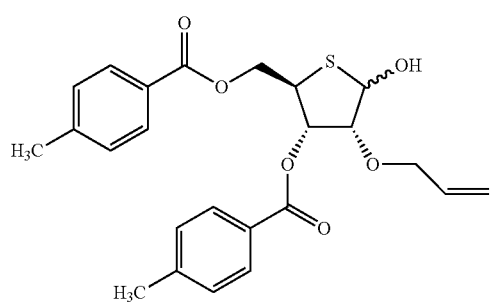
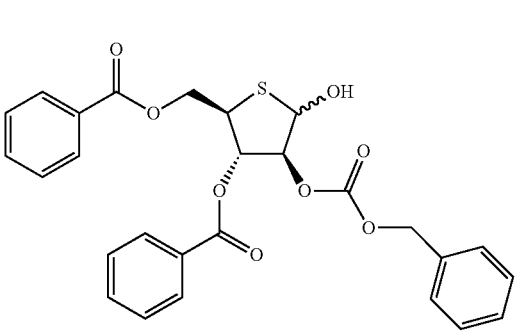
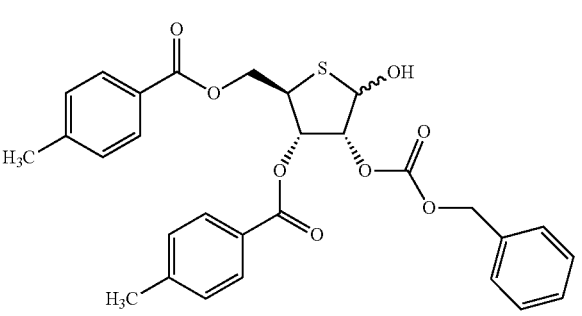
42
-continued
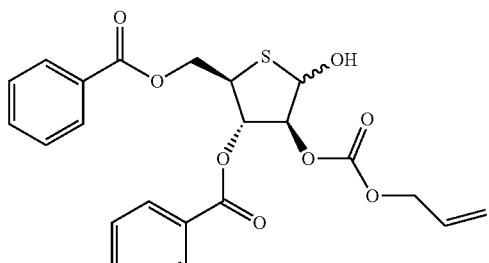
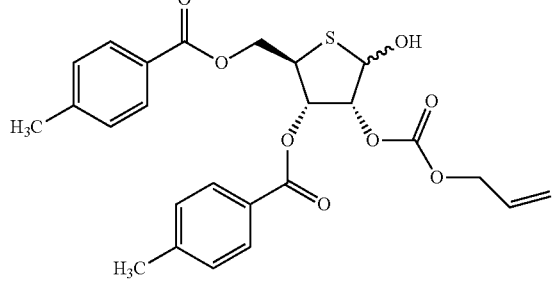
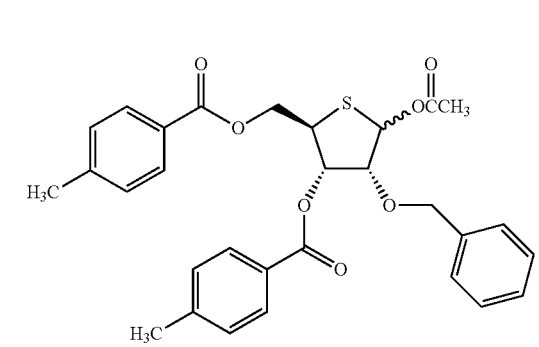
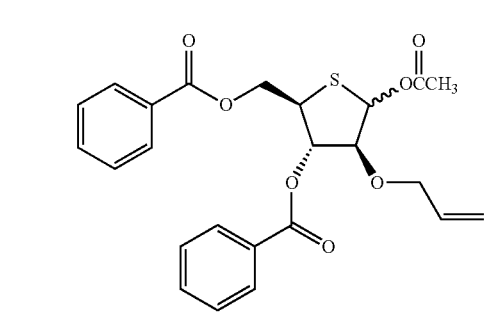

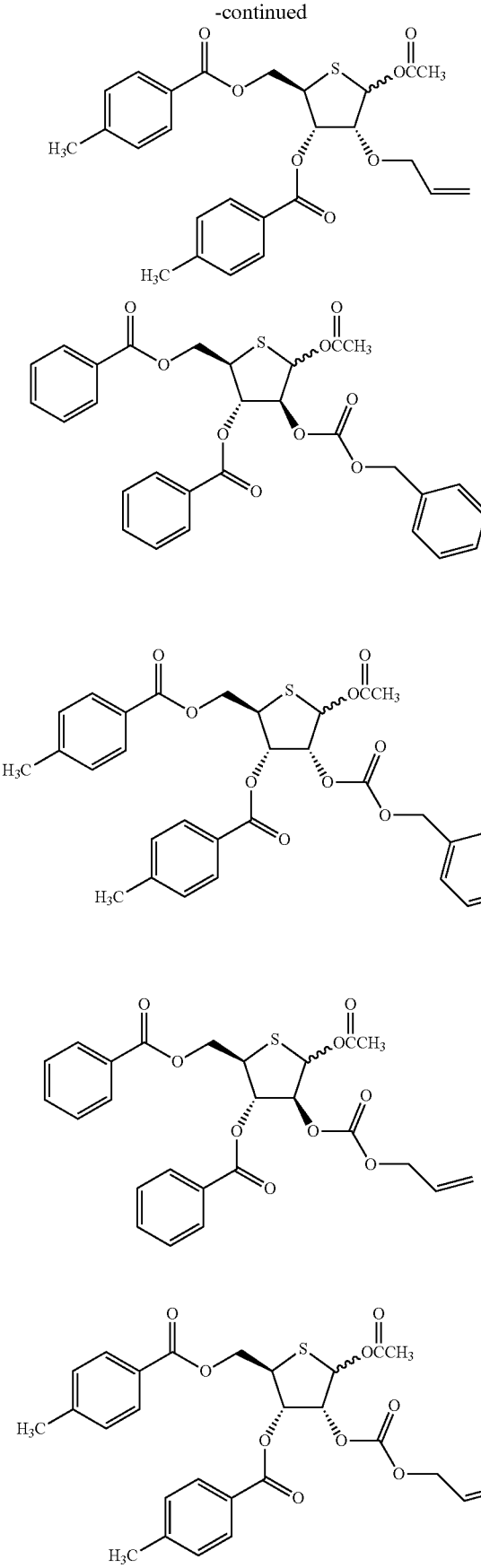
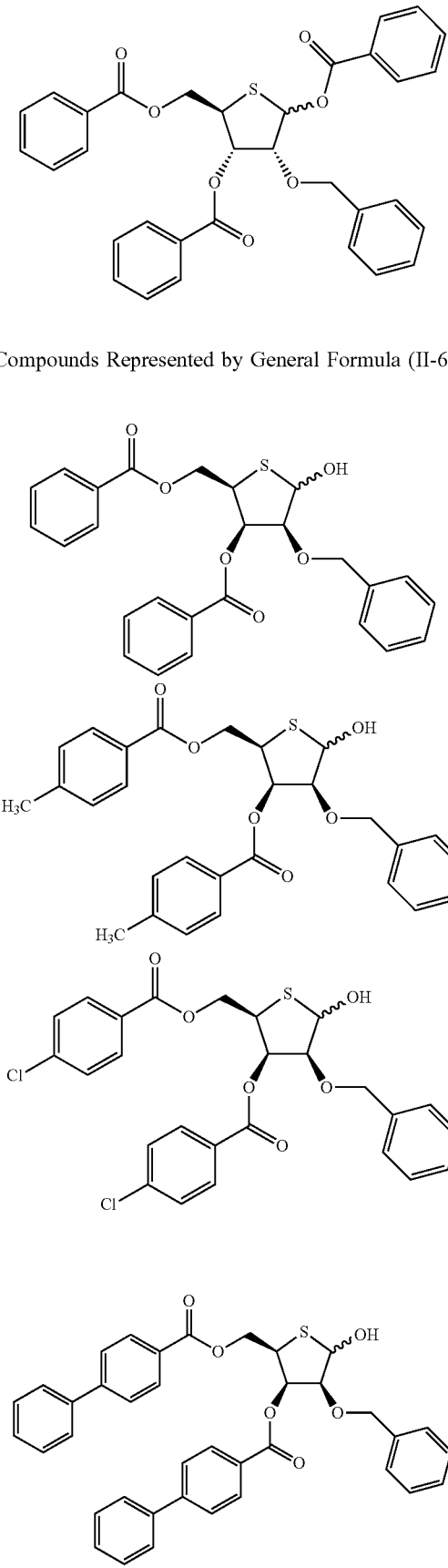
Compounds Represented by General Formula (II-6A)

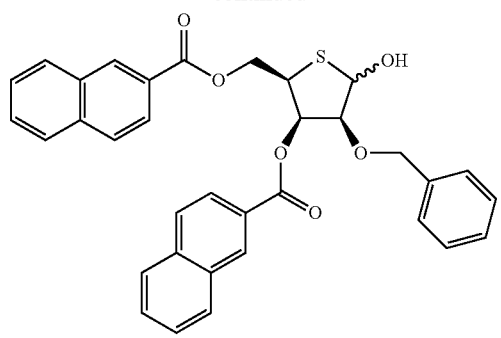
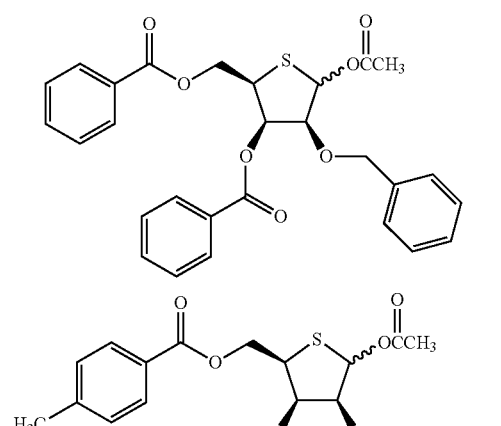
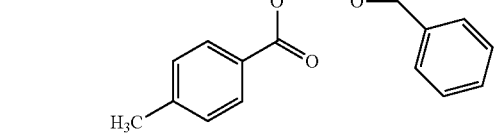
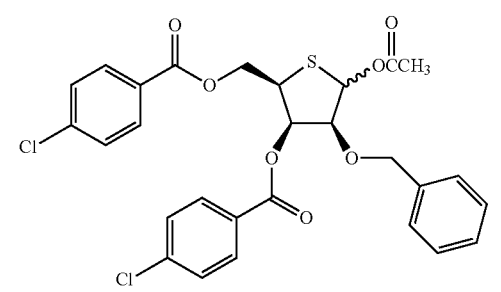
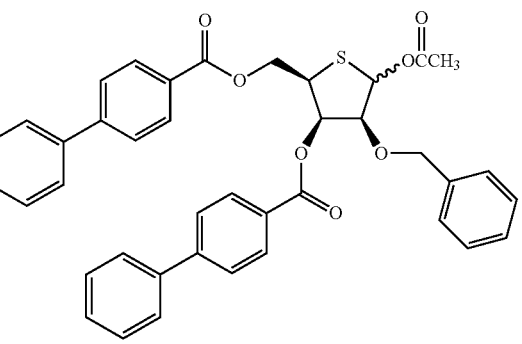
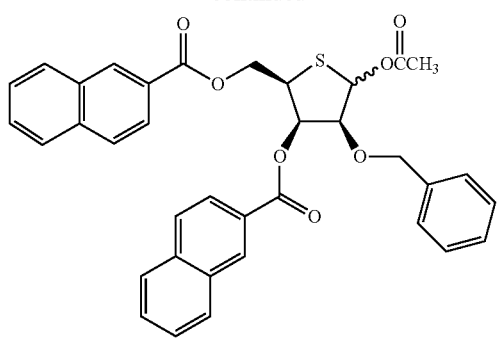
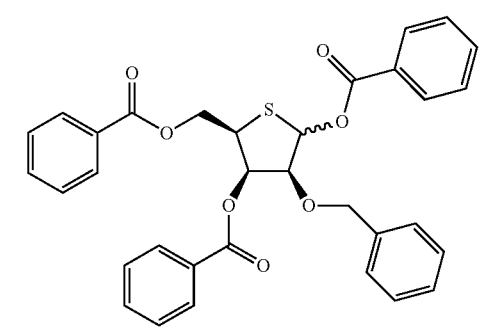
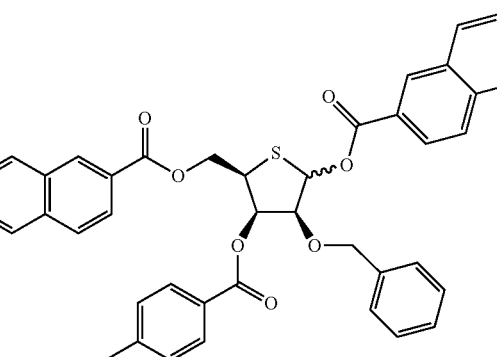
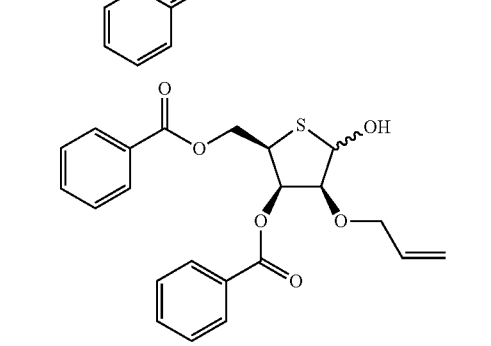
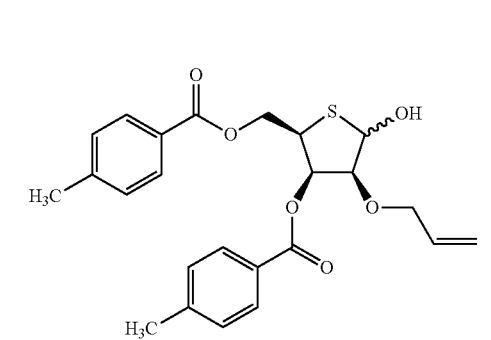

47
-continued
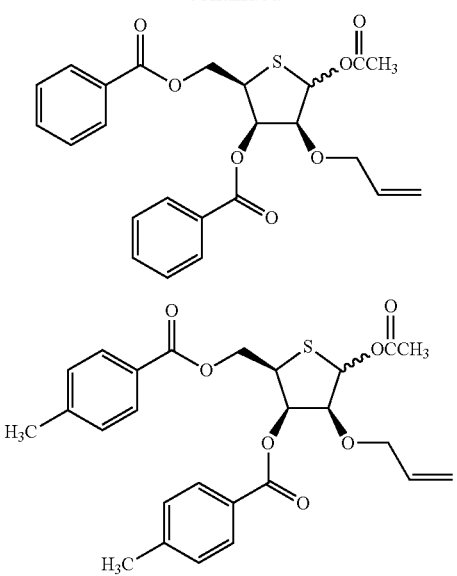
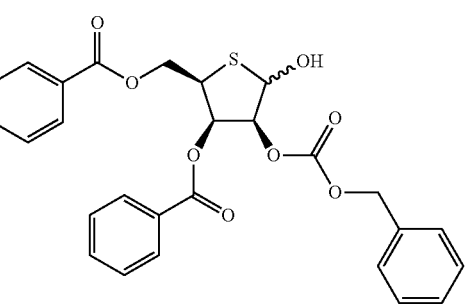
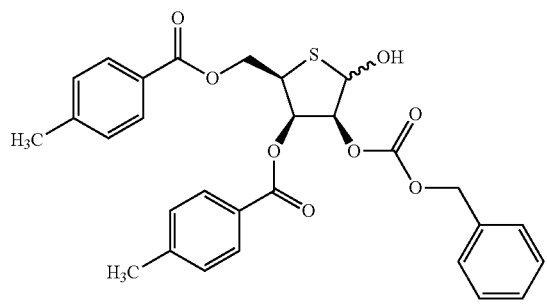
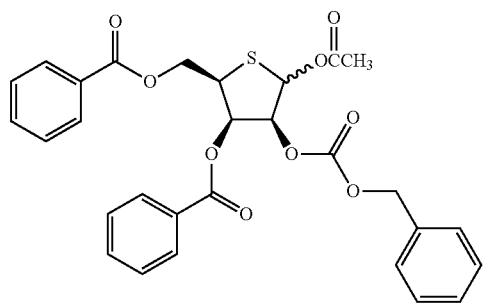
48
-continued
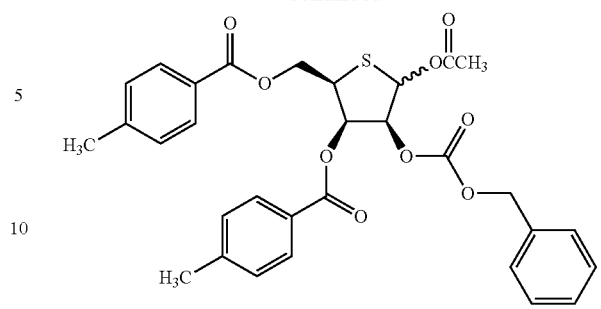
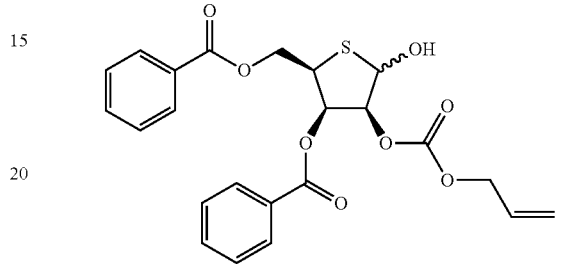
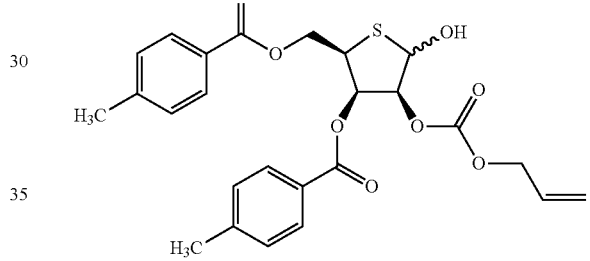
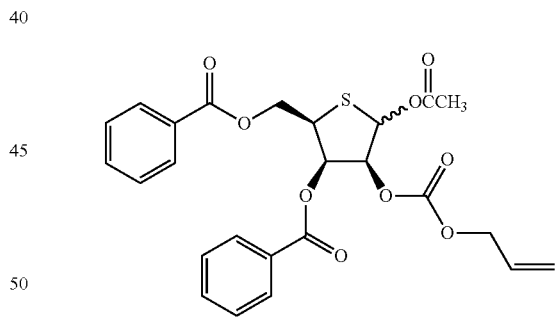
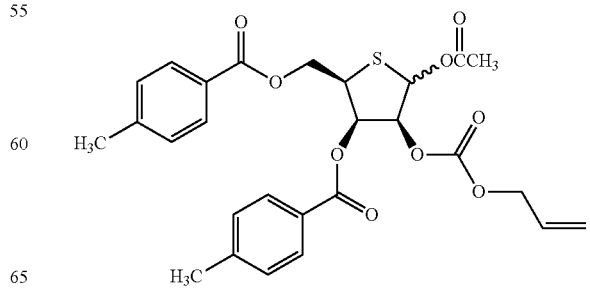

Compounds Represented by General Formula (II-6B)
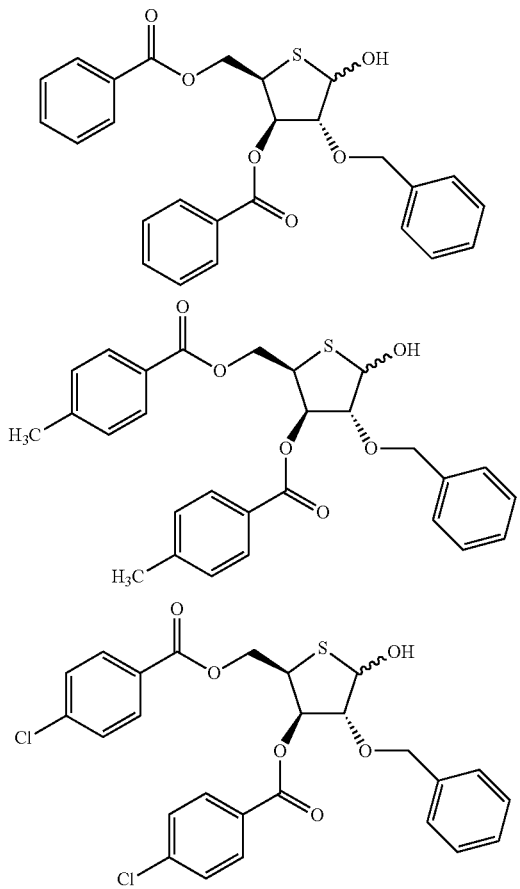
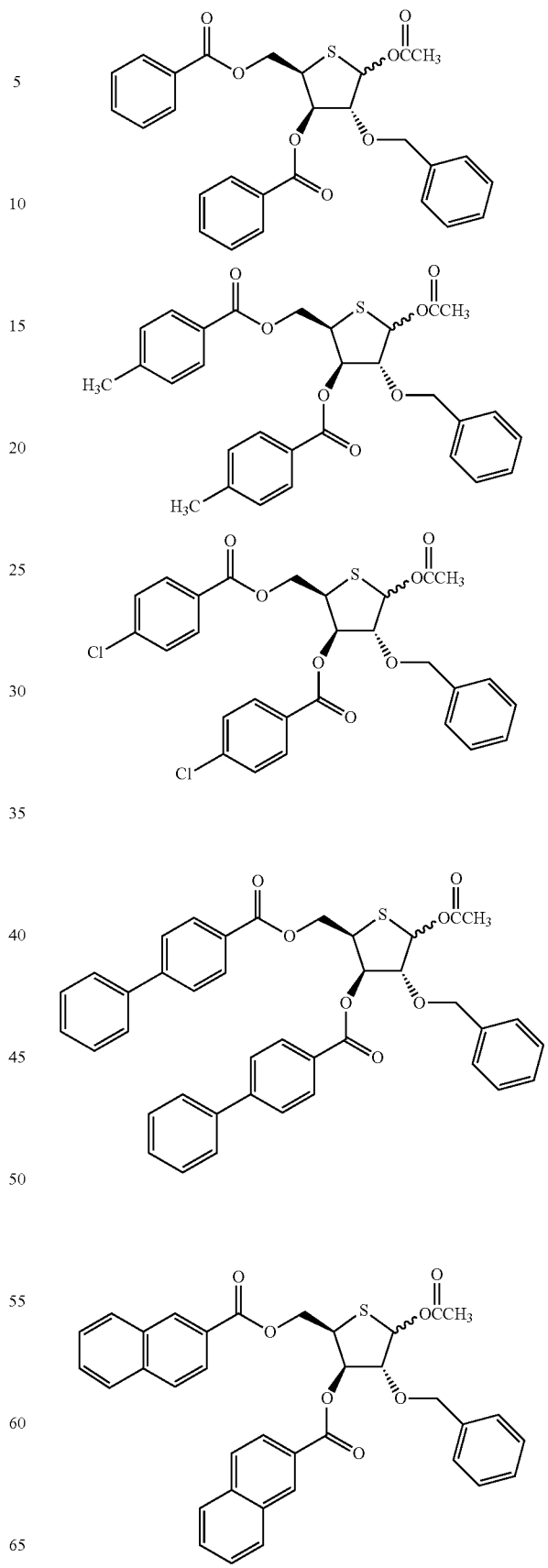

51
-continued
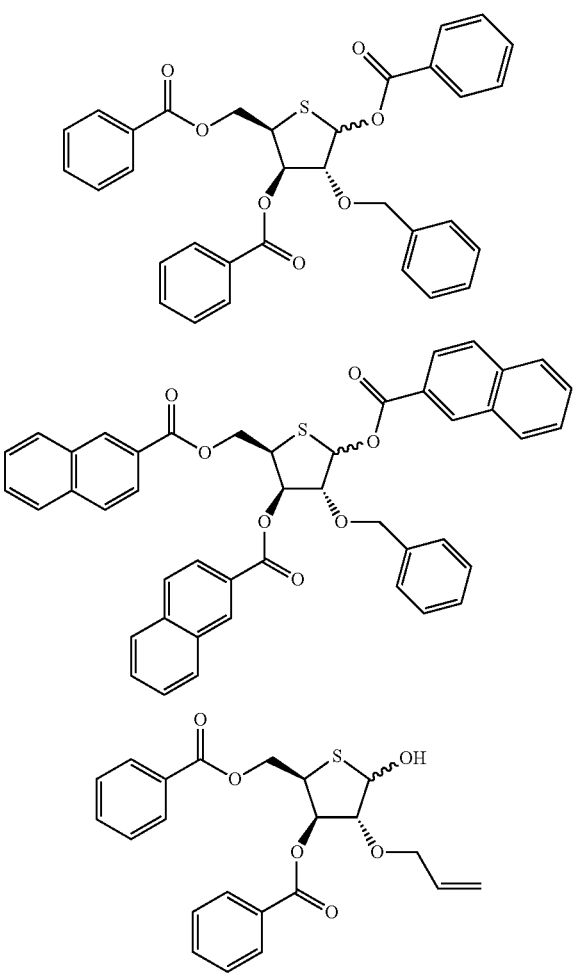
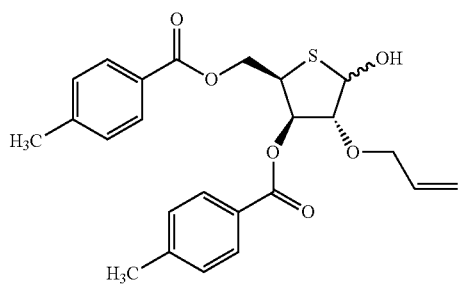
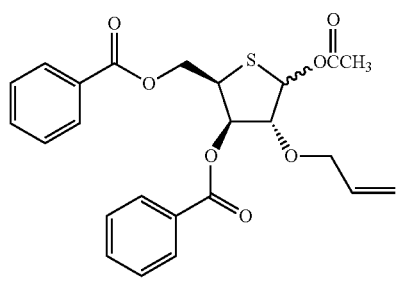
52
-continued
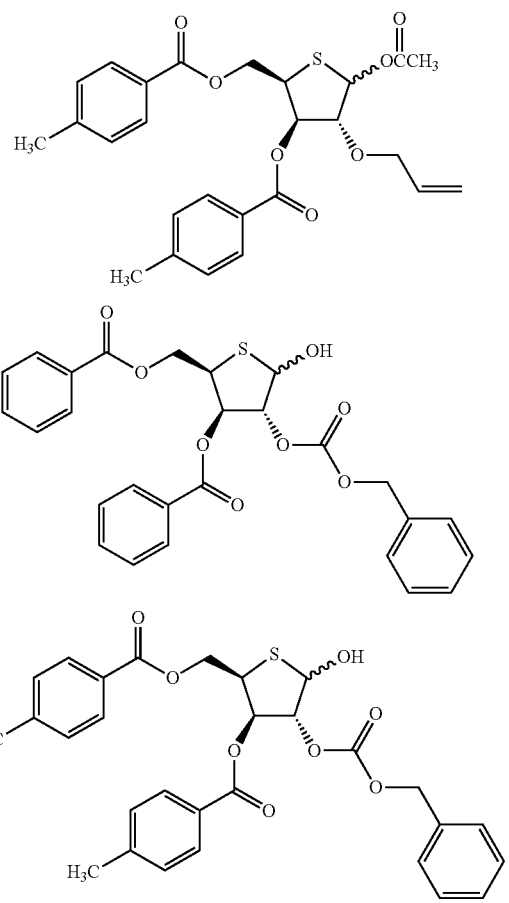
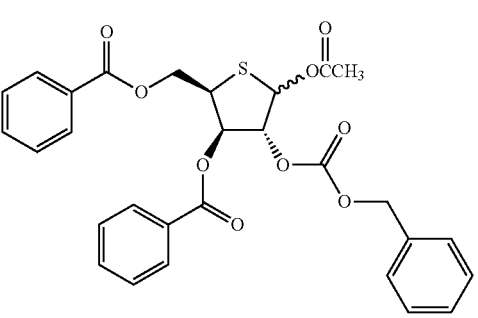
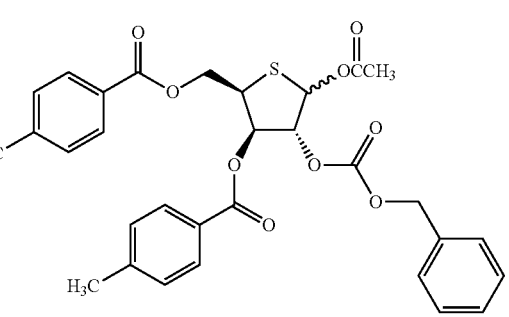

53
-continued
54
-continued
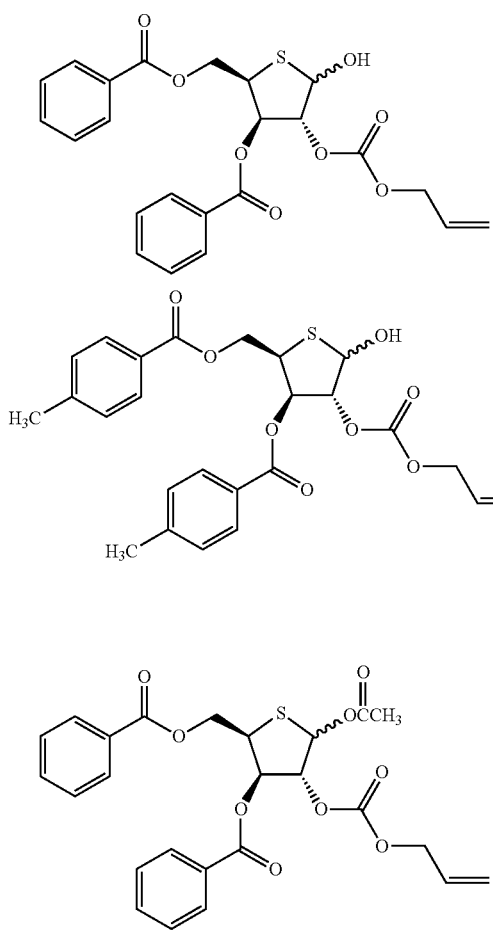
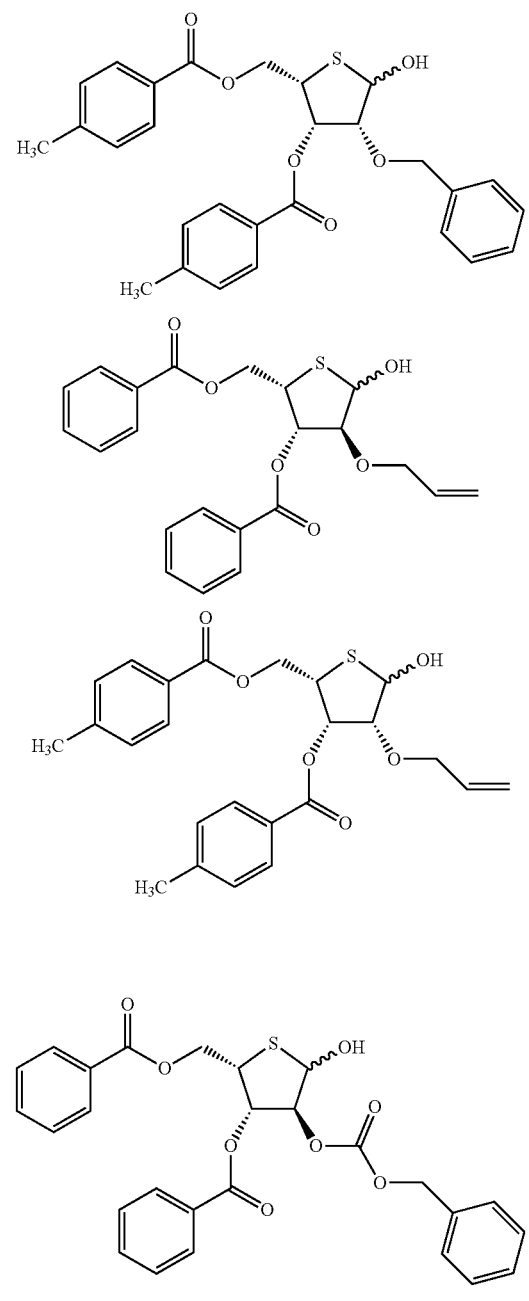
Compounds Represented by General Formula (II-7)
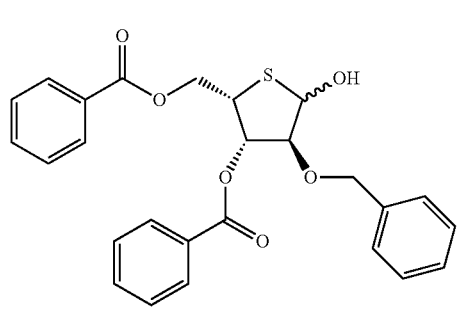
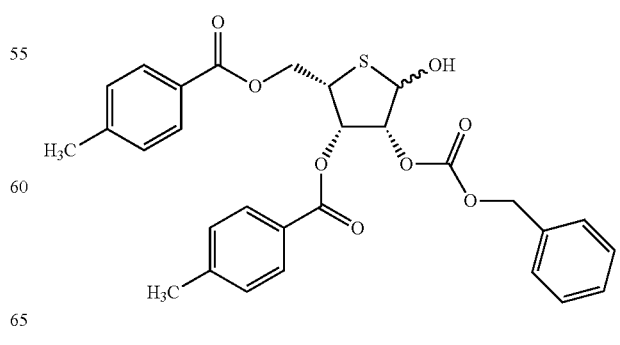

55
-continued
56
-continued
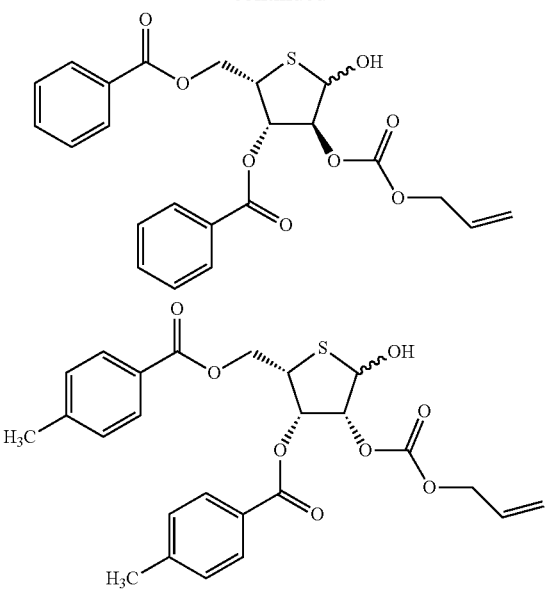
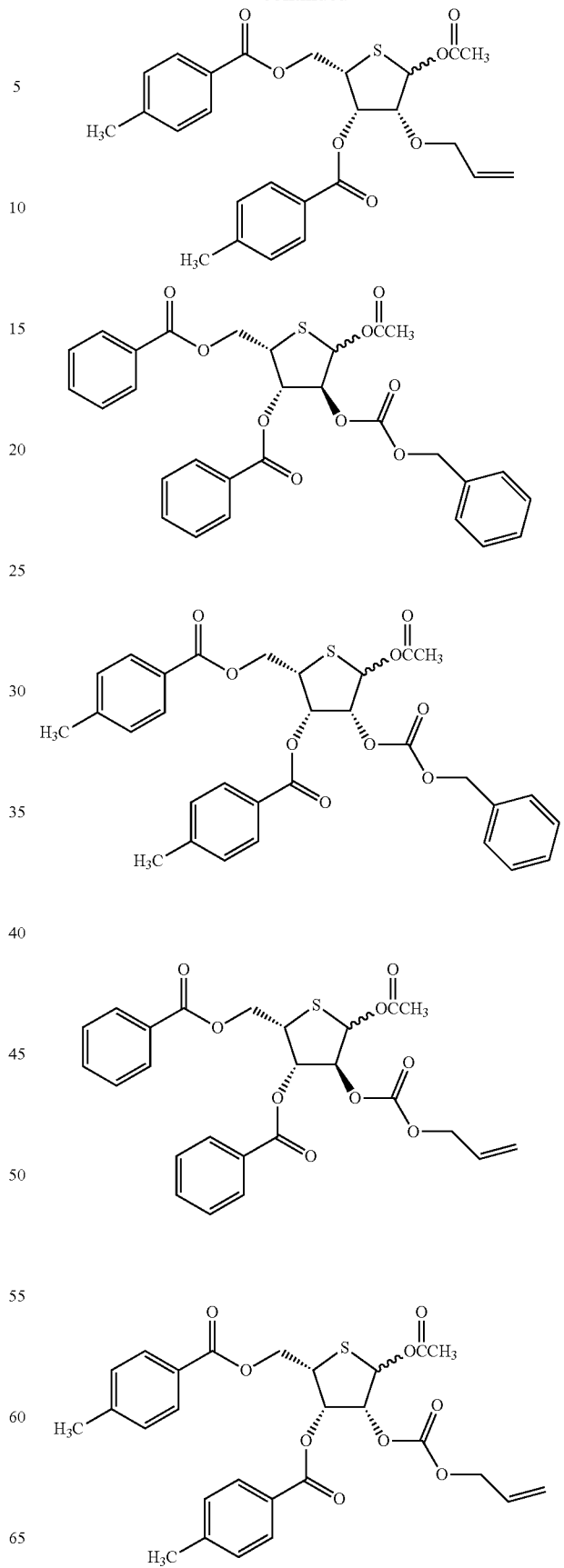

57
-continued
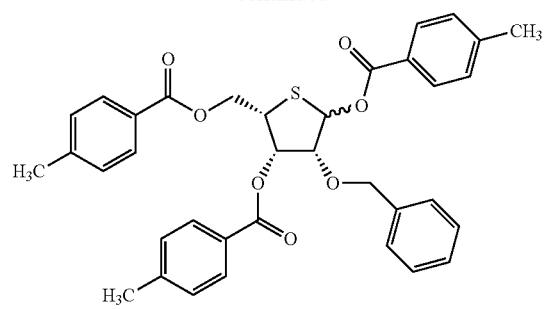
Compounds Represented by General Formula (II-8)
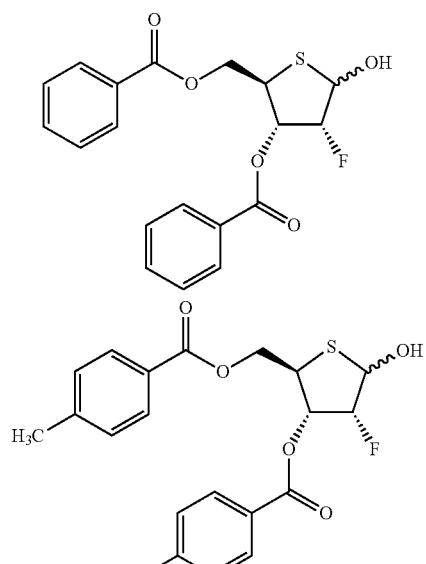
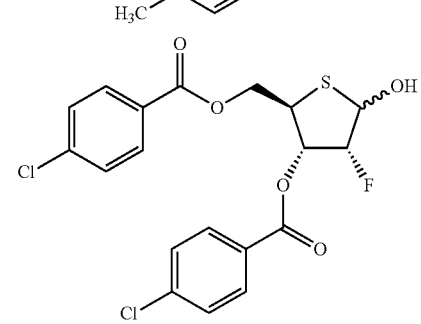
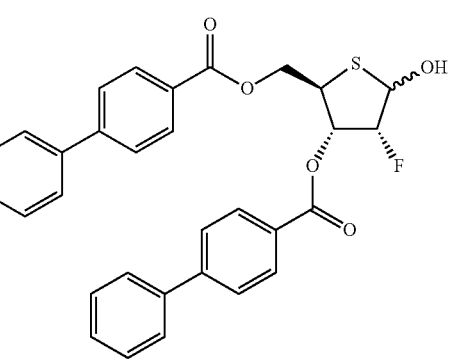
58
-continued
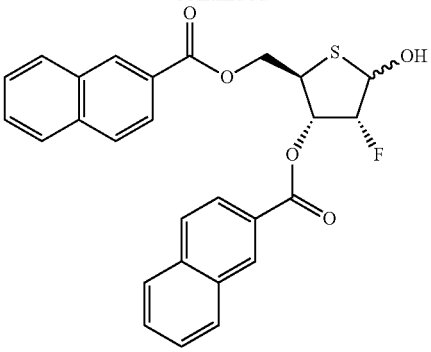
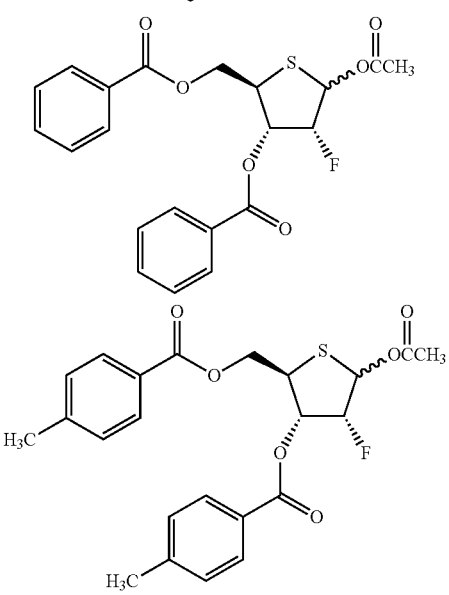
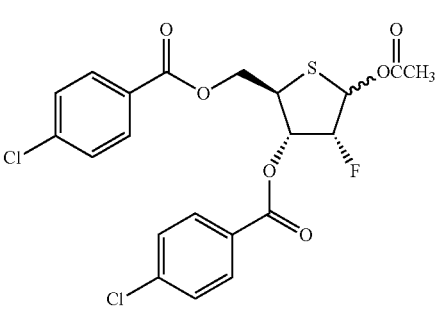
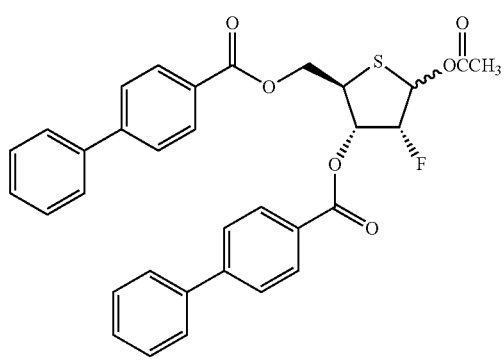

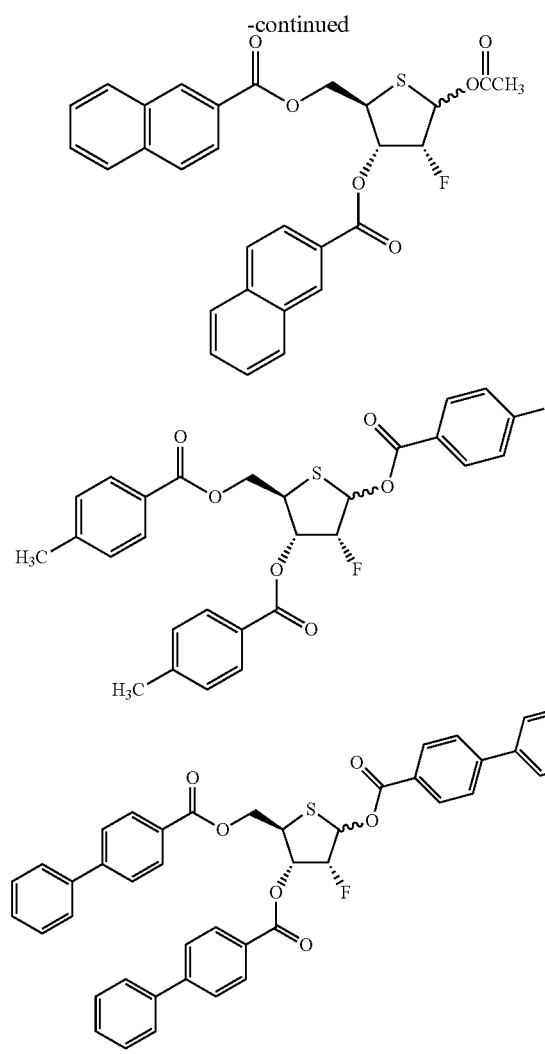
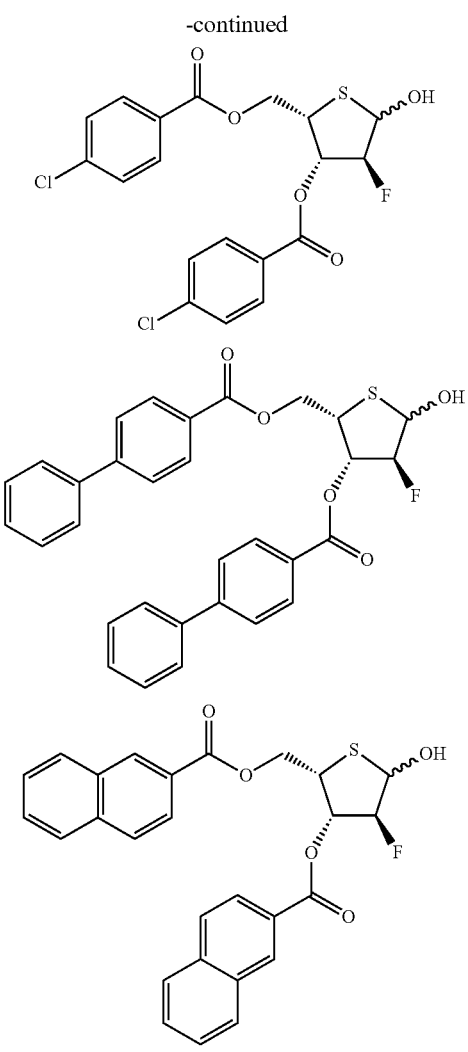
Compounds Represented by General Formula (II-9)

61
-continued
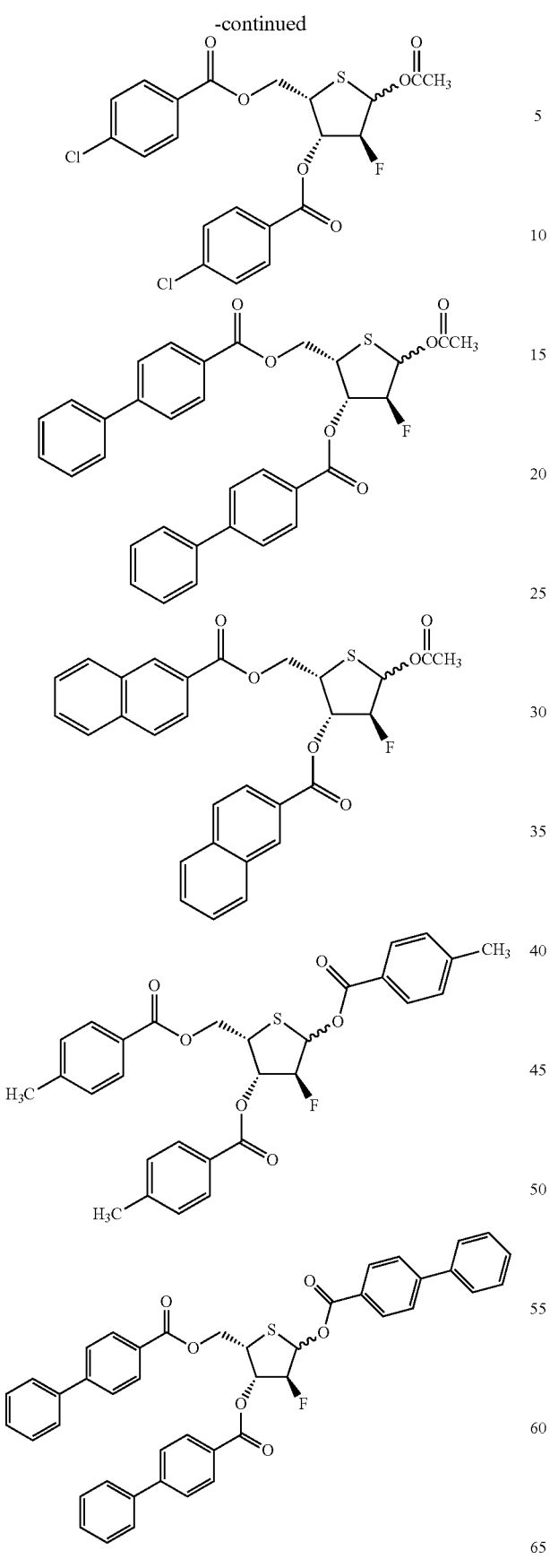
62
Compounds Represented by General Formula (II-10)
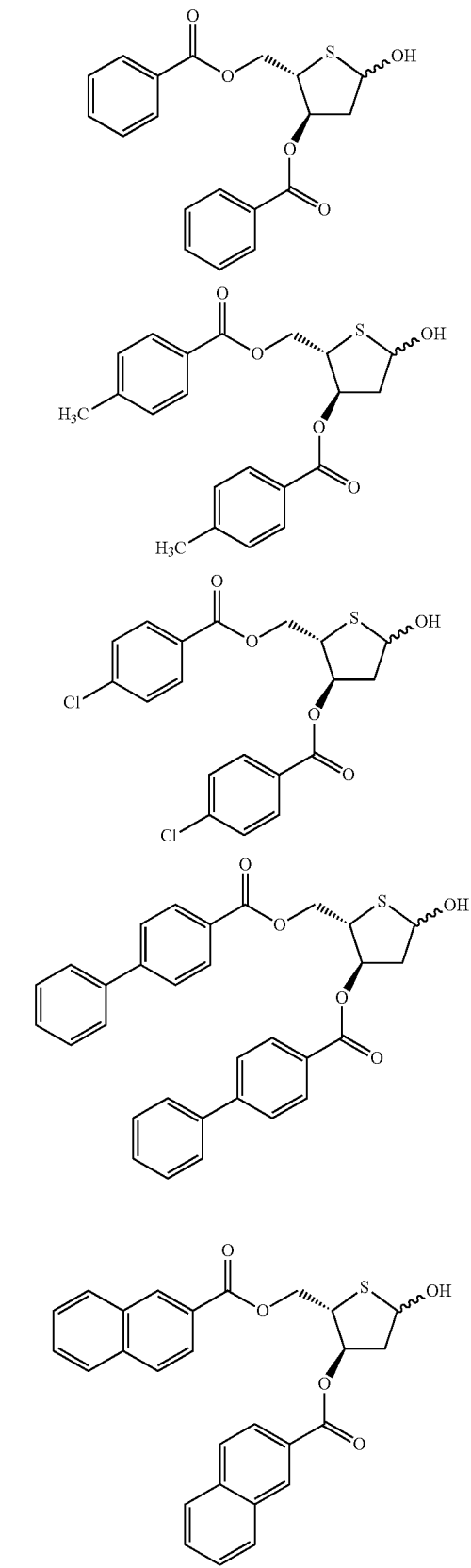

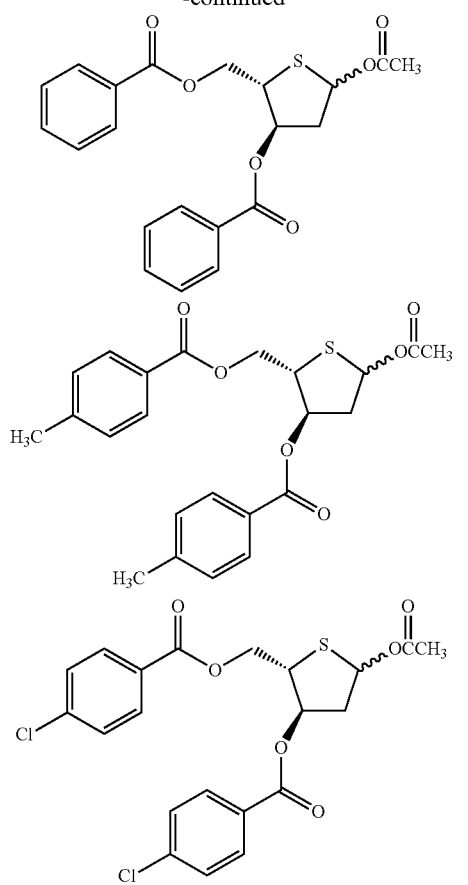
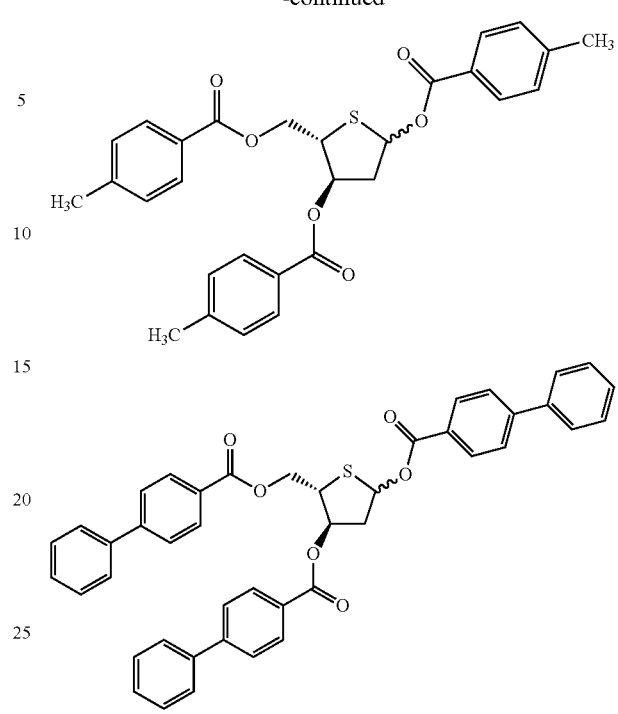
Compounds Represented by General Formula (II-11)
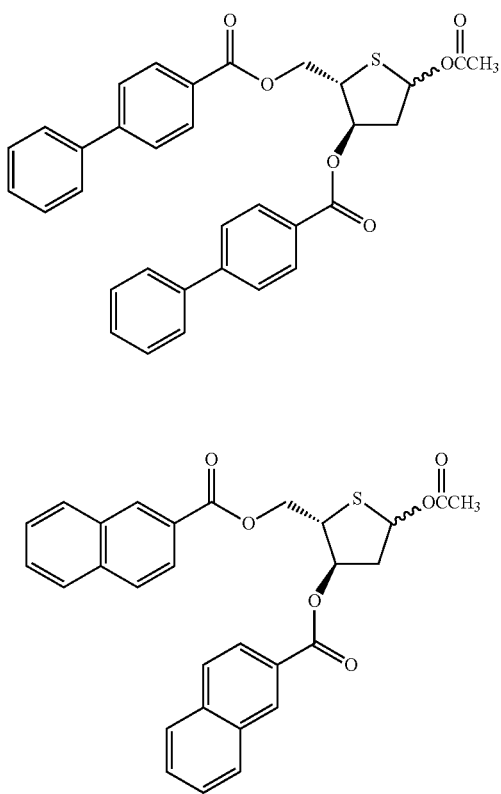
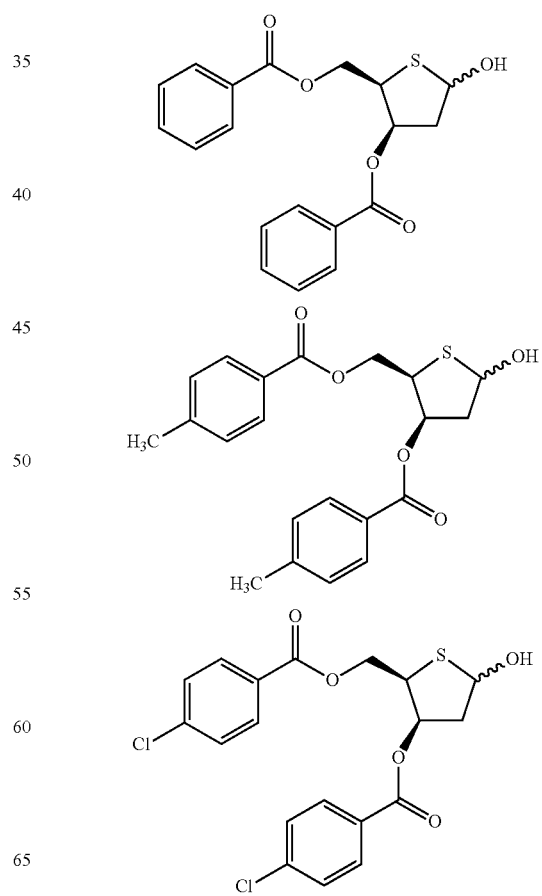

65
-continued
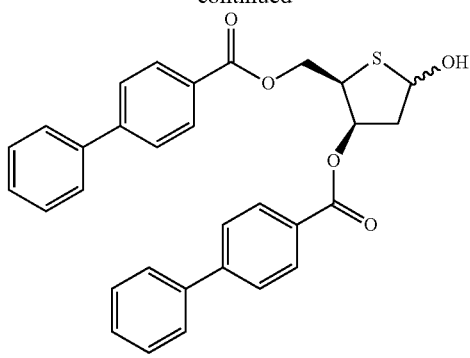
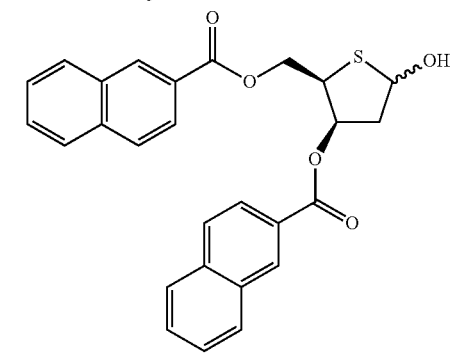
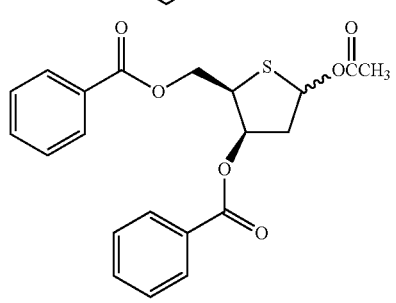
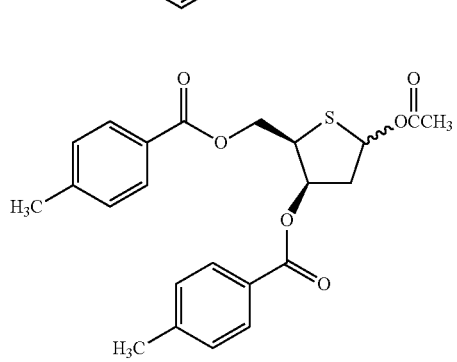
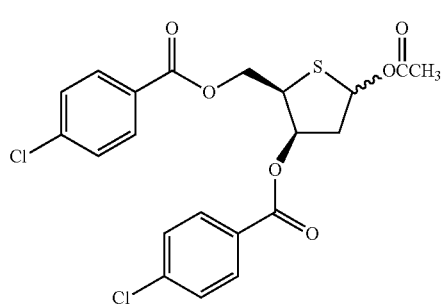
66
-continued
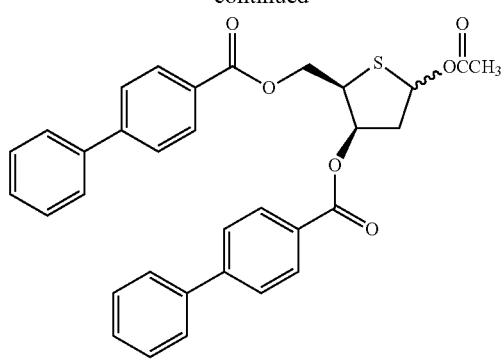
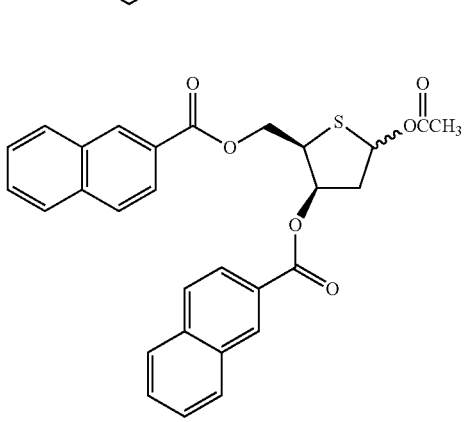
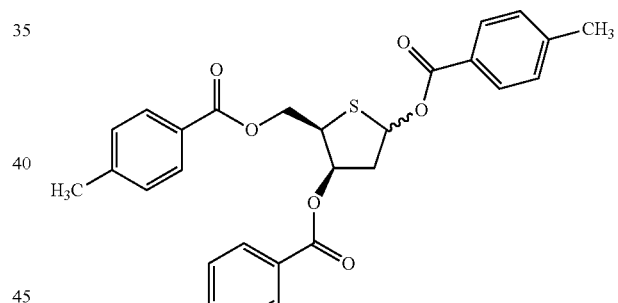
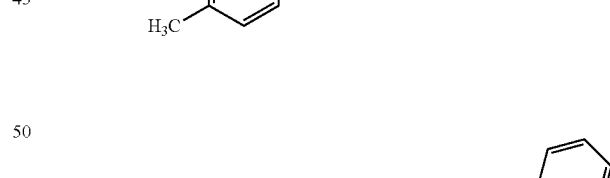
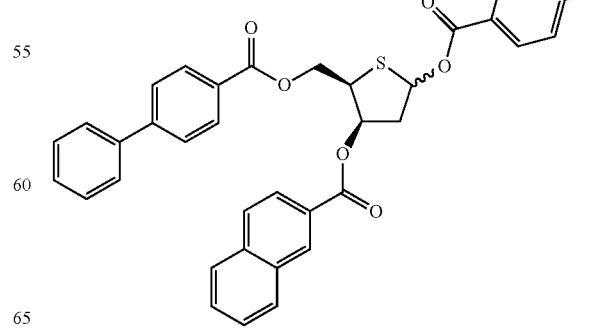

Compounds Represented by General Formula (II-12)
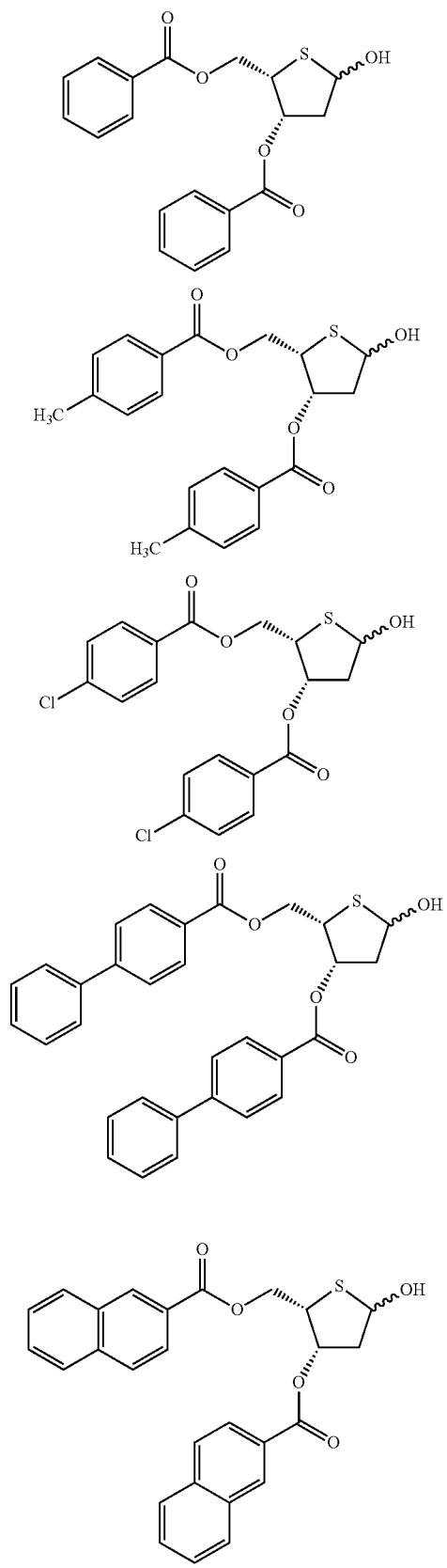
-continued
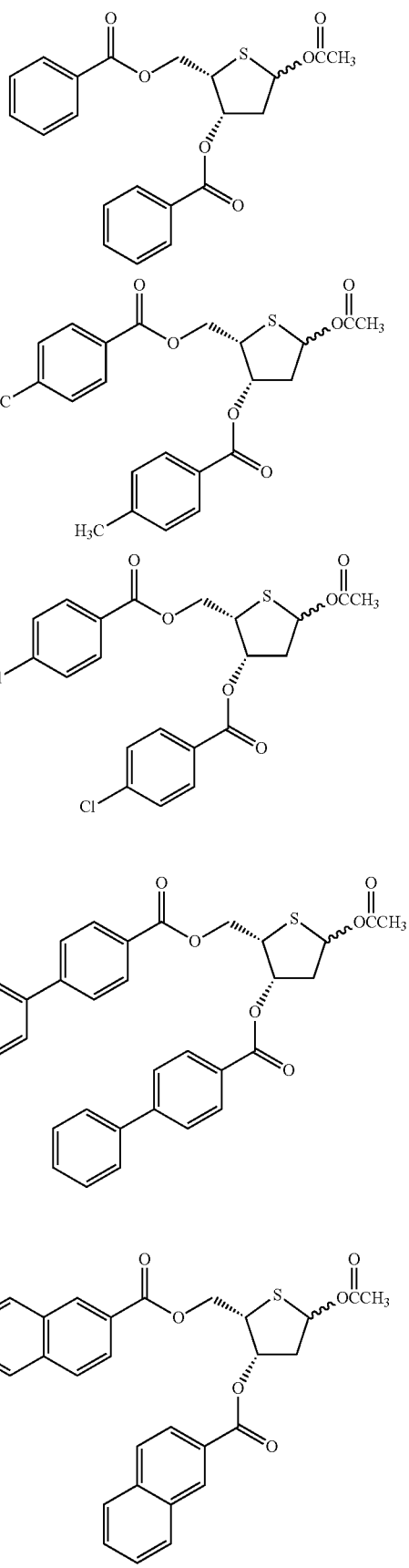

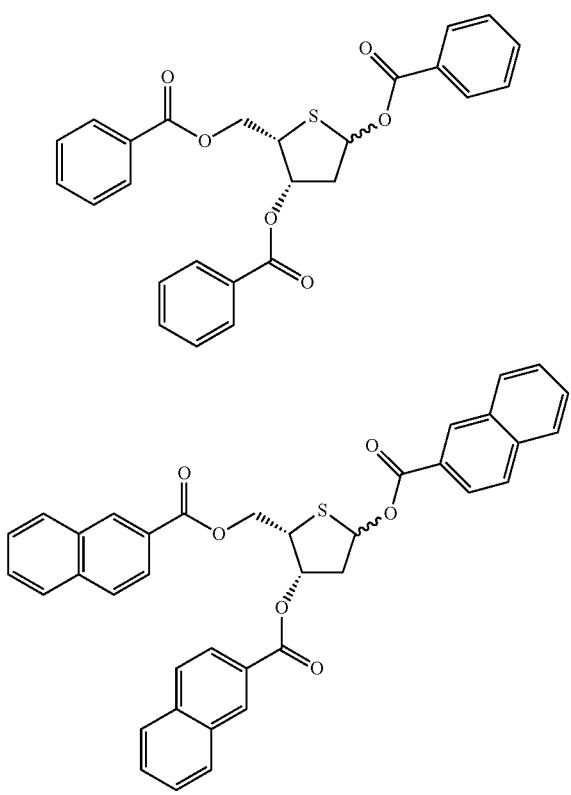
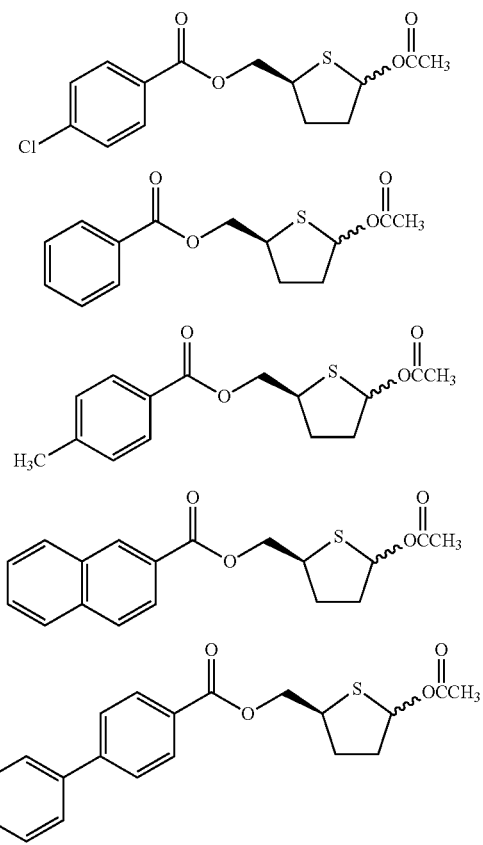
Compounds Represented by General Formula (II-13)
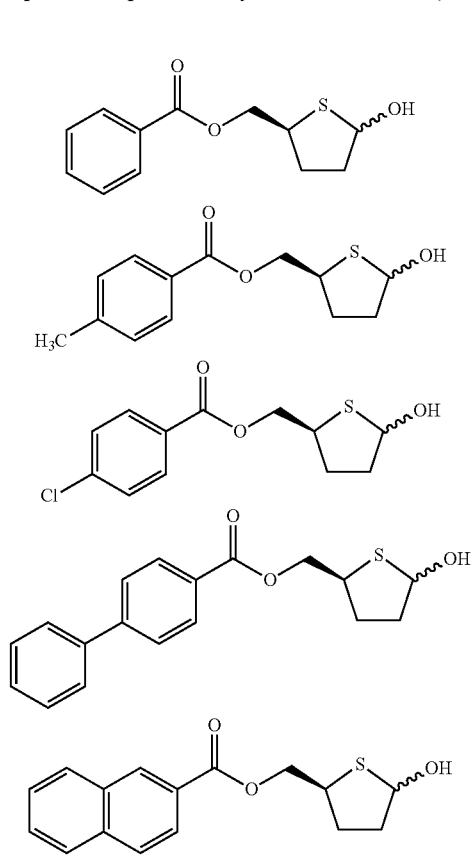
Compounds Represented by General Formula (II-14)
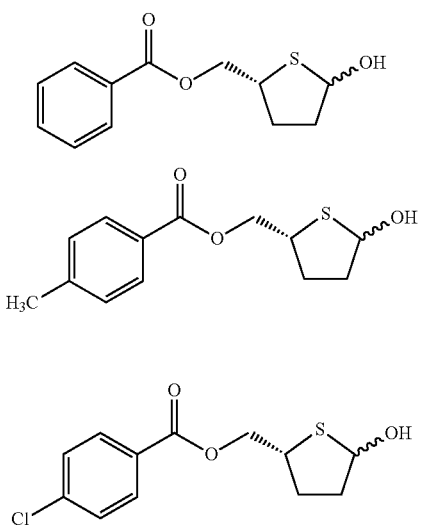

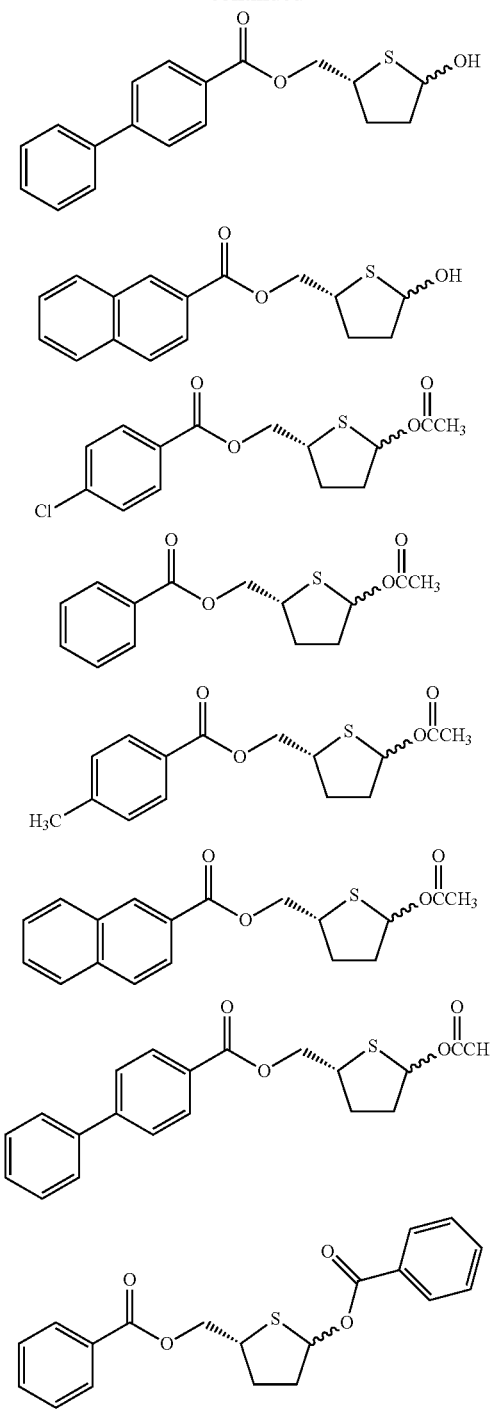

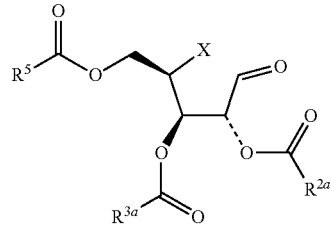
General Formula (I-1)

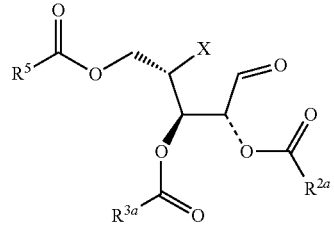
General Formula (I-2)

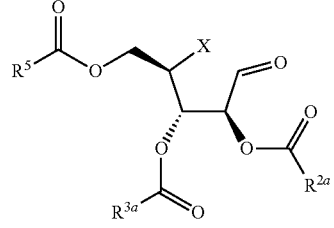
General Formula (I-3)

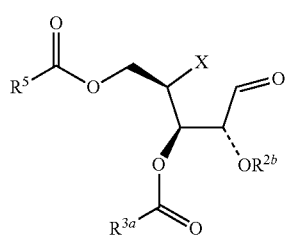
General Formula (I-4)

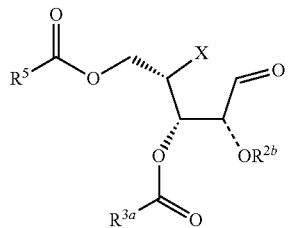
General Formula (I-5)

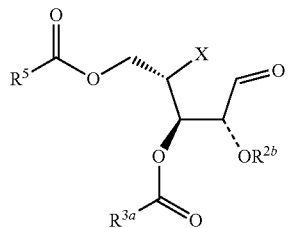
General Formula (I-6)

The compound represented by General Formula (II) of the present invention is synthesized through a step of reacting the compound represented by General Formula (I) with a sulfur compound.

<<Compounds Represented by General Formula (I)>>

Among the compounds represented by General Formula (I), compounds for synthesizing the compounds represented by General Formulas (II-1) to (II-14) are represented by the following General Formulas (I-1) to (I-14).

General Formula (I-7)

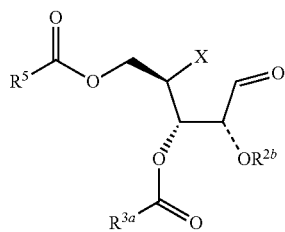

General Formula (I-8)

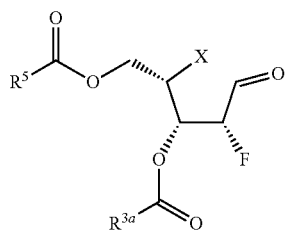

General Formula (I-9)

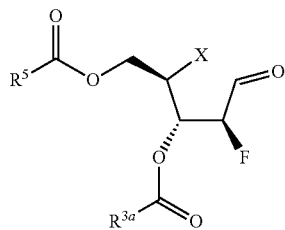

General Formula (I-10)

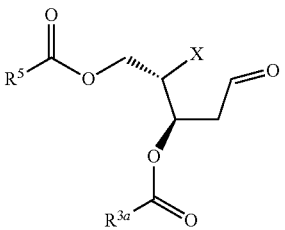

General Formula (I-11)

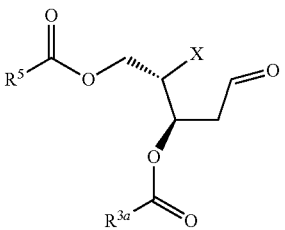

General Formula (I-12)

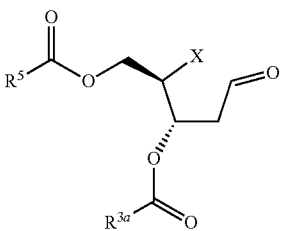

General Formula (I-13)

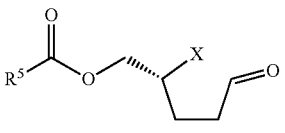

General Formula (I-14)

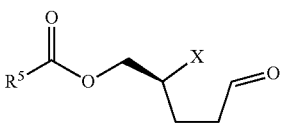

In General Formulas (I-1) to (I-14), $R^{2a}$, $R^{2b}$, $R^{3a}$, and $R^5$ have the same meaning as $R^{2a}$, $R^{2b}$, $R^{3a}$, and $R^5$ in General Formulas (II-1) to (II-14), respectively, and the preferable ranges thereof are also the same. X represents a leaving group.

Moreover, similarly to the compounds represented by each of General Formulas (II-1), (II-2), and (II-4) to (II-7), the compounds represented by each of General Formula (I-1), (I-2), and (I-4) to (I-7) having a direct bond represented by a dashed line having a constant thickness which is bonded to a thiolane ring are represented by each of the following General Formulas (I-1A), (I-1B), (I-2A), (I-2B), (I-4A) to (I-7A), and (I-4B) to (I-7B).

General Formula (I-1A)

General Formula (I-1B)

General Formula (I-2A)

General Formula (I-2B)

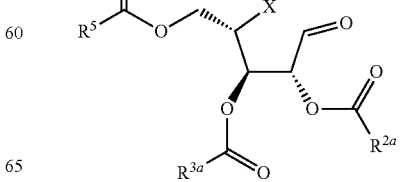

General Formula (I-4A)

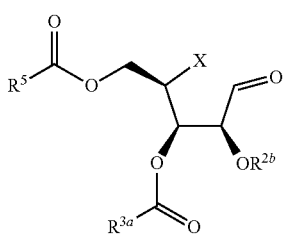

General Formula (I-4B)

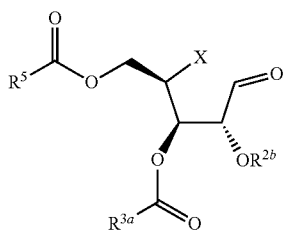

General Formula (I-5A)

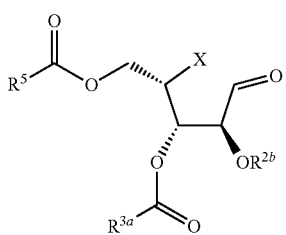

General Formula (I-5B)

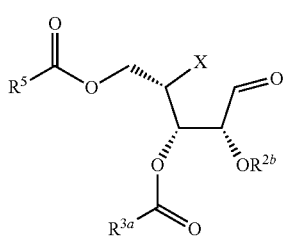

General Formula (I-6A)

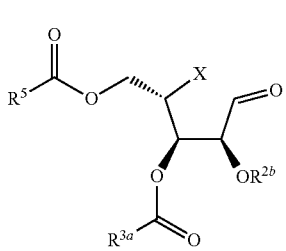

General Formula (I-6B)

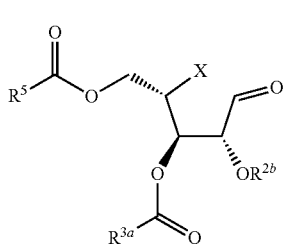

General Formula (I-7A)

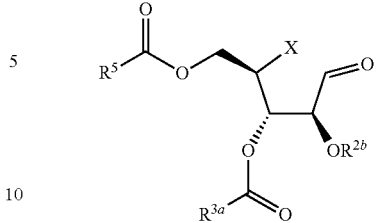

General Formula (I-7B)

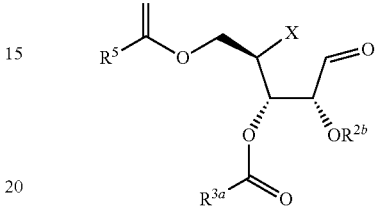

X is preferably a halogen atom, an alkylsulfonyloxy group, or an arylsulfonyloxy group.

Examples of the halogen atom include a fluorine atom, a chlorine atom, a bromine atom, and an iodine atom.

The number of carbon atoms of the alkylsulfonyloxy group is preferably 1 to 10, more preferably 1 to 6, still more preferably 1 to 3, and particularly preferably 1.

Examples of the alkylsulfonyloxy group include a methylsulfonyloxy group, an ethylsulfonyloxy group, a propylsulfonyloxy group, an isopropylsulfonyloxy group, an n-butylsulfonyloxy group, a t-butylsulfonyloxy group, an octylsulfonyloxy group, and a dodecylsulfonyloxy group.

The number of carbon atoms of the arylsulfonyloxy group is preferably 6 to 16, more preferably 6 to 12, and still more preferably 6 to 10.

Examples of the arylsulfonyloxy group include a benzenesulfonyloxy group, a toluenesulfonyloxy group, a naphthylsulfonyloxy group, a 4-chlorobenzenesulfonyloxy group, and a 2,4,5-trichlorobenzenesulfonyloxy group.

Here, using the compound of General Formula (I-1B) as a representative compound, specific examples thereof are shown below. Here, the present invention is not limited thereto.

Moreover, similarly in General Formulas (I-1A) and (I-2) to (I-14), compounds to which a leaving group shown below has been applied are exemplified.

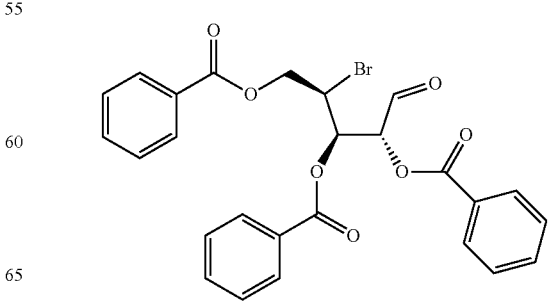

77
-continued
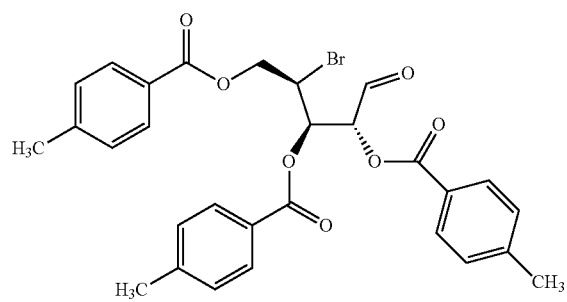
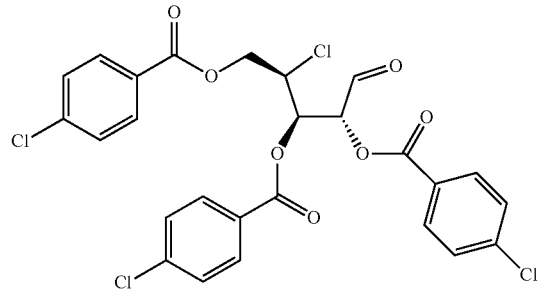
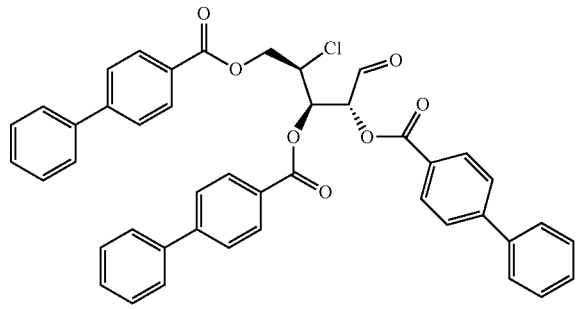
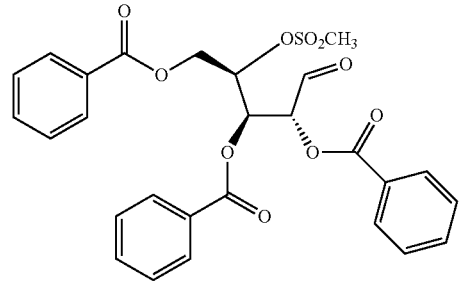
78
-continued
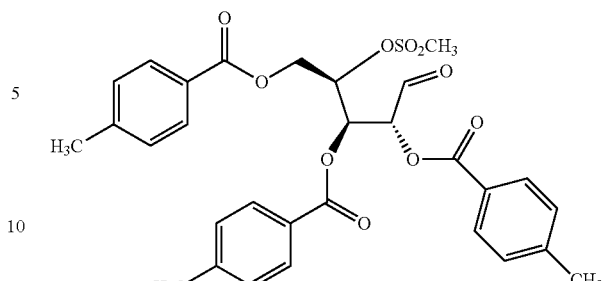
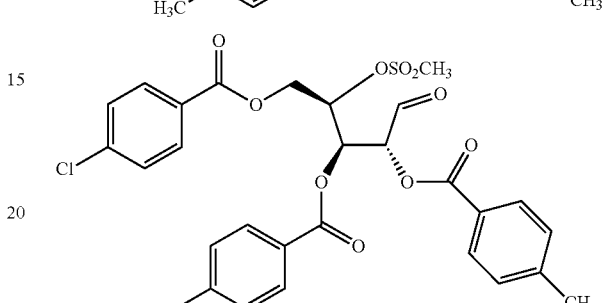
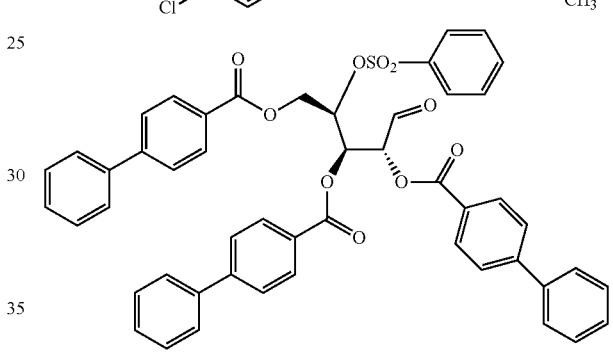
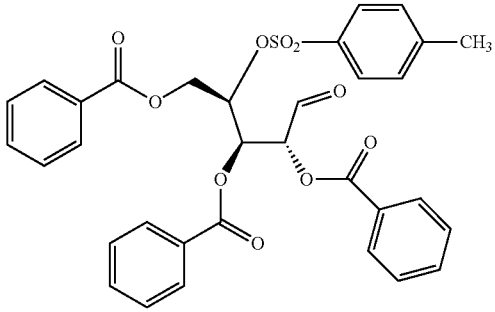

-continued

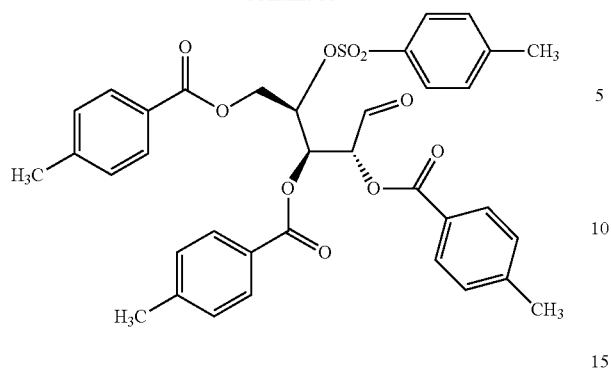

These compounds can be synthesized, for example, according to the method shown in synthesis of, representatively, a compound represented by the following General Formula (i) or by referencing this.

The compound represented by the following General Formula (i) is a compound included in General Formula (I-1B), and can be synthesized by the synthesis scheme described below.

General Formula (i)

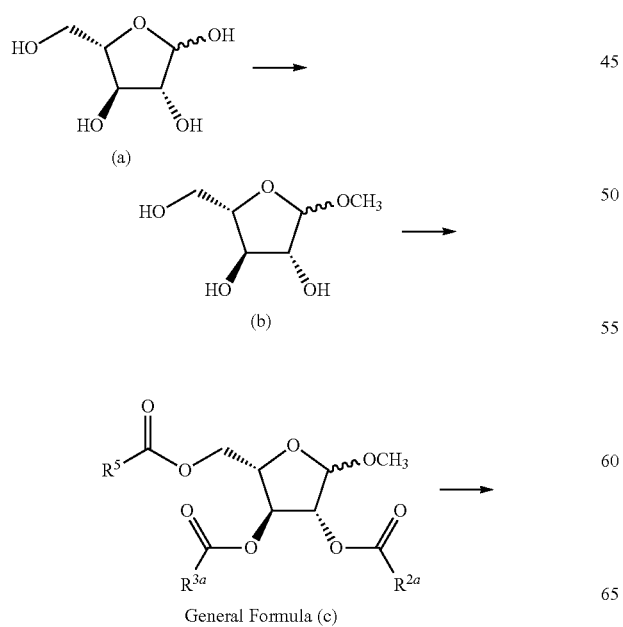

$R^{2a}$, $R^{3a}$, and $R^5$ in General Formula (i) have the same meaning as $R^{2a}$, $R^{3a}$, and $R^5$ in General Formula (I-1B), respectively, and the preferable ranges thereof are also the same.

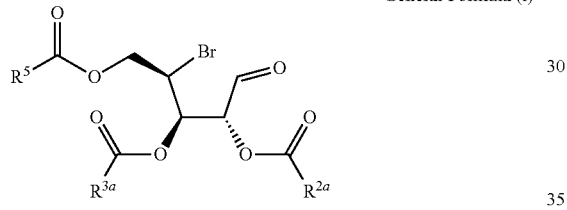

(a)

(b)

General Formula (c)

-continued

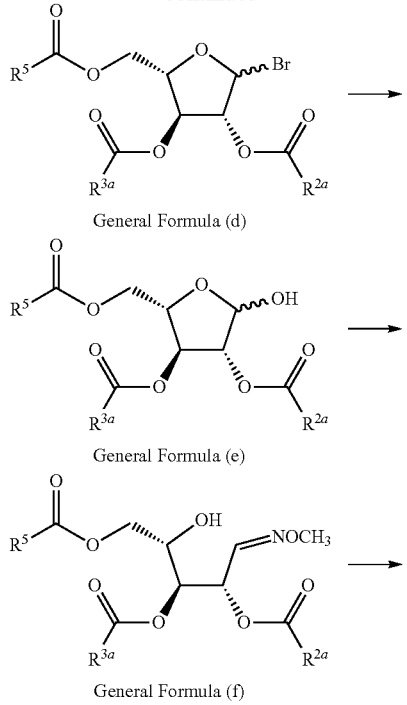

General Formula (d)

General Formula (e)

General Formula (f)

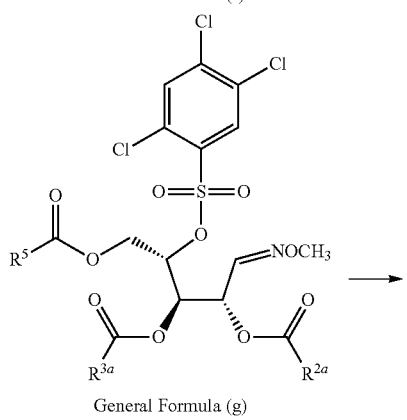

General Formula (g)

General Formula (h)

General Formula (i)

A compound (b) is synthesized by reacting a compound (a) [(3R,4R,5S)-5-(hydroxymethyl)oxolane-2,3,4-triol] with methanol under an acidic condition. Then, by reacting this with an acylating agent, a compound represented by General Formula (c) is synthesized. By reacting the compound represented by General Formula (c) with hydrogen bromide, a compound represented by General Formula (d) is synthesized. By hydrolyzing this, a compound represented by General Formula (e) is synthesized. After an oxime compound represented by General Formula (f) is synthesized by reacting the compound represented by General Formula (e) with O-methylhydroxylamine, by 2,4,5-trichlorobenzenesulfonyl chloride, a compound represented by General Formula (g) is synthesized. By reacting the compound represented by General Formula (g) with lithium bromide, a compound represented by General Formula (h) is synthesized. By acid-hydrolyzing this, oxime is converted to aldehyde, and as a result, a compound represented by General Formula (i) is synthesized.

<<Applications of Compound Represented by General Formula (II)>>

The compound represented by General Formula (II) are useful compounds for production of 1-(2-deoxy-2-fluoro-4-thio-β-D-arabinofuranosyl) cytosine, 1-(4-thio-β-D-arabinofuranosyl) cytosine useful as an antitumor agent, and the surrounding compounds thereof.

Examples of the applications of the compound represented by General Formula (II) include a compound represented by General Formula (V).

Thionucleoside represented by General Formula (V) can be synthesized by synthesizing a compound represented by General Formula (IV) directly from the compound represented by General Formula (II) or through a compound represented by General Formula (III) and deprotecting.

That is, the compound represented by General Formula (V) can be synthesized by reacting the compound represented by General Formula (II) with a silylated nucleic acid base and by deprotecting.

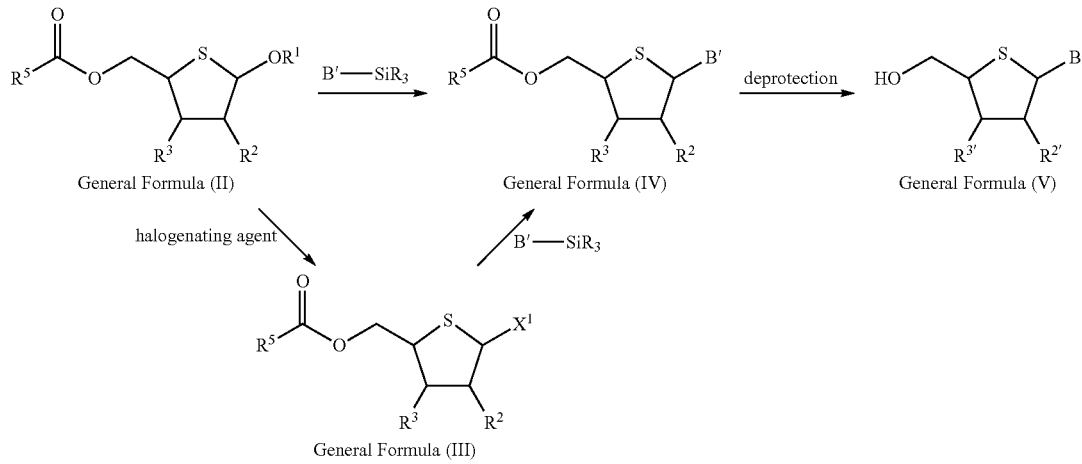

General Formula (II)  General Formula (IV)  General Formula (V)

General Formula (III)

$R^2$, $R^3$, and $R^5$ in General Formula (III) have the same meaning as $R^2$, $R^3$, and $R^5$ in General Formula (II), respectively, and the preferable ranges thereof are also the same. $X^1$ represents a halogen atom (preferably, a bromine atom).

$R^2$, $R^3$, and $R^5$ in General Formula (IV) have the same meaning as $R^2$, $R^3$, and $R^5$ in General Formula (II), respectively, and the preferable ranges thereof are also the same. B' represents a group in which the nucleic acid base or the amino group in the nucleic acid base is protected by an acyl group.

In a case where $R^2$ in General Formula (II) represents an acyloxy group, an arylmethyloxycarbonyloxy group, an allyloxycarbonyloxy group, an arylmethyloxy group, or an allyloxy group, or in a case where $R^3$ represents an acyloxy group, in General Formula (V), each of $R^{2'}$ and $R^{3'}$ represents a hydroxy group, and in the cases other than the above cases, $R^{2'}$ and $R^{3'}$ have the same meaning as $R^2$ and $R^3$ in General Formula (II), respectively. B represents a nucleic acid base.

Moreover, B'—$SiR_3$ represents a group protected by acylating a silylated nucleic acid base or the amino group in the nucleic acid base, and R represents an alkyl group (preferably a methyl group).

Here, the nucleic acid base in General Formulas (IV) and (V) means adenine which may be substituted, guanine which may be substituted, cytosine which may be substituted, thymine which may be substituted, or uracil which may be substituted, and for example, represents the following groups.

Moreover, * represents a moiety which is bonded to the 1-position of a thiolane ring.

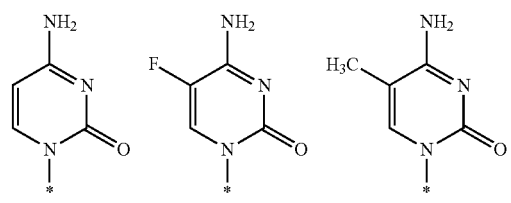

-continued

-continued

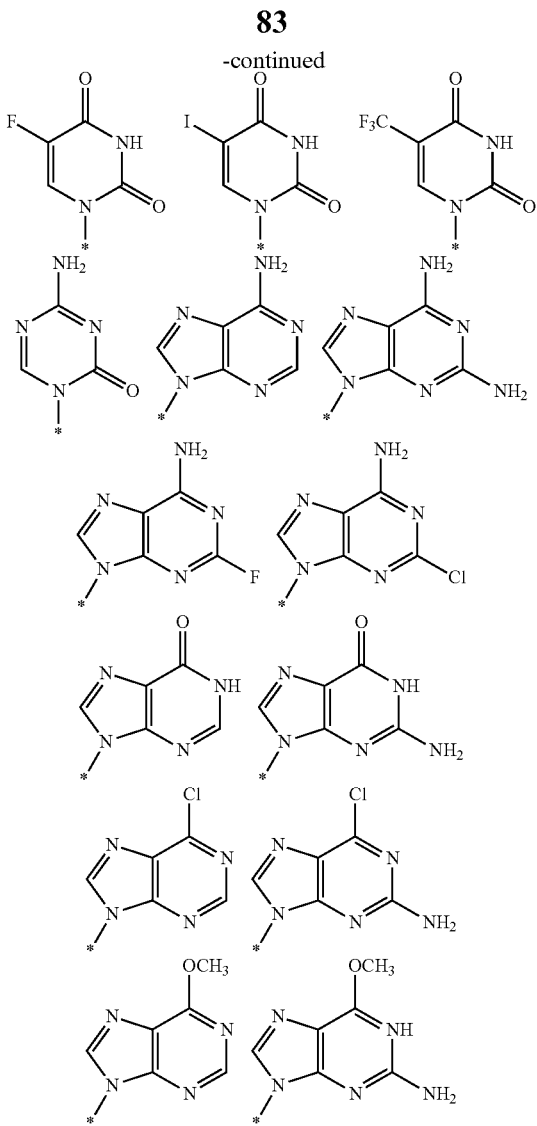

The compound represented by General Formula (III) can be synthesized by halogenating the compound represented by General Formula (II). The compound represented by General Formula (IV) can be synthesized by introducing a nucleic acid base or an amino group protector thereof by reacting a nucleic acid base or a silylated compound which is the amino group protector with the compound represented by General Formula (II) or (III).

Here, after the compound represented by General Formula (IV) is synthesized, the amino group is acylated to improve the crystallinity, and then, purification may be performed.

By deprotecting the compound represented by General Formula (IV), thionucleoside represented by General Formula (V) can be synthesized. This synthesis may be performed, for example, according to the method described in "Protective Groups in Organic Synthesis", 4th edition, pp. 696-926, (2007), published by John Wiley & Sons, INC.

EXAMPLES

Hereinafter, the present invention will be described in more detail base on examples, but the present invention is not to be interpreted as being limited thereto.

Unless otherwise specified, measurement was performed by using the following measuring instruments.

(Measuring Instruments Used)

Column Chromatography

Measuring instrument: a preparative chromatography instrument W-Prep 2XY (trade name) manufactured by YAMAZEN CORPORATION Chromatography carrier: silica gel $^1$H-NMR spectrum Measuring instrument: AVANCE 300 (trade name) manufactured by Bruker Corporation All δ values were showed in ppm.

LC/MS analysis

Measuring instrument: SQD (trade name) manufactured by WATERS

Column: BEH C18 (trade name) 1.7 μm, 2.1×30 mm manufactured by WATERS

Solvent: A liquid: 0.1% formic acid/water

B liquid: 0.1% formic acid/acetonitrile

Gradient cycle: 0.00 min (A liquid/B liquid=95/5), 2.00 min (A liquid/B liquid=5/95), 3.00 min (A liquid/B liquid=5/95), 3.01 min (A liquid/B liquid=100/0), 3.80 min (A liquid/B liquid=100/0)

Flow rate: 0.5 mL/min

Column temperature: room temperature

Ionization method: electron spray ionization method (Electron Spray Ionization: ESI positive and negative ion peaks are detected)

Detection wavelength: 254 nm

Example 1

[A] Synthesis of (3S,4R,5S)-2,4-bis(4-methylbenzoyloxy)-5-[(4-methylbenzoyloxy)methyl]thiolan-3-yl 4-methylbenzoate By reacting (2S,3R,4R)-4-bromo-1-oxo-3,5-bis((4-methylphenyl)carbonyloxy)pentan-2-yl 4-methylbenzoate with a 15% sodium hydrogen sulfide in the following manner, (3S,4R,5S)-2-hydroxy-4-((4-methylphenyl)carbonyloxy)-5-(((4-methylphenyl)carbonyloxy)methyl)thiolan-3-yl 4-methylbenzoate was obtained, and by further reacting this with 4-methylbenzoyl chloride, (3S,4R,5S)-2,4-bis(4-methylbenzoyloxy)-5-[(4-methylbenzoyloxy)methyl]thiolan-3-yl 4-methylbenzoate was synthesized.

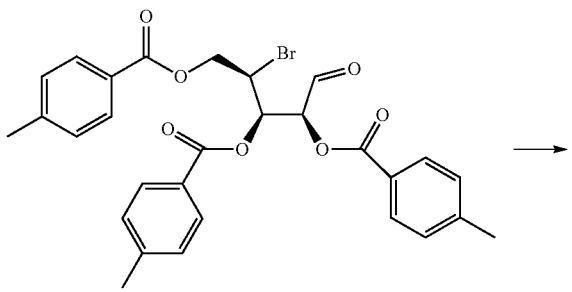

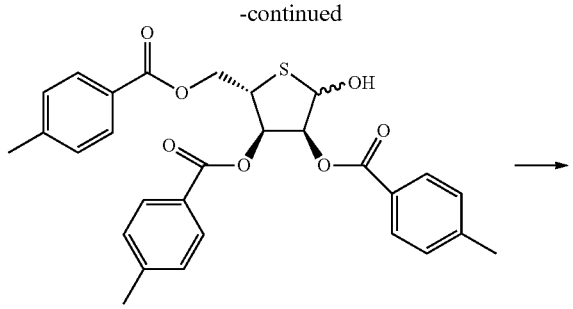

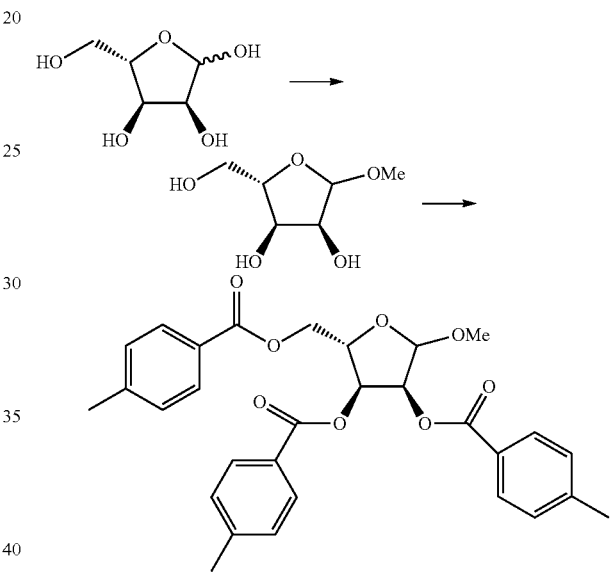

0.56 mL of a 15% sodium hydrogen sulfide aqueous solution was added dropwise to a solution of 0.57 g of (2S,3R,4R)-4-bromo-1-oxo-3,5-bis((4-methylphenyl)carbonyloxy)pentan-2-yl 4-methylbenzoate in 14 mL of N,N-dimethylformamide at 10° C. or lower, and the resultant product was stirred at 25° C. for 1.5 hours. 30 mL of ethyl acetate and 30 mL of a saturated sodium chloride aqueous solution were added to the reaction mixture, and then, the aqueous layer was removed. After the organic layer was washed sequentially three times with a sodium hydrogen carbonate aqueous solution and once with a saturated sodium chloride aqueous solution, the resultant product was dried over anhydrous sodium sulfate. The solvent was distilled off under reduced pressure, whereby a crude product of (3S,4R,5S)-2-hydroxy-4-((4-methylphenyl)carbonyloxy)-5-(((4-methylphenyl)carbonyloxy)methyl)thiolan-3-yl 4-methylbenzoate was obtained.

After 5.5 mg of N,N-dimethyl-4-aminopyridine was added to a solution of 120 mg of the obtained crude product in 2 mL of pyridine, 0.1 mL of 4-methylbenzoyl chloride was added thereto at 10° C. or lower, and the resultant product was stirred at room temperature for 6 hours. 30 mL of ethyl acetate and 30 mL of 1 N hydrochloric acid water were added to the reaction mixture, and then, the aqueous layer was removed. After the organic layer was washed sequentially with 1 N hydrochloric acid water, a sodium hydrogen carbonate aqueous solution, and a saturated sodium chloride aqueous solution, and dried over anhydrous sodium sulfate, the solvent was distilled off under reduced pressure. The obtained residue was purified by column chromatography (eluent: ethyl acetate/hexane=1/4), and as a result, two types of anomer isomers of (3S,4R,5S)-2,4-bis(4-methylbenzoyloxy)-5-[(4-methylbenzoyloxy)methyl] thiolan-3-yl 4-methylbenzoate were obtained, and one type was 89.4 mg (Rf value of TLC (eluent: ethyl acetate/hexane=1/2)=0.68) and the other type was 41.4 mg (Rf value of TLC (eluent: ethyl acetate/hexane=1/2)=0.63), respectively. Both were white amorphous materials.

The component of Rf value=0.68

$^1$H-NMR (CDCl$_3$) δ value: 2.31 (3H,s),2.36 (3H,s),2.42 (3H,s),2.44 (3H,s),4.29(1H,dt,J=8.6,5.8 Hz),4.53(1H,dd, J=5.9,11.6 Hz), 4.70(1H,dd,J=5.7,11.5 Hz),6.00 (1H,dd, J=3.6,8.6 Hz),6.17(1H,dd,J=1.8,3.5 Hz),6.28(1H,d,J=1.8 Hz),6.96(2H,d,J=8.0 Hz),7.13(2H,d,J=8.0 Hz),7.24-7.27 (4H,m),7.79(2H,d,J=8.3 Hz),7.80(2H,d,J=8.3 Hz),7.96(2H, d,J=8.2 Hz),7.97(2H,d,J=8.2 Hz)

The component of Rf value=0.63

$^1$H-NMR (CDCl$_3$) δ value: 2.36 (3H,s),2.40 (3H,s),2.41 (3H,s),2.43 (3H,s),4.16 (1H,dt,J=2.2,6.5 Hz),4.56 (2H,d, J=6.5 Hz),5.91(1H,t,J=4.7 Hz),6.07 (1H,dd,J=2.2, 4.4 Hz), 6.69 (1H,d,J=4.9 Hz),7.10 (2H,d,J=8.5 Hz),7.16 (2H,d, J=7.9 Hz),7.24-7.27 (4H,m),7.82 (2H,d,J=8.2 Hz),7.86 (2H, d,J=8.2 Hz),7.98 (2H,d,J=8.2 Hz),7.99 (2H,d,J=8.3 Hz)

[B] Synthesis of Raw Material

Moreover, (2S,3R,4R)-4-bromo-1-oxo-3,5-bis((4-methylphenyl)carbonyloxy)pentan-2-yl 4-methylbenzoate which was a raw material was synthesized through a plurality of steps in the following manner.

6.0 mL of acetyl chloride was added dropwise to a solution of 10 g of (3S,4R,5S)-5-(hydroxymethyl)oxolane-2,3,4-triol in 120 mL of methanol at 15° C. or lower, and the resultant product was stirred at 25° C. for 2 hours. 17.5 g of a 28% sodium methoxide/methanol solution and 80 mL of toluene were added to the reaction mixture, and the methanol was distilled off under reduced pressure, whereby 17.2 g of a crude product of (2S,3R,4S)-2-(hydroxymethyl)-5-methoxyoxolane-3,4-diol was obtained.

150 mL of toluene, 80 mL of water, 20 g of a 50% sodium hydroxide aqueous solution, and 0.60 g of tetrabutylammonium chloride were added to the crude product at 30° C. or lower, then, 30.9 g of 4-methylbenzoyl chloride was added dropwise thereto at 15° C. or lower over a period of 30 minutes, and the resultant product was stirred at 25° C. for 2.5 hours. 300 mL of ethyl acetate and 300 mL of water were added to the reaction liquid, and then, the aqueous layer was removed. After the organic layer was washed sequentially with 400 mL (two times) of water and 400 mL (two times) of a saturated sodium chloride aqueous solution and dried over anhydrous sodium sulfate, the solvent was distilled off under reduced pressure, whereby 33.6 g of a crude product of (3S,4S,5S)-2-methoxy-4-((4-methylphenyl)carbonyloxy)-5-(((4-methylphenyl)carbonyloxy)methyl)oxolan-3-yl 4-methylbenzoate was obtained as a pale yellow oil. The crude product was used in the next step without purification. As a result of ¹H-NMR measurement, the crude product was an anomer mixture of about 80:20.

¹H-NMR (CDCl₃) δ value: 2.35-2.45(9H,m),3.40(2.4H, s),3.47(0.6H,s),4.49(0.8H, d,J=6.2,12.8 Hz),4.56-4.63 (0.4H,m),4.68-4.73(1.8H,m),5.13(0.8H,s),5.30(0.2H,dd, J=40.4,70.1 Hz),5.37(0.2H,d,J=4.4 Hz),5.64(0.8H,d,J=4.8 Hz),5.69(0.2H,dd,J=3.4,7.1 Hz),5.84(0.8H,dd,J=4.8,6.6 Hz),7.10-7.32(6H,m),7.77-8.04(6H, m)

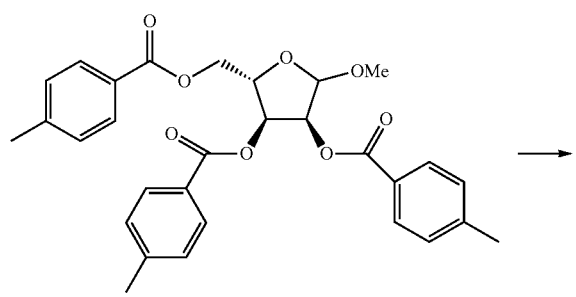

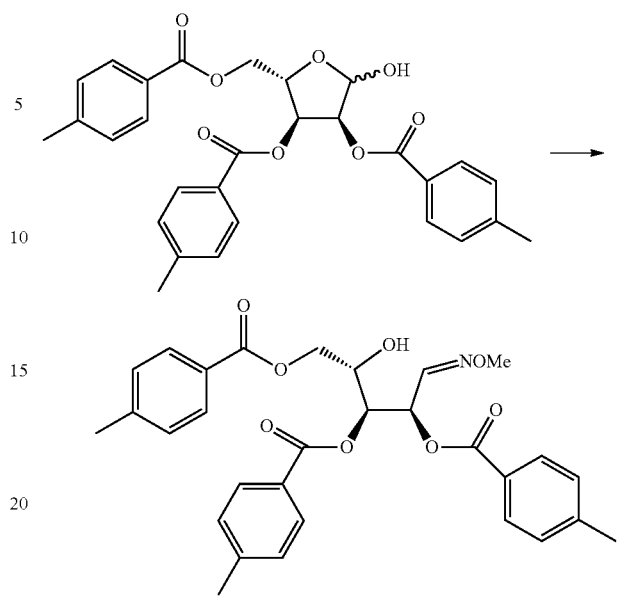

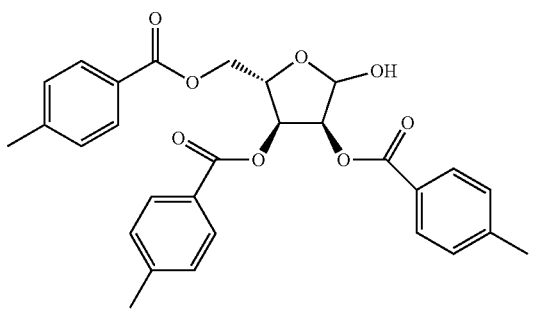

26.9 mL of water was added to a solution of 26.9 g of the crude product of (3S,4S,5S)-2-methoxy-4-((4-methylphenyl)carbonyloxy)-5-(((4-methylphenyl)carbonyloxy) methyl)oxolan-3-yl 4-methylbenzoate in 323 mL of trifluoroacetic acid at 10° C., and the resultant product was stirred at 40° C. for 1.5 hours. About 280 mL of trifluoroacetic acid was distilled off under reduced pressure, and 750 mL of ethyl acetate and 750 mL of a 10% sodium hydrogen carbonate aqueous solution were added to the residue. After the aqueous layer was removed, the organic layer was washed sequentially with 750 mL of a 10% sodium hydrogen carbonate aqueous solution, 750 mL of water, and 750 mL of a saturated sodium chloride aqueous solution, and dried over anhydrous sodium sulfate. The solvent was distilled off under reduced pressure, and the resultant product was purified by column chromatography (eluent: ethyl acetate/hexane=1/3→1/2), whereby 11.4 g of (3S,4S,5S)-2-hydroxy-4-((4-methylphenyl)carbonyloxy)-5-(((4-methylphenyl)carbonyloxy)methyl)oxolan-3-yl 4-methylbenzoate was obtained as a white amorphous material. As a result of ¹H-NMR measurement, the above-obtained material was an anomer mixture of about 67:33.

¹H-NMR (CDCl₃) δ value: 2.36-2.40(9H,m),3.32-3.34 (1H,m),4.51-4.79(3H,m),5.48(0.33H,dd,J=4.4,6.2 Hz),5.61 (0.67H,d, J=2.4 Hz),5.65(0.67H,d,J=4.9 Hz),5.75-5.79 (0.66H,m),5.86(0.67H,dd,J=5.0,6.2 Hz),7.10-7.27(6H,m), 7.77-7.98(6H,m)

12.0 mL of pyridine, 6.1 g of p-toluenesulfonic acid monohydrate, and 3.6 g of O-methylhydroxylamine hydrochloride were added to a solution of 12.0 g of (3S,4S,5S)-2-hydroxy-4-((4-methylphenyl)carbonyloxy)-5-(((4-methylphenyl)carbonyloxy)methyl)oxolan-3-yl 4-methylbenzoate in 38.4 mL of methanol at 25° C., and the resultant product was stirred at 40° C. for 2.5 hours. 400 mL of ethyl acetate and 400 mL of water were added to the reaction mixture, and then, the aqueous layer was removed. After the organic layer was washed sequentially two times with a 10% sodium chloride aqueous solution, two times with 1 N hydrochloric acid water, once with a sodium hydrogen carbonate aqueous solution, and once with a saturated sodium chloride aqueous solution, and dried over anhydrous sodium sulfate, the solvent was distilled off under reduced pressure, whereby 12.3 g of (2R,3S,4S)-4-hydroxy-1-(methoxyimino)-3,5-bis((4-methylphenyl)carbonyloxy) pentan-2-yl 4-methylbenzoate was obtained as a white amorphous material. As a result of ¹H-NMR measurement, the above-obtained material was an oxime isomer mixture of about 75:25.

¹H-NMR (CDCl₃) δ value: 2.38-2.41(9H,m),3.09(0.75H, d,J=5.8 Hz),3.25(0.25H,d, J=6.0 Hz),3.91(2.25H,s),4.02 (0.75H,s), 4.26-4.43(2H,m),4.59-4.64(1H,m),5.76(0.75H, dd,J=3.3,7.9 Hz),5.82(0.25H,dd,J=2.8,8.6 Hz),6.13(0.75H, dd,J=3.3,6.9 Hz),6.53(0.25H,dd,J=2.8,6.1 Hz),6.90(0.25H, d,J=6.1 Hz),7.12-7.26(6H, m),7.5 (0.75H,d,J=6.9 Hz),7.84-7.93(6H,m)

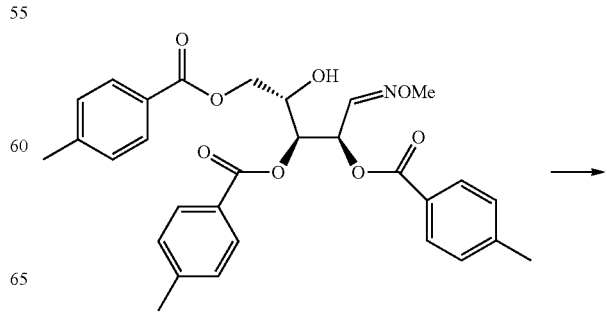

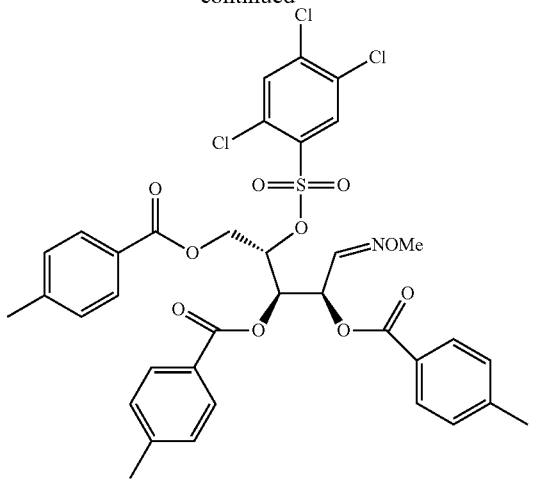

After 6.7 g of 2,4,5-trichlorobenzenesulfonyl chloride was added to a solution of 6.4 g of (2R,3S,4S)-4-hydroxy-1-(methoxyimino)-3,5-bis((4-methylphenyl)carbonyloxy) pentan-2-yl 4-methylbenzoate in 25.6 mL of acetonitrile at 25° C., 2.6 mL of N-methylimidazole was added dropwise thereto at 0° C. to 10° C., and the resultant product was stirred at 25° C. for 2 hours. 120 mL of ethyl acetate and 120 mL of water were added to the reaction mixture, and then, the aqueous layer was removed. After the organic layer was washed sequentially two times with a 10% sodium chloride aqueous solution, once with 1 N hydrochloric acid water, once with a sodium hydrogen carbonate aqueous solution, and once with a saturated sodium chloride aqueous solution, and dried over anhydrous sodium sulfate, the solvent was distilled off under reduced pressure, whereby 9.7 g of a crude product of (2R,3R,4S)-1-(methoxyimino)-3,5-bis((4-methylphenyl)carbonyloxy)-4-(((2,4,5-trichlorobenz ene)sulfonyl)oxy)pentan-2-yl 4-methylbenzoate was obtained as a pale yellow amorphous material. The crude product was used in the next step without further purification. As a result of $^1$H-NMR measurement, the crude product was an oxime isomer mixture of about 75:25.

$^1$H-NMR (CDCl$_3$) δ value: 2.41-2.43(9H,m),3.84(2.25H, s),3.96(0.75H,s),4.60(0.25,dd,J=7.6,12.8 Hz),4.65(0.75dd, J=7.7,12.7 Hz),4.81(0.75H,dd,J=2.9,12.7 Hz),4.93(0.28H, dd,J=2.7,12.8 Hz),5.40-5.45(0.25H,m),5.48-5.52(0.75H,m), 5.92(0.75H,dd,J=3.6,5.4 Hz),6.98-6.02(1H,m),6.52(0.25H, dd,J=4.8,5.6 Hz),6.89(0.25H,d,J=5.6 Hz),7.19-7.35(7H,m), 7.53(0.75H,d,J=6.3 Hz), 7.75-8.00(7H,m)

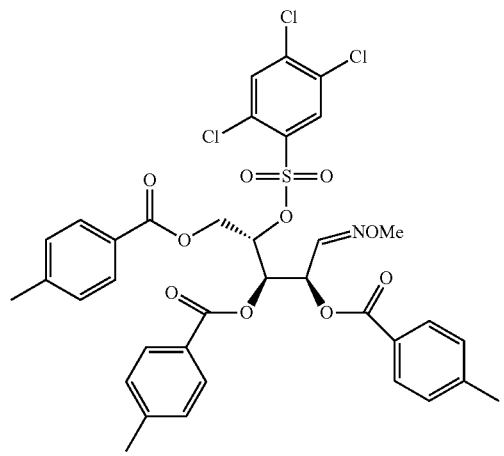

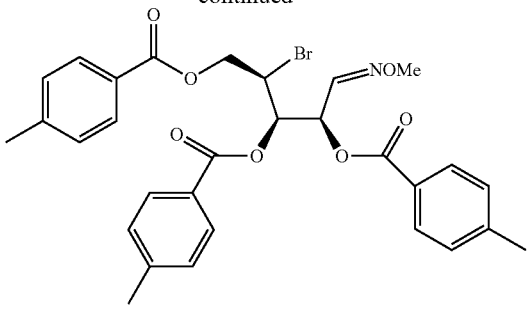

2.0 g of lithium bromide was added to a mixed solution of 9.1 g of the crude product of (2R,3R,4S)-1-(methoxyimino)-3,5-bis((4-methylphenyl)carbonyloxy)-4-(((2,4,5-trichlorobenz ene)sulfonyl)oxy)pentan-2-yl 4-methylbenzoate in 9.1 mL of tetrahydrofuran and 7.8 mL of 1,2-dimethylimidazole at 25° C., and the resultant product was stirred at 48° C. for 5 hours. After 300 mL of ethyl acetate and 100 mL of water were added to the reaction mixture, the aqueous layer was removed, then, the resultant product was dried over anhydrous sodium sulfate, and the solvent was distilled off under reduced pressure. The obtained residue was purified by column chromatography (eluent: ethyl acetate/hexane=1/3), whereby 5.5 g of (2R,3R,4R)-4-bromo-1-(methoxyimino)-3,5-bis((4-methylphenyl)carbonyloxy)-pentan-2-yl 4-methylbenzoate was obtained as a white amorphous material. As a result of $^1$H-NMR measurement, the above-obtained material was an oxime isomer mixture of about 77:23.

$^1$H-NMR (CDCl$_3$) δ value: 2.41-2.43(9H,m),3.70(2.31H, s),3.80(0.69H,s),4.50-4.77(3H,m),5.91-6.01(1.75H,m),6.50 (0.25H,t,J=6.4 Hz),6.80(0.25H,d,J=6.2 Hz),7.22-7.28(6H, m),7.45(0.75H,d,J=6.3 Hz),17.90-8.00(6H,m)

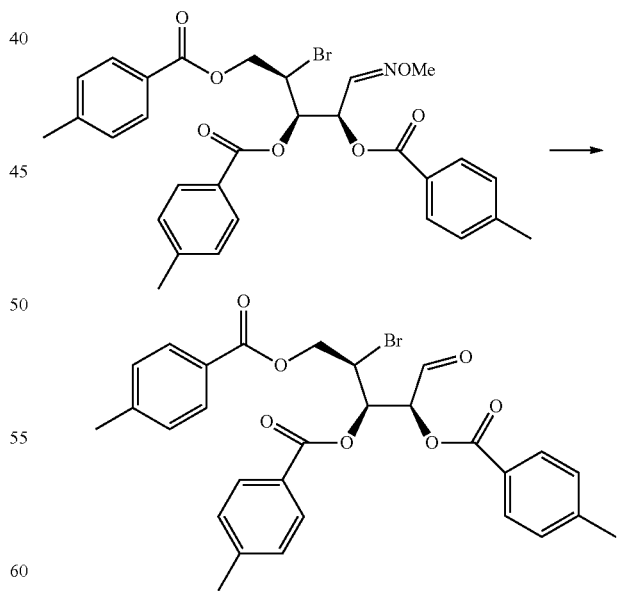

15.6 mL of a 50% glyoxylic acid aqueous solution was added to a solution of 5.2 g of (2R,3R,4R)-4-bromo-1-(methoxyimino)-3,5-bis((4-methylphenyl)carbonyloxy)-pentan-2-yl 4-methylbenzoate in 60 mL of acetonitrile, and the resultant product was stirred at 75° C. for 9.5 hours. The reaction mixture was cooled to room temperature, then, 270 mL of ethyl acetate and 90 mL of water were added thereto, and the aqueous layer was removed. After the organic layer was washed sequentially three times with a 10% sodium chloride aqueous solution, once with a sodium hydrogen carbonate aqueous solution, and three times with a saturated sodium chloride aqueous solution, and dried over anhydrous sodium sulfate, the solvent was distilled off under reduced pressure. The obtained residue was purified by column chromatography (eluent: ethyl acetate/hexane=1/3→1/2), whereby 3.8 g of (2S,3R,4R)-4-bromo-1-oxo-3,5-bis((4-methylphenyl)carbonyloxy)pentan-2-yl 4-methylbenzoate was obtained as a white amorphous material.

$^1$H-NMR (CDCl$_3$) δ value: 2.41-2.43(9H,m),(1H,dd, J=6.4,10.4 Hz),4.72-4.82(2H,m),5.64(1H,dd,J=1.0,7.4 Hz), 5.98(1H,dd, J=3.1,7.4 Hz),7.23-7.29(6H,m),7.92-7.99(6H, m),9.69(1H,d,J=0.96 Hz)

Example 2

[A] Synthesis of (3S,4R,5S)-2,4-bis(4-phenylbenzoyloxy)-5-[(4-phenylbenzoyloxy)methyl]thiolan-3-yl 4-phenylbenzoate By reacting (2S,3R,4R)-4-bromo-1-oxo-3,5-bis((4-phenylphenyl)carbonyloxy)pentan-2-yl 4-phenylbenzoate with a 15% sodium hydrogen sulfide in the following manner, (3S,4R,5S)-2-hydroxy-4-((4-phenylphenyl)carbonyloxy)-5-(((4-phenylphenyl)carbonyloxy)methyl)thiolan-3-yl 4-phenylbenzoate was obtained, and by further reacting the hydroxyl group thereof with 4-phenylbenzoyl chloride, (3S,4R,5S)-2,4-bis(4-phenylbenzoyloxy)-5-[(4-phenylbenzoyloxy)methyl]thiolan-3-yl 4-phenylbenzoate was synthesized.

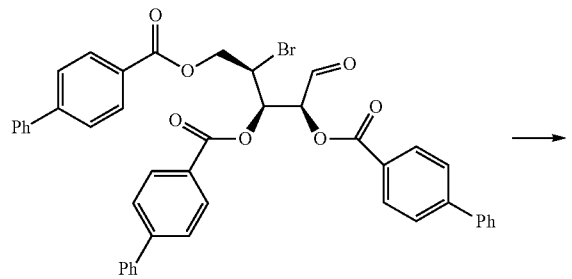

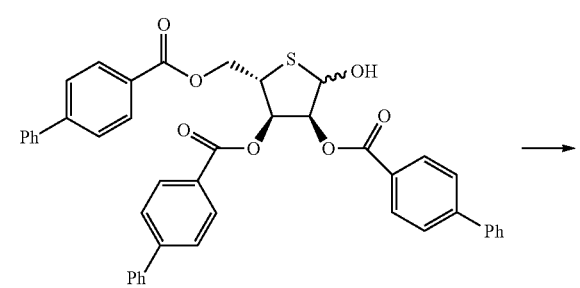

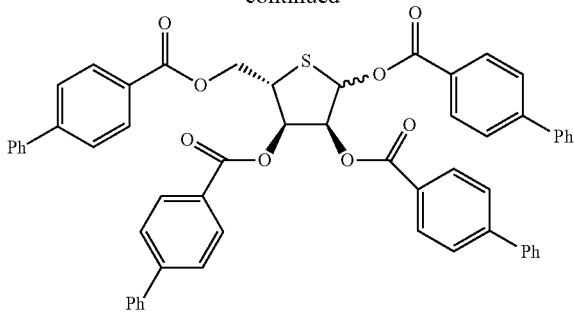

1.9 mL of a 15% sodium hydrogen sulfide aqueous solution was added dropwise to a solution of 2.6 g of the crude product of (2S,3R,4R)-4-bromo-1-oxo-3,5-bis((4-phenylphenyl)carbonyloxy)pentan-2-yl 4-phenylbenzoate in 48 mL of N,N-dimethylformamide at 10° C. or lower, and the resultant product was stirred at 25° C. for 1.5 hours. 150 mL of ethyl acetate and 150 mL of a saturated sodium chloride aqueous solution were added to the reaction mixture, and then, the aqueous layer was removed. After the organic layer was washed sequentially three times with a sodium hydrogen carbonate aqueous solution and once with a saturated sodium chloride aqueous solution, the resultant product was dried over anhydrous sodium sulfate. The solvent was distilled off under reduced pressure, whereby a crude product of (3S,4R,5S)-2-hydroxy-4-((4-phenylphenyl)carbonyloxy)-5-(((4-phenylphenyl)carbonyloxy) methyl)thiolan-3-yl 4-phenylbenzoate was obtained.

After 3 mg of N,N-dimethyl-4-aminopyridine was added to a solution of 69 mg of the crude product in 1 mL of pyridine, 85 mg of 4-phenylbenzoyl chloride was added thereto at 10° C. or lower, and the resultant product was stirred at room temperature for 2.5 hours and allowed to stand for 3 days. 30 mL of ethyl acetate and 30 mL of 1 N hydrochloric acid water were added to the reaction mixture, and then, the aqueous layer was removed. After the organic layer was washed sequentially with 1 N hydrochloric acid water, a sodium hydrogen carbonate aqueous solution, and a saturated sodium chloride aqueous solution, and dried over anhydrous sodium sulfate, the solvent was distilled off under reduced pressure. The obtained residue was recrystallized from ethyl acetate/hexane, whereby 67 mg of (3S,4R,5S)-2,4-bis(4-phenylbenzoyloxy)-5-[(4-phenylbenzoyloxy) methyl]thiolan-3-yl 4-phenylbenzoate was obtained as a white solid. As a result of $^1$H-NMR measurement, the above-obtained solid was an anomer mixture of about 60:40.

$^1$H-NMR (CDCl$_3$) δ value: 4.26(0.4H,dt,J=1.8,6.4 Hz), 4.38(0.6H,dt,J=8.6,5.3 Hz),4.59-4.67(1.4H,m),4.75(0.6H, dd,J=6.0,11.7 Hz),6.02(0.4H,t,J=4.6 Hz),6.14(0.6H,dd, J=3.6,8.6 Hz),6.22(0.4H,dd,J=1.9,4.3 Hz),6.28(0.6H, dd,J=1.7,3.5 Hz),6.37(0.6H,d,J=1.7 Hz),6.78(0.4H,d,J=4.9 Hz),7.27-7.77(28H,m),7.96-8.04(4H, m),8.15-8.26(4H,m)

[B] Synthesis of Raw Material

Moreover, (2S,3R,4R)-4-bromo-1-oxo-3,5-bis((4-phenylphenyl)carbonyloxy)pentan-2-yl 4-phenylbenzoate which was a raw material was synthesized through a plurality of steps in the following manner.

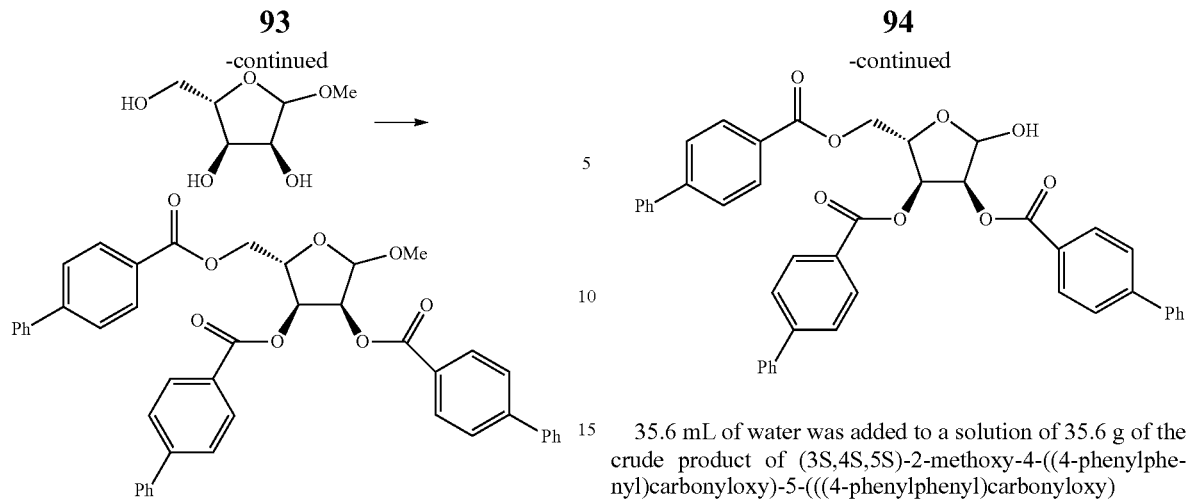

4.5 mL of acetyl chloride was added dropwise to a solution of 7.5 g of (3S,4R,5S)-5-(hydroxymethyl)oxolane-2,3,4-triol in 75 mL of methanol at 15° C. or lower, and the resultant product was stirred at 25° C. for 2 hours. 13.1 g of a 28% sodium methoxide/methanol solution and 60 mL of toluene were added to the reaction mixture, and the methanol was distilled off under reduced pressure, whereby 13.5 g of a crude product of (2S,3R,4S)-2-(hydroxymethyl)-5-methoxyoxolane-3,4-diol was obtained.

100 mL of toluene, 60 mL of water, 15 g of a 50% sodium hydroxide aqueous solution, and 0.45 g of tetrabutylammonium chloride were added to the crude product at 30° C. or lower, then, a solution of 32.6 g of 4-phenylbenzoyl chloride in 150 mL of THF was added thereto ten times by being divided at 15° C. or lower, and the resultant product was stirred at 25° C. for 2.5 hours. 200 mL of ethyl acetate and 200 mL of water were added to the reaction liquid, and then, the aqueous layer was removed. After the organic layer was washed sequentially with 300 mL (two times) of water and 300 mL (two times) of a saturated sodium chloride aqueous solution and dried over anhydrous sodium sulfate, the solvent was distilled off under reduced pressure, whereby 36.8 g of a crude product of (3S,4S,5S)-2-methoxy-4-((4-phenylphenyl)carbonyloxy)-5-(((4-phenylphenyl)carbonyloxy)methyl)oxolan-3-yl 4-phenylbenzoate was obtained as a white amorphous material. The crude product was used in the next step without purification. As a result of ¹H-NMR measurement, the crude product was an anomer mixture of about 87:13.

¹H-NMR (CDCl₃) δ value: 3.46(2.61H,s),3.53(0.39H,s), 4.56-4.62(1H,m),4.68-4.80(2H,m),5.20(0.87H,s),5.39-5.44 (0.26H, m),5.73(0.87H,d,J=4.8 Hz),5.77(0.13H,dd,J=3.5, 6.8 Hz),5.93(0.87H,dd,J=4.8,6.6 Hz),7.26-7.77(21H,m), 7.95-8.18(6H,m)

35.6 mL of water was added to a solution of 35.6 g of the crude product of (3S,4S,5S)-2-methoxy-4-((4-phenylphenyl)carbonyloxy)-5-(((4-phenylphenyl)carbonyloxy)methyl)oxolan-3-yl 4-phenylbenzoate in 427 mL of trifluoroacetic acid at 10° C., and the resultant product was stirred at 40° C. for 1.5 hours. About 370 mL of trifluoroacetic acid was distilled off under reduced pressure, then, 750 mL of ethyl acetate and 750 mL of a 10% sodium hydrogen carbonate aqueous solution were added to the residue, and the insoluble materials were removed by filtration using Celite. After the aqueous layer was removed, the organic layer was washed sequentially with 500 mL (five times) of a 10% sodium hydrogen carbonate aqueous solution and 500 mL (two times) of a saturated sodium chloride aqueous solution, and dried over anhydrous sodium sulfate. The solvent was distilled off under reduced pressure, and the resultant product was purified by column chromatography (eluent: ethyl acetate/hexane=1/3→1/2), whereby 10.6 g of (3S,4S,5S)-2-hydroxy-4-((4-phenylphenyl)carbonyloxy)-5-(((4-phenylphenyl)carbonyloxy)methyl)oxolan-3-yl 4-phenylbenzoate was obtained as a pale yellow amorphous material. As a result of ¹H-NMR measurement, the above-obtained material was an anomer mixture of about 57:43.

¹H-NMR (CDCl₃) δ value: 3.28(1H,brs),4.60-4.86(3H, m),5.57(0.43H,dd,J=4.4,6.3 Hz),5.6(0.57H,brs),5.75(0.57H, dd,J=0.8, 4.8 Hz),5.84-5.87(0.86H,m),5.96(0.57H,dd,J=4.8, 6.2 Hz),7.37-7.70(21H,m),7.96-8.22(6H,m)

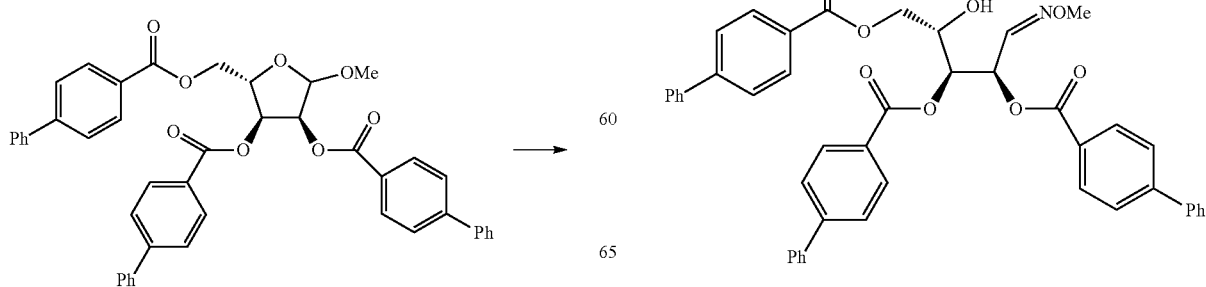

7.2 mL of pyridine, 3.6 g of p-toluenesulfonic acid monohydrate, and 2.1 g of O-methylhydroxylamine hydrochloride were added to a solution of 9.6 g of (3S,4S,5S)-2-hydroxy-4-((4-phenylphenyl)carbonyloxy)-5-(((4-phenylphenyl)carbonyloxy)methyl)oxolan-3-yl 4-phenylbenzoate in 30.7 mL of methanol at 25° C., and the resultant product was stirred at 40° C. for 2 hours. 250 mL of ethyl acetate and 250 mL of water were added to the reaction mixture, and then, the aqueous layer was removed. After the organic layer was washed sequentially two times with a 10% sodium chloride aqueous solution, two times with 1 N hydrochloric acid water, once with a sodium hydrogen carbonate aqueous solution, and once with a saturated sodium chloride aqueous solution, and dried over anhydrous sodium sulfate, the solvent was distilled off under reduced pressure, whereby 9.66 g of (2R,3S,4S)-4-hydroxy-1-(methoxyimino)-3,5-bis((4-phenylphenyl)carbonyloxy)pentan-2-yl 4-phenylbenzoate was obtained as a pale yellow amorphous material. As a result of $^1$H-NMR measurement, the above-obtained material was an oxime isomer mixture of about 77:23.

$^1$H-NMR (CDCl$_3$) δ value: 3.08(0.77H,brs),3.27(0.23H,brs),3.94(2.31H,s),4.06(0.69H, s),4.32-4.53(2H,m),4.66-4.72(1H, m),5.87(0.77H,dd,J=3.3,7.9 Hz),5.92(0.23H,dd,J=2.7,8.7 Hz),6.21(0.77H,dd,J=3.3,6.8 Hz),6.62(0.23H,dd,J=2.8,6.1 Hz),6.97(0.23H,d,J=6.1 Hz),7.38-7.68(21.77H,m),8.04-8.12(6H,m)

added to the reaction mixture, and then, the aqueous layer was removed. After the organic layer was washed sequentially two times with a 10% sodium chloride aqueous solution, once with 1 N hydrochloric acid water, once with a sodium hydrogen carbonate aqueous solution, and once with a saturated sodium chloride aqueous solution, and dried over anhydrous sodium sulfate, the solvent was distilled off under reduced pressure, and the resultant product was purified by column chromatography (eluent: ethyl acetate/hexane=1/4), whereby 3.7 g of (2R,3R,4S)-1-(methoxyimino)-3,5-bis((4-phenylphenyl)carbonyloxy)-4-(((2,4,5-trichlorobenz ene)sulfonyl)oxy)pentan-2-yl 4-phenylbenzoate was obtained as a white amorphous material. As a result of $^1$H-NMR measurement, the above-obtained material was an oxime isomer mixture of about 72:28.

$^1$H-NMR (CDCl$_3$) δ value: 3.88(2.16H,s),4.00(0.84H,s),4.68(0.28H,dd,J=7.4,12.8 Hz),4.73(0.72H,dd,J=7.5,12.7 Hz),4.91(0.72H,dd,J=2.9,12.7 Hz),4.93(0.28H,dd,J=2.7,12.8 Hz),5.49-5.54(0.28H,m),5.56-5.61(0.72H,m), 6.02 (0.72H,dd,J=3.7,5.2 Hz),6.07-6.11(1H,m),6.62(0.28H,dd,J=4.8,5.6 Hz),6.97 (0.28H,d,J=5.6 Hz),7.38-7.72 (22.72H,m),7.95-8.18(7H,m)

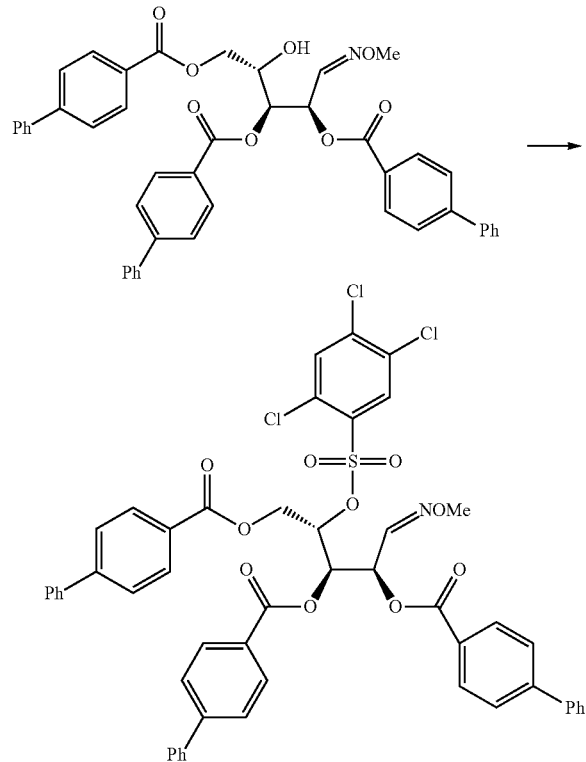

After 3.6 g of 2,4,5-trichlorobenzenesulfonyl chloride was added to a mixed solution of 4.6 g of (2R,3S,4S)-4-hydroxy-1-(methoxyimino)-3,5-bis((4-phenylphenyl)carbonyloxy)pentan-2-yl 4-phenylbenzoate in 18.5 mL of acetonitrile and 10 mL of tetrahydrofuran at 25° C., 1.4 mL of N-methylimidazole was added dropwise thereto at 0° C. to 10° C., and the resultant product was stirred at 25° C. for 2 hours. 90 mL of ethyl acetate and 90 mL of water were

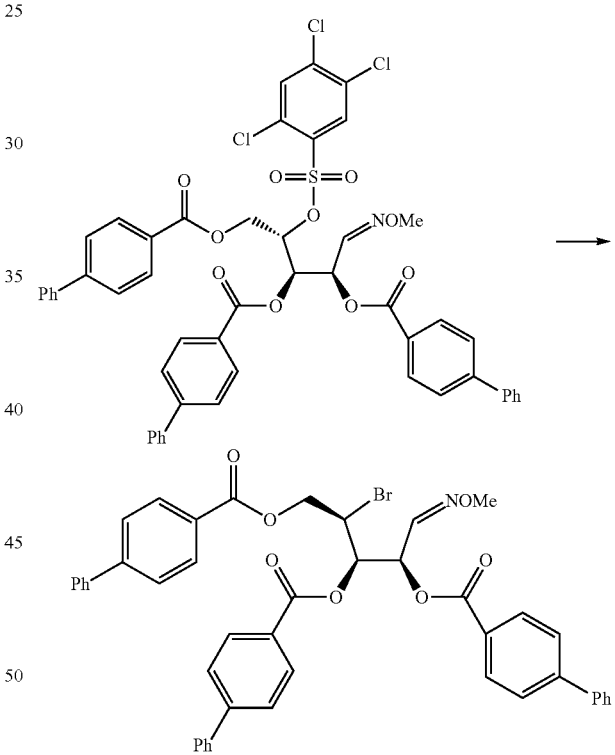

0.67 g of lithium bromide was added to a mixed solution of 3.7 g of (2R,3R,4S)-1-(methoxyimino)-3,5-bis((4-phenylphenyl)carbonyloxy)-4-(((2,4,5-trichlorobenz ene)sulfonyl)oxy)pentan-2-yl 4-phenylbenzoate in 3.7 mL of tetrahydrofuran and 3.2 mL of 1,2-dimethylimidazole at 25° C., and the resultant product was stirred at 48° C. for 5 hours. After 150 mL of ethyl acetate and 50 mL of water were added to the reaction mixture, the aqueous layer was removed, then, the resultant product was dried over anhydrous sodium sulfate, and the solvent was distilled off under reduced pressure, whereby 4.6 g of (2R,3R,4R)-4-bromo-1-(methoxyimino)-3,5-bis((4-phenylphenyl)carbonyloxy)pentan-2-yl 4-phenylbenzoate was obtained as a white solid.

As a result of $^1$H-NMR measurement, the above-obtained solid was an oxime isomer mixture of about 74:26.

$^1$H-NMR (CDCl$_3$) δ value: 3.75(2.22H,s), 3.86(0.78H,s), 4.60-4.66(1H,m),4.73-4.78(1H,m),4.81-4.87(1H,m),6.01-6.10(1.74H,m),6.59(0.26H,t,J=6.3 Hz),6.88(0.26H,d,J=6.2 Hz),7.39-7.71(21.74H,m),8.09-8.19(6H,m)

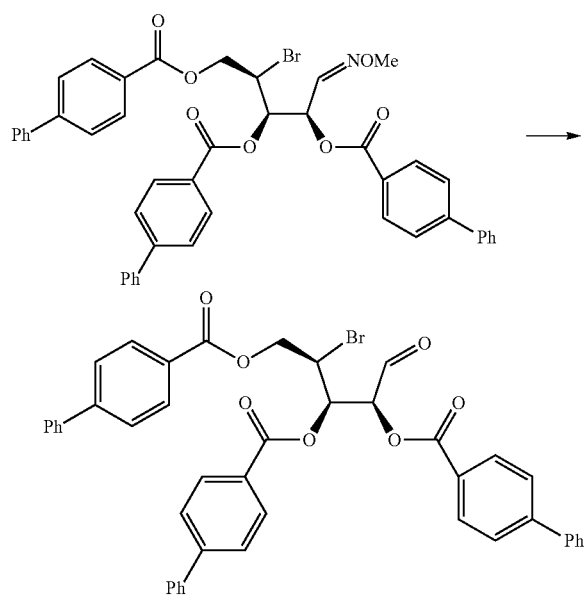

28 mL of a 50% glyoxylic acid aqueous solution was added to a solution of 4.2 g of (2R,3R,4R)-4-bromo-1-(methoxyimino)-3,5-bis((4-phenylphenyl)carbonyloxy)pentan-2-yl 4-phenylbenzoate in 320 mL of acetonitrile, and the resultant product was stirred at 75° C. for 19 hours. The reaction mixture was cooled to room temperature, then, 330 mL of ethyl acetate and 110 mL of water were added thereto, and the aqueous layer was removed. After the organic layer was washed sequentially three times with a 10% sodium chloride aqueous solution, once with a sodium hydrogen carbonate aqueous solution, and three times with a saturated sodium chloride aqueous solution, and dried over anhydrous sodium sulfate, the solvent was distilled off under reduced pressure, whereby 2.9 g of a crude product of (2S,3R,4R)-4-bromo-1-oxo-3,5-bis((4-phenylphenyl)carbonyloxy)pentan-2-yl 4-phenylbenzoate was obtained as a pale yellow amorphous material. The crude product was used in the next step without further purification.

$^1$H-NMR (CDCl$_3$) δ value: 4.65(1H,dd,J=6.7,11.0 Hz), 4.80-4.91(2H,m),5.74(1H,dd, J=0.8,7.3 Hz),6.08(1H,dd, J=3.1,7.2 Hz), 7.39-7.72(21H,m),8.10-8.19(6H,m),9.77(1H, d,J=0.8 Hz)

Example 3

[A] Synthesis of (3R,4R,5S)-2,4-bis(4-methylbenzoyloxy)-5-[(4-methylbenzoyloxy)methyl]thiolan-3-yl 4-methylbenzoate By reacting (2R,3R,4R)-4-bromo-1-oxo-3,5-bis((4-methylphenyl)carbonyloxy)pentan-2-yl 4-methylbenzoate with a 15% sodium hydrogen sulfide in the following manner, (3R,4R,5S)-2-hydroxy-4-((4-methylphenyl)carbonyloxy)-5-(((4-methylphenyl)carbonyloxy)methyl)thiolan-3-yl 4-methylbenzoate was obtained, and by further reacting the hydroxyl group thereof with 4-methylbenzoyl chloride, (3R, 4R,5S)-2,4-bis(4-methylbenzoyloxy)-5-[(4-methylbenzoyloxy)methyl]thiolan-3-yl 4-methylbenzoate was synthesized.

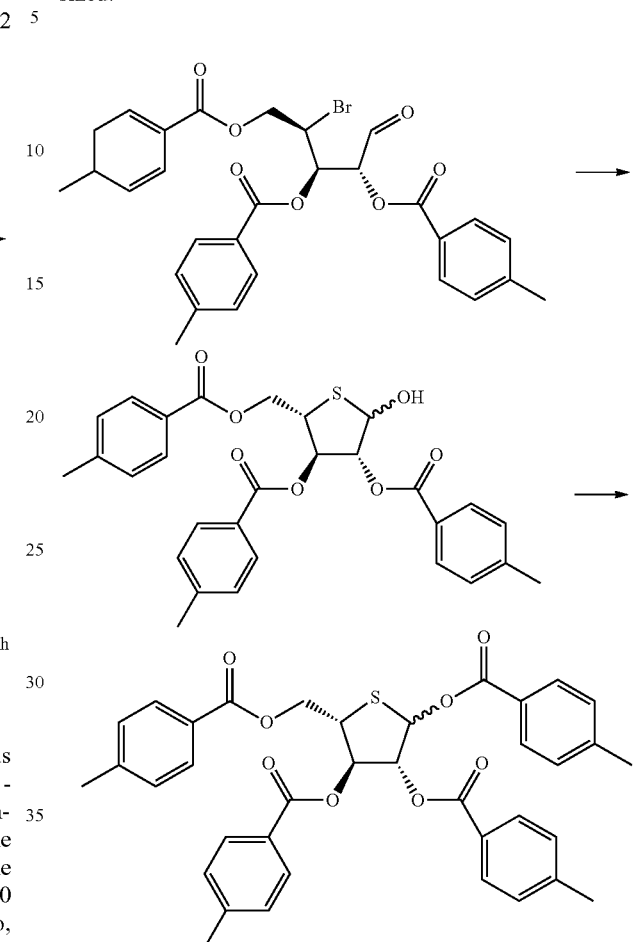

1.6 mL of a 15% sodium hydrogen sulfide aqueous solution was added dropwise to a solution of 1.2 g of the oily crude product of (2R,3R,4R)-4-bromo-1-oxo-3,5-bis((4-methylphenyl)carbonyloxy)pentan-2-yl 4-methylbenzoate in 12 mL of N,N-dimethylformamide at 10° C. or lower, and the resultant product was stirred at 25° C. for 1.5 hours. 50 mL of ethyl acetate and 50 mL of a saturated sodium chloride aqueous solution were added to the reaction mixture, and then, the aqueous layer was removed. After the organic layer was washed sequentially three times with a sodium hydrogen carbonate aqueous solution and once with a saturated sodium chloride aqueous solution, the resultant product was dried over anhydrous magnesium sulfate. The solvent was distilled off under reduced pressure, whereby a crude product of (3R,4R,5S)-2-hydroxy-4-((4-methylphenyl)carbonyloxy)-5-(((4-methylphenyl)carbonyloxy)methyl)thiolan-3-yl 4-methylbenzoate was obtained.

After 10 mg of N,N-dimethyl-4-aminopyridine was added to a solution of 204 mg of the obtained crude product in 2 mL of pyridine, 62.3 µL of 4-methylbenzoyl chloride was added thereto at 10° C. or lower, and the resultant product was stirred at room temperature for 1 hour. 30 mL of ethyl acetate and 30 mL of 1 N hydrochloric acid water were added to the reaction mixture, and then, the aqueous layer was removed. After the organic layer was washed sequentially with a sodium hydrogen carbonate aqueous solution and a saturated sodium chloride aqueous solution, and dried over anhydrous sodium sulfate, the solvent was distilled off under reduced pressure. The obtained residue was purified by column chromatography (eluent: ethyl acetate/hexane=1/4), and as a result, two types of anomer isomers of (3R,4R,5S)-2,4-bis(4-methylbenzoyloxy)-5-[(4-methylbenzoyloxy)methyl]thiolan-3-yl 4-methylbenzoate were obtained, and one type was 66.3 mg (Rf value of TLC (eluent: ethyl acetate/hexane=1/2)=0.68) and the other type was 183 mg (Rf value of TLC (eluent: ethyl acetate/hexane=1/2)=0.62), respectively. Both were white amorphous materials.

The component of Rf value=0.68
$^1$H-NMR (CDCl$_3$) δ value: 2.38-2.42(12H,m),4.23(1H,dt, J=3.6,7.5 Hz),4.54(1H,dd, J=7.3,11.3 Hz),4.74(1H,dd, J=7.9,11.3 Hz), 5.90(1H,t,J=3.3 Hz),6.14(1H,dd,J=2.0,3.2 Hz),6.43(1H,d,J=1.6 Hz),7.15-7.28(8H,m),7.90-7.98(8H,m)

The component of Rf value=0.62
$^1$H-NMR (CDCl$_3$) δ value: 2.31(3H,s),2.34(3H,s),2.38 (3H,s),2.42(3H,s),3.91(1H,dt,J=7.7,6.2 Hz),4.52(1H,dd, J=6.2,11.5 Hz), 4.67(1H,dd,J=6.1,11.5 Hz),5.85(1H,dd, J=4.5,9.8 Hz),6.31(1H,dd,J=7.8,9.8 Hz),6.50(1H,d,J=4.5 Hz),6.95(2H,d,J=8.0 Hz),7.14(2H,d,J=8.0 Hz),7.19(2H,d, J=8.0 Hz),7.22(2H,d,J=8.0 Hz),7.77(2H,d,J=8.2 Hz),7.85 (2H,d,J=8.1 Hz),7.87(2H,d,J=8.2 Hz), 7.91(2H,d,J=8.2 Hz)

[B] Synthesis of Raw Material

Moreover, (2R,3R,4R)-4-bromo-1-oxo-3,5-bis((4-methylphenyl)carbonyloxy)pentan-2-yl 4-methylbenzoate which was a raw material was synthesized through a plurality of steps in the following manner.

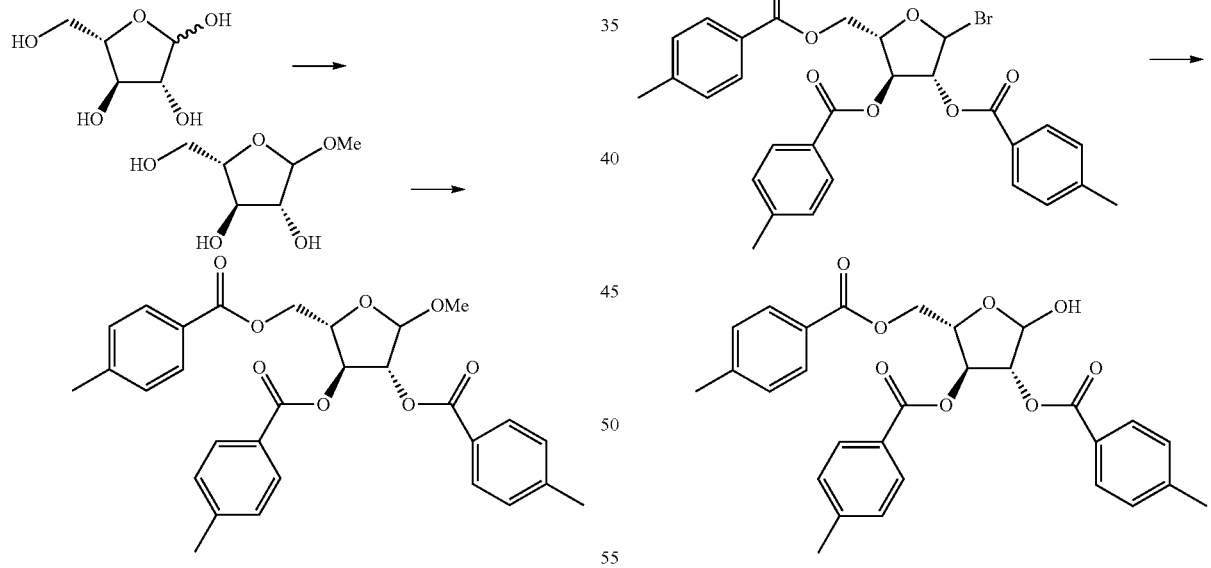

5.8 mL of acetyl chloride was added dropwise to a solution of 9.6 g of (3R,4R,5S)-5-(hydroxymethyl)oxolane-2,3,4-triol in 96 mL of methanol at 15° C. or lower, and the resultant product was stirred at 25° C. for 1 hour. 17.5 mL of a 28% sodium methoxide/methanol solution and 80 mL of toluene were added to the reaction mixture, and the methanol was distilled off under reduced pressure, whereby 18.3 g of a crude product of (2S,3R,4R)-2-(hydroxymethyl)-5-methoxyoxolane-3,4-diol was obtained.

48 mL of toluene, 38.4 mL of a 25% sodium hydroxide aqueous solution, and 0.58 g of tetrabutylammonium chloride were added to the crude product at 30° C. or lower, then, 25.3 mL of 4-methylbenzoyl chloride was added dropwise thereto at 15° C. or lower over a period of 1 hour, and the resultant product was stirred at 25° C. for 3 hours. After the aqueous layer was removed, the organic layer was washed sequentially with 50 mL of water and 50 mL of a saturated sodium chloride aqueous solution and dried over anhydrous sodium sulfate, the solvent was distilled off under reduced pressure, whereby 29.6 g of (3R,4S,5S)-2-methoxy-4-((4-methylphenyl)carbonyloxy)-5-(((4-methylphenyl)carbonyloxy)methyl)oxolan-3-yl 4-methylbenzoate was obtained as a white solid. As a result of $^1$H-NMR measurement, the above-obtained solid was an anomer mixture of about 75:25.

$^1$H-NMR (CDCl$_3$) δ value: 2.37-2.43(9H,m),3.36(0.75H, s),3.48(2.25H,s),4.43-4.48(0.25H,m),4.53-4.57(0.75H,m), 4.59-4.69(1H,m),4.74(0.25H,dd,J=4.5,11.7 Hz),4.83 (0.75H,dd,J=3.3,11.7 Hz),5.16(0.75H,s),5.33(0.25H,d,J=4.5 Hz),5.46(0.25H,dd,J=4.5,6.9 Hz),5.49(0.75H,d,J=1.2 Hz), 5.55(0.75H,d,J=5.1 Hz),5.93(0.25H,dd,J=5.1,6.9 Hz),7.16-7.28(6H,m),7.86-7.98(6H,m)

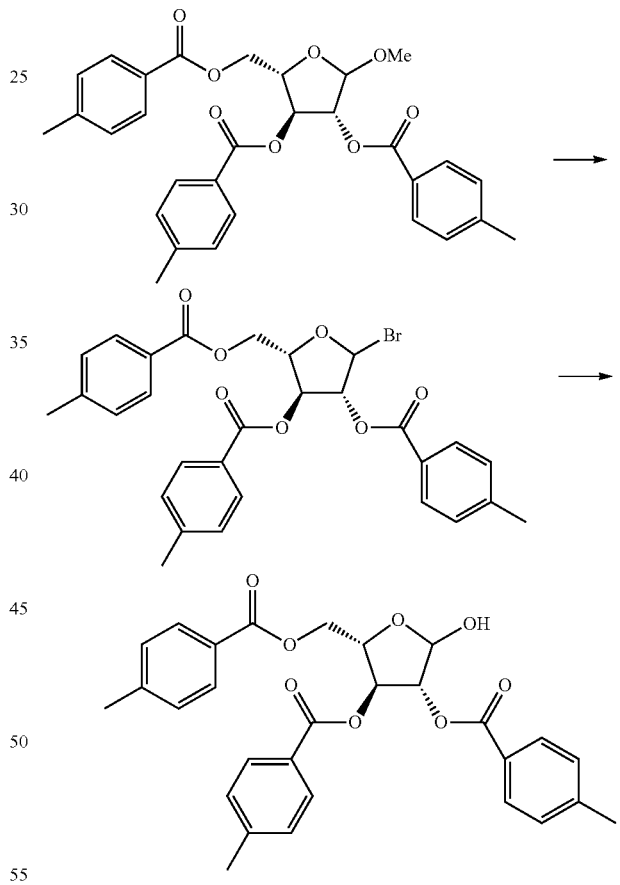

28 mL of a 30% hydrogen bromide/acetic acid solution was added to a mixed solution of 29.6 g of (3R,4S,5S)-2-methoxy-4-((4-methylphenyl)carbonyloxy)-5-(((4-methylphenyl)carbonyloxy)methyl)oxolan-3-yl 4-methylbenzoate in 29.6 mL of acetic acid and 35.3 mL of toluene at 25° C., and the resultant product was stirred at the same temperature for 2 hours. 114 mL of hexane was added to the reaction mixture, and the solid was collected by filtration, whereby 24.4 g of (3R,4S,5S)-2-bromo-4-((4-methylphenyl)carbonyloxy)-5-(((4-methylphenyl)carbonyloxy)methyl)oxolan-3-yl 4-methylbenzoate was obtained as a white solid.

7.3 g of sodium hydrogen carbonate was added to a mixed solution of 24 g of (3R,4S,5S)-2-bromo-4-((4-methylphenyl)carbonyloxy)-5-(((4-methylphenyl)carbonyloxy)methyl)oxolan-3-yl 4-methylbenzoate in 57 mL of toluene, 29 mL of water, and 36 mL of acetonitrile at 25° C., and the resultant product was stirred at 55° C. for 6.5 hours. 30 mL of a 10% sodium hydrogen carbonate aqueous solution was added to the reaction mixture, and the aqueous layer was removed. After the organic layer was washed with 180 mL of a 10% sodium chloride aqueous solution and dried over anhydrous magnesium sulfate, the solvent was distilled off under reduced pressure, whereby 17.3 g of (3R,4S,5S)-2-hydroxy-4-((4-methylphenyl)carbonyloxy)-5-(((4-methylphenyl)carbonyloxy)methyl)oxolan-3-yl 4-methylbenzoate was obtained as a white solid. As a result of $^1$H-NMR measurement, the above-obtained solid was an anomer mixture of about 75:25.

$^1$H-NMR (CDCl$_3$) δ value: 2.35-2.41(9H,m),3.36(0.75H,brs),3.63(0.25H,brs),4.41-4.46(0.25H,m),4.62(0.75H,dd,J=5.0,11.3 Hz),4.73-4.83(2H,m),5.51-5.55(1.75H,m),5.66(0.75H,d,J=3.9 Hz),5.79-5.86(0.5H,m),7.13-7.28(6H,m),7.86-7.98(6H,m)

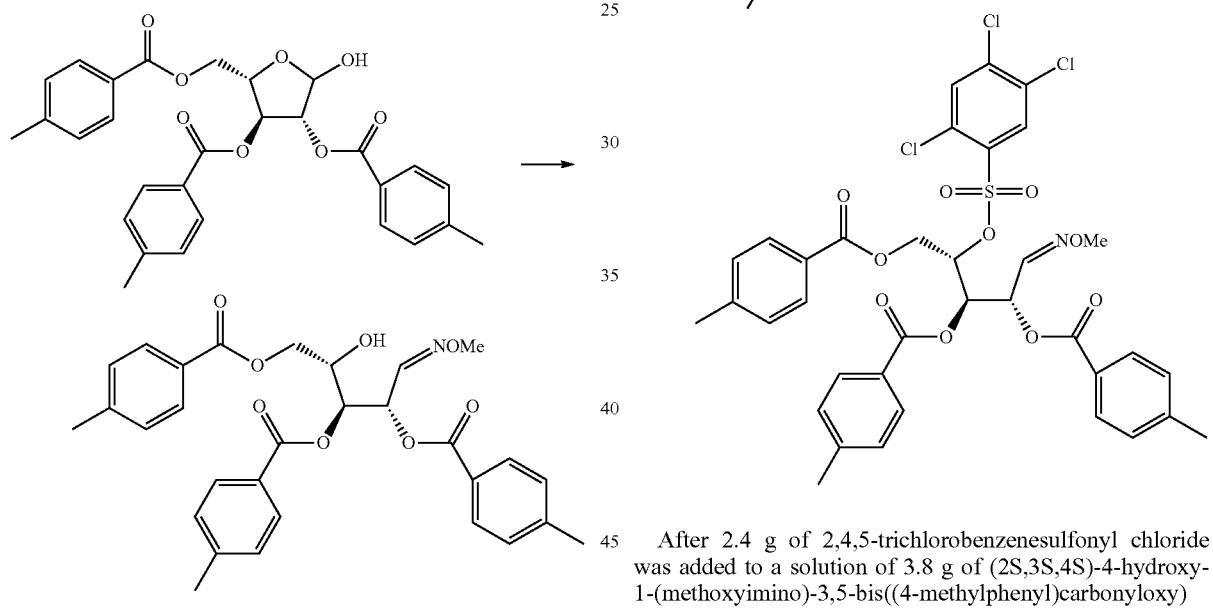

16.5 mL of pyridine, 8.2 g of p-toluenesulfonic acid monohydrate, and 4.9 g of O-methylhydroxylamine hydrochloride were added to a solution of 17.3 g of (3R,4S,5S)-2-hydroxy-4-((4-methylphenyl)carbonyloxy)-5-(((4-methylphenyl)carbonyloxy)methyl)oxolan-3-yl 4-methylbenzoate in 52 mL of methanol at 25° C., and the resultant product was stirred at the same temperature for 5 hours and at 35° C. for 2 hours. 1.0 g of p-toluenesulfonic acid monohydrate and 1.0 g of O-methylhydroxylamine hydrochloride were added to the reaction liquid, and the resultant product was allowed to stand overnight. 100 mL of ethyl acetate and 100 mL of water were added to the reaction mixture, and then, the aqueous layer was removed. After the organic layer was washed sequentially two times with a 10% sodium chloride aqueous solution, two times with 1 N hydrochloric acid water, once with a sodium hydrogen carbonate aqueous solution, and once with a saturated sodium chloride aqueous solution, and dried over anhydrous sodium sulfate, the solvent was distilled off under reduced pressure, whereby 17.9 g of (2S,3S,4S)-4-hydroxy-1-(methoxyimino)-3,5-bis((4-methylphenyl)carbonyloxy)pentan-2-yl 4-methylbenzoate was obtained as a colorless oily material. As a result of $^1$H-NMR measurement, the above-obtained material was an oxime isomer mixture of about 75:25.

$^1$H-NMR (CDCl$_3$) δ value: 2.39-2.43 (9H,m), 3.41(1H,d,J=5.4 Hz),3.79(2.25H,s),3.96(0.75H,s),4.18-4.29(1H,m),4.34-4.42(1H,m),4.52-4.60(1H,m),5.66(0.75H,dd,J=3.4,8.3 Hz),5.84(0.25H,dd,J=2.7,8.4 Hz),6.18(0.75H, dd,J=3.4,6.0 Hz),6.57(0.25H,dd,J=2.7,5.4 Hz),6.76(0.25H,d,J=5.4 Hz),7.19-7.29(6H,m),7.45(0.75H,d,J=6.0 Hz),7.88-8.01(6H,m)

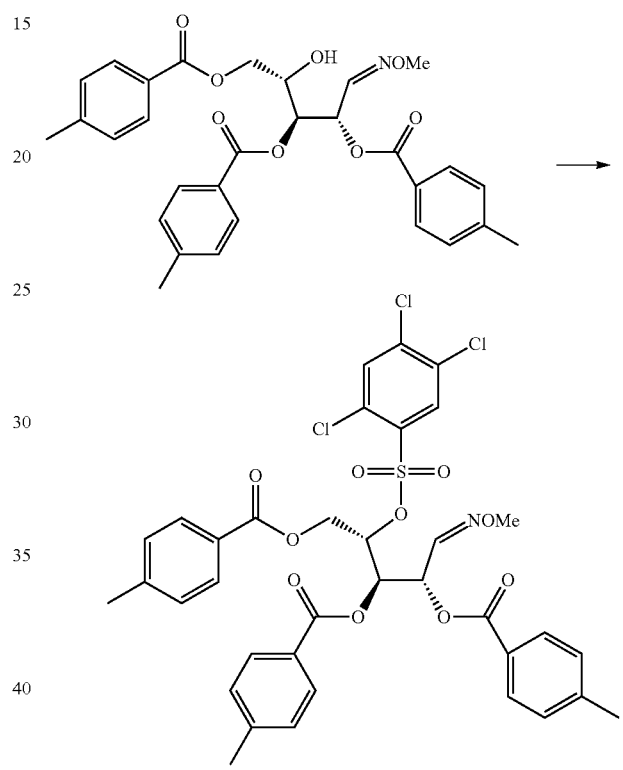

After 2.4 g of 2,4,5-trichlorobenzenesulfonyl chloride was added to a solution of 3.8 g of (2S,3S,4S)-4-hydroxy-1-(methoxyimino)-3,5-bis((4-methylphenyl)carbonyloxy)pentan-2-yl 4-methylbenzoate in 13.5 mL of acetonitrile at 25° C., 1.5 mL of N-methylimidazole was added dropwise thereto at 0° C. to 10° C., and the resultant product was stirred at 10° C. for 6 hours. 20 mL of ethyl acetate and 20 mL of water were added to the reaction mixture, and then, the aqueous layer was removed. After the organic layer was washed sequentially two times with a 10% sodium chloride aqueous solution, once with hydrochloric acid, once with a sodium hydrogen carbonate aqueous solution, and once with a saturated sodium chloride aqueous solution, and dried over anhydrous sodium sulfate, the solvent was distilled off under reduced pressure, whereby 5.1 g of (2S,3R,4S)-1-(methoxyimino)-3,5-bis((4-methylphenyl)carbonyloxy)-4-(((2,4,5-trichlorobenz ene)sulfonyl)oxy)pentan-2-yl 4-methylbenzoate was obtained as a colorless oily material.

As a result of $^1$H-NMR measurement, the above-obtained material was an oxime isomer mixture of about 75:25.

$^1$H-NMR (CDCl$_3$) δ value: 2.40-2.42(9H,m),3.83(2.25H,s),3.91(0.75H,s),4.63-4.78(2H,m),5.39-5.45(0.25H,m),5.46-5.53(0.75H,m),5.93-5.99(1.5H,m),6.04(0.25H,dd, J=5.1,4.3 Hz),6.34(0.25H,dd,J=4.3,5.1 Hz),6.72(0.25H,d, J=5.1 Hz),7.19-7.27(67H,m),7.48(0.75H,d,J=5.4 Hz), 7.75-7.97(67H,m)

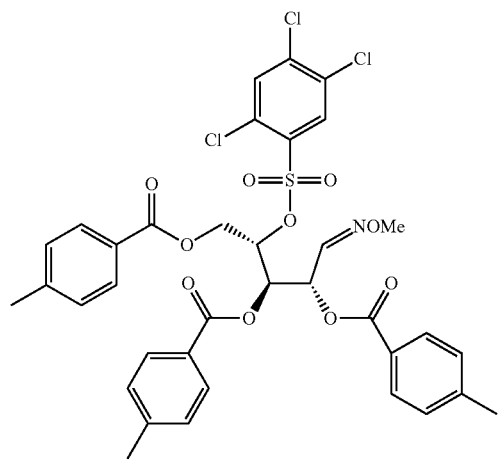

1.1 g of lithium bromide was added to a mixed solution of 4.9 g of (2S,3R,4S)-1-(methoxyimino)-3,5-bis((4-methylphenyl)carbonyloxy)-4-(((2,4,5-trichlorobenz ene)sulfonyl)oxy)pentan-2-yl 4-methylbenzoate in 4.4 mL of tetrahydrofuran and 3.7 mL of 1,2-dimethylimidazole at 10° C. or lower, and the resultant product was stirred at 48° C. for 6.5 hours. 8 mL of ethyl acetate and 8 mL of water were added to the reaction mixture, and then, the aqueous layer was removed. After the organic layer was dried over anhydrous sodium sulfate, the solvent was distilled off under reduced pressure, and the resultant product was purified by column chromatography (eluent: ethyl acetate/hexane=1/4), whereby 2.7 g of (2S,3R,4R)-4-bromo-1-(methoxyimino)-3,5-bis((4-methylphenyl)carbonyloxy)pentan-2-yl 4-methylbenzoate was obtained as a colorless oily material.

As a result of $^1$H-NMR measurement, the above-obtained material was an oxime isomer mixture of about 80:20.

$^1$H-NMR (CDCl$_3$) δ value: 2.33-2.41(9H,m),3.84(2.4H, s),3.88(0.6H,s),4.47(0.8H, dd,J=9.9,13.3 Hz),4.57-4.61 (0.4H,m),4.68-4.76(1.8H,m),6.04-6.12(1.8H,m),6.43(0.2H, t,J=5.3 Hz),6.76(0.2H,d,J=5.5 Hz),7.10-7.26(6H, m),7.53 (0.8H,d,J=4.7 Hz),7.77-8.00(6H,m)

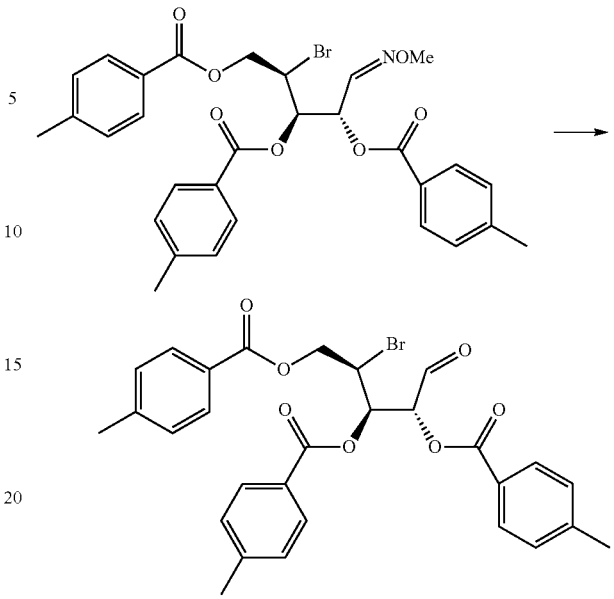

3.7 mL of a 50% glyoxylic acid aqueous solution was added to a solution of 2.5 g of (2S,3R,4R)-4-bromo-1-(methoxyimino)-3,5-bis((4-methylphenyl)carbonyloxy)-pentan-2-yl 4-methylbenzoate in 10 mL of acetonitrile, and the resultant product was stirred at 75° C. for 12 hours. The reaction mixture was cooled to room temperature, then, 30 mL of ethyl acetate and 10 mL of water were added thereto, and the aqueous layer was removed. After the organic layer was washed sequentially with a 10% sodium chloride aqueous solution and a mixed liquid of a sodium hydrogen carbonate aqueous solution and a saturated sodium chloride aqueous solution, and dried over anhydrous sodium sulfate, the solvent was distilled off under reduced pressure, whereby 2.4 g of a oily crude product of (2R,3R,4R)-4-bromo-1-oxo-3,5-bis((4-methylphenyl)carbonyloxy)pentan-2-yl 4-methylbenzoate was obtained. The crude product was used in the next step without further purification.

Example 4

[A-1] (3R,4R,5S)-2-hydroxy-4-((4-phenylphenyl) carbonyloxy)-5-(((4-phenylphenyl)carbonyloxy) methyl)thiolan-3-yl 4-phenylbenzoate and acetylated product thereof By reacting (2R,3R,4R)-4-bromo-1-oxo-3,5-bis((4-phenylphenyl)carbonyloxy)pentan-2-yl 4-phenylbenzoate with 15% sodium hydrogen sulfide in the following manner, (3R,4R,5S)-2-hydroxy-4-((4-phenylphenyl)carbonyloxy)-5-(((4-phenylphenyl)carbonyloxy)methyl)thiolan-3-yl 4-phenylbenzoate was synthesized.

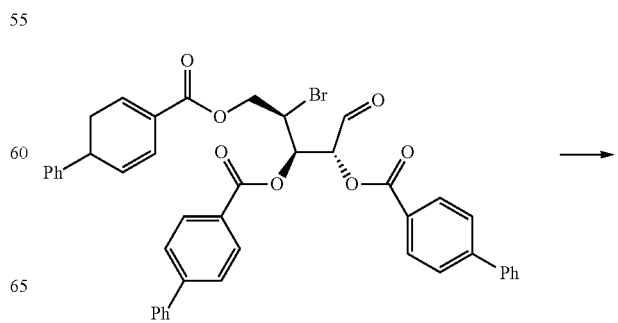

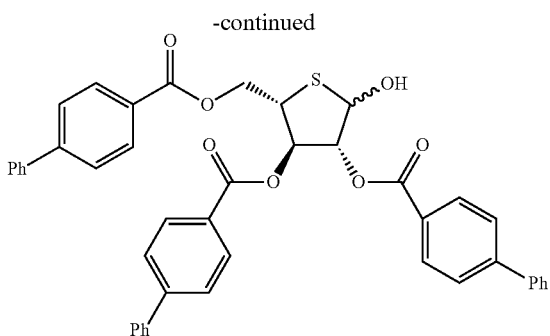

1.2 mL of a 15% sodium hydrogen sulfide aqueous solution was added dropwise to a solution of 1.6 g of the crude product of (2R,3R,4R)-4-bromo-1-oxo-3,5-bis((4-phenylphenyl)carbonyloxy)pentan-2-yl 4-phenylbenzoate in 16 mL of N,N-dimethylformamide at 10° C. or lower, and the resultant product was stirred at 25° C. for 1.5 hours. 150 mL of ethyl acetate and 100 mL of a saturated sodium chloride aqueous solution were added to the reaction mixture, and then, the aqueous layer was removed. After the organic layer was washed sequentially three times with a sodium hydrogen carbonate aqueous solution and once with a saturated sodium chloride aqueous solution, the resultant product was dried over anhydrous magnesium sulfate, and the solvent was concentrated under reduced pressure. The concentrated residue was recrystallized from tetrahydrofuran/ethyl acetate (1/10), whereby 0.2 g of (3R,4R,5S)-2-hydroxy-4-((4-phenylphenyl)carbonyloxy)-5-(((4-phenylphenyl)carbonyloxy)methyl)thiolan-3-yl 4-phenylbenzoate was obtained as a white crystal. As a result of $^1$H-NMR measurement, the above-obtained crystal was a substantially single anomer.

$^1$H-NMR (CDCl$_3$) δ value: 2.67(1H,d,J=4.1 Hz),3.93(1H, dd,J=7.0,13.4 Hz),4.67-4.88(2H,m),5.67(1H,dd,J=4.1,9.1 Hz),5.70(1H,t,J=4.1 Hz),6.34(1H,dd,J=7.0,9.1 Hz),7.26-7.64(21H,m),8.00-8.13(6H,m)

0.01 g of N,N-dimethyl-4-aminopyridine, 0.17 mL of pyridine, and 0.22 mL of acetic anhydride were added to a mixed solution of 0.2 g of the white crystal of (3R,4R,5S)-2-hydroxy-4-((4-phenylphenyl)carbonyloxy)-5-(((4-phenylphenyl)carbonyloxy)methyl)thiolan-3-yl 4-phenylbenzoate in 6 mL of ethyl acetate and 16 mL of tetrahydrofuran, and the resultant product was stirred at room temperature for 3.5 hours. 30 mL of ethyl acetate and 20 mL of 0.5 N hydrochloric acid water were added to the reaction mixture, and then, the aqueous layer was removed. After the organic layer was washed sequentially four times with a sodium hydrogen carbonate aqueous solution and once with a saturated sodium chloride aqueous solution, and dried over anhydrous sodium sulfate, the solvent was distilled off under reduced pressure. The obtained residue was purified by column chromatography (eluent: ethyl acetate/hexane=1/2), and recrystallized from methanol, whereby 0.12 g of (3R,4R,5S)-2-(acetyloxy)-4-((4-phenylphenyl)carbonyloxy)-5-(((4-phenylphenyl)carbonyloxy)methyl)thiolan-3-yl 4-phenylbenzoate was obtained as a white crystal. As a result of $^1$H-NMR measurement, the above-obtained crystal was a substantially single anomer.

$^1$H-NMR (CDCl$_3$) δ value: 2.10(1H,s),3.94(1H,dd,J=7.2, 13.6 Hz),4.60(1H,dd,J=6.0, 11.3 Hz),4.72(1H,dd,J=7.1,11.3 Hz),5.79(1H,dd,J=4.5,9.9 Hz),6.30(1H,dd,J=7.7,9.9 Hz), 6.40(1H,d,J=4.5 Hz),7.35-7.70(21H,m),7.96-8.13(6H,m)

[A-2] Synthesis of (3R,4R,5S)-2,4-bis(4-phenylbenzoyloxy)-5-[(4-phenylbenzoyloxy)methyl]thiolan-3-yl 4-phenylbenzoate By reacting (2R,3R,4R)-4-bromo-1-oxo-3,5-bis((4-phenylphenyl)carbonyloxy)pentan-2-yl 4-phenylbenzoate with a 15% sodium hydrogen sulfide in the following manner, (3R,4R,5S)-2-hydroxy-4-((4-phenylphenyl)carbonyloxy)-5-(((4-phenylphenyl)carbonyloxy)methyl)thiolan-3-yl 4-phenylbenzoate was obtained, and by further reacting the hydroxyl group thereof with 4-phenylbenzoyl chloride, (3R,4R,5S)-2,4-bis(4-phenylbenzoyloxy)-5-[(4-phenylbenzoyloxy)methyl]thiolan-3-yl 4-phenylbenzoate was synthesized.

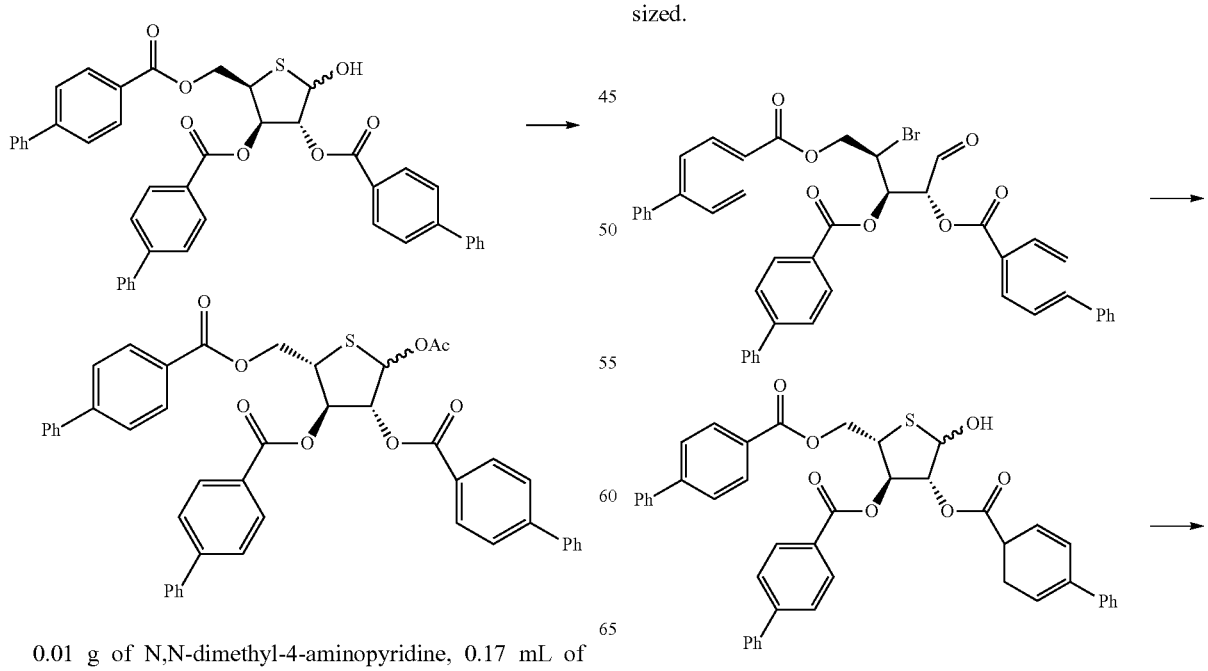

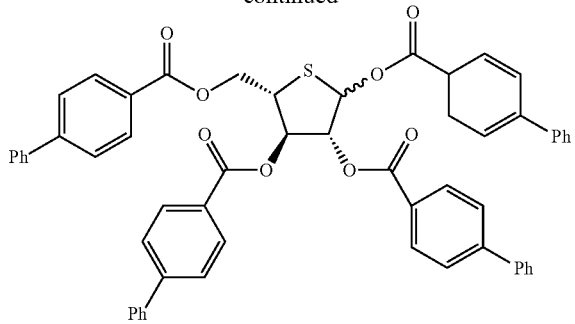

0.36 mL of a 15% sodium hydrogen sulfide aqueous solution was added dropwise to a solution of 0.6 g of the crude product of (2R,3R,4R)-4-bromo-1-oxo-3,5-bis((4-phenylphenyl)carbonyloxy)pentan-2-yl 4-phenylbenzoate in 8 mL of N,N-dimethylformamide at 10° C. or lower, and the resultant product was stirred at 25° C. for 1 hour. 30 mL of ethyl acetate and 30 mL of a saturated sodium chloride aqueous solution were added to the reaction mixture, and then, the aqueous layer was removed. After the organic layer was washed sequentially with a sodium hydrogen carbonate aqueous solution and a saturated sodium chloride aqueous solution, the resultant product was dried over anhydrous magnesium sulfate. The solvent was distilled off under reduced pressure, whereby a crude product of (3R,4R,5S)-2-hydroxy-4-((4-phenylphenyl)carbonyloxy)-5-(((4-phenylphenyl)carbonyloxy)methyl)thiolan-3-yl 4-phenylbenzoate was obtained.

After 19 mg of N,N-dimethyl-4-aminopyridine was added to a solution of the obtained crude product of (3R,4R,5S)-2-hydroxy-4-((4-phenylphenyl)carbonyloxy)-5-(((4-phenylphenyl)carbonyloxy)methyl)thiolan-3-yl 4-phenylbenzoate in 5 mL of pyridine, 250 mg of 4-phenylbenzoyl chloride was added thereto at 10° C. or lower, and the resultant product was stirred at room temperature for 12 hours. After 170 mg of 4-phenylbenzoyl chloride was additionally added to the reaction liquid, the resultant product was allowed to react for 6 hours, then, 30 mL of ethyl acetate and 30 mL of 1 N hydrochloric acid water were added thereto, and the aqueous layer was removed. After the organic layer was washed sequentially with 1 N hydrochloric acid water, a sodium hydrogen carbonate aqueous solution, and a saturated sodium chloride aqueous solution, and dried over anhydrous sodium sulfate, the solvent was distilled off under reduced pressure. The obtained residue was recrystallized from ethyl acetate/methanol, whereby 88 mg of (3R,4R,5S)-2,4-bis(4-phenylbenzoyloxy)-5-[(4-phenylbenzoyloxy)methyl]thiolan-3-yl 4-phenylbenzoate was obtained as a white crystal. The filtrate was concentrated under reduced pressure, and the resultant product was recrystallized from ethyl acetate/methanol, whereby 316 mg of (3R,4R,5S)-2,4-bis(4-phenylbenzoyloxy)-5-[(4-phenylbenzoyloxy)methyl]thiolan-3-yl 4-phenylbenzoate was obtained as a white solid. As a result of $^1$H-NMR measurement, the first crystal was a substantially single anomer, and the second crystal was an anomer mixture of about 88:12.

First Crystal
$^1$H-NMR (CDCl$_3$) δ value: 4.31-4.37(1H,m),4.66(1H,dd, J=6.8,11.3 Hz),4.82(1H,dd, J=8.3,11.2 Hz),6.02(1H,t,J=3.4 Hz),6.25(1H,dd,J=2.2,3.1 Hz),6.51(1H,d,J=1.8 Hz),7.35-7.72(28H, m),8.06-8.17(8H,m)

Second Crystal
$^1$H-NMR (CDCl$_3$) δ value: 4.02(0.88H,dt,J=7.9,5.7 Hz), 4.32-4.38(0.12H,m),4.61-4.74(1.88H,m),4.83(0.12H,dd, J=8.2,11.3 Hz),5.94(0.88H,dd, J=4.5,10.0 Hz),6.03(0.12H, t,J=3.4 Hz), 6.25(0.12H,dd,J=2.1,3.3 Hz),6.45(0.88H,dd, J=8.0,10.0 Hz),6.51(0.12H,d,J=1.8 Hz),6.60(0.88H,dd, J=4.5 Hz),7.25-7.72(28H,m),7.95-8.17(8H,m)

[B] 4-Amino-1-[(2R,3R,4R,5S)-3,4-dihydroxy-5-(hydroxymethyl)thiolan-2-yl]-1,2-dihydropyrimidine-2-one 4-Amino-1-[(2R,3R,4R,5S)-3,4-dihydroxy-5-(hydroxymethyl)thiolan-2-yl]-1,2-dihydropyrimidine-2-one was synthesized in the following manner.

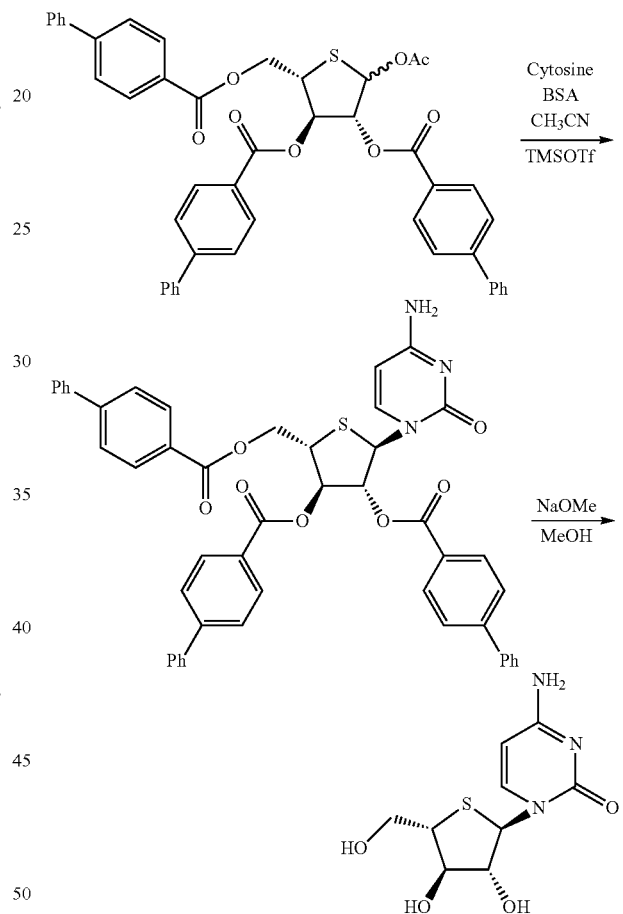

2.2 mg of cytosine and 0.070 mL of N,O-bis(trimethylsilyl)acetamide were added to a solution of 10.0 mg of (3R,4R,5S)-2-(acetyloxy)-4-((4-phenylphenyl)carbonyloxy)-5-(((4-phenylphenyl)carbonyloxy)methyl)thiolan-3-yl 4-phenylbenzoate in 0.5 mL of acetonitrile, and the resultant product was irradiated with microwaves (microwave reaction apparatus (INITIATOR SIXTY (product name, manufactured by Biotage)), 120° C., 5 minutes, 2.45 GHz, 0 W to 240 W). After the reaction mixture was cooled to room temperature, 4.8 μL of trimethylsilyl trifluoromethanesulfonate was added thereto, and the resultant product was irradiated with microwaves (microwave reaction apparatus (INITIATOR SIXTY (product name, manufactured by Biotage)), 120° C., 10 minutes, 2.45 GHz, 0 W to 240 W). The solvent of the reaction mixture was distilled off under reduced pressure, and the obtained residue was purified by silica gel column chromatography (eluent: ethyl acetate/hexane=1/4→1/0), whereby 6.8 mg of [(2S,3R,4R,5R)-5-(4-amino-2-oxo-1,2-dihydropyrimidin-1-yl)-3,4-bis[(4-phenylphenyl)carbonyloxy]thiolan-2-yl]methyl 4-phenylbenzoate was obtained as a white solid.

LC/MS
Retention time: 2.61 minutes
[M+H] 800.7

Moreover, the obtained $^1$H-NMR spectrum was broad, and thus, it was not possible to determine the δ value.

9 μL of a 5 M sodium methoxide-methanol solution was added to a solution of 6.8 mg of [(2S,3R,4R,5R)-5-(4-amino-2-oxo-1,2-dihydropyrimidin-1-yl)-3,4-bis[(4-phenylphenyl)carbonyloxy]thiolan-2-yl]methyl 4-phenylbenzoate in 1.0 mL of methanol, and the resultant product was stirred at room temperature for 1 hour. Acetic acid was added to the reaction mixture, and the solvent was distilled off under reduced pressure. The obtained residue was purified by silica gel column chromatography (eluent: ethyl acetate/methanol=1/0→3/2), whereby 1.8 mg of 4-amino-1-[(2R,3R,4R,5S)-3,4-dihydroxy-5-(hydroxymethyl)thiolan-2-yl]-1,2-dihydropyrimidine-2-one was obtained as a white solid.

LC/MS
Retention time: 0.21 minutes
[M+H] 260.3

$^1$H-NMR (CD$_3$OD) δ value: 3.57-3.69(2H,m),3.86-3.98 (2H,m),4.09(1H,t,J=6.6 Hz),5.94(2H,d,J=7.9 Hz),6.02(2H,d,J=6.6 Hz), 8.06(1H,d,J=7.3 Hz)

[C] Synthesis of Raw Material

Moreover, (2R,3R,4R)-4-bromo-1-oxo-3,5-bis((4-phenylphenyl)carbonyloxy)pentan-2-yl 4-phenylbenzoate which was a raw material was synthesized through a plurality of steps in the following manner.

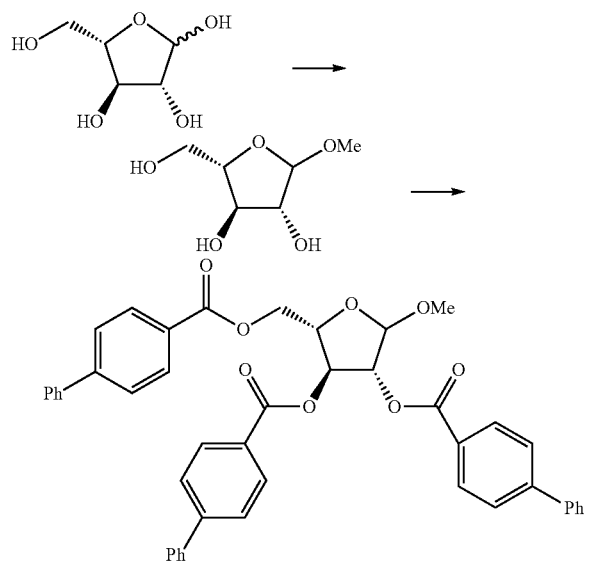

3.0 mL of acetyl chloride was added dropwise to a solution of 5.0 g of (3R,4R,5S)-5-(hydroxymethyl)oxolane-2,3,4-triol in 96 mL of methanol at 15° C. or lower, and the resultant product was stirred at 25° C. for 1.5 hours. 8.8 g of a 28% sodium methoxide/methanol solution and 40 mL of toluene were added to the reaction mixture, and the methanol was distilled off under reduced pressure, whereby 9.3 g of a crude product of (2S,3R,4R)-2-(hydroxymethyl)-5-methoxyoxolane-3,4-diol was obtained.

48 mL of toluene, 30 mL of a 8.3% sodium hydroxide aqueous solution, and 0.3 g of tetrabutylammonium chloride were added to the crude product at 30° C. or lower, then, a solution of 21.7 g of 4-phenylbenzoyl chloride in 110 mL of tetrahydrofuran was added dropwise thereto at 15° C. or lower over a period of 1 hour, and the resultant product was stirred at 25° C. for 3 hours. After the aqueous layer was removed, the organic layer was washed sequentially three times with 100 mL of water and two times with 100 mL of a saturated sodium chloride aqueous solution and dried over anhydrous sodium sulfate, and the solvent was distilled off under reduced pressure. The obtained residue was recrystallized from ethyl acetate/hexane (1/1), whereby 9.7 g of (3R,4S,5S)-2-methoxy-4-((4-phenylphenyl)carbonyloxy)-5-(((4-phenylphenyl)carbonyloxy)methyl)oxolan-3-yl 4-phenylbenzoate was obtained as a white crystal. As a result of $^1$H-NMR measurement, the above-obtained crystal was a single anomer.

$^1$H-NMR (CDCl$_3$) δ value: 3.53(3H,s),4.60(1H,dd,J=3.8, 8.5 Hz),4.78(1H,dd,J=4.1, 12.0 Hz),4.92(1H,dd,J=3.3,12.0 Hz),5.24(1H,s),5.56(1H,d,J=1.2 Hz),5.67(1H,d,J=5.0 Hz), 7.31-7.70 (21H, m),8.06(2H,d,J=8.6 Hz),8.12(2H,d,J=8.6 Hz),8.16(2H,d,J=8.6 Hz)

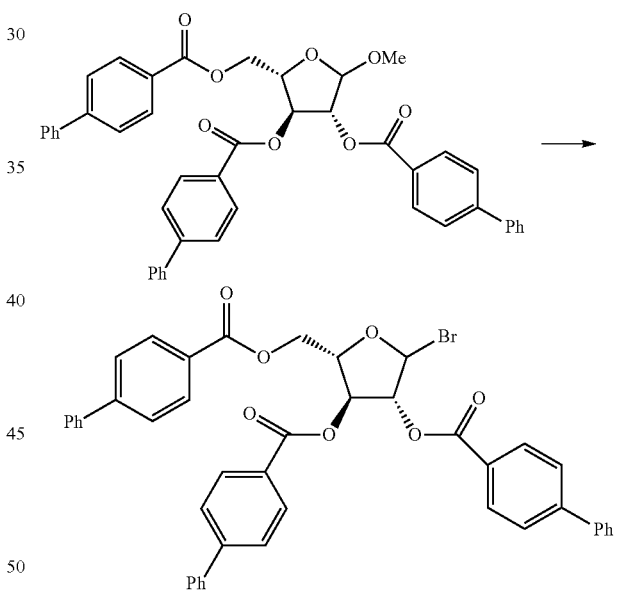

After 11.2 mL of a 30% hydrogen bromide/acetic acid solution was added to a mixed solution of 11 g of (3R,4S,5S)-2-methoxy-4-((4-phenylphenyl)carbonyloxy)-5-(((4-phenylphenyl)carbonyloxy)methyl)oxolan-3-yl 4-phenylbenzoate in 11 mL of acetic acid and 110 mL of dichloromethane at 25° C., the resultant product was stirred at the same temperature for 2 hours, and the solvent was concentrated under reduced pressure. The obtained residue was reslurried from ethyl acetate/hexane (1/1), whereby 10.7 g of (3R,4S,5S)-2-bromo-4-((4-phenylphenyl)carbonyloxy)-5-(((4-phenylphenyl)carbonyloxy)methyl)oxolan-3-yl 4-phenylbenzoate was obtained as a white solid.

$^1$H-NMR (CDCl$_3$) δ value: 4.84-5.00(3H,m),5.73(1H,d, J=4.1 Hz),6.01(1H,s),6.69(1H,s),7.32-7.74(21H,m),8.02 (2H,d,J=8.6 Hz),8.12(2H,d,J=8.6 Hz),8.22(2H,d,J=8.6 Hz)

111

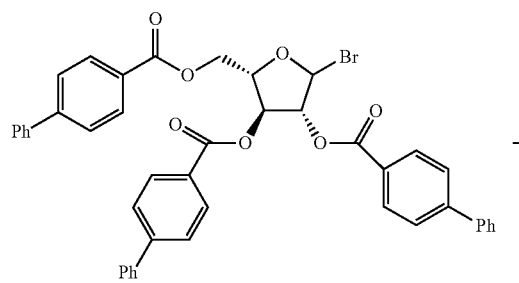

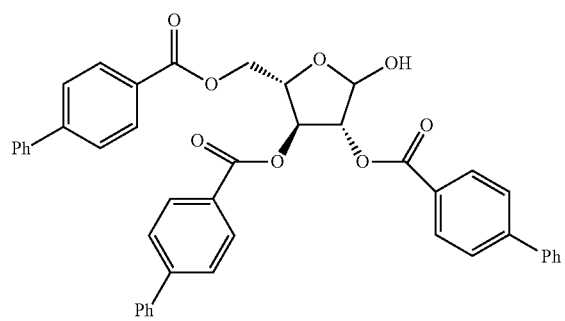

1.5 g of sodium hydrogen carbonate was added to a mixed solution of 10 g of (3R,4S,5S)-2-bromo-4-((4-phenylphenyl)carbonyloxy)-5-(((4-phenylphenyl)carbonyloxy)methyl)oxolan-3-yl 4-phenylbenzoate in 100 mL of tetrahydrofuran and 30 mL of water at 25° C., and the resultant product was stirred at 55° C. for 2.5 hours. 100 mL of ethyl acetate and 1,000 mL of a 10% sodium hydrogen carbonate aqueous solution were added to the reaction mixture, and then, the aqueous layer was removed. After the organic layer was washed with 100 mL of a 10% sodium chloride aqueous solution and dried over anhydrous sodium sulfate, the solvent was distilled off under reduced pressure, whereby 9.9 g of (3R,4S,5S)-2-hydroxy-4-((4-phenylphenyl)carbonyloxy)-5-(((4-phenylphenyl)carbonyloxy)methyl)oxolan-3-yl 4-phenylbenzoate was obtained as a white solid. As a result of ¹H-NMR measurement, the above-obtained solid was an anomer mixture of about 77:23.

¹H-NMR (CDCl₃) δ value: 3.06(0.77H,d,J=3.7 Hz),3.41 (0.23H,d,J=5.5 Hz),4.49-4.54(0.23H,m),4.72-4.89(2.77H, m),5.59-5.63(1H,m),5.67(0.77H,d,J=4.5 Hz),5.74(0.77H,d, J=3.7 Hz), 5.87(0.23H,t,J=5.0 Hz),5.95(0.23H, t,J=5.3 Hz), 7.33-7.70(21H,m),8.05-8.18(6H,m)

112

-continued

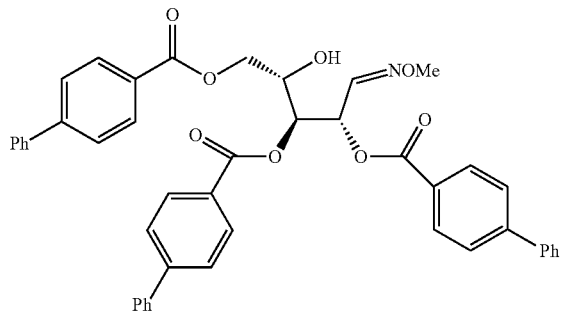

7.1 mL of pyridine, 3.5 g of p-toluenesulfonic acid monohydrate, and 2.1 g of O-methylhydroxylamine hydrochloride were added to a mixed solution of 9.5 g of (3R, 4S,5S)-2-hydroxy-4-((4-phenylphenyl)carbonyloxy)-5-(((4-phenylphenyl)carbonyloxy)methyl)oxolan-3-yl 4-phenylbenzoate in 61 mL of methanol and 95 mL of tetrahydrofuran at 25° C., and the resultant product was stirred at the same temperature for 5 hours. 150 mL of ethyl acetate and 150 mL of water were added to the reaction mixture, and then, the aqueous layer was removed. After the organic layer was washed sequentially two times with a 10% sodium chloride aqueous solution, two times with 1 N hydrochloric acid water, once with a sodium hydrogen carbonate aqueous solution, and once with a saturated sodium chloride aqueous solution, and dried over anhydrous sodium sulfate, the solvent was distilled off under reduced pressure, whereby 9.9 g of (2S,3S,4S)-4-hydroxy-1-(methoxyimino)-3,5-bis((4-phenylphenyl)carbonyloxy)pentan-2-yl 4-phenylbenzoate was obtained as a white amorphous material. As a result of ¹H-NMR measurement, the above-obtained material was an oxime isomer mixture of about 70:30.

¹H-NMR (CDCl₃) δ value: 3.44-3.47(1H,m),3.83(2.1H, s),4.00(0.9H,s),4.26-4.37(1H,m),4.46-4.52(1H,m),4.61-4.68(1H,m), 5.76(0.7H,dd,J=3.5,8.1 Hz),5.93(0.3H,dd, J=2.8,8.3 Hz),6.26(0.7H,dd,J=3.5,6.0 Hz),6.66(0.3H, dd,J=2.8,5.2 Hz),6.84(0.3H,d,J=5.2 Hz),7.38-7.73(21.7H, m),8.05-8.21(6H,m)

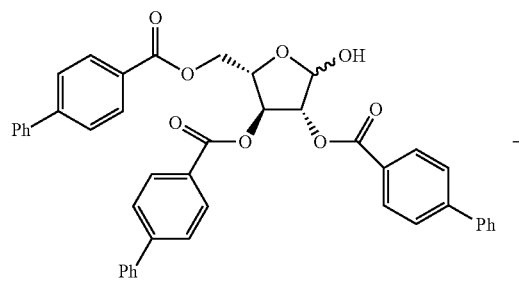

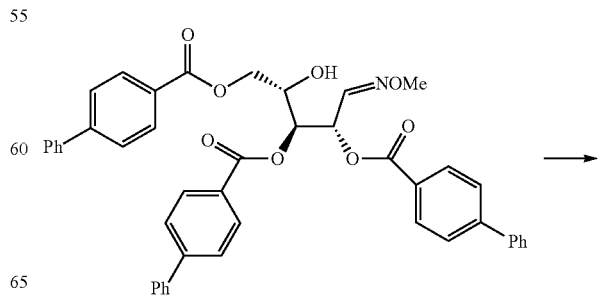

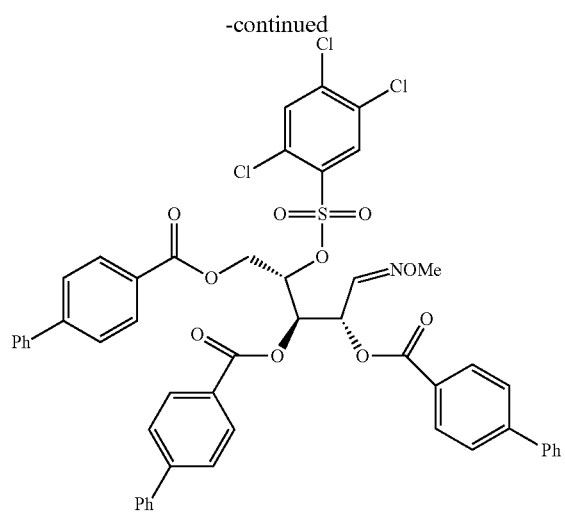

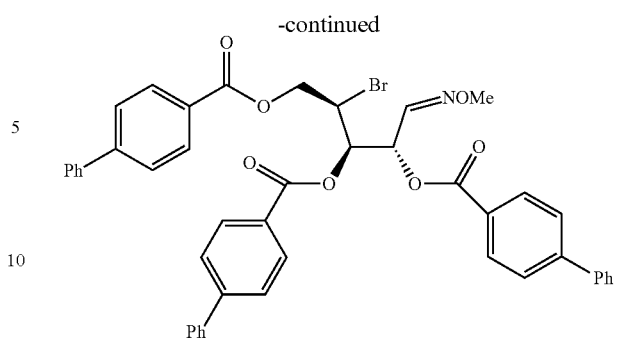

After 2.0 g of 2,4,5-trichlorobenzenesulfonyl chloride was added to a mixed solution of 4.0 g of (2S,3S,4S)-4-hydroxy-1-(methoxyimino)-3,5-bis((4-phenylphenyl)carbonyloxy)pentan-2-yl 4-phenylbenzoate in 16 mL of acetonitrile and 20 mL of tetrahydrofuran at 25° C., 1.3 mL of N-methylimidazole was added dropwise thereto at 0° C. to 10° C., and the resultant product was stirred at 10° C. for 10 hours. 50 mL of ethyl acetate and 50 mL of water were added to the reaction mixture, and then, the aqueous layer was removed. After the organic layer was washed sequentially two times with a 10% sodium chloride aqueous solution, once with hydrochloric acid, once with a sodium hydrogen carbonate aqueous solution, and once with a saturated sodium chloride aqueous solution, and dried over anhydrous sodium sulfate, the solvent was distilled off under reduced pressure, whereby 5.2 g of (2S,3R,4S)-1-(methoxyimino)-3,5-bis((4-phenylphenyl)carbonyloxy)-4-(((2,4,5-trichlorobenz ene)sulfonyl)oxy)pentan-2-yl 4-phenylbenzoate was obtained as a white amorphous material. As a result of $^1$H-NMR measurement, the above-obtained material was an oxime isomer mixture of about 70:30.

$^1$H-NMR (CDCl$_3$) δ value: 3.87(2.1H,s),3.97(0.9H,s), 4.71-4.87(2H,m),5.48-5.53(0.3H,m),5.55-5.59(0.7H,m), 6.02-6.09(1.4H,m),6.12(0.3H,dd,J=4.4,5.1 Hz),6.42 (0.3H, dd,J=4.4,5.2 Hz),6.79(0.3H,d,J=5.2 Hz),7.38-7.71(22.7H, m),7.94-8.17(7H,m)

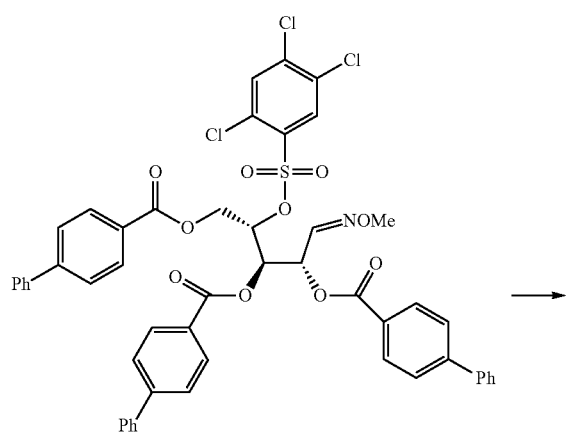

0.57 g of lithium bromide was added to a mixed solution of 3 g of (2S,3R,4S)-1-(methoxyimino)-3,5-bis((4-phenylphenyl)carbonyloxy)-4-(((2,4,5-trichlorobenz ene)sulfonyl)oxy)pentan-2-yl 4-phenylbenzoate in 3 mL of tetrahydrofuran and 2.6 mL of 1,2-dimethylimidazole at 10° C. or lower, and the resultant product was stirred at 40° C. for 6 hours. 40 mL of ethyl acetate and 40 mL of water were added to the reaction mixture, and then, the aqueous layer was removed. After the organic layer was dried over anhydrous sodium sulfate, the solvent was distilled off under reduced pressure, and the resultant product was purified by column chromatography (eluent: ethyl acetate/hexane=1/4→1/3), whereby 2.0 g of (2S,3R,4R)-4-bromo-1-(methoxyimino)-3,5-bis((4-phenylphenyl)carbonyloxy)pentan-2-yl 4-phenylbenzoate was obtained as a white amorphous material. As a result of $^1$H-NMR measurement, the above-obtained material was an oxime isomer mixture of about 80:20.

$^1$H-NMR (CDCl$_3$) δ value: 3.88(2.4H,s),3.93(0.6H,s), 4.56(0.8H,dd,J=10.0,13.5 Hz),4.64-4.69(0.4H,m),4.78-4.85 (1.8H,m), 6.11-6.22(1.8H,m),6.52(0.2H,t,J=5.5 Hz),6.83 (0.2H,d,J=5.5 Hz),7.36-7.68(21.8H,m),7.96-8.19(6H,m)

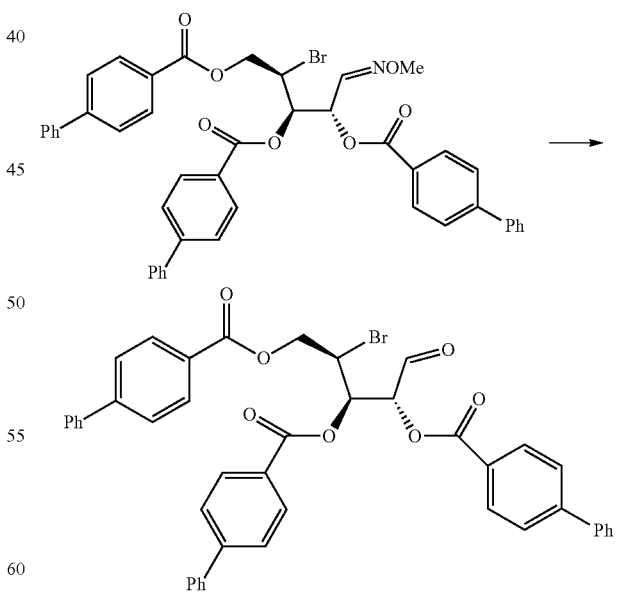

4.2 mL of a 50% glyoxylic acid aqueous solution was added to a solution of 1.8 g of (2S,3R,4R)-4-bromo-1-(methoxyimino)-3,5-bis((4-phenylphenyl)carbonyloxy)pentan-2-yl 4-phenylbenzoate in 23 mL of acetonitrile, and the resultant product was stirred at 75° C. for 12 hours. The reaction mixture was cooled to room temperature, then, 30 mL of ethyl acetate and 30 mL of water were added thereto, and the aqueous layer was removed. After the organic layer was washed sequentially three times with a 10% sodium chloride aqueous solution, once with a sodium hydrogen carbonate aqueous solution, and once with a saturated sodium chloride aqueous solution, and dried over anhydrous sodium sulfate, the solvent was distilled off under reduced pressure, whereby 1.7 g of a crude product of (2R,3R,4R)-4-bromo-1-oxo-3,5-bis((4-phenylphenyl)carbonyloxy)pentan-2-yl 4-phenylbenzoate was obtained as a white amorphous material. The crude product was used as a raw material without further purification.

$^1$H-NMR (CDCl$_3$) δ value: 4.70(1H,dd,J=7.1,11.6 Hz), 4.81-4.91(2H,m),5.90(1H,d, J=5.5 Hz),6.08(1H,dd,J=3.6, 5.5 Hz),7.39-7.66(21H,m),8.04-8.15(6H,m),9.79(1H,s)

Example 5

[A] Synthesis of (3R,4R,5S)-2,4-bis((naphthalen-2-yl)carbonyloxy)-5-[((naphthalen-2-yl)carbonyloxy)methyl]thiolan-3-yl naphthalene-2-carboxylate By reacting (2R,3R,4R)-4-bromo-1-oxo-3,5-bis((naphthalen-2-yl)carbonyloxy)pentan-2-yl naphthalene-2-carboxylate with a 15% sodium hydrogen sulfide in the following manner, (3R,4R,5S)-2-hydroxy-4-((naphthalen-2-yl)carbonyloxy)-5-(((naphthalen-2-yl)carbonyloxy)methyl)thiolan-3-yl naphthalene-2-carboxylate was obtained, and by further reacting this with (naphthalen-2-yl)carbonyl chloride, (3R,4R,5S)-2,4-bis((naphthalen-2-yl)carbonyloxy)-5-[((naphthalen-2-yl)carbonyloxy)methyl]thiolan-3-yl naphthalene-2-carboxylate was synthesized.

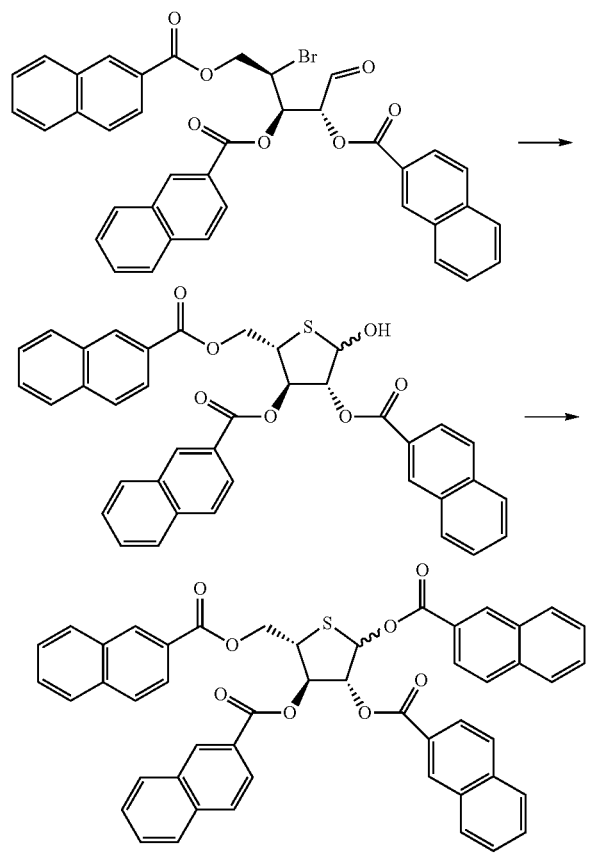

1.65 mL of a 15% sodium hydrogen sulfide aqueous solution was added dropwise to a solution of 2 g of (2R, 3R,4R)-4-bromo-1-oxo-3,5-bis((naphthalen-2-yl)carbonyloxy)pentan-2-yl naphthalene-2-carboxylate in 41 mL of N,N-dimethylformamide at 10° C. or lower, and the resultant product was stirred at 25° C. for 1 hour. 100 mL of ethyl acetate and 100 mL of a saturated sodium chloride aqueous solution were added to the reaction mixture, and then, the aqueous layer was removed. After the organic layer was washed sequentially three times with a sodium hydrogen carbonate aqueous solution and once with a saturated sodium chloride aqueous solution, the resultant product was dried over anhydrous magnesium sulfate. The solvent was distilled off under reduced pressure, whereby a crude product of (3R,4R,5S)-2-hydroxy-4-((naphthalen-2-yl)carbonyloxy)-5-(((naphthalen-2-yl)carbonyloxy)methyl)thiolan-3-yl naphthalene-2-carboxylate was obtained.

After 4.8 mg of N,N-dimethyl-4-aminopyridine was added to a solution of 125 mg of the obtained crude product in 1 mL of pyridine, 46 mL of (naphthalen-2-yl)carbonyl chloride was added thereto at 10° C. or lower, and the resultant product was stirred at room temperature for 10 hours. 30 mL of ethyl acetate and 30 mL of 1 N hydrochloric acid water were added to the reaction mixture, and then, the aqueous layer was removed. After the organic layer was washed sequentially with 1 N hydrochloric acid water, a sodium hydrogen carbonate aqueous solution, and a saturated sodium chloride aqueous solution, and dried over anhydrous sodium sulfate, the solvent was distilled off under reduced pressure. The obtained residue was purified by column chromatography (eluent: ethyl acetate/hexane=1/3), and as a result, two types of anomer isomers of (3R,4R,5S)-2,4-bis((naphthalen-2-yl)carbonyloxy)-5-[((naphthalen-2-yl)carbonyloxy)methyl]thiolan-3-yl naphthalen-2-carboxylate were obtained, and one type was 50 mg (Rf value of TLC (eluent: ethyl acetate/hexane=1/2)=0.71) and the other type was 86 mg (Rf value of TLC (eluent: ethyl acetate/hexane=1/2)=0.69), respectively. Both were white amorphous materials.

The component of Rf value=0.71
$^1$H-NMR (CDCl$_3$) δ value: 4.43-4.50(1H,m),4.76(1H,dd, J=6.9,11.3 Hz),4.97(1H,dd, J=8.4,11.2 Hz),6.16(1H,t,J=2.8 Hz),6.38(1H,dd,J=1.9,2.7 Hz),6.64(1H,d,J=1.2 Hz),7.31-8.14(28H, m),8.56(1H,s),8.64(1H,s),8.66(1H,s), 8.71(1H,s)

The component of Rf value=0.69
$^1$H-NMR (CDCl$_3$) δ value: 4.08-4.17(1H,m),4.76(1H,dd, J=5.7,11.5 Hz),4.85(1H,dd, J=6.9,11.5 Hz),6.08(1H,dd, J=4.5,9.7 Hz), 6.58(1H,dd,J=8.9,9.8 Hz),6.71(1H,d,J=4.5 Hz),7.38-8.04(24H,m),8.41(1H,s),8.41(1H,s),8.56(1H,s), 8.59(1H,s)

[B] Synthesis of Raw Material

Moreover, (2R,3R,4R)-4-bromo-1-oxo-3,5-bis((naphthalen-2-yl)carbonyloxy)pentan-2-yl naphthalene-2-carboxylate which was a raw material was synthesized through a plurality of steps in the following manner.

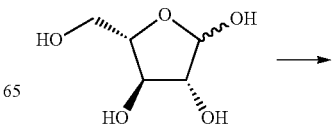

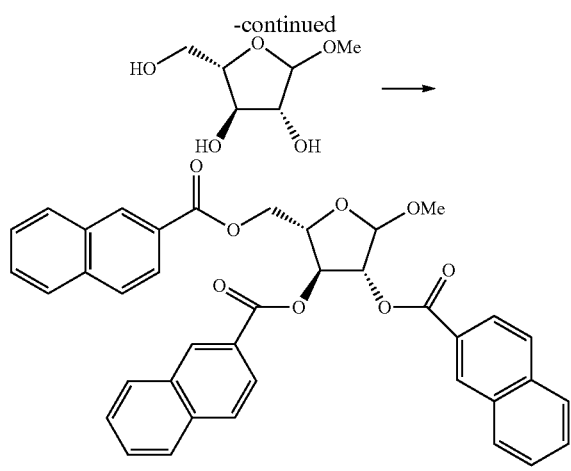

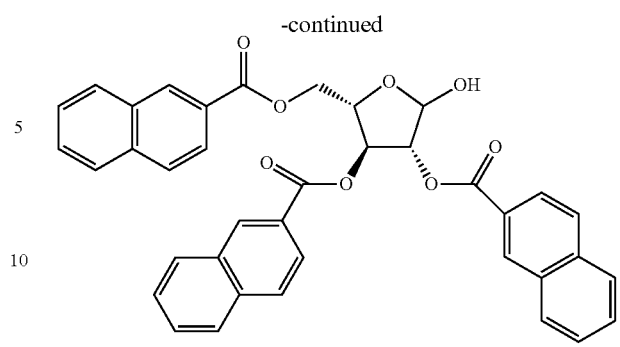

6.0 mL of acetyl chloride was added dropwise to a solution of 10 g of (3R,4R,5S)-5-(hydroxymethyl)oxolane-2,3,4-triol in 100 mL of methanol at 15° C. or lower, and the resultant product was stirred at 25° C. for 1.5 hours. 17.5 g of a 28% sodium methoxide/methanol solution and 80 mL of toluene were added to the reaction mixture, and the methanol was distilled off under reduced pressure, whereby 18.6 g of a crude product of (2S,3R,4R)-2-(hydroxymethyl)-5-methoxyoxolane-3,4-diol was obtained.

After 150 mL of toluene, 100 mL of a 10% sodium hydroxide aqueous solution, and 0.6 g of tetrabutylammonium chloride were added to the crude product at 30° C. or lower, a solution of 38 g of naphthalene-2-carbonyl chloride in 50 mL of tetrahydrofuran was added dropwise thereto at 15° C. or lower over a period of 1 hour, then, the resultant product was stirred at 25° C. for 2 hours, and 300 mL of ethyl acetate and 300 mL of water were added thereto. After the aqueous layer was removed, the organic layer was washed two times with 400 mL of a 10% sodium chloride aqueous solution and dried over anhydrous sodium sulfate, and the solvent was distilled off under reduced pressure, whereby 44 g of (3R,4S,5S)-2-methoxy-4-((naphthalen-2-yl)carbonyloxy)-5-(((naphthalen-2-yl)carbonyloxy)methyl)oxolan-3-yl 4-naphthalene-2-carboxylate was obtained as a pale yellow oily material. As a result of $^1$H-NMR measurement, the above-obtained material was an anomer mixture of about 85:15.

$^1$H-NMR (CDCl$_3$) δ value: 3.44(0.45H,s),3.57(2.55H,s), 4.62-4.67(0.15H,m),4.71(0.85H,dd,J=4.4,8.5 Hz),4.76-4.87 (1.15H, m),5.01(0.85H,dd,J=3.5,12.0 Hz),5.31(0.85H,s), 5.46(0.15H,d,J=4.3 Hz),5.59-5.66(0.15H,m),5.66(0.85H,d, J=1.2 Hz),5.78(0.85H,d,J=4.9 Hz),6.12-6.20(0.15H,m), 7.41-8.21(18H,m),8.54-8.79(3H,m)

49.5 mL of water was added to a solution of 33 g of (3R,4S,5S)-2-methoxy-4-((naphthalen-2-yl)carbonyloxy)-5-(((naphthalen-2-yl)carbonyloxy)methyl)oxolan-3-yl naphthalene-2-carboxylate in 330 mL of trifluoroacetic acid at 25° C., and the resultant product was stirred at 40° C. for 4.5 hours. About 280 mL of trifluoroacetic acid was distilled off under reduced pressure, then, 450 mL of ethyl acetate and 500 mL of a 10% sodium hydrogen carbonate aqueous solution were added to the residue, and the insoluble materials were removed by filtration using Celite. After the aqueous layer was removed, the organic layer was washed sequentially with 500 mL of a 10% sodium hydrogen carbonate aqueous solution, 500 mL of water, and 500 mL of a saturated sodium chloride aqueous solution, and dried over anhydrous sodium sulfate. The solvent was distilled off under reduced pressure, and the resultant product was purified by column chromatography (eluent: ethyl acetate/hexane=1/2), whereby 15.6 g of (3R,4S,5S)-2-hydroxy-4-((naphthalen-2-yl)carbonyloxy)-5-(((naphthalen-2-yl)carbonyloxy)methyl)oxolan-3-yl naphthalene-2-carboxylate was obtained as a white amorphous material. As a result of $^1$H-NMR measurement, the above-obtained material was an anomer mixture of about 75:25.

$^1$H-NMR (CDCl$_3$) δ value: 3.13(0.75H,brs),3.45(0.25H, brs),4.59-4.64(0.25H,m),4.79-4.98(2.75H,m),5.70-5.73(1H, m),5.77(0.75H,d,J=4.7 Hz),5.81(0.75H,brs),5.94(0.25H, brs),6.06(0.25H,t,J=5.4 Hz),7.31-8.12(18H,m), 8.53-8.69 (3H,m)

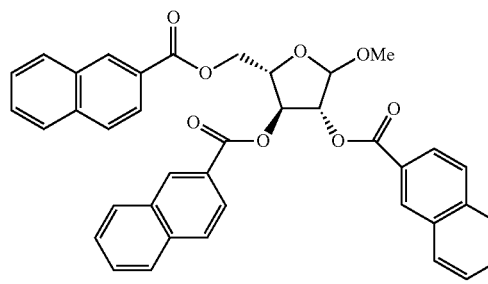

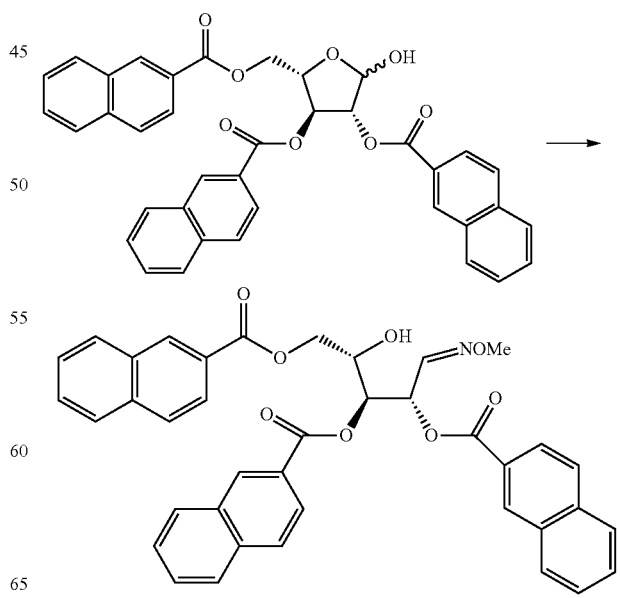

15.6 mL of pyridine, 7.8 g of p-toluenesulfonic acid monohydrate, and 4.7 g of O-methylhydroxylamine hydrochloride were added to a solution of 18.6 g of (3R,4S,5S)-2-hydroxy-4-((naphthalen-2-yl)carbonyloxy)-5-(((naphthalen-2-yl)carbonyloxy)methyl)oxolan-3-yl naphthalene-2-carboxylate in 120 mL of methanol at 25° C., and the resultant product was stirred at 40° C. for 3 hours. After about 90 mL of methanol was distilled off under reduced pressure, 100 mL of ethyl acetate and 150 mL of water were added thereto, and the aqueous layer was removed. After the organic layer was washed sequentially two times with a 10% sodium chloride aqueous solution, two times with 1 N hydrochloric acid water, once with a sodium hydrogen carbonate aqueous solution, and once with a saturated sodium chloride aqueous solution, and dried over anhydrous sodium sulfate, the solvent was distilled off under reduced pressure, whereby 20.6 g of (2S,3S,4S)-4-hydroxy-1-(methoxyimino)-3,5-bis((naphthalen-2-yl)carbonyloxy)pentan-2-yl naphthalene-2-carboxylate was obtained as a white amorphous material. As a result of $^1$H-NMR measurement, the above-obtained material was an oxime isomer mixture of about 70:30.

$^1$H-NMR (CDCl$_3$) δ value: 3.53-3.57(1H,m),3.82(2.1H,s),4.01(0.9H,s),4.39-4.48(1H,m),4.54-4.61(1H,m),4.68-4.75(1H,m), 5.86(0.7H,dd,J=3.7,8.0 Hz),6.02(0.3H,dd, J=2.9,8.1 Hz),6.35(0.7H,dd,J=3.7,6.0 Hz),6.74(0.3H, dd,J=2.9,5.2 Hz),6.92(0.3H,d,J=5.2 Hz),7.46-8.16(18.7H, m),8.57-8.71(3H,m)

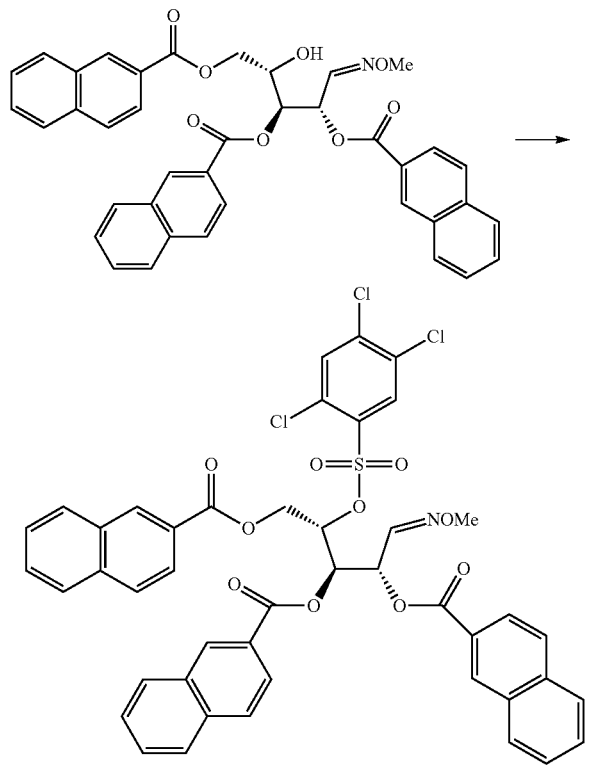

After 4.9 g of 2,4,5-trichlorobenzenesulfonyl chloride was added to a solution of 7.5 g of (2S,3S,4S)-4-hydroxy-1-(methoxyimino)-3,5-bis((naphthalen-2-yl)carbonyloxy)pentan-2-yl naphthalene-2-carboxylate in 30 mL of acetonitrile at 25° C., 2.5 mL of N-methylimidazole was added dropwise thereto at 0° C. to 10° C., and the resultant product was stirred at 10° C. for 3 hours. 150 mL of ethyl acetate and 150 mL of water were added to the reaction mixture, and then, the aqueous layer was removed. After the organic layer was washed sequentially two times with a 10% sodium chloride aqueous solution, once with hydrochloric acid, once with a sodium hydrogen carbonate aqueous solution, and once with a saturated sodium chloride aqueous solution, and dried over anhydrous sodium sulfate, the solvent was distilled off under reduced pressure, whereby 9.7 g of (2S,3R,4S)-1-(methoxyimino)-3,5-bis((naphthalen-2-yl)carbonyloxy)-4-(((2,4,5-trichlorobenz ene)sulfonyl)oxy)pentan-2-yl naphthalene-2-carboxylate was obtained as a white amorphous material.

As a result of $^1$H-NMR measurement, the above-obtained material was an oxime isomer mixture of about 70:30.

$^1$H-NMR (CDCl$_3$) δ value: 3.86(2.1H,s),3.95(0.9H,s), 4.81-4.93(2H,m),5.58-5.69(1H,m),6.12-6.21(1.7H,m),6.52 (0.3H,dd, J=4.0,5.1 Hz),6.88(0.3H,d,J=5.2 Hz),7.50-8.10 (20.7H,m),8.59-8.70(3H,m)

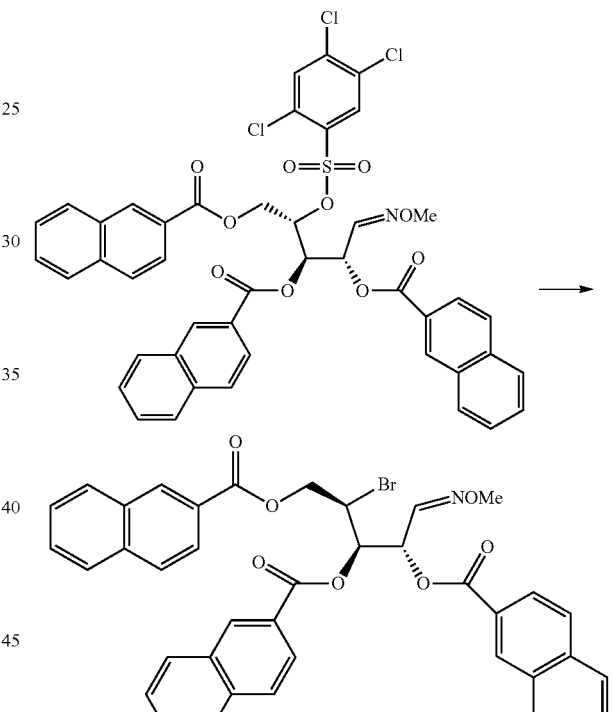

1.2 g of lithium bromide was added to a mixed solution of 6.0 g of (2S,3R,4S)-1-(methoxyimino)-3,5-bis((naphthalen-2-yl)carbonyloxy)-4-(((2,4,5-trichlorobenz ene)sulfonyl)oxy)pentan-2-yl naphthalene-2-carboxylate in 6.5 mL of tetrahydrofuran and 5.5 mL of 1,2-dimethylimidazole at 10° C. or lower, and the resultant product was stirred at 48° C. for 6 hours. 40 mL of ethyl acetate and 30 mL of water were added to the reaction mixture, and then, the aqueous layer was removed. After the organic layer was dried over anhydrous sodium sulfate, the solvent was distilled off under reduced pressure, and the resultant product was purified by column chromatography (eluent: ethyl acetate/hexane=1/3), whereby 7.6 g of (2S,3R,4R)-4-bromo-1-(methoxyimino)-3,5-bis((naphthalen-2-yl)carbonyloxy)pentan-2-yl naphthalene-2-carboxylate was obtained as a white solid. As a result of $^1$H-NMR measurement, the above-obtained solid was an oxime isomer mixture of about 80:20.

$^1$H-NMR (CDCl$_3$) δ value: 3.86(2.4H,s),3.92(0.6H,s), 4.65(0.8H,dd,J=9.8,13.3 Hz),4.70-4.91(2.2H,m),6.19-6.27 (1.8H,m), 6.60(0.2H,t,J=5.5 Hz),6.90(0.2H,d,J=5.6 Hz), 7.25-8.14(18.8H,m),8.43-8.69(3H,m)

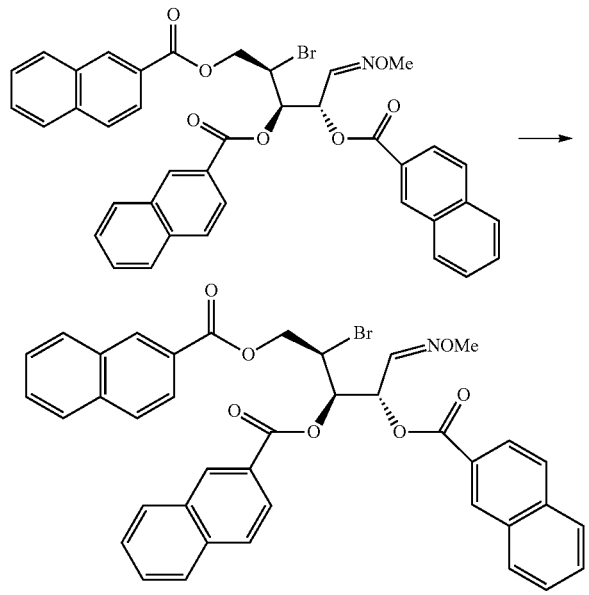

4.5 mL of a 50% glyoxylic acid aqueous solution was added to a solution of 3.5 g of (2S,3R,4R)-4-bromo-1-(methoxyimino)-3,5-bis((naphthalen-2-yl)carbonyloxy) pentan-2-yl naphthalene-2-carboxylate in 30 mL of acetonitrile, and the resultant product was stirred at 75° C. for 12 hours. The reaction mixture was cooled to room temperature, then, 200 mL of ethyl acetate and 150 mL of water were added thereto, and the aqueous layer was removed. After the organic layer was washed sequentially three times with a 10% sodium chloride aqueous solution, once with a sodium hydrogen carbonate aqueous solution, and three times with a saturated sodium chloride aqueous solution, and dried over anhydrous sodium sulfate, the solvent was distilled off under reduced pressure. The obtained residue was purified by column chromatography (eluent: ethyl acetate/hexane=1/ 2→1/1), whereby 3.5 g of a oily crude product of (2R,3R, 4R)-4-bromo-1-oxo-3,5-bis((naphthalen-2-yl)carbonyloxy) pentan-2-yl naphthalene-2-carboxylate was obtained as a white amorphous material.

$^1$H-NMR (CDCl$_3$) δ value: 4.79(1H,dd,J=7.2,11.7 Hz), 4.89-5.00(2H,m),5.97(1H,d, J=5.5 Hz),6.16(1H,dd,J=3.7, 5.5 Hz),7.43-8.09(18H,m),8.51(1H,s),8.53(1H,s),8.65(1H, s),9.84(1H,s)

Example 6

[A] Synthesis of (3S,4R,5R)-2,4-bis(4-phenylbenzoyloxy)-5-[(4-phenylbenzoyloxy)methyl]thiolan-3-yl 4-phenylbenzoate By reacting (2S,3R,4S)-4-(methanesulfonyloxy)-1-oxo-3, 5-bis((4-phenylphenyl)carbonyloxy)pentan-2-yl 4-phenylbenzoate with a 15% sodium hydrogen sulfide in the following manner, (3S,4R,5R)-2-hydroxy-4-((4-phenylphenyl) carbonyloxy)-5-(((4-phenylphenyl)carbonyloxy)methyl) thiolan-3-yl 4-phenylbenzoate was obtained, and by further reacting the hydroxyl group thereof with 4-phenylbenzoyl chloride, (3S,4R,5R)-2,4-bis(4-phenylbenzoyloxy)-5-[(4-phenylbenzoyloxy)methyl]thiolan-3-yl 4-phenylbenzoate was synthesized.

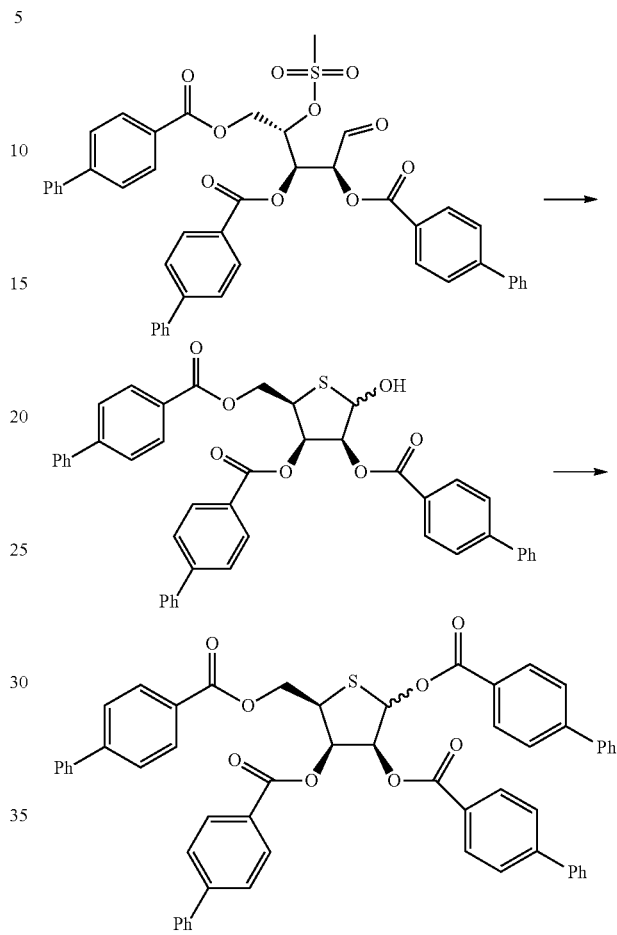

1.2 mL of a 15% sodium hydrogen sulfide aqueous solution was added dropwise to a solution of 1.7 g of (2S,3R,4S)-4-(methanesulfonyloxy)-1-oxo-3,5-bis((4-phenylphenyl)carbonyloxy)pentan-2-yl 4-phenylbenzoate in 31 mL of N,N-dimethylformamide at 10° C. or lower, and the resultant product was stirred at 25° C. for 1.5 hours. 100 mL of ethyl acetate and 100 mL of a saturated sodium chloride aqueous solution were added to the reaction mixture, and then, the aqueous layer was removed. After the organic layer was washed sequentially three times with a sodium hydrogen carbonate aqueous solution and once with a saturated sodium chloride aqueous solution, the resultant product was dried over anhydrous sodium sulfate. The solvent was distilled off under reduced pressure, whereby a crude product of (3S,4R,5R)-2-hydroxy-4-((4-phenylphenyl)carbonyloxy)-5-(((4-phenylphenyl)carbonyloxy)methyl)thiolan-3-yl 4-phenylbenzoate was obtained.

After 5 mg of N,N-dimethyl-4-aminopyridine was added to a solution of 146 mg of the crude product in 3 mL of pyridine, 198 mg of 4-phenylbenzoyl chloride was added thereto at 10° C. or lower, and the resultant product was stirred at room temperature for 8 hours and allowed to stand overnight. 30 mL of ethyl acetate and 30 mL of 1 N hydrochloric acid water were added to the reaction mixture, and then, the aqueous layer was removed. After the organic layer was washed sequentially with 1 N hydrochloric acid water, a sodium hydrogen carbonate aqueous solution, and a saturated sodium chloride aqueous solution, and dried over anhydrous sodium sulfate, the solvent was distilled off under reduced pressure. The obtained residue was recrystallized from ethyl acetate/methanol, whereby 97 mg of (3S,4R,5R)-2,4-bis(4-phenylbenzoyloxy)-5-[(4-phenylbenzoyloxy)methyl]thiolan-3-yl 4-phenylbenzoate was obtained as a white crystal. As a result of ¹H-NMR measurement, the above-obtained crystal was an anomer mixture of about 60:40.

¹H-NMR (CDCl₃) δ value: 4.31(0.4H,dd,J=7.1,12.3 Hz), 4.50(0.6H,dd,J=6.7,13.1 Hz),4.66-4.97(2H,m),5.81(0.4H,t, J=4.4 Hz), 6.21-6.28(1.2H,m),6.47-6.52(1H,m),6.71(0.4H, d,J=5.0 Hz),7.36-7.77(28H,m),7.93-8.26(8H, m)

[B] Synthesis of Raw Material

Moreover, (2S,3R,4S)-4-(methanesulfonyloxy)-1-oxo-3,5-bis((4-phenylphenyl)carbonyloxy)pentan-2-yl 4-phenylbenzoate which was a raw material was synthesized through a plurality of steps in the following manner.

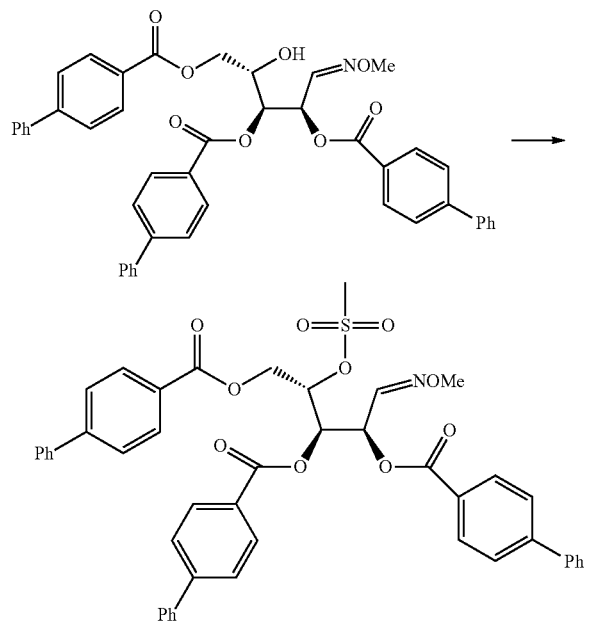

After 2.0 mL of triethylamine and 1.0 mL of methanesulfonyl chloride were added dropwise to a mixed solution of 4.6 g of (2R,3S,4S)-4-hydroxy-1-(methoxyimino)-3,5-bis((4-phenylphenyl)carbonyloxy)pentan-2-yl 4-phenylbenzoate in 18.5 mL of acetonitrile and 10 mL of tetrahydrofuran at 10° C. or lower, the resultant product was stirred at 25° C. for 2 hours. After 0.4 mL of triethylamine and 0.2 mL of methanesulfonyl chloride were added dropwise to the reaction liquid, the resultant product was stirred at 25° C. for 1 hour, then, 100 mL of ethyl acetate and 100 mL of water were added thereto, and the aqueous layer was removed. After the organic layer was washed sequentially two times with a 10% sodium chloride aqueous solution, once with 1 N hydrochloric acid water, once with a sodium hydrogen carbonate aqueous solution, and once with a saturated sodium chloride aqueous solution, and dried over anhydrous sodium sulfate, the solvent was distilled off under reduced pressure. The concentrated residue was purified by column chromatography (eluent: ethyl acetate/hexane=1/2), whereby 3.1 g of (2R,3R,4S)-4-(methanesulfonyloxy)-1-(methoxyimino)-3,5-bis((4-phenylphenyl)carbonyloxy)pentan-2-yl 4-phenylbenzoate was obtained as a white amorphous material. As a result of ¹H-NMR measurement, the above-obtained material was an oxime isomer mixture of about 75:25.

¹H-NMR (CDCl₃) δ value: 3.17(0.75H,s),3.21(2.25H,s), 3.91(2.25H,s),4.01(0.75H,s),4.56(0.25H,dd,J=6.5,12.8 Hz), 4.62(0.75H,dd,J=6.8,12.6 Hz),4.98(0.75H,dd,J=2.9,12.6 Hz),5.02(0.25H,dd, J=2.8,12.8 Hz),5.53-5.55(1H,m),6.07-6.17(1.75H,m),6.60(0.25H,dd,J=3.9,5.4 Hz),6.97(0.25H,d, J=5.4 Hz),7.39-7.72(21.75H,m),8.08-8.20(6H,m)

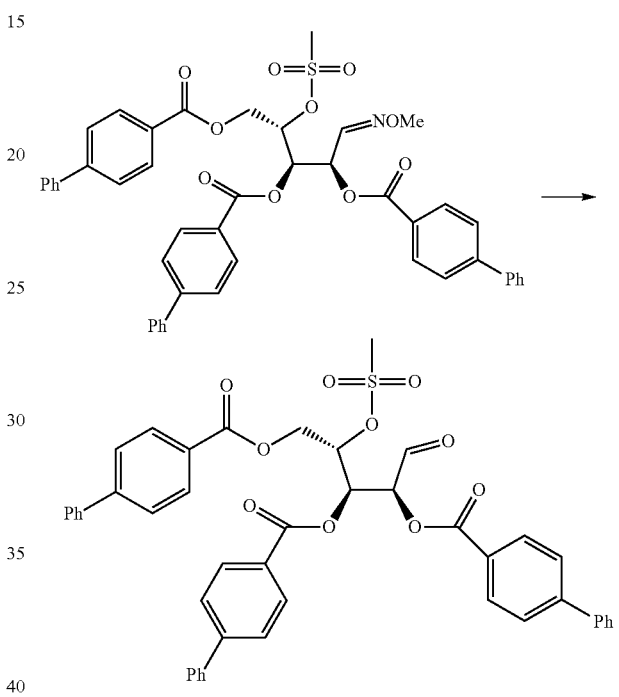

6.9 mL of a 50% glyoxylic acid aqueous solution was added to a solution of 3.0 g of (2R,3R,4S)-4-(methanesulfonyloxy)-1-(methoxyimino)-3,5-bis((4-phenylphenyl)carbonyloxy)pentan-2-yl 4-phenylbenzoate in 100 mL of acetonitrile, and the resultant product was stirred at 75° C. for 10 hours. The reaction mixture was cooled to room temperature, then, 240 mL of ethyl acetate and 80 mL of water were added thereto, and the aqueous layer was removed. After the organic layer was washed sequentially three times with a 10% sodium chloride aqueous solution, once with a sodium hydrogen carbonate aqueous solution, and three times with a saturated sodium chloride aqueous solution, and dried over anhydrous sodium sulfate, the solvent was distilled off under reduced pressure. The obtained residue was purified by column chromatography (eluent: ethyl acetate/hexane=1/2→1/1), whereby 1.7 g of (2S,3R,4S)-4-(methanesulfonyloxy)-1-oxo-3,5-bis((4-phenylphenyl)carbonyloxy)pentan-2-yl 4-phenylbenzoate was obtained as a white amorphous material.

¹H-NMR (CDCl₃) δ value: 3.17(3H,s),4.55(1H,dd,J=5.2, 12.9 Hz),5.00(1H,dd,J=2.7, 12.8 Hz), 5.64-5.69(1H,m),5.93 (1H,d,J=2.8 Hz),6.18(1H,dd,J=2.8,8.1 Hz),7.38-7.75(21H, m),8.07-8.28(6H,m),9.79(1H,s)

Example 7

[A] Synthesis of (3S,4R,5R)-2-hydroxy-4-((4-methylphenyl)carbonyloxy)-5-(((4-methylphenyl)carbonyloxy)methyl)thiolan-3-yl 4-methylbenzoate and acylated product thereof By reacting (2S,3R,4S)-4-(methanesulfonyloxy)-1-oxo-3,5-bis((4-methylphenyl)carbonyloxy)pentan-2-yl 4-methylbenzoate with 15% sodium hydrogen sulfide in the following manner, (3S,4R,5R)-2-hydroxy-4-((4-methylphenyl)carbonyloxy)-5-(((4-methylphenyl)carbonyloxy)methyl)thiolan-3-yl 4-methylbenzoate and an acylated product thereof were synthesized.

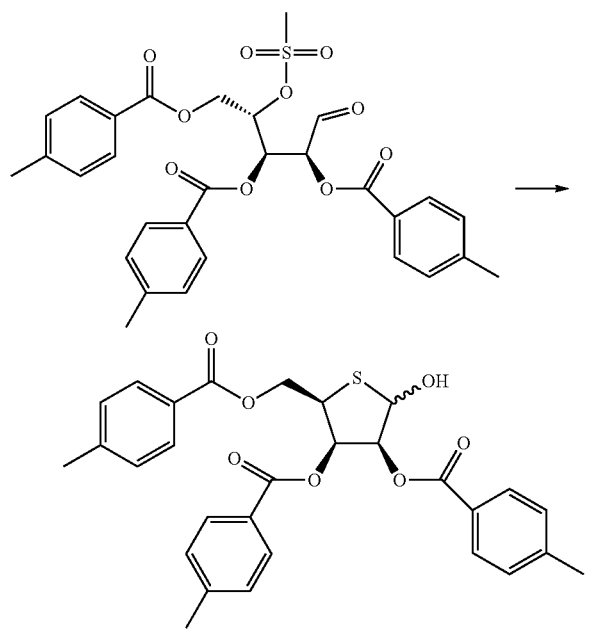

0.48 mL of a 15% sodium hydrogen sulfide aqueous solution was added dropwise to a solution of 0.5 g of (2S,3R,4S)-4-(methanesulfonyloxy)-1-oxo-3,5-bis((4-methylphenyl)carbonyloxy)pentan-2-yl 4-methylbenzoate in 12 mL of N,N-dimethylformamide at 10° C. or lower, and the resultant product was stirred at 25° C. for 1 hour. 25 mL of ethyl acetate and 25 mL of a saturated sodium chloride aqueous solution were added to the reaction mixture, and then, the aqueous layer was removed. After the organic layer was washed sequentially three times with a sodium hydrogen carbonate aqueous solution and once with a saturated sodium chloride aqueous solution, the resultant product was dried over anhydrous sodium sulfate. The solvent was concentrated under reduced pressure, and the obtained residue was purified by column chromatography (eluent: ethyl acetate/hexane=1/3), whereby 0.29 g of (3S,4R,5R)-2-hydroxy-4-((4-methylphenyl)carbonyloxy)-5-(((4-methylphenyl)carbonyloxy)methyl)thiolan-3-yl 4-methylbenzoate was obtained as a white amorphous material. As a result of $^1$H-NMR measurement, the above-obtained material was an anomer mixture of about 79:21.

$^1$H-NMR (CDCl$_3$) δ value: 2.37-2.43(9H,m),2.71(0.79H, brs),2.87(0.21H,d,J=11.7 Hz), 4.06-4.12(0.21H,m),4.44 (0.79H,dd, J=7.1,13.5 Hz),4.55-4.70(2H,m),5.43(0.21H,dd, J=3.8,5.8 Hz),5.65(0.79H,dd,J=3.8,5.8 Hz),5.74-5.75(1H, m),6.12(0.79H,dd,J=3.7,6.1 Hz),6.33(0.21H,t,J=4.6 Hz), 7.12-7.28(6H,m),7.76-7.93(6H,m)

A reaction was performed in the same manner as in the above reaction except that the solvent was changed from N,N-dimethylformamide to dimethylsulfoxide, whereby 0.28 g of (3S,4R,5R)-2-hydroxy-4-((4-methylphenyl)carbonyloxy)-5-(((4-methylphenyl)carbonyloxy)methyl)thiolan-3-yl 4-methylbenzoate was obtained as a white amorphous material. As a result of $^1$H-NMR measurement, the above-obtained material was an anomer mixture of about 79:21.

A reaction was performed in the same manner as in the above reaction except that the solvent was changed from N,N-dimethylformamide to acetone, whereby 0.23 g of (3S,4R,5R)-2-hydroxy-4-((4-methylphenyl)carbonyloxy)-5-(((4-methylphenyl)carbonyloxy)methyl)thiolan-3-yl 4-methylbenzoate was obtained as a white amorphous material. As a result of $^1$H-NMR measurement, the above-obtained material was an anomer mixture of about 79:21.

A reaction was performed in the same manner as in the above reaction except that the solvent was changed from N,N-dimethylformamide to ethanol, whereby 0.24 g of (3S,4R,5R)-2-hydroxy-4-((4-methylphenyl)carbonyloxy)-5-(((4-methylphenyl)carbonyloxy)methyl)thiolan-3-yl 4-methylbenzoate was obtained as a white amorphous material. As a result of $^1$H-NMR measurement, the above-obtained material was an anomer mixture of about 79:21.

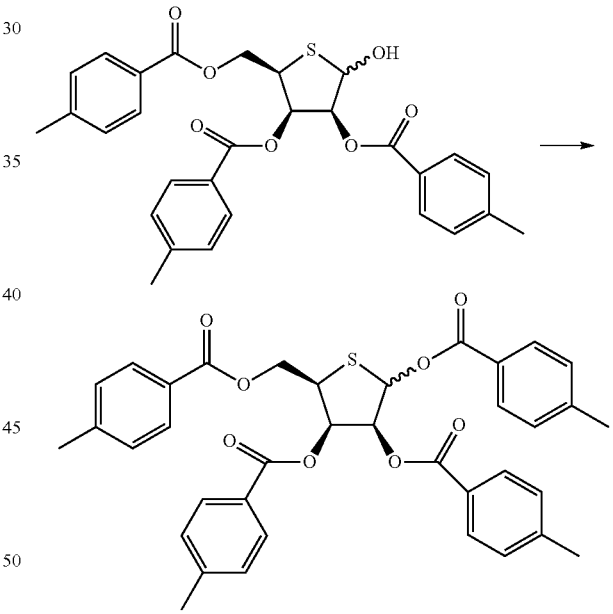

After 7.6 mg of N,N-dimethyl-4-aminopyridine was added to a solution of 165 mg of (3S,4R,5R)-2-hydroxy-4-((4-methylphenyl)carbonyloxy)-5-(((4-methylphenyl)carbonyloxy)methyl)thiolan-3-yl 4-methylbenzoate in 2 mL of pyridine, 50 µL of p-methylbenzoyl chloride was added thereto at 10° C. or lower, and the resultant product was stirred at room temperature for 6 hours. 30 mL of ethyl acetate and 30 mL of 1 N hydrochloric acid water were added to the reaction mixture, and then, the aqueous layer was removed. After the organic layer was washed sequentially with 1 N hydrochloric acid water, a sodium hydrogen carbonate aqueous solution, and a saturated sodium chloride aqueous solution, and dried over anhydrous sodium sulfate, the solvent was distilled off under reduced pressure. The obtained residue was purified by column chromatography (eluent: ethyl acetate/hexane=1/4), and as a result, two types of anomer isomers of (3S,4R,5R)-2,4-bis(4-methylbenzoyloxy)-5-[(4-methylbenzoyloxy)methyl]thiolan-3-yl 4-methylbenzoate were obtained, and one type was 130 mg (Rf value of TLC (eluent: ethyl acetate/hexane=1/2)=0.71) and the other type was 45 mg (Rf value of TLC (eluent: ethyl acetate/hexane=1/2)=0.63), respectively. Both were white amorphous materials.

The component of Rf value=0.71

$^1$H-NMR (CDCl$_3$) δ value: 2.37(3H,s),2.39(3H,s),2.41(3H,s),2.42(3H,s),4.39(1H,dd,J=7.2,13.2 Hz),4.62(1H,dd,J=7.4,11.1 Hz),4.75(1H,dd,J=7.2,11.1 Hz),6.10-6.17(2H,m),6.41(1H,d, J=3.4 Hz),7.13(2H,d,J=8.0 Hz),7.17(2H,d,J=8.1 Hz),7.24-7.27(4H,m),7.78(2H,d,J=7.8 Hz),7.85(2H,d,J=8.2 Hz),7.94-7.97(4H,m)

The component of Rf value=0.63

$^1$H-NMR (CDCl$_3$) δ value: 2.34(3H,s),2.38(6H,s),2.43(3H,s),4.16-4.22(1H,m),4.58-4.70(2H,m),5.71(1H,dd,J=4.0,5.1 Hz), 6.38(1H,t,J=4.6 Hz),6.62(1H,d,J=5.1 Hz), 7.03(2H,d,J=8.0 Hz),7.11(2H,d,J=8.0 Hz),7.15(2H,d,J=8.0 Hz),7.19(2H,d,J=8.0 Hz),7.77(4H,t,J=8.1 Hz),7.83(2H,d,J=8.2 Hz),7.98(2H,d=8.2 Hz)

[B] Synthesis of Raw Material

Moreover, (2S,3R,4S)-4-(methanesulfonyloxy)-1-oxo-3,5-bis((4-methylphenyl)carbonyloxy)pentan-2-yl 4-methylbenzoate which was a raw material was synthesized through a plurality of steps in the following manner.

chloric acid water, once with a sodium hydrogen carbonate aqueous solution, and once with a saturated sodium chloride aqueous solution, and dried over anhydrous sodium sulfate, the solvent was distilled off under reduced pressure, whereby 7.3 g of a crude product of (2R,3R,4S)-4-(methanesulfonyloxy)-1-(methoxyimino)-3,5-bis((4-methylphenyl)carbonyloxy)pentan-2-yl 4-methylbenzoate was obtained as a white amorphous material. The crude product was used in the next step without further purification. As a result of $^1$H-NMR measurement, the above-obtained crude product was an oxime isomer mixture of about 76:24.

$^1$H-NMR (CDCl$_3$) δ value: 2.40-2.42(9H,m),3.11(0.72H,s),3.16(2.28H,s),3.87(2.28H,s),3.97(0.72H,s),4.47(0.24H,dd,J=6.7, 12.7 Hz),4.53(0.76H,dd,J=7.1,12.6 Hz),4.89(0.76H,dd,J=2.7,12.6 Hz),4.94(0.24H,dd,J=2.8,12.8 Hz), 5.43-5.49(1H,m),5.98-6.08(1.76H,m),6.51(0.24H,dd,J=4.1, 5.5 Hz),6.90(0.24H,d,J=5.5 Hz), 7.22-7.27(6H,m),7.54(0.76H,d,J=6.1 Hz),7.88-7.80(6H, m)

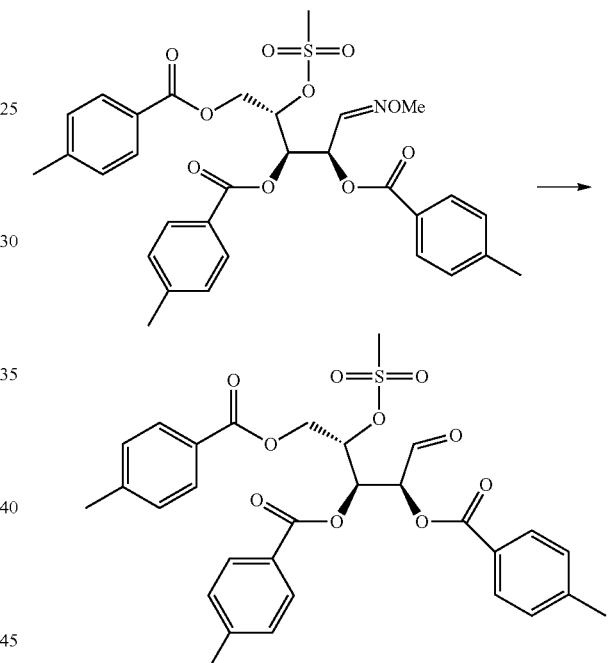

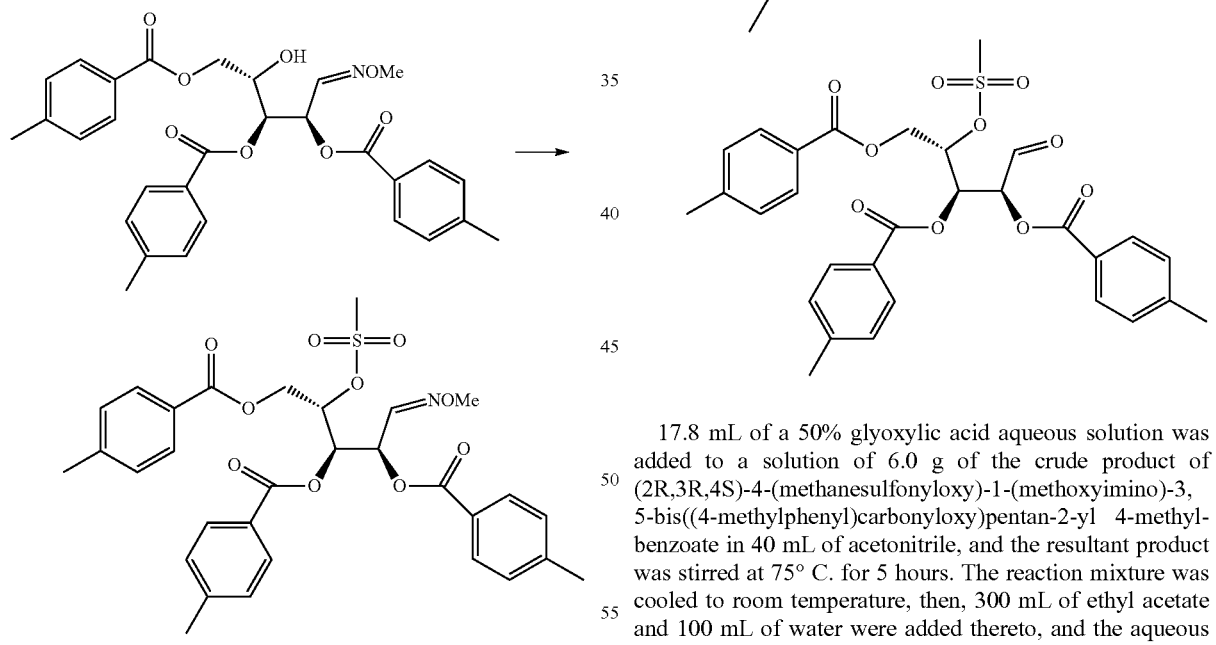

After 3.7 mL of triethylamine and 1.9 mL of methanesulfonyl chloride were added dropwise to a solution of 6.4 g of (2R,3S,4S)-4-hydroxy-1-(methoxyimino)-3,5-bis((4-methylphenyl)carbonyloxy)pentan-2-yl 4-methylbenzoate in 64 mL of ethyl acetate at 10° C. or lower, the resultant product was stirred at 25° C. for 2 hours. 60 mL of ethyl acetate and 120 mL of water were added to the reaction mixture, and then, the aqueous layer was removed. After the organic layer was washed sequentially two times with a 10% sodium chloride aqueous solution, once with 1 N hydro- 17.8 mL of a 50% glyoxylic acid aqueous solution was added to a solution of 6.0 g of the crude product of (2R,3R,4S)-4-(methanesulfonyloxy)-1-(methoxyimino)-3,5-bis((4-methylphenyl)carbonyloxy)pentan-2-yl 4-methylbenzoate in 40 mL of acetonitrile, and the resultant product was stirred at 75° C. for 5 hours. The reaction mixture was cooled to room temperature, then, 300 mL of ethyl acetate and 100 mL of water were added thereto, and the aqueous layer was removed. After the organic layer was washed sequentially three times with a 10% sodium chloride aqueous solution, once with a sodium hydrogen carbonate aqueous solution, and three times with a saturated sodium chloride aqueous solution, and dried over anhydrous sodium sulfate, the solvent was distilled off under reduced pressure. The obtained residue was purified by column chromatography (eluent: ethyl acetate/hexane=1/2→1/1), whereby 4.6 g of (2S,3R,4S)-4-(methanesulfonyloxy)-1-oxo-3,5-bis((4-methylphenyl)carbonyloxy)pentan-2-yl 4-methylbenzoate was obtained as a white amorphous material.

$^1$H-NMR (CDCl$_3$) δ value: 2.40-2.44(9H,m),3.10(3H,s), 4.46(1H,dd,J=5.4,12.9 Hz),4.92(1H,dd,J=2.5,12.8 Hz),5.55-5.61(1H,m),5.83(1H,d,J=2.9 Hz),6.07(1H,dd,J=2.8,8.0 Hz), 7.21-7.31(6H,m),7.87-8.08(6H,m),9.72(1H,s)

Example 8

[A] Synthesis of (3R,4R,5R)-2,4-bis(4-methylbenzoyloxy)-5-[(4-methylbenzoyloxy)methyl]thiolan-3-yl 4-methylbenzoate By reacting (2R,3R,4S)-4-(methanesulfonyloxy)-1-oxo-3,5-bis((4-methylphenyl)carbonyloxy)pentan-2-yl 4-methylbenzoate with a 15% sodium hydrogen sulfide in the following manner, (3R,4R,5R)-2-hydroxy-4-((4-methylphenyl)carbonyloxy)-5-(((4-methylphenyl)carbonyloxy)methyl)thiolan-3-yl 4-methylbenzoate was obtained, and by further reacting the hydroxyl group thereof with 4-methylbenzoyl chloride, (3R,4R,5R)-2,4-bis(4-methylbenzoyloxy)-5-[(4-methylbenzoyloxy)methyl]thiolan-3-yl 4-methylbenzoate was synthesized.

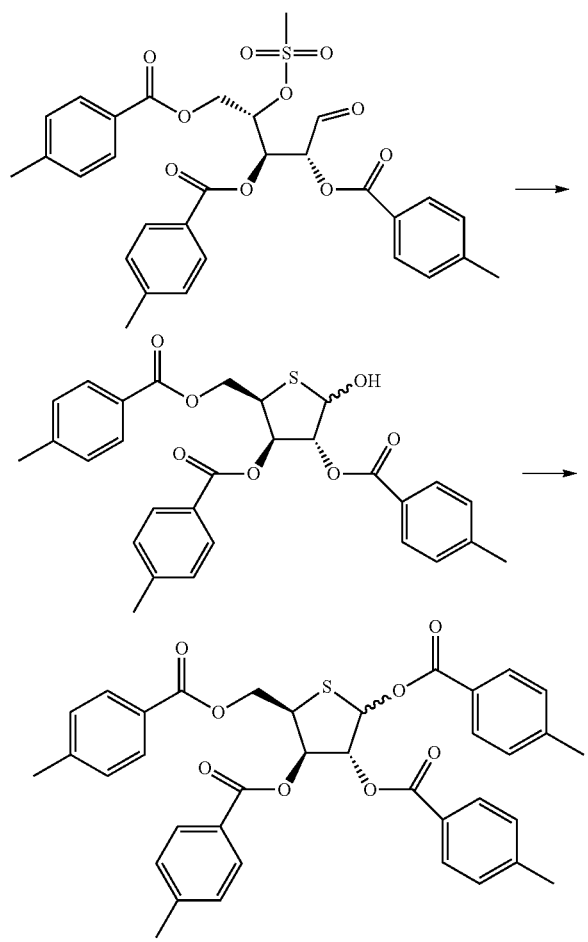

1.2 mL of a 15% sodium hydrogen sulfide aqueous solution was added dropwise to a solution of 0.90 g of (2R,3R,4S)-4-(methanesulfonyloxy)-1-oxo-3,5-bis((4-methylphenyl)carbonyloxy)pentan-2-yl 4-methylbenzoate in 10 mL of N,N-dimethylformamide at 10° C. or lower, and the resultant product was stirred at 25° C. for 1.5 hours. 50 mL of ethyl acetate and 50 mL of a saturated sodium chloride aqueous solution were added to the reaction mixture, and then, the aqueous layer was removed. After the organic layer was washed sequentially three times with a sodium hydrogen carbonate aqueous solution and once with a saturated sodium chloride aqueous solution, the resultant product was dried over anhydrous magnesium sulfate. The solvent was distilled off under reduced pressure, whereby a crude product of (3R,4R,5R)-2-hydroxy-4-((4-methylphenyl)carbonyloxy)-5-(((4-methylphenyl)carbonyloxy)methyl)thiolan-3-yl 4-methylbenzoate was obtained.

After 20 mg of N,N-dimethyl-4-aminopyridine was added to a solution of 0.25 g of the obtained crude product in 5 mL of pyridine, 100 µL of 4-methylbenzoyl chloride was added thereto at 10° C. or lower, and the resultant product was stirred at room temperature for 10 hours. 30 mL of ethyl acetate and 30 mL of 1 N hydrochloric acid water were added to the reaction mixture, and then, the aqueous layer was removed. After the organic layer was washed sequentially with a sodium hydrogen carbonate aqueous solution and a saturated sodium chloride aqueous solution, and dried over anhydrous sodium sulfate, the solvent was distilled off under reduced pressure. The obtained residue was purified by column chromatography (eluent: ethyl acetate/hexane=1/4), whereby 0.24 g of (3R,4R,5R)-2,4-bis(4-methylbenzoyloxy)-5-[(4-methylbenzoyloxy)methyl]thiolan-3-yl 4-methylbenzoate was obtained as a white amorphous material. As a result of $^1$H-NMR measurement, the above-obtained material was an anomer mixture of about 62:38.

$^1$H-NMR (CDCl$_3$) δ value: 2.35-2.45(12H,m),4.26 (0.62H,dt,J=8.3,7.0 Hz),4.40-4.47(1H,m),4.61(1H,dd,J=6.5, 11.6 Hz),4.76(0.38H,dd,J=7.2,10.7 Hz),5.96 (0.38H,t,J=4.6 Hz),6.09(0.62H, dd,J=4.5,10.0 Hz),6.17(0.62H,dd, J=7.3, 10.0 Hz),6.25(0.38H,dd,J=2.0,4.0 Hz),6.32(0.38H,d,J=1.8 Hz),7.05-7.28(8H,m),7.76-8.01(8H,m)

[B] Synthesis of Raw Material

Moreover, (2R,3R,4S)-4-(methanesulfonyloxy)-1-oxo-3,5-bis((4-methylphenyl)carbonyloxy)pentan-2-yl 4-methylbenzoate which was a raw material was synthesized through a plurality of steps in the following manner.

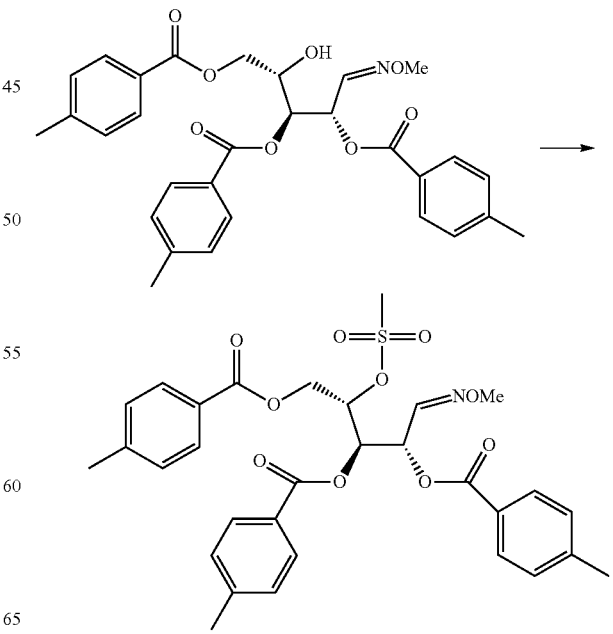

After 0.67 mL of methanesulfonyl chloride was added to a solution of 3.8 g of (2S,3S,4S)-4-hydroxy-1-(methoxyimino)-3,5-bis((4-methylphenyl)carbonyloxy)pentan-2-yl 4-methylbenzoate in 13.5 mL of acetonitrile at 25° C., 1.5 mL of N-methylimidazole was added dropwise thereto at 10° C. or lower, and the resultant product was stirred at 10° C. for 4 hours. 20 mL of ethyl acetate and 20 mL of water were added to the reaction mixture, and then, the aqueous layer was removed. After the organic layer was washed sequentially two times with a 10% sodium chloride aqueous solution, once with 1 N hydrochloric acid water, once with a sodium hydrogen carbonate aqueous solution, and once with a saturated sodium chloride aqueous solution, and dried over anhydrous sodium sulfate, the solvent was distilled off under reduced pressure. The obtained residue was purified by column chromatography (eluent: ethyl acetate/hexane=1/2), whereby 3.5 g of (2S,3R,4S)-4-(methanesulfonyloxy)-1-(methoxyimino)-3,5-bis((4-methylphenyl)carbonyloxy)pentan-2-yl 4-methylbenzoate was obtained as a colorless oily material.

As a result of $^1$H-NMR measurement, the above-obtained material was an oxime isomer mixture of about 70:30.

$^1$H-NMR (CDCl$_3$) δ value: 2.38-2.41(9H,m),3.02(0.9H,s),3.08(2.1H,s),3.83(2.1H, s),3.95(0.9H,s),4.50-4.59(1H,m),4.79-4.87(1H,m),5.38-5.50(1H,m),6.02(0.7H,s),6.02(0.7H, dd,J=5.3, 13.9 Hz),6.10(0.3H,dd,J=4.0,5.9 Hz), 6.38(0.3H,dd,J=4.1,5.1 Hz),6.73(0.3H,d,J=5.2 Hz),7.20-7.27(6H,m),7.47(0.7H,d,J=5.3 Hz),7.91-8.00(6H,m)

14.3 mL of a 30% formalin aqueous solution and 0.49 mL of 2 N hydrochloric acid water were added to a solution of 1.2 g of (2S,3R,4S)-4-(methanesulfonyloxy)-1-(methoxyimino)-3,5-bis((4-methylphenyl)carbonyloxy)pentan-2-yl 4-methylbenzoate in 19.3 mL of acetone, and the resultant product was stirred at 50° C. for 2.5 hours. The reaction mixture was cooled to room temperature, then, 30 mL of ethyl acetate and 30 mL of water were added thereto, and the aqueous layer was removed. After the organic layer was washed sequentially two times with water and once with a saturated sodium chloride aqueous solution and dried over anhydrous sodium sulfate, the solvent was distilled off under reduced pressure. The obtained residue was purified by column chromatography (eluent: ethyl acetate/hexane=1/2→1/1), whereby 0.93 g of (2R,3R,4S)-4-(methanesulfonyloxy)-1-oxo-3,5-bis((4-methylphenyl)carbonyloxy)pentan-2-yl 4-methylbenzoate was obtained as a colorless oily material.

$^1$H-NMR (CDCl$_3$) δ value: 2.41-2.43 (9H,m),3.04(3H,s), 4.54(1H,dd,J=6.0,12.7 Hz),4.87(1H,dd,J=2.8,12.7 Hz),5.47-5.52(1H,m),5.72(1H,d,J=2.7 Hz),6.05(1H,dd,J=2.7,7.0 Hz), 7.23-7.30(6H,m),7.94(4H,d,J=8.2 Hz),8.01(2H,d,J=8.2 Hz), 9.68(1H,s)

Example 9

[A] Synthesis of (3R,4R,5R)-2,4-bis(4-phenylbenzoyloxy)-5-[(4-phenylbenzoyloxy)methyl]thiolan-3-yl 4-phenylbenzoate By reacting (2R,3R,4S)-4-(methanesulfonyloxy)-1-oxo-3,5-bis((4-phenylphenyl)carbonyloxy)pentan-2-yl 4-phenylbenzoate with a 15% sodium hydrogen sulfide in the following manner, (3R,4R,5R)-2-hydroxy-4-((4-phenylphenyl)carbonyloxy)-5-(((4-phenylphenyl)carbonyloxy)methyl)thiolan-3-yl 4-phenylbenzoate was obtained, and by further reacting the hydroxyl group thereof with 4-phenylbenzoyl chloride, (3R,4R,5R)-2,4-bis(4-phenylbenzoyloxy)-5-[(4-phenylbenzoyloxy)methyl]thiolan-3-yl 4-phenylbenzoate was synthesized.

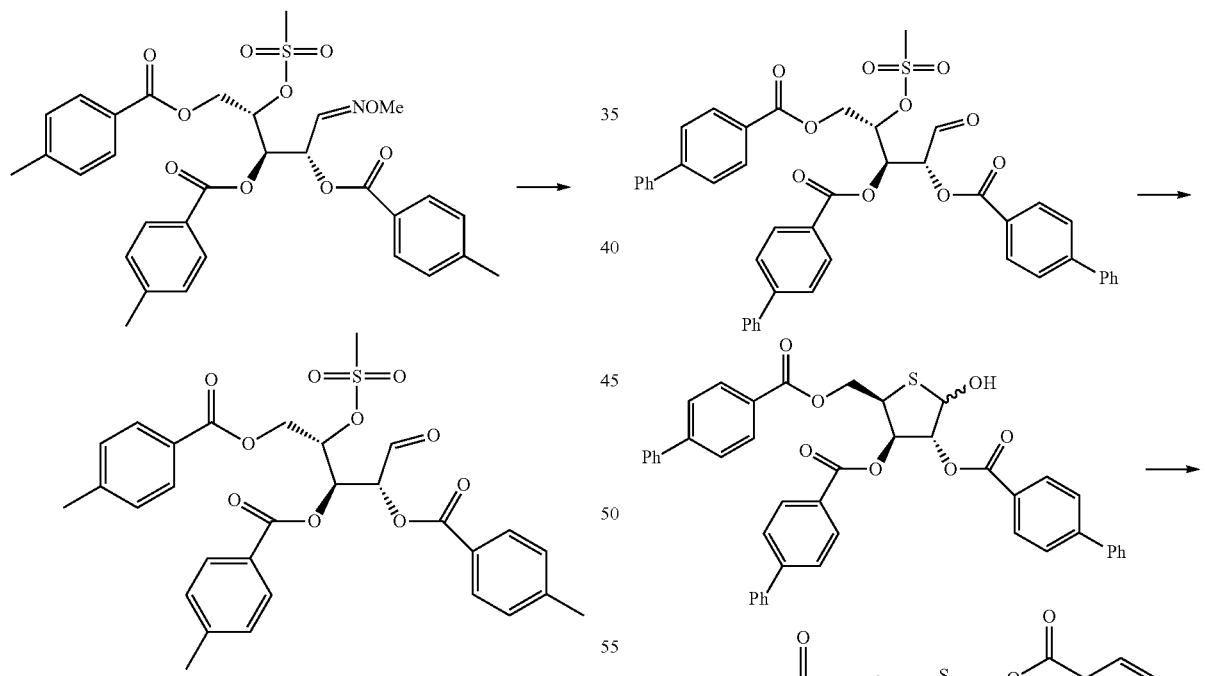

1.2 mL of a 15% sodium hydrogen sulfide aqueous solution was added dropwise to a solution of 1.65 g of (2R,3R,4S)-4-(methanesulfonyloxy)-1-oxo-3,5-bis((4-phenylphenyl)carbonyloxy)pentan-2-yl 4-phenylbenzoate in 21.5 mL of N,N-dimethylformamide at 10° C. or lower, and the resultant product was stirred at 25° C. for 1.5 hours. 100 mL of ethyl acetate and 100 mL of a saturated sodium chloride aqueous solution were added to the reaction mixture, and then, the aqueous layer was removed. After the organic layer was washed sequentially three times with a sodium hydrogen carbonate aqueous solution and once with a saturated sodium chloride aqueous solution, and dried over anhydrous sodium sulfate, the solvent was concentrated under reduced pressure, whereby a crude product of (3R,4R,5R)-2-hydroxy-4-((4-phenylphenyl)carbonyloxy)-5-(((4-phenylphenyl)carbonyloxy)methyl)thiolan-3-yl 4-phenylbenzoate was obtained.

After 9.5 mg of N,N-dimethyl-4-aminopyridine was added to a solution of 0.28 g of the obtained crude product in 5 mL of pyridine, 171 mg of 4-phenylbenzoyl chloride was added thereto at 10° C. or lower, and the resultant product was stirred at room temperature for 4 hours. 30 mL of ethyl acetate and 30 mL of 1 N hydrochloric acid water were added to the reaction mixture, and then, the aqueous layer was removed. After the organic layer was washed sequentially with 1 N hydrochloric acid water, a sodium hydrogen carbonate aqueous solution, and a saturated sodium chloride aqueous solution, and dried over anhydrous sodium sulfate, the solvent was distilled off under reduced pressure. The obtained residue was recrystallized from ethyl acetate/methanol, whereby 231 mg of (3R,4R,5R)-2,4-bis(4-phenylbenzoyloxy)-5-[(4-phenylbenzoyloxy)methyl]thiolan-3-yl 4-phenylbenzoate was obtained as an orange solid. The filtrate was concentrated under reduced pressure, and the resultant product was recrystallized from ethyl acetate/methanol, whereby 17 mg of (3R,4R,5R)-2,4-bis(4-phenylbenzoyloxy)-5-[(4-phenylbenzoyloxy)methyl]thiolan-3-yl 4-phenylbenzoate was obtained as a thin yellow solid. As a result of $^1$H-NMR measurement, the first crystal was an anomer mixture of 77:23, and the second crystal was an anomer mixture of 23:77.

First Crystal $^1$H-NMR (CDCl$_3$) δ value: 4.33-4.39(0.77H,m),4.44-4.53 (1H,m),4.68-4.79(1H,m), 4.90(0.23H,dd,J=7.4,11.5 Hz), 6.03-6.06(0.23H,m),6.19(0.77H,dd,J=4.5,10.2 Hz),6.28 (0.77H,dd,J=7.3,10.2 Hz),6.40-6.42(0.46H,m),6.63(0.77H, d,J=4.5 Hz),7.36-7.71(28H,m),7.91-8.18(8H,m)

Second Crystal $^1$H-NMR (CDCl$_3$) δ value: 4.33-4.39(0.23H,m),4.44-4.53 (1H,m),4.68-4.79(1H,m), 4.92(0.77H,dd,J=7.4,11.4 Hz), 6.03-6.06(0.77H,m),6.19(0.23H,dd,J=4.6,10.2 Hz),6.28 (0.23H,dd,J=7.3,10.2 Hz),6.40-6.41(1.54H,m),6.63(0.23H, d,J=4.5 Hz),7.36-7.71(28H,m),7.91-8.18(8H,m)

[B] Synthesis of Raw Material

Moreover, (2R,3R,4S)-4-(methanesulfonyloxy)-1-oxo-3,5-bis((4-phenylphenyl)carbonyloxy)pentan-2-yl 4-phenylbenzoate which was a raw material was synthesized through a plurality of steps in the following manner.

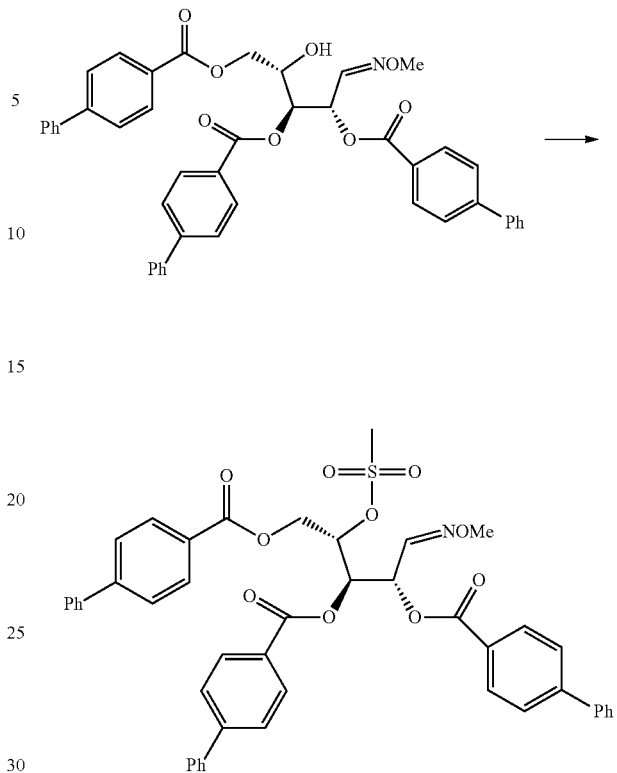

After 0.58 mL of methanesulfonyl chloride was added to a mixed solution of 4.1 g of (2S,3S,4S)-4-hydroxy-1-(methoxyimino)-3,5-bis((4-phenylphenyl)carbonyloxy)pentan-2-yl 4-phenylbenzoate in 16.4 mL of acetonitrile and 21 mL of tetrahydrofuran at 25° C., 1.2 mL of N-methylimidazole was added dropwise thereto at 10° C. or lower, and the resultant product was stirred at 10° C. for 2 hours. 0.04 mL of methanesulfonyl chloride and 0.18 mL of N-methylimidazole were additionally added thereto, and the resultant product was further stirred for 2 hours. 150 mL of ethyl acetate and 150 mL of water were added to the reaction mixture, and then, the aqueous layer was removed. After the organic layer was washed sequentially two times with a 10% sodium chloride aqueous solution, once with 1 N hydrochloric acid water, once with a sodium hydrogen carbonate aqueous solution, and once with a saturated sodium chloride aqueous solution, and dried over anhydrous sodium sulfate, the solvent was distilled off under reduced pressure. The obtained residue was purified by column chromatography (eluent: ethyl acetate/hexane=1/3→1/2), whereby 4.2 g of (2S,3R,4S)-4-(methanesulfonyloxy)-1-(methoxyimino)-3,5-bis((4-phenylphenyl)carbonyloxy)pentan-2-yl 4-phenylbenzoate was obtained as a white amorphous material. As a result of $^1$H-NMR measurement, the above-obtained material was an oxime isomer mixture of about 70:30.

$^1$H-NMR (CDCl$_3$) δ value: 3.09(0.9H,s),3.15(2.1H,s), 3.87(2.1H,s),4.00(0.9H,s),4.59-4.68(1H,m),4.87-4.93(1H, m),5.47-5.57(1H,m),6.10(0.7H,s),6.10(0.7H,dd,J=5.4,14.3 Hz),6.18(0.3H, dd,J=4.1,6.0 Hz),6.47(0.3H,dd,J=4.1,5.2 Hz),6.79 (0.3H,d,J=5.2 Hz),7.39-7.71(21.7H,m),8.10-8.19 (6H,m)

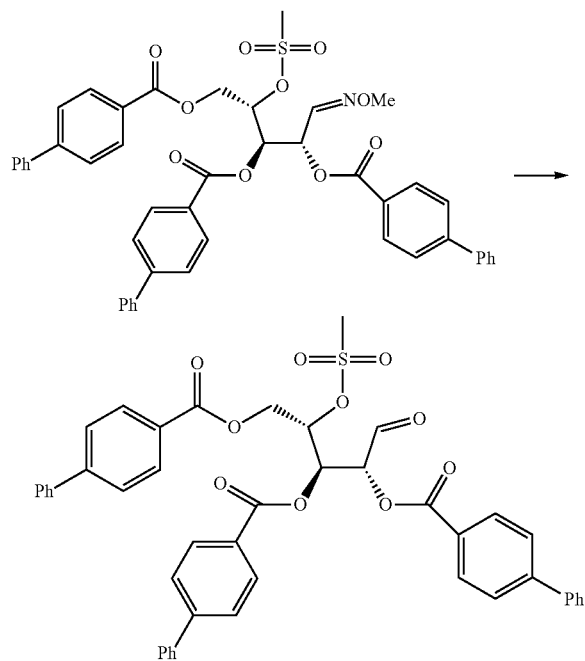

3.8 mL of a 50% glyoxylic acid aqueous solution was added to a solution of 3.4 g of (2S,3R,4S)-4-(methanesulfonyloxy)-1-(methoxyimino)-3,5-bis((4-phenylphenyl)carbonyloxy)pentan-2-yl 4-phenylbenzoate in 20 mL of acetonitrile, and the resultant product was stirred at 75° C. for 5 hours. The reaction mixture was cooled to room temperature, then, 40 mL of ethyl acetate and 30 mL of water were added thereto, and the aqueous layer was removed. After the organic layer was washed sequentially three times with a 10% sodium chloride aqueous solution, once with a sodium hydrogen carbonate aqueous solution, and three times with a saturated sodium chloride aqueous solution, and dried over anhydrous sodium sulfate, the solvent was distilled off under reduced pressure. The obtained residue was purified by column chromatography (eluent: ethyl acetate/hexane=1/2→1/1), whereby 2.1 g of (2R,3R,4S)-4-(methanesulfonyloxy)-1-oxo-3,5-bis((4-phenylphenyl)carbonyloxy)pentan-2-yl 4-phenylbenzoate was obtained as a white amorphous material.

$^1$H-NMR (CDCl$_3$) δ value: 3.11(3H,s),4.64(1H,dd,J=5.7, 12.7 Hz),4.96(1H,dd,J=3.0, 12.7 Hz),5.56-5.61(1H,m),5.81(1H,d,J=2.6 Hz),6.15(1H,dd,J=2.6,7.2 Hz),7.40-7.73(21H, m),8.11-8.23(6H,m),9.75(1H,s)

Example 10

[A] Synthesis of (3R,4R,5R)-2,4-bis((naphthalen-2-yl)carbonyloxy)-5-[((naphthalen-2-yl)carbonyloxy)methyl]thiolan-3-yl naphthalene-2-carboxylate By reacting (2R,3R,4S)-4-(methanesulfonyloxy)-1-oxo-3,5-bis((naphthalen-2-yl)carbonyloxy)pentan-2-yl naphthalene-2-carboxylate with a 15% sodium hydrogen sulfide in the following manner, (3R,4R,5R)-2-hydroxy-4-((naphthalen-2-yl)carbonyloxy)-5-(((naphthalen-2-yl)carbonyloxy)methyl)thiolan-3-yl naphthalene-2-carboxylate was obtained, and by further reacting this with (naphthalen-2-yl)carbonyl chloride, (3R,4R,5R)-2,4-bis((naphthalen-2-yl)carbonyloxy)-5-[((naphthalen-2-yl)carbonyloxy)methyl]thiolan-3-yl naphthalene-2-carboxylate was synthesized.

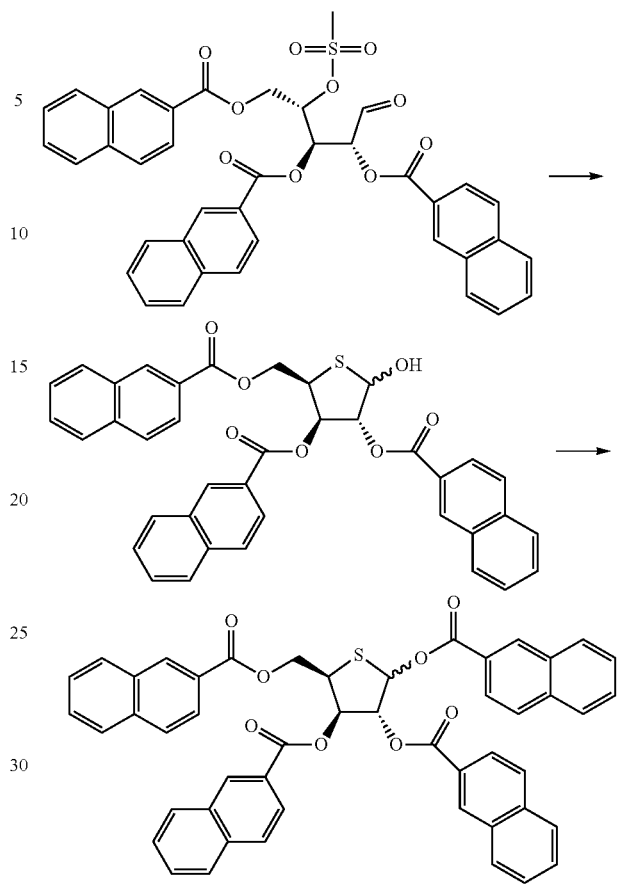

3.7 mL of a 15% sodium hydrogen sulfide aqueous solution was added dropwise to a solution of 4.6 g of (2R,3R,4S)-4-(methanesulfonyloxy)-1-oxo-3,5-bis((naphthalen-2-yl)carbonyloxy)pentan-2-yl naphthalene-2-carboxylate in 93 mL of N,N-dimethylformamide at 10° C. or lower, and the resultant product was stirred at 25° C. for 1 hour. 150 mL of ethyl acetate and 150 mL of a saturated sodium chloride aqueous solution were added to the reaction mixture, and then, the aqueous layer was removed. After the organic layer was washed sequentially three times with a sodium hydrogen carbonate aqueous solution and once with a saturated sodium chloride aqueous solution, the resultant product was dried over anhydrous sodium sulfate. The solvent was distilled off under reduced pressure, whereby a crude product of (3R,4R,5R)-2-hydroxy-4-((naphthalen-2-yl)carbonyloxy)-5-(((naphthalen-2-yl)carbonyloxy)methyl)thiolan-3-yl naphthalene-2-carboxylate was obtained.

After 5 mg of N,N-dimethyl-4-aminopyridine was added to a solution of 134 mg of the obtained crude product in 1.3 mL of pyridine, 81 mg of (naphthalen-2-yl)carbonyl chloride was added thereto at 10° C. or lower, and the resultant product was stirred at 25° C. for 18 hours. 30 mL of ethyl acetate and 30 mL of 1 N hydrochloric acid water were added to the reaction mixture, and then, the aqueous layer was removed. After the organic layer was washed sequentially with 1 N hydrochloric acid water, a sodium hydrogen carbonate aqueous solution, and a saturated sodium chloride aqueous solution, and dried over anhydrous sodium sulfate, the solvent was distilled off under reduced pressure. The obtained residue was purified by column chromatography (eluent: ethyl acetate/hexane=1/2), whereby 130 mg of (3R,4R,5R)-2,4-bis((naphthalen-2-yl)carbonyloxy)-5-[((naphthalen-2-yl)carbonyloxy)methyl]thiolan-3-yl naphthalene-2-carboxylate was obtained as a white amorphous material.

As a result of ¹H-NMR measurement, the above-obtained material was an anomer mixture of about 71:29.

¹H-NMR(CDCl₃)δ value: 4.33-4.39(0.71H,m),4.56-4.64 (1H,m),4.77-4.86(1H, m),4.99 (0.29H,dd,J=7.4,11.4 Hz), 6.19-6.22(0.29H,m),6.33-6.42(1.42H,m),6.51-6.52(0.58H, m),6.74 (0.71H,d,J=4.2 Hz),7.24-8.12(24H,m), 8.37-8.69 (4H,m)

[B] Synthesis of Raw Material

Moreover, (2R,3R,4S)-4-(methanesulfonyloxy)-1-oxo-3,5-bis((naphthalen-2-yl)carbonyloxy)pentan-2-yl naphthalene-2-carboxylate which was a raw material was synthesized through a plurality of steps in the following manner.

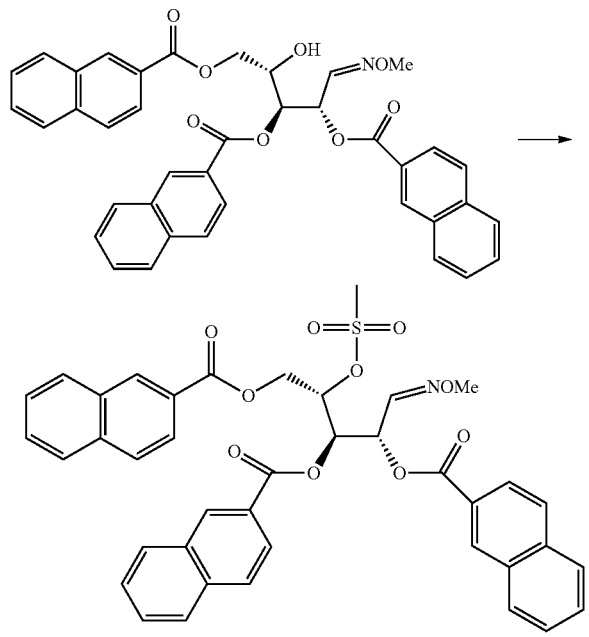

After 1.2 mL of methanesulfonyl chlorid was added to a solution of 6.5 g of (2S,3S,4S)-4-hydroxy-1-(methoxyimino)-3,5-bis((naphthalen-2-yl)carbonyloxy)pentan-2-yl naphthalene-2-carboxylate in 65 mL of acetonitrile at 25° C., 2.3 mL of triethylamine was added dropwise thereto at 10° C. or lower, and the resultant product was stirred at 10° C. for 3 hours. 150 mL of ethyl acetate and 150 mL of water were added to the reaction mixture, and then, the aqueous layer was removed. After the organic layer was washed sequentially two times with a 10% sodium chloride aqueous solution, once with 1 N hydrochloric acid water, once with a sodium hydrogen carbonate aqueous solution, and once with a saturated sodium chloride aqueous solution, and dried over anhydrous sodium sulfate, the solvent was distilled off under reduced pressure, whereby 8.4 g of a crude product of (2S,3R,4S)-4-(methanesulfonyloxy)-1-(methoxyimino)-3,5-bis((naphthalen-2-yl)carbonyloxy) pentan-2-yl naphthalene-2-carboxylate was obtained as a white amorphous material. The crude product was used in the next step without purification. As a result of ¹H-NMR measurement, the above-obtained crude product was an oxime isomer mixture of about 67:33.

¹H-NMR(CDCl₃) δ value: 3.08(0.99H,s),3.15(2.01H,s), 3.87(2.01H,s),3.99(0.99H,s),4.69-4.78(1H,m),4.96-5.04 (1H,m),5.55-5.60(0.33H,m),5.62-5.67(0.67H,m),6.17-6.24 (1.34H,m),6.26(0.33H,dd,J=4.2,5.5 Hz),6.56(0.33H,dd, J=4.3,5.2 Hz),6.88(0.33H,d,J=5.2 Hz),7.49-7.63(6.67H,m), 7.81-7.95(9H,m),8.02-8.12(3H,m),8.62-8.68(3H,m)

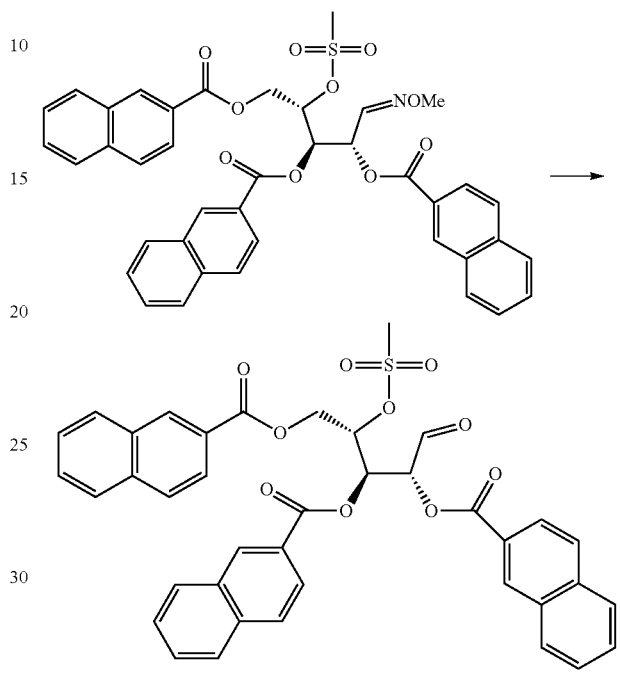

9.0 mL of a 50% glyoxylic acid aqueous solution was added to a solution of 7.2 g of the crude product of (2S,3R,4S)-4-(methanesulfonyloxy)-1-(methoxyimino)-3,5-bis((naphthalen-2-yl)carbonyloxy) pentan-2-yl naphthalene-2-carboxylate in 36 mL of acetonitrile, and the resultant product was stirred at 75° C. for 6 hours. The reaction mixture was cooled to room temperature, then, 300 mL of ethyl acetate and 100 mL of water were added thereto, and the aqueous layer was removed. After the organic layer was washed sequentially three times with a 10% sodium chloride aqueous solution, once with a sodium hydrogen carbonate aqueous solution, and three times with a saturated sodium chloride aqueous solution, and dried over anhydrous sodium sulfate, the solvent was distilled off under reduced pressure. The obtained residue was purified by column chromatography (eluent: ethyl acetate/hexane=1/2→1/1), whereby 5.4 g of (2R,3R,4S)-4-(methanesulfonyloxy)-1-oxo-3,5-bis ((naphthalen-2-yl)carbonyloxy)pentan-2-yl naphthalene-2-carboxylate was obtained as a white amorphous material.

¹H-NMR (CDCl₃) δ value: 3.09(3H,s),4.75(1H,dd,J=6.0, 12.6 Hz),5.04(1H,dd,J=3.1,12.6 Hz),5.70(1H,m),5.92(1H,d, J=2.8 Hz),6.22(1H,dd,J=2.8,6.6 Hz),7.46-8.15(18H,m),8.62 (1H,s),8.68(1H,s),8.72(1H,s),9.82(1H,s)

Example 11

[A] (3S,4S,5S)-2-hydroxy-4-(4-methylbenzoyloxy)-5-[(4-methylbenzoyloxy)methyl]thiolan-3-yl 4-methylbenzoate and acetylated product thereof By reacting (2R,3S,4S)-2-((methanesulfonyl)oxy)-5-oxo-pentane-1,3,4-triyl tris(4-methylbenzoate) with hydrate of sodium hydrogen sulfide in the following manner, (3S,4S,5S)-2-hydroxy-4-(4-methylbenzoyloxy)-5-[(4-methylbenzoyloxy)methyl]thiolan-3-yl 4-methylbenzoate and an acetylated product thereof were synthesized.

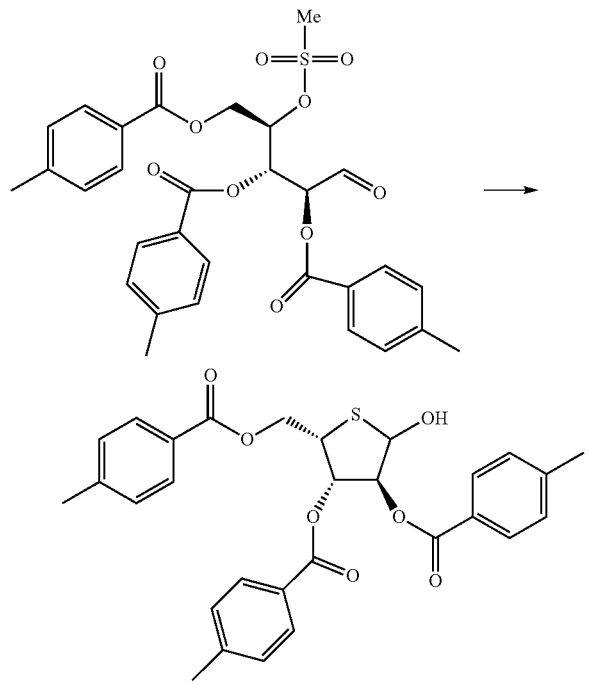

187 mg of sodium monohydrogen sulfide n-hydrate was added to a solution of 0.972 g of (2R,3S,4S)-2-((methanesulfonyl)oxy)-5-oxopentane-1,3,4-triyl tris(4-methylbenzoate) in 14.7 mL of N,N-dimethylformamide under ice-cooling, and the resultant product was stirred for 1 hour under ice-cooling. Thereafter, the resultant product was stirred at room temperature for 1 hour. Ethyl acetate and a saline solution were added to the reaction mixture. After the organic layer was collected by separation, the organic layer was washed with a saturated saline solution, and dried over anhydrous sodium sulfate. The solvent was distilled off under reduced pressure, whereby a crude product of (3S,4S,5S)-2-hydroxy-4-(4-methylbenzoyloxy)-5-[(4-methylbenzoyloxy)methyl]thiolan-3-yl 4-methylbenzoate was obtained.

LC/MS

Retention time: 1.99 minutes, 2.02 minutes

[M+H–H₂O] 503.4

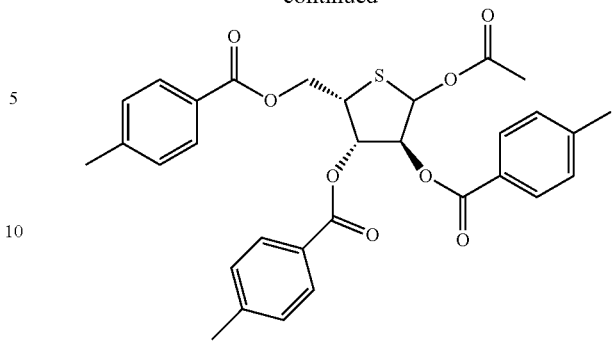

8.7 mL of tetrahydrofuran, 0.237 mL of acetic anhydride, 0.417 mL of triethylamine, and 4-dimethylaminopyridine (one piece) were added to the obtained crude product of (3S,4S,5S)-2-hydroxy-4-(4-methylbenzoyloxy)-5-[(4-methylbenzoyloxy)methyl]thiolan-3-yl 4-methylbenzoate, and the resultant product was stirred at room temperature for 2.5 hours. Ethyl acetate and water were added to the reaction mixture. After the organic layer was collected by separation, the organic layer was washed with a saturated saline solution and dried over anhydrous sodium sulfate, and the solvent was distilled off under reduced pressure. The obtained residue was purified by silica gel column chromatography (hexane/ethyl acetate=95:5 to 60:40). Methanol was added to the obtained solid, and the resultant product was stirred. The solid was collected by filtration, whereby 146 mg of (3S,4S,5S)-2-(acetyloxy)-4-(4-methylbenzoyloxy)-5-[(4-methylbenzoyloxy)methyl]thiolan-3-yl 4-methylbenzoate was obtained as a brown solid. As a result of ¹H-NMR measurement, the above-obtained solid was a substantially single anomer.

LC/MS

Retention time: 2.17 minutes

[M+H–AcOH] 503.4

¹H-NMR (CDCl₃) δ value: 2.08(1H,s),2.34(3H,s),2.38(3H,s),2.38(3H,s),4.15-4.23(1H,m),4.37-4.43(1H,m),4.54-4.60(1H,m),5.94(1H,dd,J=4.5,10.5 Hz),6.06(1H,dd,J=7.6,17.7 Hz),6.31(1H,d,J=4.5 Hz),7.10-7.24(6H,m), 7.75-7.92(6H,m)

[B] 4-Amino-1-[(2S,3S,4S,5S)-3,4-dihydroxy-5-(hydroxymethyl)thiolan-2-yl]-1,2-dihydropyrimidine-2-one 4-Amino-1-[(2S,3S,4S,5S)-3,4-dihydroxy-5-(hydroxymethyl)thiolan-2-yl]-1,2-dihydropyrimidine-2-one was synthesized in the following manner.

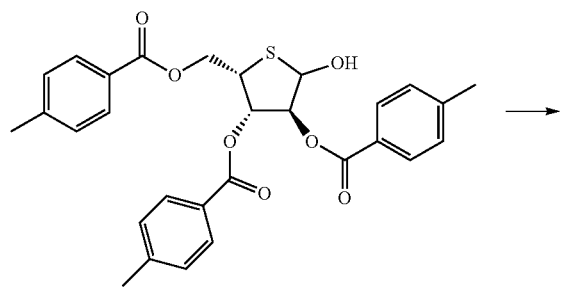

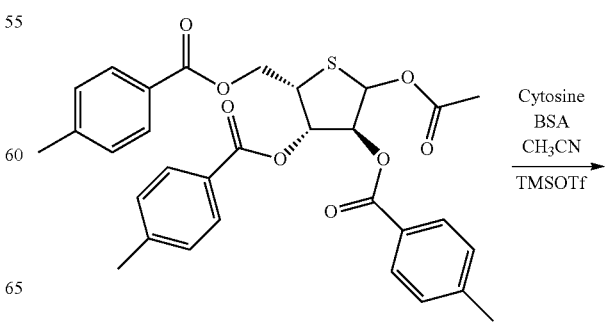

-continued

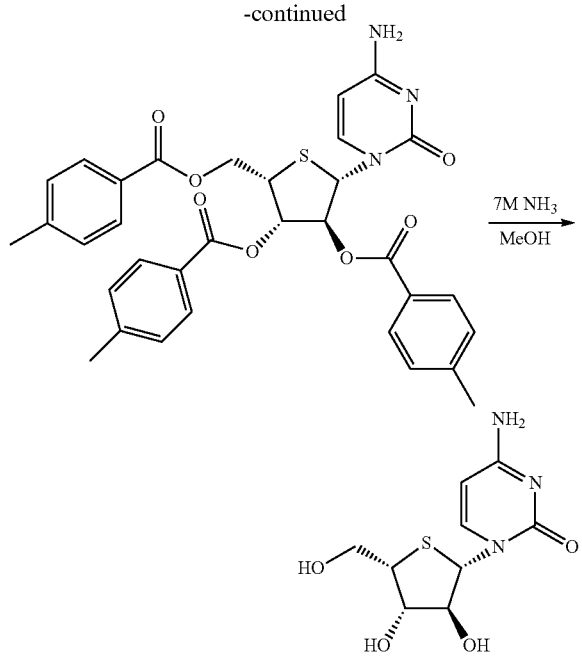

11.9 mg of cytosine and 0.070 mL of N,O-bis(trimethylsilyl)acetamide were added to a solution of 40.2 mg of (3S,4S,5S)-2-(acetyloxy)-4-((4-methylphenyl)carbonyloxy)-5-[((4-methylphenyl)carbonyloxy)methyl]thiolan-3-yl 4-methylbenzoate in 0.8 mL of acetonitrile, and the resultant product was stirred at 70° C. for 1 hour in a nitrogen atmosphere. 0.026 mL of trimethylsilyl trifluoromethanesulfonate was added thereto, followed by stirring at 70° C. for 7 hours, and 0.026 mL of trimethylsilyl trifluoromethanesulfonate was further added thereto, followed by stirring at 70° C. for 3.5 hours. Ethyl acetate and water were added to the reaction mixture, and then, the aqueous layer was removed. The organic layer was dried over anhydrous sodium sulfate, and the solvent was concentrated under reduced pressure. The obtained residue was purified by silica gel column chromatography (eluent: ethyl acetate/hexane=4/1 →1/0 to methanol/ethyl acetate=0/1→1/9), whereby 38.7 mg of [(2S,3S,4S,5S)-5-(4-amino-2-oxo-1,2-dihydropyrimidin-1-yl)-3,4-bis[(4-methylphenyl)carbonyloxy]thiolan-2-yl]methyl 4-methylbenzoate was obtained as a brown solid. As a result of $^1$H-NMR measurement, the above-obtained solid was a substantially single anomer. By the NOESY spectrum, the three-dimension of the anomeric position was determined to be S.

LC/MS

Retention time: 1.77 minutes

[M+H] 614.5

$^1$H-NMR (CD$_3$OD) δ value: 2.34(3H,s),2.37(3H,s),2.39 (3H,s),4.28-4.36(1H,m),4.62(1H,dd,J=11.9,4.0 Hz),4.91 (1H,d,J=6.6 Hz),5.79(1H,d,J=7.3 Hz),5.97(1H,dd,J=7.9,6.6 Hz),6.23(1H,t,J=7.3 Hz),6.47(1H,d,J=6.6 Hz),7.8(6H,t, J=8.6 Hz),7.26(6H,d,J=7.9 Hz),7.78(4H,t,J=8.6 Hz),7.88 (2H,d,J=7.9 Hz),8.12(1H,d,J=7.9 Hz)

0.046 mL of a 7 M ammonia-methanol solution was added to a solution of 19.8 mg of [(2S,3S,4S,5S)-5-(4-amino-2-oxo-1,2-dihydropyrimidin-1-yl)-3,4-bis[(4-methylphenyl)carbonyloxy]thiolan-2-yl]methyl 4-methylbenzoate in 0.4 mL of methanol, and the resultant product was stirred at room temperature for 1.5 hours. 0.46 mL of a 7 M ammonia-methanol solution was further added thereto, and the resultant product was stirred for 4 hours. The solvent of the reaction mixture was concentrated under reduced pressure. The obtained residue was purified by silica gel column chromatography (eluent: methanol/ethyl acetate=0/1→1/1), whereby 4.0 mg of 4-amino-1-[(2S,3S,4S,5S)-3,4-dihydroxy-5-(hydroxymethyl)thiolan-2-yl]-1,2-dihydropyrimidine-2-one was obtained as a brown solid.

LC/MS

Retention time: 0.21 minutes

[M+H] 260.2

$^1$H-NMR (CD$_3$OD) δ value: 3.73-3.81(1H,m),3.84-4.02 (2H,m),4.17-4.25(2H,m),5.86(1H,d,J=7.3 Hz),5.95(1H,d, J=3.3 Hz),8.37(1H,d,J=7.3 Hz)

[C] Synthesis of Raw Material

Moreover, (2R,3S,4S)-2-((methanesulfonyl)oxy)-5-oxopentane-1,3,4-triyl tris(4-methylbenzoate) which was a raw material was synthesized through a plurality of steps in the following manner.

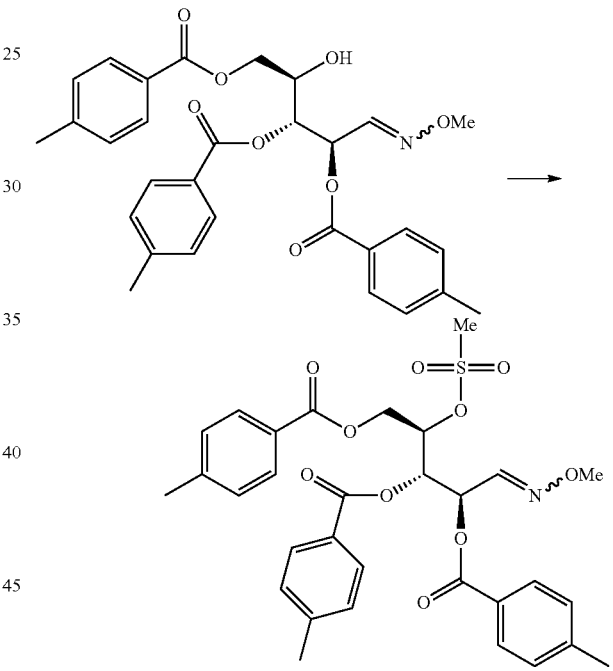

After 0.183 mL of methanesulfonyl chloride and 0.217 mL of 1-methylimidazole were added to a solution of 0.97 g of (2R,3R,4R)-2-hydroxy-5-(methoxyimino)pentane-1,3, 4-triyl tris(4-methylbenzoate) in 9.7 mL of acetonitrile at room temperature, the resultant product was stirred at room temperature for 12.5 hours. Ethyl acetate and water were added to the reaction mixture. After the organic layer was collected by separation, the organic layer was washed with a saturated saline solution and dried over anhydrous sodium sulfate, and the solvent was distilled off under reduced pressure. The obtained residue was purified by silica gel column chromatography (hexane:ethyl acetate=90:10 to 50:50), whereby 1.02 g of (2R,3S,4R)-5-(methoxyimino)-2-((methanesulfonyl)oxy)pentane-1,3,4-triyl tris(4-methylbenzoate) was obtained as a white foamy material. As a result of $^1$H-NMR measurement, the above-obtained material was an oxime isomer of about 68:32.

LC/MS
Retention time: 2.05 minutes
[M+H] 612.5
$^1$H-NMR (CDCl$_3$) δ value: 2.35-2.45(9H,m),3.02(0.96H, s),3.08(2.04H,s),3.83(2.04H,s),3.95(0.96H,s),4.49-4.61(1H, m),4.76-4.88(1H,m),5.36-5.56(1H,m),5.97-6.11(1.68H,m), 6.35-6.41(0.32H,m),6.72(0.32H,d,J=5.3 Hz),7.17-7.31(6H, m),6.72(0.68H,d,J=5.3 Hz),7.88-8.01(6H,m)

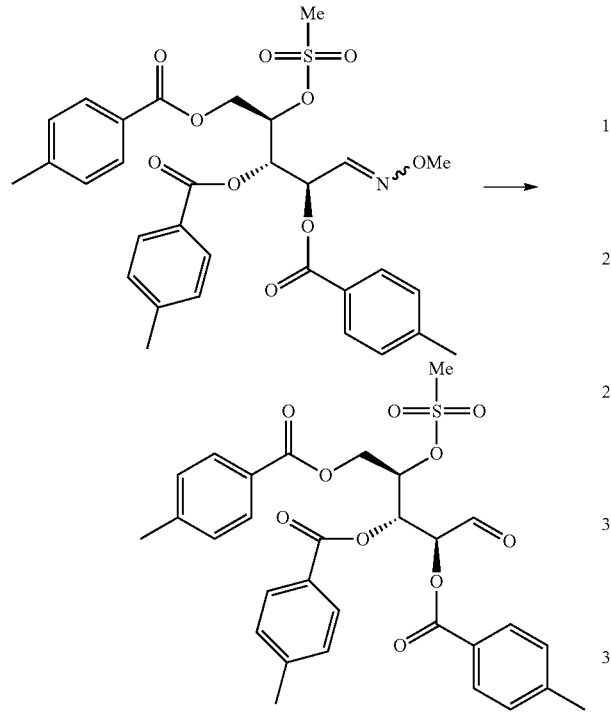

2 mL of 35% formaldehyde liquid and 1.2 mL of 4 N hydrochloric acid were added to a solution of 1.02 g of (2R,3S,4R)-5-(methoxyimino)-2-((methanesulfonyl)oxy) pentane-1,3,4-triyl tris(4-methylbenzoate)(E/Z mixture) in 10 mL of acetone at room temperature, and the resultant product was stirred at room temperature for 3.5 hours. Ethyl acetate and water were added to the reaction mixture. After the organic layer was collected by separation, the organic layer was washed with a saturated sodium hydrogen carbonate aqueous solution, and dried over anhydrous sodium sulfate. The solvent was distilled off under reduced pressure, whereby 0.97 g of a crude product of (2R,3S,4S)-2-((methanesulfonyl)oxy)-5-oxopentane-1,3,4-triyl tris(4-methylbenzoate) was obtained as a white foamy material. The crude product was used as a raw material without further purification.
LC/MS
Retention time: 1.90 minutes
[M+H]:583.4

Example 12

[A] (2R,3R,4R)-4-(benzyloxy)-5-hydroxy-2-((4-methylbenzoyloxy)methyl)thiolan-3-yl 4-methylbenzoate and acetylated product thereof By reacting (2S,3R,4R)-4-(benzyloxy)-2-bromo-3-(4-methylbenzoyloxy)-5-oxopentyl 4-methylbenzoate with sodium hydrogen sulfide in the following manner, (2R,3R, 4R)-4-(benzyloxy)-5-hydroxy-2-((4-methylbenzoyloxy) methyl)thiolan-3-yl 4-methylbenzoate was synthesized.

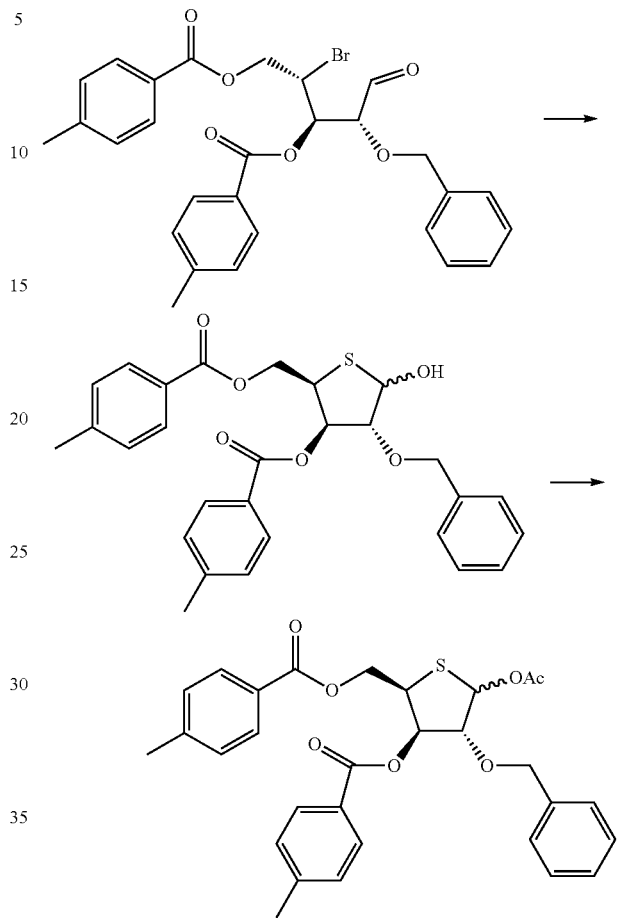

A solution of 1.1 g of sodium hydrogen sulfide in 50 mL of N-methylpyrrolidone was added dropwise to a solution of 4.3 g of the crude product of (2S,3R,4R)-4-(benzyloxy)-2-bromo-3-(4-methylbenzoyloxy)-5-oxopentyl 4-methylbenzoate in 50 mL of N-methylpyrrolidone under ice-cooling, and the resultant product was stirred at room temperature for 3.5 hours. 300 mL of ethyl acetate, 400 mL of water, and 200 mL of a saturated sodium chloride aqueous solution were added to the reaction mixture, and then, the aqueous layer was removed. After the organic layer was dried over anhydrous sodium sulfate, the solvent was distilled off under reduced pressure, and 50 mL of tetrahydrofuran was added to the obtained residue, whereby a solution of (2R,3R,4R)-4-(benzyloxy)-5-hydroxy-2-((4-methylbenzoyloxy)methyl) thiolan-3-yl 4-methylbenzoate in tetrahydrofuran was obtained.

After 3.0 mL of triethylamine and 1.0 mL of acetic anhydride were added to this solution, 0.07 g of N,N-dimethyl-4-aminopyridine was added thereto, and the resultant product was stirred at room temperature for 2 hours. The reaction mixture was distilled off under reduced pressure, and the obtained residue was purified by column chromatography (eluent: ethyl acetate/hexane=0/1→1/4), whereby 2.4 g of (2R,3R,4R)-5-(acetyloxy)-4-(benzyloxy)-2-((4-methylbenzoyloxy)methyl)thiolan-3-yl 4-methylbenzoate was obtained as a pale yellow amorphous material. As a result of $^1$H-NMR measurement, the above-obtained material was an anomer mixture of about 74:26.

$^1$H-NMR (CDCl$_3$) δ value: 1.94(2.22H,s),2.16(0.78H,s),2.33-2.48(6H,m),4.17-4.32(1H,m),4.37-4.58(1H,m),4.58-4.78(3H,m),5.71(0.74H,dd,J=4.6,5.3 Hz),5.77(0.26H,dd,J=7.6,9.6 Hz),6.04(0.74H,d,J=2.0 Hz),6.16(0.26H,d,J=4.0 Hz),7.04-7.37(9H,m),7.76-7.95(4H,m)

[B] Synthesis of Raw Material

Moreover, (2S,3R,4R)-4-(benzyloxy)-2-bromo-3-(4-methylbenzoyloxy)-5-oxopentyl 4-methylbenzoate which was a raw material was synthesized through a plurality of steps in the following manner.

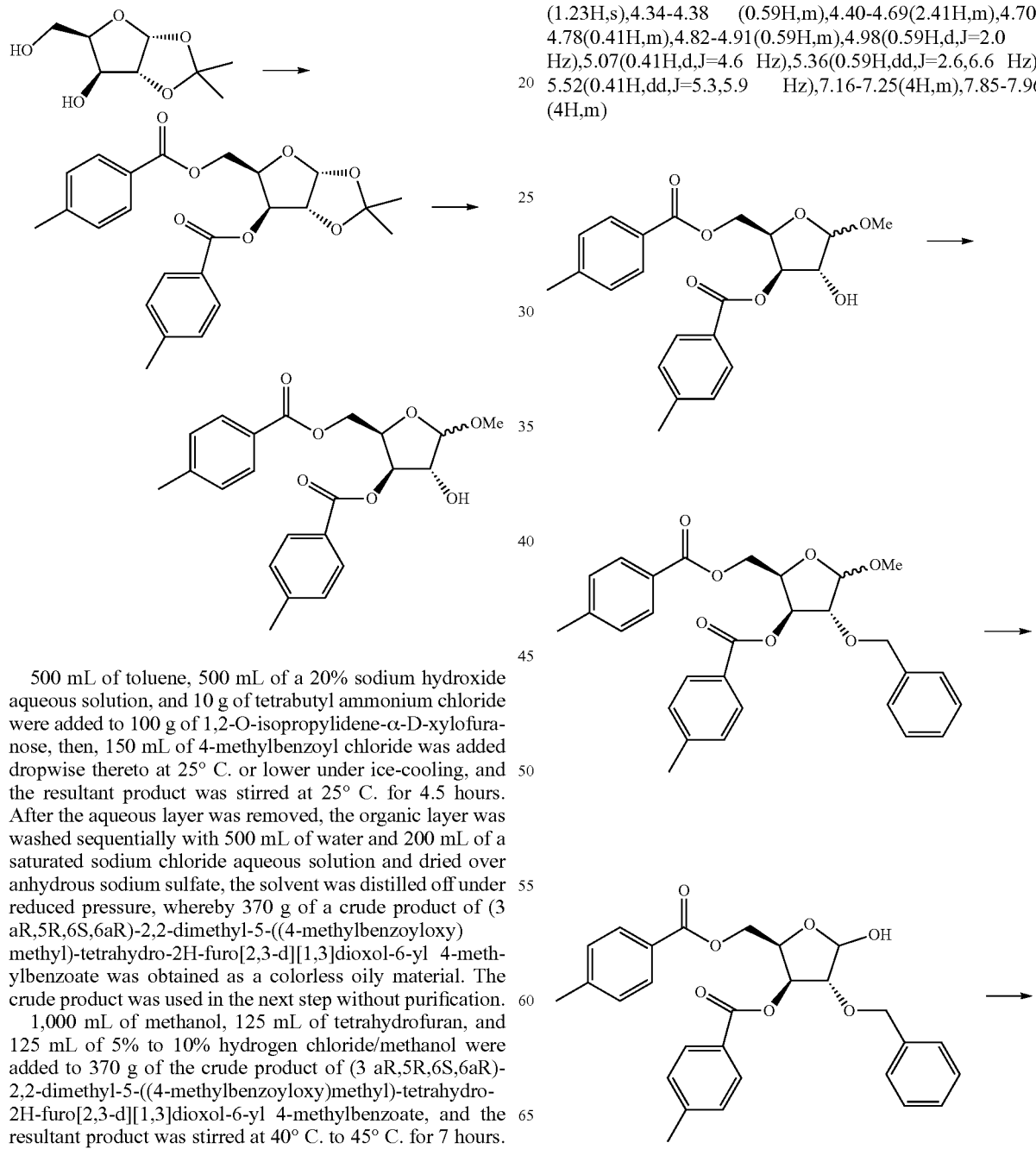

500 mL of toluene, 500 mL of a 20% sodium hydroxide aqueous solution, and 10 g of tetrabutyl ammonium chloride were added to 100 g of 1,2-O-isopropylidene-α-D-xylofuranose, then, 150 mL of 4-methylbenzoyl chloride was added dropwise thereto at 25° C. or lower under ice-cooling, and the resultant product was stirred at 25° C. for 4.5 hours. After the aqueous layer was removed, the organic layer was washed sequentially with 500 mL of water and 200 mL of a saturated sodium chloride aqueous solution and dried over anhydrous sodium sulfate, the solvent was distilled off under reduced pressure, whereby 370 g of a crude product of (3 aR,5R,6S,6aR)-2,2-dimethyl-5-((4-methylbenzoyloxy)methyl)-tetrahydro-2H-furo[2,3-d][1,3]dioxol-6-yl 4-methylbenzoate was obtained as a colorless oily material. The crude product was used in the next step without purification.

1,000 mL of methanol, 125 mL of tetrahydrofuran, and 125 mL of 5% to 10% hydrogen chloride/methanol were added to 370 g of the crude product of (3 aR,5R,6S,6aR)-2,2-dimethyl-5-((4-methylbenzoyloxy)methyl)-tetrahydro-2H-furo[2,3-d][1,3]dioxol-6-yl 4-methylbenzoate, and the resultant product was stirred at 40° C. to 45° C. for 7 hours. After the reaction mixture was distilled off under reduced pressure, 1,000 mL of toluene was added thereto, then, the organic layer was washed sequentially with 500 mL of water, 500 mL of a saturated sodium hydrogen carbonate aqueous solution, 500 mL of water, and 200 mL of a saturated sodium chloride aqueous solution, and dried over anhydrous sodium sulfate. The solvent was distilled off under reduced pressure, whereby 215 g of a crude product of (2R,3R,4R)-4-hydroxy-5-methoxy-2-((4-methylbenzoyloxy)methyl)oxolan-3-yl 4-methylbenzoate was obtained as a colorless oily material. The crude product was used in the next step without purification. As a result of $^1$H-NMR measurement, the above-obtained crude product was an anomer mixture of about 59:41.

$^1$H-NMR (CDCl$_3$) δ value: 2.40(6H,s),2.85(0.59H,d,J=3.3 Hz),2.97(0.41H,d,J=7.3 Hz),3.45(1.77H,s),3.54(1.23H,s),4.34-4.38 (0.59H,m),4.40-4.69(2.41H,m),4.70-4.78(0.41H,m),4.82-4.91(0.59H,m),4.98(0.59H,d,J=2.0 Hz),5.07(0.41H,d,J=4.6 Hz),5.36(0.59H,dd,J=2.6,6.6 Hz),5.52(0.41H,dd,J=5.3,5.9 Hz),7.16-7.25(4H,m),7.85-7.96 (4H,m)

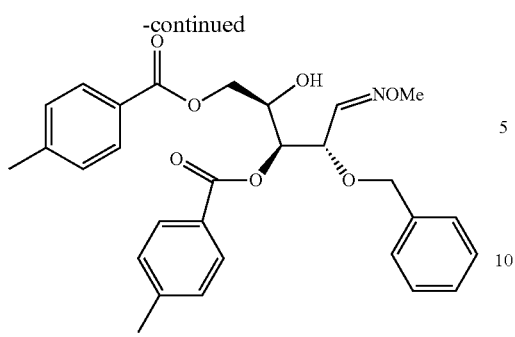

25 g of benzyl 2,2,2-trichloroacetimidate and 0.6 mL of trifluoromethanesulfonic acid were added to a solution of the crude product of (2R,3R,4R)-4-hydroxy-5-methoxy-2-((4-methylbenzoyloxy)methyl)oxolan-3-yl 4-methylbenzoate in 100 mL of dichloromethane, and the resultant product was stirred at room temperature for 4 hours. After the reaction mixture was allowed to stand at room temperature for 12 hours, 100 mL of dichloromethane and 200 mL of water were added thereto, and the aqueous layer was removed. The organic layer was washed sequentially with a saturated sodium hydrogen carbonate aqueous solution, water, and a saturated sodium chloride aqueous solution, and dried over anhydrous sodium sulfate. The solvent was distilled off under reduced pressure, whereby 47.3 g of a crude product of (2R,3S,4R)-4-(benzyloxy)-5-methoxy-2-((4-methylbenzoyloxy)methyl)oxolan-3-yl 4-methylbenzoate was obtained as a yellow oily material. As a result of $^1$H-NMR measurement, the above-obtained crude product was an anomer mixture of about 57:43. The crude product was used in the next step without purification.

100 mL of acetic acid and 90 mL of 2 M hydrochloric acid were added to 47 g of the crude product of (2R,3S,4R)-4-(benzyloxy)-5-methoxy-2-((4-methylbenzoyloxy)methyl)oxolan-3-yl 4-methylbenzoate, and the resultant product was heated and stirred at 90° C. for 3.5 hours. 400 mL of ethyl acetate and 400 mL of water were added to the reaction mixture, and then, the aqueous layer was removed. The organic layer was washed sequentially with water, a saturated sodium hydrogen carbonate aqueous solution, water, and a saturated sodium chloride aqueous solution, and dried over anhydrous sodium sulfate. After the solvent was distilled off under reduced pressure, 100 mL of methanol was added to the obtained residue, whereby a solution of (2R,3S,4R)-4-(benzyloxy)-5-hydroxy-2-((4-methylbenzoyloxy)methyl)oxolan-3-yl 4-methylbenzoate in methanol was obtained.

13.4 mL of triethylamine and 10.4 g of O-methylhydroxylamine hydrochloride were added to this solution, and the resultant product was stirred at room temperature for 1 hour. After the solvent was distilled off under reduced pressure, 200 mL of ethyl acetate and 200 mL of water were added to the obtained residue, and the aqueous layer was removed. The organic layer was washed with a saturated sodium chloride aqueous solution, dried over anhydrous sodium sulfate, and the solvent was distilled off under reduced pressure. The obtained residue was purified by column chromatography (eluent: ethyl acetate/hexane=0/1 →1/4), whereby 10.5 g of (2R,3S,4S)-4-(benzyloxy)-2-hydroxy-5-(methoxyimino)-3-(4-methylbenzoyloxy)pentyl 4-methylbenzoate was obtained as a colorless oily material. As a result of $^1$H-NMR measurement, the above-obtained material was an oxime isomer mixture of about 80:20.

$^1$H-NMR (CDCl$_3$) δ value: 2.36-2.44(6H,m),2.89-2.94 (0.8H,m),3.01-3.05(0.2H,m),3.78(0.6H,s),3.87(2.4H,s), 4.27-4.51(4H,m),4.56-4.74(1.8H,m),5.09(0.20H,dd,J=5.3, 6.6 Hz),5.50(0.8H,dd,J=2.0,5.9 Hz),5.56(0.2H,dd,J=2.6,5.3 Hz),6.85(0.2H,d,J=6.6 Hz),7.13-7.34(9H,m),7.44(0.80H,d, J=7.9 Hz),7.80-8.00(4H,m)

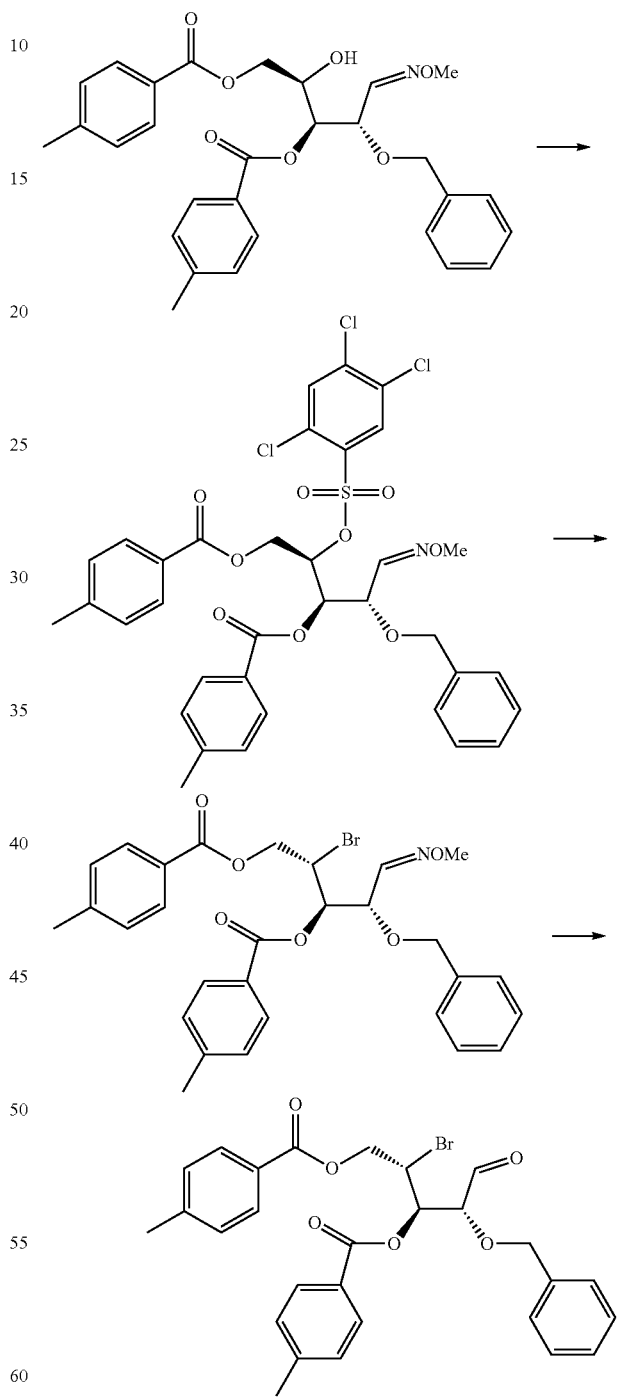

7.8 g of 2,4,5-trichlorobenzenesulfonyl chloride and 3.0 g of N-methylimidazole were added to a solution of 9.5 g of (2R,3S,4S)-4-(benzyloxy)-2-hydroxy-5-(methoxyimino)-3-(4-methylbenzoyloxy)pentyl 4-methylbenzoate in 100 mL of acetonitrile under ice-cooling, and the resultant product was stirred at room temperature for 1.5 hours. 500 mL of ethyl acetate and 300 mL of water were added to the reaction mixture, and then, the aqueous layer was removed. After the organic layer was washed with a saturated sodium chloride aqueous solution and dried over anhydrous sodium sulfate, the solvent was distilled off under reduced pressure, and 50 mL of 1,2-dimethylimidazole was added to the obtained residue, whereby a solution of (2R,3R,4S)-4-(benzyloxy)-5-(methoxyimino)-3-(4-methylbenzoyloxy)-2-((2,4,5-trichlorobenz enesulfonyl)oxy)pentyl 4-methylbenzoate in 1,2-dimethylimidazole was obtained.

1.6 g of lithium bromide was added to this solution, and the resultant product was stirred at 50° C. to 60° C. for 4 hours. 200 mL of ethyl acetate, 100 mL of water, and 100 mL of a saturated sodium chloride aqueous solution were added to the reaction mixture, and then, the aqueous layer was removed. The organic layer was washed with a 25% lithium bromide aqueous solution and dried over anhydrous sodium sulfate, and the solvent was distilled off under reduced pressure. The obtained residue was purified by column chromatography (eluent: ethyl acetate/hexane=0/1→1/4), whereby 5.8 g of (2S,3R,4S)-4-(benzyloxy)-2-bromo-5-(methoxyimino)-3-(4-methylbenzoyloxy)pentyl 4-methylbenzoate was obtained as a brown oily material.

6 mL of a 35% formaldehyde aqueous solution and 0.6 mL of concentrated hydrochloric acid were added to a solution of 5.8 g of (2S,3R,4S)-4-(benzyloxy)-2-bromo-5-(methoxyimino)-3-(4-methylbenzoyloxy)pentyl 4-methylbenzoate in 60 mL of acetone, and the resultant product was stirred at 40° C. to 50° C. for 1 hour. 200 mL of ethyl acetate and 200 mL of a saturated sodium hydrogen carbonate aqueous solution were added to the reaction mixture under ice-cooling, and then, the aqueous layer was removed. After the organic layer was washed with water and a saturated sodium chloride aqueous solution, the organic layer was dried over anhydrous sodium sulfate, and the solvent was distilled off under reduced pressure, whereby 4.3 g of a crude product of (2S,3R,4R)-4-(benzyloxy)-2-bromo-3-(4-methylbenzoyloxy)-5-oxopentyl 4-methylbenzoate was obtained as a pale yellow oily material. The crude product was used as a raw material without further purification.

Example 13

[A] (2S,3S,4S)-3-(benzoyloxy)-4-fluoro-5-hydroxy-thiolan-2-yl)methyl benzoate and acetylated product thereof By reacting (2R,3R,4S)-3-(benzoyloxy)-4-fluoro-2-(methanesulfonyloxy)-5-oxopentyl benzoate with 15% sodium hydrogen sulfide in the following manner, (2S,3S,4S)-3-(benzoyloxy)-4-fluoro-5-hydroxythiolan-2-yl)methyl benzoate was synthesized.

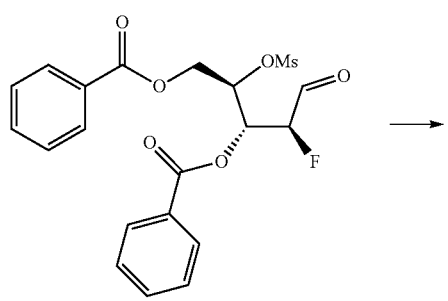

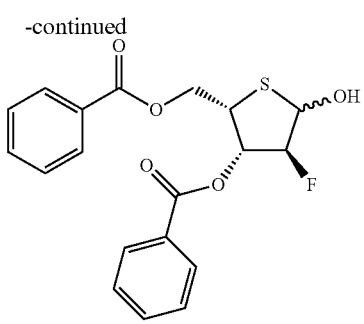

1.27 mL of a 15% sodium hydrogen sulfide aqueous solution was added to a solution of 1.0 g of ((2R,3R,4S)-3-(benzoyloxy)-4-fluoro-2-(methanesulfonyloxy)-5-oxo-pentyl benzoate in 20 mL of N,N-dimethylformamide at 0° C. to 10° C., and the resultant product was stirred at room temperature for 2 hours. Ethyl acetate and a saturated sodium chloride aqueous solution were added to the reaction mixture, and the organic layer was collected by separation. The organic layer was washed with a saturated sodium chloride aqueous solution, and dried over anhydrous magnesium sulfate. The solvent was distilled off under reduced pressure, and the obtained residue was purified by silica gel column chromatography, whereby 0.52 g of ((2S,3S,4S)-3-(benzoyloxy)-4-fluoro-5-hydroxythiolan-2-yl)methyl benzoate was obtained as a colorless oily material.

$^1$H-NMR (CDCl$_3$) δ value: 8.04-7.87(4H,m),7.63-7.50 (2H,m),7.48-7.34(4H,m),5.98(0.44H,dq,J=6.0,8.7 Hz),5.91 (0.56H,ddd,J=4.2,5.1,10.8 Hz),5.65(0.44H,ddd,J=3.9,8.1, 9.6 Hz),5.56(0.56H,ddd,J=1.1,8.7,13.1 Hz),5.35(0.56H,ddd, J=1.6,3.5,47.8 Hz),5.22(0.44H,ddd,J=3.9,6.1,50.6 Hz),4.67 (1.12H,d,J=6.9 Hz),4.55-4.33(1.32H,m),4.28(0.56H,dd, J=6.9,12.3 Hz),2.73(0.44H,dd,J=2.4,8.1 Hz),2.52(0.56H,d, J=8.7 Hz)

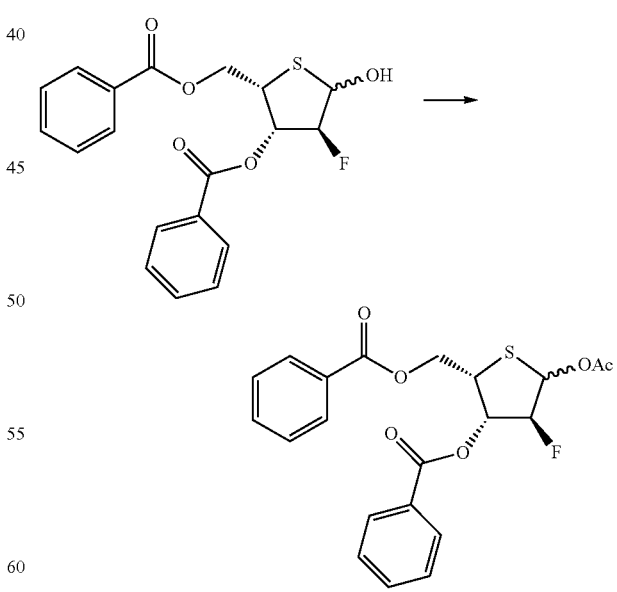

1.5 mL of pyridine, 0.85 mL of acetic anhydride, and 50 mg of N,N-dimethyl-4-aminopyridine were added to a solution of 1.74 g of ((2S,3S,4S)-3-(benzoyloxy)-4-fluoro-5-hydroxythiolan-2-yl)methyl benzoate in 20 mL of ethyl acetate at 0° C. to 10° C., and the resultant product was allowed to stand at room temperature for 17 hours. The reaction mixture was concentrated under reduced pressure, and the obtained residue was purified by silica gel column chromatography, whereby 1.50 g of ((2S,3S,4S)-5-(acetyloxy)-3-(benzoyloxy)-4-fluorothiolan-2-yl)methyl benzoate was obtained as a colorless oily material.

$^1$H-NMR (CDCl$_3$) δ value: 8.07-7.95(3.12H,m),7.87-7.81 (0.88H,m),7.62-7.30(6H,m),6.20(0.44H,dd,J=2.2,4.5 Hz), 6.11(0.56H,dd,J=2.4,16.5 Hz),6.01-5.90(0.44H,m),5.91-5.82(0.56H,m),5.54(0.56H,ddd,J=2.4,5.1,48.9 Hz),5.44 (0.44H,ddd,J=4.5,9.3,50.7 Hz),4.67(0.56H,dd,J=6.9,11.7 Hz),4.58-4.47(1H,m),4.37(0.44H,dd,J=5.1,11.7 Hz),4.24-4.17(1H,m),2.19(1.32H,s),2.01(1.68H,s)

[B] Synthesis of Raw Material

Moreover, (2R,3R,4S)-3-(benzoyloxy)-4-fluoro-2-(methanesulfonyloxy)-5-oxopentyl benzoate which was a raw material was synthesized through a plurality of steps in the following manner.

(Step 1)

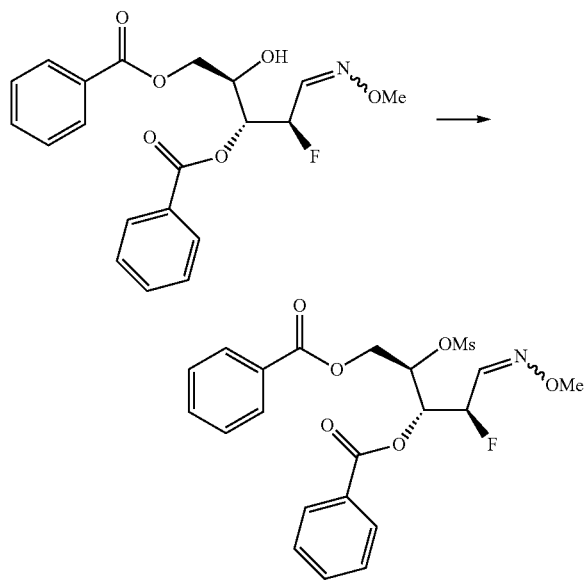

5.0 mL of methanesulfonyl chloride was added dropwise to a mixed solution of 12.8 g of (2R,3R,4R)-3-(benzoyloxy)-4-fluoro-2-hydroxy-5-(methoxyimino)pentyl benzoate in 100 mL of ethyl acetate and 18 mL of triethylamine at 0° C. to 10° C., and the resultant product was stirred at room temperature for 4 hours. Ethyl acetate and water were added to the reaction mixture, and the organic layer was collected by separation. The organic layer was washed sequentially with water and a saturated sodium chloride aqueous solution, and dried over anhydrous magnesium sulfate. The solvent was distilled off under reduced pressure, and the obtained residue was purified by silica gel column chromatography, whereby 14.4 g of (2R,3R,4R)-3-(benzoyloxy)-4-fluoro-2-(methanesulfonyloxy)-5-(methoxyimino)pentyl benzoate was obtained as a colorless oily material.

$^1$H-NMR (CDCl$_3$) δ value: 8.11-8.03(4H,m),7.66-7.55 (2H,m),7.52-7.38(4.75H,m),6.85(0.25H,dd,J=4.5,11.1 Hz), 6.09-6.00(0.25H,m),5.99-5.74(1H,m),5.56-5.35(1.75H,m), 4.87(0.75H,dd,J=2.8,12.8 Hz),4.86(0.25H, dd,J=2.8,12.8 Hz),4.48(0.75H,dd,J=6.0,12.6 Hz),4.46(0.25H,dd,J=6.6, 12.6 Hz),3.92(0.75H,s),3.85(2.25H,s),3.14(2.25H,s),3.13 (0.75H,s)

(Step 2)

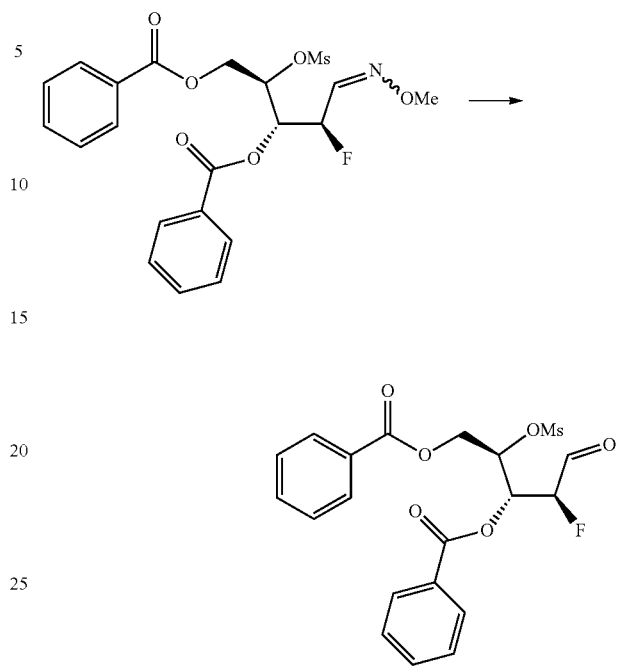

80 mL of a 37% formaldehyde aqueous solution and 1.3 mL of 9% hydrochloric acid were added to a solution of 9.6 g of (2R,3R,4R)-3-(benzoyloxy)-4-fluoro-2-(methanesulfonyloxy)-5-(methoxyimino)pentyl benzoate in 100 mL of acetone at room temperature, and the resultant product was stirred at room temperature for 3 hours. Next, 3.0 mL of 9% hydrochloric acid was added thereto, and the resultant product was stirred for 12 hours. The acetone of reaction mixture was distilled off under reduced pressure, then, ethyl acetate was added to the obtained aqueous solution, and the organic layer was collected by separation. The organic layer was washed sequentially with a saturated sodium chloride aqueous solution, a saturated sodium hydrogen carbonate aqueous solution, and a saturated sodium chloride aqueous solution, and dried over anhydrous magnesium sulfate. The solvent was distilled off under reduced pressure, and the obtained residue was purified by silica gel column chromatography, whereby 8.1 g of (2R,3R,4S)-3-(benzoyloxy)-4-fluoro-2-(methanesulfonyloxy)-5-oxopentyl benzoate was obtained as a colorless oily material.

$^1$H-NMR (CDCl$_3$) δ value: 9.75(1H,d,J=6.9 Hz),8.10-8.00(4H,m),7.66-7.55(2H,m),7.51-7.41(4H,m),5.93(1H, ddd,J=1.9,7.1,24.8 Hz),5.47(1H,ddd,J=2.8,5.8,7.1 Hz),5.30 (1H,dd,J=1.9,46.4 Hz),4.91(1H,dd,J=2.8,12.9 Hz), 4.48(1H, dd,J=5.8,12.9 Hz),3.14(3H,s)

Example 14

[A] ((2S)-5-hydroxythiolan-2-yl)methyl 4-methylbenzoate and acetylated product thereof By reacting (2R)-2-bromo-5-oxopentyl 4-methylbenzoate with 15% sodium hydrogen sulfide in the following manner, ((2S)-5-hydroxythiolan-2-yl)methyl 4-methylbenzoate was synthesized.

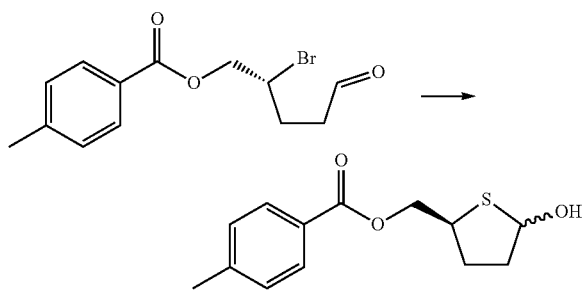

0.78 mL of a 15% sodium hydrogen sulfide aqueous solution was added to a solution of 0.32 g of (2R)-2-bromo-5-oxopentyl 4-methylbenzoate in 5 mL of N,N-dimethylformamide at 0° C. to 10° C., and the resultant product was stirred at 0° C. to 10° C. for 2 hours. Ethyl acetate and a saturated sodium chloride aqueous solution were added to the reaction mixture, and the organic layer was collected by separation. The organic layer was washed with a saturated sodium chloride aqueous solution, and dried over anhydrous magnesium sulfate. The solvent was distilled off under reduced pressure, and the obtained residue was purified by silica gel column chromatography, whereby 0.18 g of ((2S)-5-hydroxythiolan-2-yl)methyl 4-methylbenzoate was obtained as a colorless oily material.

$^1$H-NMR (CDCl$_3$) δ value: 7.96-7.90(2H,m),7.28-7.22 (2H,m),5.63-5.55(1H,m),4.54(0.55H,dd,J=6.6,11.1 Hz), 4.40(0.55H, dd,J=6.9,11.1 Hz),4.27-4.17(0.90H,m),3.99-3.77(1H,m),2.45-1.95(8H,m)

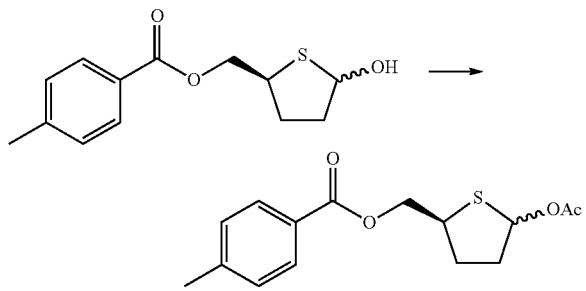

0.3 mL of pyridine, 0.18 mL of acetic anhydride, and 12 mg of N,N-dimethyl-4-aminopyridine were added to a solution of 0.24 g of ((2S)-5-hydroxythiolan-2-yl)methyl 4-methylbenzoate in 10 mL of ethyl acetate at 0° C. to 10° C., and the resultant product was allowed to stand at room temperature for 16 hours. The reaction mixture was concentrated under reduced pressure, and the obtained residue was purified by silica gel column chromatography, whereby 0.29 g of ((2S)-5-(acetyloxy)thiolan-2-yl)methyl 4-methylbenzoate was obtained as a colorless oily material.

$^1$H-NMR (CDCl$_3$) δ value: 7.96-7.89(2H,m),7.27-7.20 (2H,m),6.20-6.14(1H,m),4.54(0.52H,dd,J=6.4,11.1 Hz), 4.33(0.52H, dd,J=7.2,11.1 Hz),4.28-4.16(0.96H,m),3.91-3.75(1H,m),2.43-1.89(10H,m)

[B] Synthesis of Raw Material

Moreover, (2R)-2-bromo-5-oxopentyl 4-methylbenzoate which was a raw material was synthesized through a plurality of steps in the following manner.

(Step 1)

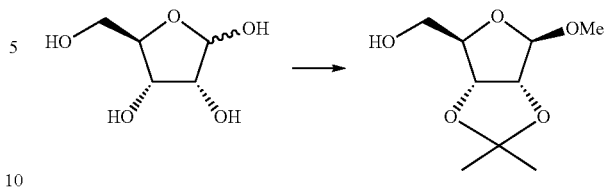

3 mL of concentrated hydrochloric acid was added to a mixed solution of 30 g of (3R,4S,5R)-5-(hydroxymethyl) oxolane-2,3,4-triol (D-ribose) in 120 mL of methanol and 120 mL of acetone at room temperature, and the resultant product was heated to reflux for 90 minutes. 5 mL of triethylamine was added to the reaction mixture, and 100 mL of the solvent was distilled off under reduced pressure. Ethyl acetate was added to the obtained aqueous solution, and the organic layer was collected by separation three times. The collected organic layer was dried over anhydrous magnesium sulfate, and the solvent was distilled off under reduced pressure, whereby 34.5 g of ((3aR,4R,6aR)-6-methoxy-2,2-dimethyl-tetrahydro-2H-furo(3,4-d)(1,3)dioxol-4-yl)methanol was obtained as a pale yellow oily material.

$^1$H-NMR (CDCl$_3$) δ value: 4.98(1H,s),4.84(1H,d,J=5.9 Hz),4.59(1H,d,J=5.9 Hz),4.44(1H,t,J=2.7 Hz),3.74-3.57 (2H,m),3.44(3H,s),3.22(1H,dd,J=2.9,10.4 Hz),1.49(3H,s), 1.32(3H,s)

(Step 2)

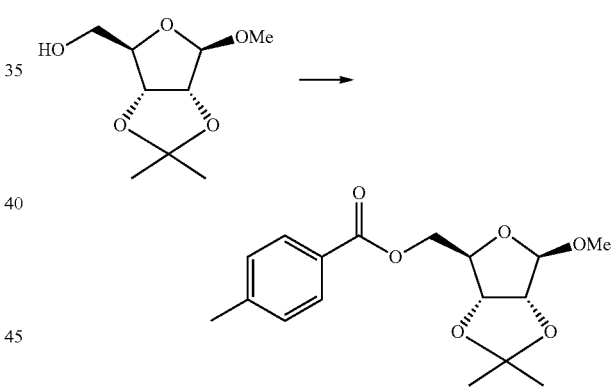

28.3 g of 4-methylbenzoyl chloride and 0.61 g of N,N-dimethyl-4-aminopyridine were added to a mixed solution of 34 g of ((3aR,4R,6aR)-6-methoxy-2,2-dimethyl-tetrahydro-2H-furo(3,4-d)(1,3)dioxol-4-yl)methanol in 200 mL of ethyl acetate and 35 mL of triethylamine at 0° C. to 10° C., and the resultant product was stirred at room temperature for 2 hours. Next, 5 mL of 4-methylbenzoyl chloride and 15 mL of triethylamine were added thereto, and the resultant product was stirred for 3 hours. Ethyl acetate and water were added to the reaction mixture, and the organic layer was collected by separation. The organic layer was washed sequentially with water and a saturated sodium chloride aqueous solution, and dried over anhydrous magnesium sulfate. The solvent was distilled off under reduced pressure, and the obtained residue was purified by silica gel column chromatography, whereby 53 g of ((3aR,4R,6aR)-6-methoxy-2,2-dimethyl-tetrahydro-2H-furo(3,4-d)(1,3)dioxol-4-yl)methyl 4-methylbenzoate was obtained as a pale yellow oily material.

¹H-NMR (CDCl₃) δ value: 7.96(2H,d,J=8.1 Hz),7.24(2H, d,J=8.1 Hz),5.02(1H,s),4.77(1H,dd,J=0.6,6.0 Hz),4.65(1H, d,J=6.0 Hz),4.53(1H, dt, J=0.6,6.9 Hz),4.36(1H,dd,J=6.9, 13.9 Hz),4.32(1H,dd,J=6.9,13.9 Hz),3.34(3H,s), 2.41(3H,s), 1.50(3H,s),1.34(3H,s)
(Step 3)

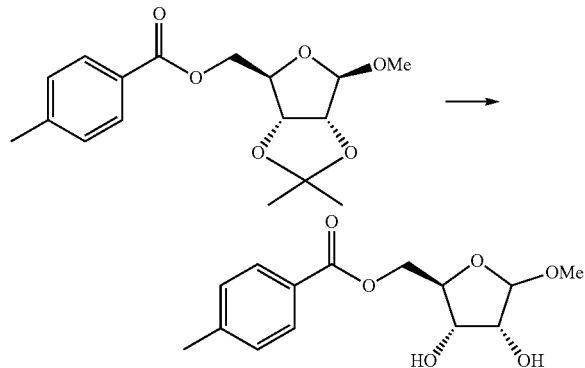

1.16 g of (7,7-dimethyl-2-oxobicyclo(2,2,1)heptan-1-yl) methanesulfonic acid (10-camphorsulfonic acid) was added to a solution of 32.2 g of ((3aR,4R,6aR)-6-methoxy-2,2-dimethyl-tetrahydro-2H-furo(3,4-d)(1,3)dioxol-4-yl)methyl 4-methylbenzoate in 800 mL of methanol, and 400 mL of the solvent was distilled off by heating to reflux. Next, 400 mL of methanol and 10 mL of water were added thereto, and 400 mL of the solvent was distilled off by heating to reflux. Next, 400 mL of methanol was added thereto, and 400 mL of the solvent was distilled off by heating to reflux. 5 g of sodium hydrogen carbonate was added thereto, and the solvent was distilled off under reduced pressure. Next, ethyl acetate and a saturated sodium chloride aqueous solution were added thereto, and the organic layer was collected by separation two times and dried over anhydrous magnesium sulfate. The solvent was distilled off under reduced pressure, and the precipitated solid was washed with ethyl acetate/hexane, whereby 16.3 g of ((2R,3S,4R)-3,4-dihydroxy-5-methoxyoxolan-2-yl)methyl 4-methylbenzoate was obtained as a white solid.

¹H-NMR (CDCl₃) δ value: 7.96(2H,d,J=8.1 Hz),7.24(2H, d,J=8.1 Hz),4.88(1H, br),4.56(1H,dd,J=3.9,11.9 Hz),4.47-4.38(2H,m),4.28-4.21(1H,m),4.11-4.06(1H,m),3.33(3H,s), 2.59(1H,d,J=3.3 Hz),2.53(1H,d,J=7.1 Hz),2.41(3H,s)
(Step 4)

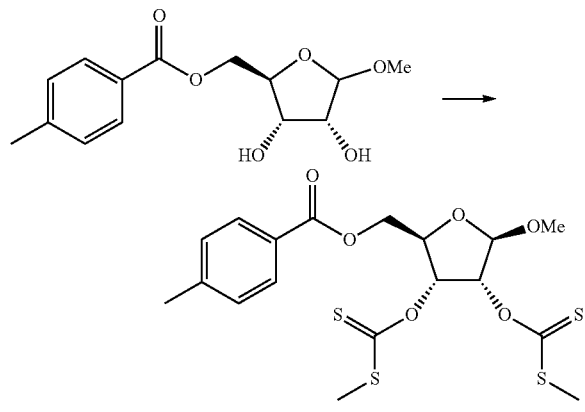

8.0 g of sodium hydride (in oil) was added to a mixed solution of 14.1 g of ((2R,3S,4R)-3,4-dihydroxy-5-methoxyoxolan-2-yl)methyl 4-methylbenzoate in 350 mL of tetrahydrofuran and 30 mL of carbon disulfide at 0° C. to 10° C. over a period of 15 minutes, and the resultant product was stirred at room temperature for 30 minutes. Next, 85.1 g of methyl iodide was added thereto, and the resultant product was stirred for 90 minutes. Ethyl acetate and water were added to the reaction mixture, and the organic layer was collected by separation. The organic layer was washed sequentially with water and a saturated sodium chloride aqueous solution, and dried over anhydrous magnesium sulfate. The solvent was distilled off under reduced pressure, and the obtained residue was purified by silica gel column chromatography, whereby 21.9 g of ((2R,3R,4R)-5-methoxy-3,4-bis(((methylsulfanyl)methanethioyl)oxy)oxolan-2-yl)methyl 4-methylbenzoate was obtained as a pale yellow oily material.

¹H-NMR (CDCl₃) δ value: 7.97(2H,d,J=8.1 Hz),7.24(2H, d,J=8.1 Hz),6.37(1H,dd,J=5.0,6.3 Hz),6.16(1H,dd,J=0.9,5.0 Hz),5.16(1H,d,J=0.9 Hz),4.74-4.68(1H,m),4.62(1H,dd, J=4.1,11.9 Hz),4.45(1H,dd,J=4.7,11.9 Hz),3.38(3H,s),2.59 (3H,s),2.55(3H,s),2.41(3H,s)
(Step 5)

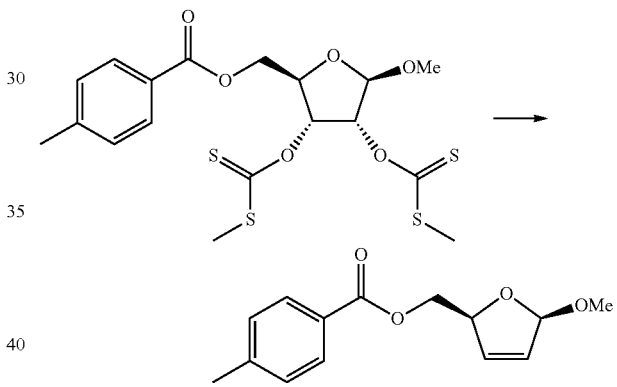

A solution of 35 g of tributyltin hydride and 2 g of 2,2'-azobis(2-methyl propionitrile)(AIBN) in 80 mL of toluene was added dropwise to a solution of 27.8 g of ((2R,3R, 4R)-5-methoxy-3,4-bis(((methylsulfanyl)methanethioyl) oxy)oxolan-2-yl)methyl 4-methylbenzoate in 300 mL of toluene over a period of 75 minutes while heating to reflux, and the resultant product was stirred for 90 minutes while heating to reflux. The reaction mixture was purified by silica gel column chromatography, whereby 13.7 g of ((2S)-5-methoxy-2,5-dihydrofuran-2-yl)methyl 4-methylbenzoate was obtained as a colorless oily material.

¹H-NMR (CDCl₃) δ value: 7.97(2H,d,J=8.1 Hz),7.23(2H, d,J=8.1 Hz),6.23-6.18(1H,m),5.96-5.91(1H,m),5.76-5.73 (1H,m),5.06-4.99(1H,m),4.44(1H,dd,J=4.2,11.6 Hz),4.36 (1H,dd,J=5.6,11.6 Hz),3.41(3H,s),2.41(3H,s)
(Step 6)

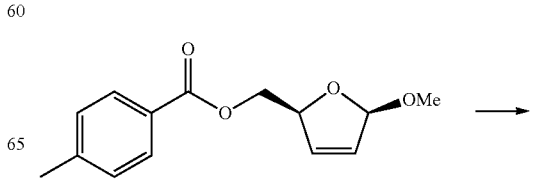

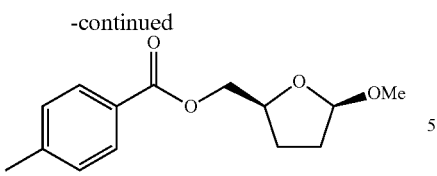

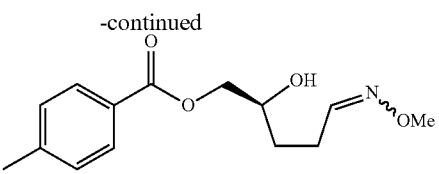

3.6 g of 5% palladium on carbon was added to a mixed solution of 4.2 g of ((2S)-5-methoxy-2,5-dihydrofuran-2-yl)methyl 4-methylbenzoate in 40 mL of propane-2-ol and 10 mL of water, and the resultant product was stirred at room temperature for 19 hours in a hydrogen atmosphere at 1 atm. Next, 1.8 g of 5% palladium on carbon was added thereto, and the resultant was stirred at room temperature for 3 hours in a hydrogen atmosphere at 1 atm. The reaction mixture was filtered using Celite, then, the filtrate was distilled off under reduced pressure, and the obtained residue was purified by silica gel column chromatography, whereby 3.2 g of ((2S)-5-methoxyoxolan-2-yl)methyl 4-methylbenzoate was obtained as a colorless oily material.

$^1$H-NMR (CDCl$_3$) δ value: 7.98(2H,d,J=8.4 Hz),7.24(2H,d,J=8.4 Hz),5.03(1H,d,J=3.6 Hz),4.49-4.24(3H,m),3.24(3H,s),2.41(3H,s),2.11-1.86(4H,m)

(Step 7)

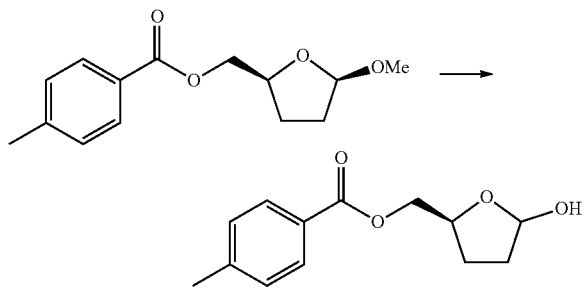

1.26 g of concentrated sulfuric acid was added to a mixed solution of 3.2 g of ((2S)-5-methoxyoxolan-2-yl)methyl 4-methylbenzoate in 130 mL of acetic acid and 130 mL of water at room temperature, and the resultant was stirred at room temperature for 2 hours. Ethyl acetate was added to the reaction mixture, and the organic layer was collected by separation two times. After the organic layer was washed sequentially with a saturated sodium hydrogen carbonate aqueous solution and a saturated sodium chloride aqueous solution, the resultant product was dried over anhydrous magnesium sulfate. The solvent was distilled off under reduced pressure, and the obtained residue was purified by silica gel column chromatography, whereby 2.8 g of ((2S)-5-hydroxyoxolan-2-yl)methyl 4-methylbenzoate was obtained as a colorless oily material.

$^1$H-NMR (CDCl$_3$) δ value: 8.00-7.90(2H,m),7.28-7.20(2H,m),5.64(0.5H,d,J=3.9 Hz),5.46(0.5H,d,J=3.6 Hz),4.64-4.55(0.5H,m),4.47-4.34(2H,m),4.26(0.5H,dd,J=6.0,11.4 Hz),2.72(0.5H, br),2.62(0.5H, br),2.41(3H,s),2.33-1.71(4H,m)

(Step 8)

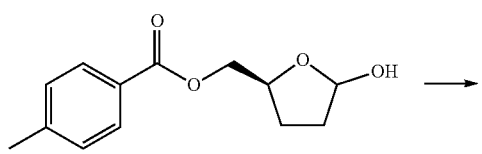

6.2 mL of pyridine, 3.08 g of p-toluenesulfonic acid monohydrate and 1.8 g of O-methylhydroxylamine hydrochloride were added to a solution of 2.8 g of ((2S)-5-hydroxyoxolan-2-yl)methyl 4-methylbenzoate in 20 mL of methanol, and the resultant product was stirred at room temperature for 5 hours. Ethyl acetate and a saturated sodium chloride aqueous solution were added to the reaction mixture, and the organic layer was collected by separation two times. The organic layer was washed sequentially with water and a saturated sodium chloride aqueous solution, and dried over anhydrous magnesium sulfate. The solvent was distilled off under reduced pressure, and the obtained residue was purified by silica gel column chromatography, whereby 2.6 g of (2S)-2-hydroxy-5-(methoxyimino)pentyl 4-methylbenzoate was obtained as a colorless oily material.

$^1$H-NMR (CDCl$_3$) δ value: 7.96-7.90(2H,m),7.44(0.60H,t,J=5.7 Hz),7.28-7.22(2H,m),6.72(0.40H,t,J=5.9 Hz),4.41-4.21(2H,m),4.07-3.92(1H,m),3.88(1.20H,s),3.82(1.80H,s),2.64-2.31(5H,m),1.84-1.67(2H,m)

(Step 9)

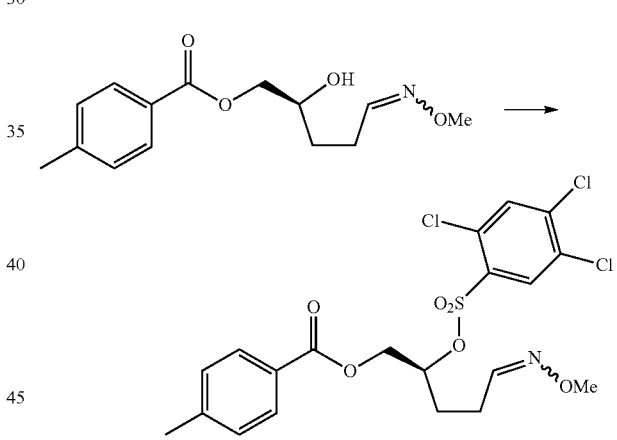

0.62 g of 2,4,5-trichlorobenzenesulfonyl chloride and 0.24 mL of N-methylimidazole were added to a solution of 0.53 g of (2S)-2-hydroxy-5-(methoxyimino)pentyl 4-methylbenzoate in 10 mL of acetonitrile at 0° C. to 10° C., and the resultant product was stirred at room temperature for 3 hours. Next, 0.1 g of 2,4,5-trichlorobenzenesulfonyl chloride was added thereto, and the resultant product was stirred for 1 hour. Next, 0.1 mL of N-methylimidazole and 0.05 g of 2,4,5-trichlorobenzenesulfonyl chloride were added thereto, and the resultant product was stirred for 1 hour. After ethyl acetate and water were added to the reaction mixture, the organic layer was collected by separation, washed with a saturated sodium chloride aqueous solution, and dried over anhydrous magnesium sulfate. The solvent was distilled off under reduced pressure, and the obtained residue was purified by silica gel column chromatography, whereby 0.67 g of (2S)-5-(methoxyimino)-2-((2,4,5-trichlorobenzenesulfonyl)oxy)pentyl 4-methylbenzoate was obtained as a white solid.

¹H-NMR (CDCl₃) δ value: 8.06(1H,s),7.71(2H,d,J=8.1 Hz),7.42-7.36(1.58H,m),7.21(2H,d,J=8.1 Hz),6.70(0.42H,t,J=5.5 Hz),5.11(0.58H,ddd,J=3.3,6.7,12.8 Hz),5.03(0.42H,ddd,J=3.2,6.4,12.8 Hz),4.50-4.34(2H,m),3.87(1.26H,s),3.82(1.74H,s),2.58-2.35(5H,m),2.12-1.98(2H,m)

(Step 10)

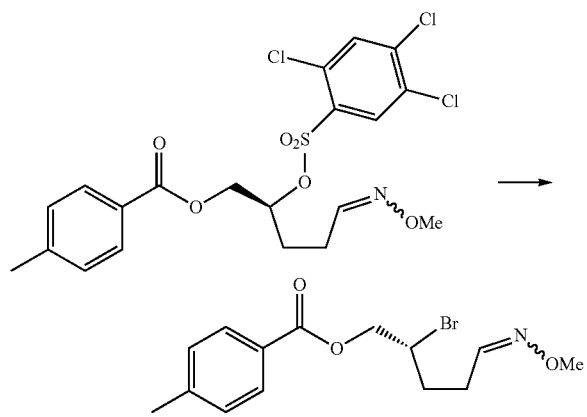

0.23 g of lithium bromide was added to a solution of 0.67 g of (2S)-5-(methoxyimino)-2-((2,4,5-trichlorobenzenesulfonyl)oxy)pentyl 4-methylbenzoate in 2.6 mL of 1,3-dimethyl-2-imidazolidinone three times by being divided at room temperature, and the resultant product was stirred at 40° C. for 2 hours. The reaction mixture was purified by silica gel column chromatography, whereby 0.41 g of (2R)-2-bromo-5-(methoxyimino)pentyl 4-methylbenzoate was obtained as a colorless oily material.

¹H-NMR (CDCl₃) δ value: 7.98-7.92(2H,m),7.41(0.58H,t,J=5.6 Hz),7.29-7.22(2H,m),6.68(0.42H,t,J=5.4 Hz),4.63-4.45(2H,m),4.35-4.17(1H,m),3.87(1.26H,s),3.81(1.74H,s),2.70-1.89(7H,m)

(Step 11)

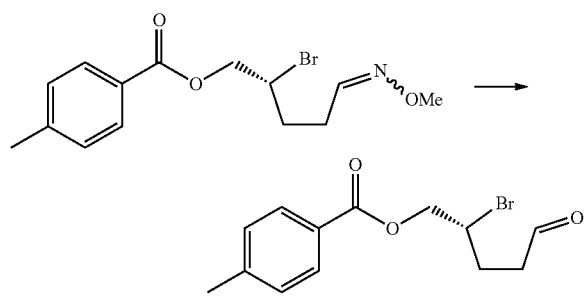

1 mL of a 37% formaldehyde aqueous solution and 0.04 mL of 9% hydrochloric acid were added to a solution of 0.41 g of (2R)-2-bromo-5-(methoxyimino)pentyl 4-methylbenzoate in 6 mL of acetone at room temperature, and the resultant product was stirred at room temperature for 60 minutes. Next, 1 mL of 37% formaldehyde aqueous solution was added thereto, and the resultant product was stirred for 90 minutes. Next, 1 mL of 37% formaldehyde aqueous solution was added thereto, and the resultant product was stirred for 60 minutes. Ethyl acetate and a saturated sodium hydrogen carbonate aqueous solution were added to the reaction mixture, and the organic layer was collected by separation. The organic layer was washed sequentially with water and a saturated sodium chloride aqueous solution, and dried over anhydrous magnesium sulfate. The solvent was distilled off under reduced pressure, and the obtained residue was purified by silica gel column chromatography, whereby 0.33 g of (2R)-2-bromo-5-oxopentyl 4-methylbenzoate was obtained as a colorless oily material.

¹H-NMR (CDCl₃) δ value: 9.84(1H,s),7.95(2H,d,J=8.0 Hz),7.26(2H,d,J=8.0 Hz),4.55(2H,ddd,J=6.3,11.7,28.2 Hz),4.36-4.25(1H,m),2.90-2.68(2H,m),2.46-2.32(4H,m),2.18-2.03(1H,m)

Example 15

[A] ((2S)-5-hydroxythiolan-2-yl)methyl 4-phenylbenzoate and acetylated product thereof By reacting (2R)-2-bromo-5-oxopentyl 4-phenylbenzoate with a sodium hydrogen sulfide aqueous solution in the following manner, ((2S)-5-hydroxythiolan-2-yl)methyl 4-phenylbenzoate was synthesized.

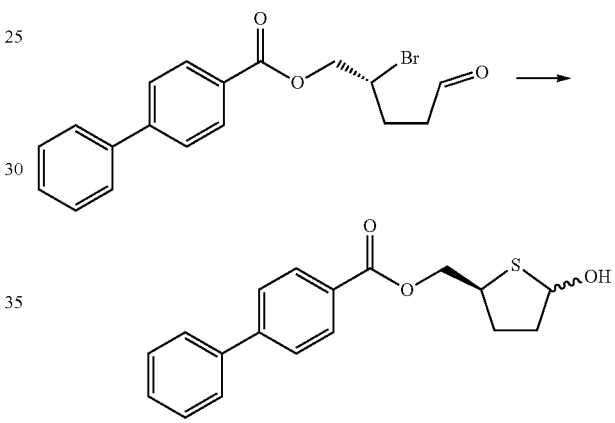

0.3 mL of a 15% sodium hydrogen sulfide aqueous solution was added to a solution of 0.15 g of (2R)-2-bromo-5-oxopentyl 4-phenylbenzoate in 4 mL of N,N-dimethylformamide at 0° C. to 10° C., and the resultant product was stirred at 0° C. to 10° C. for 1 hour and stirred at room temperature for 1 hour. The reaction mixture was purified by silica gel column chromatography, whereby 0.17 g of a mixture of ((2S)-5-hydroxythiolan-2-yl)methyl 4-phenylbenzoate and N,N-dimethylformamide was obtained. The mixture was used in the next step without further purification.

¹H-NMR (CDCl₃) δ value: 8.14-8.08(2H,m),7.70-7.59(4H,m),7.51-7.36(3H,m),5.64-5.56(1H,m),4.58(0.53H,dd,J=6.6,11.1 Hz),4.44(0.53H,dd,J=6.9,11.1 Hz),4.32-4.20(0.94H,m),4.02-3.80(1H,m),2.42-1.97(5H,m)

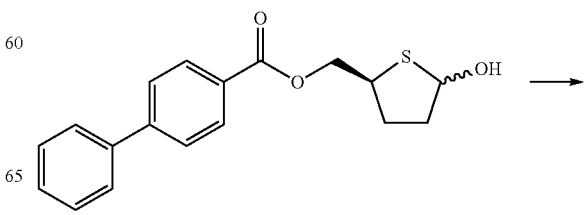

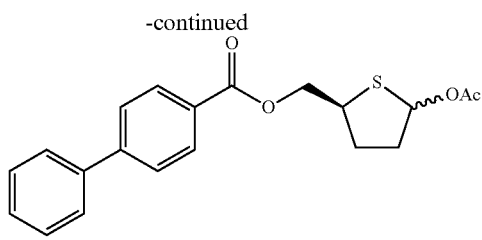

95 µL of acetic anhydride and 6 mg of N,N-dimethyl-4-aminopyridine were added to a mixed solution of 0.15 g of the mixture of ((2S)-5-hydroxythiolan-2-yl)methyl 4-phenylbenzoate and N,N-dimethylformamide in 5 mL of ethyl acetate and 161 µL of pyridine at 0° C. to 10° C., and the resultant product was allowed to stand at room temperature overnight. The reaction mixture was concentrated under reduced pressure, and the obtained residue was purified by silica gel column chromatography, whereby 59 mg of ((2S)-5-(acetyloxy)thiolan-2-yl)methyl 4-phenylbenzoate was obtained as a colorless oily material.

$^1$H-NMR (CDCl$_3$) δ value: 8.14-8.07(2H,m),7.70-7.59(4H,m),7.51-7.36(3H,m),6.21-6.16(1H,m),4.58(0.54H,dd,J=6.4,11.0 Hz),4.42-4.20(1.46H,m),3.94-3.78(1H,m),2.42-1.91(7H,m)

[B] Synthesis of Raw Material

Moreover, (2R)-2-bromo-5-oxopentyl 4-phenylbenzoate which was a raw material was synthesized through a plurality of steps in the following manner.

(Step 1)

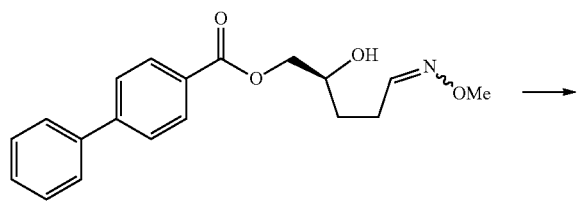

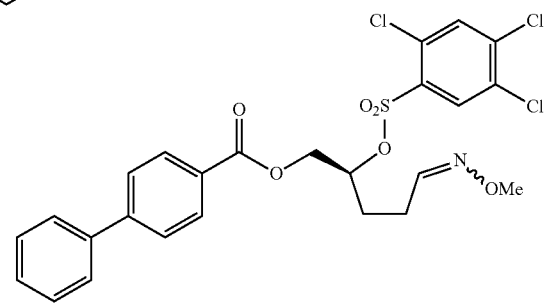

0.24 g of 2,4,5-trichlorobenzenesulfonyl chloride and 96 µL of N-methylimidazole were added to a solution of 0.26 g of (2S)-2-hydroxy-5-(methoxyimino)pentyl 4-phenylbenzoate in 5 mL of acetonitrile at room temperature, and the resultant product was stirred at room temperature for 135 minutes. Next, 0.12 g of 2,4,5-trichlorobenzenesulfonyl chloride and 96 µL of N-methylimidazole were added thereto, and the resultant product was stirred for 75 minutes. After ethyl acetate and water were added to the reaction mixture, the insoluble materials were separated by filtration, and the organic layer was collected by separation. The organic layer was washed with a saturated sodium chloride aqueous solution, and dried over anhydrous magnesium sulfate. The solvent was distilled off under reduced pressure, and the obtained residue was purified by silica gel column chromatography, whereby 0.35 g of (2S)-5-(methoxyimino)-2-((2,4,5-trichlorobenzenesulfonyl)oxy)pentyl 4-phenylbenzoate was obtained.

$^1$H-NMR (CDCl$_3$) δ value: 8.09(1H,s),7.94-7.88(2H,m),7.71-7.60(4H,m),7.52-7.37(4.65H,m),6.70(0.35H,t,J=5.4 Hz),5.19-5.01(1H,m),4.54-4.39(2H,m),3.88(1.05H,s),3.82(1.95H,s),2.63-2.38(2H,m),2.14-1.99(2H,m)

(Step 2)

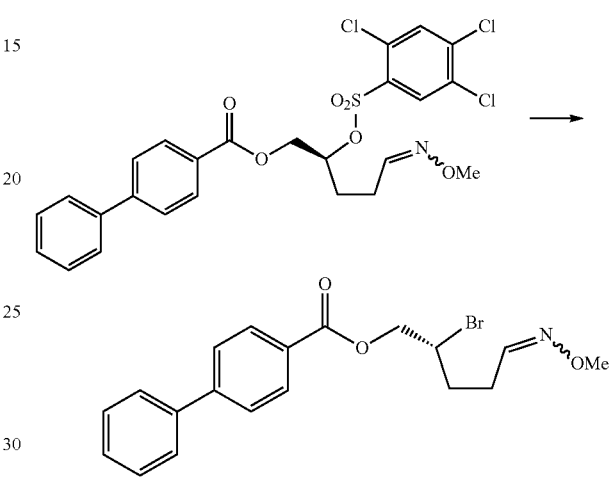

0.11 g of lithium bromide was added to a solution of 0.35 g of (2S)-5-(methoxyimino)-2-((2,4,5-trichlorobenzenesulfonyl)oxy)pentyl 4-phenylbenzoate in 2 mL of 1,3-dimethyl-2-imidazolidinone at room temperature, and the resultant product was stirred at 40° C. for 2 hours. The reaction mixture was purified by silica gel column chromatography, whereby 0.18 g of (2R)-2-bromo-5-(methoxyimino)pentyl 4-phenyl benzoate was obtained as a colorless oily material.

$^1$H-NMR (CDCl$_3$) δ value: 8.16-8.10(2H,m),7.71-7.59(4H,m),7.52-7.37(3.59H,m),6.69(0.41H,t,J=5.5 Hz),4.67-4.49(2H,m), 4.37-4.20(1H,m),3.88(1.23H,s),3.82(1.77H,s),2.71-1.94(4H,m)

(Step 3)

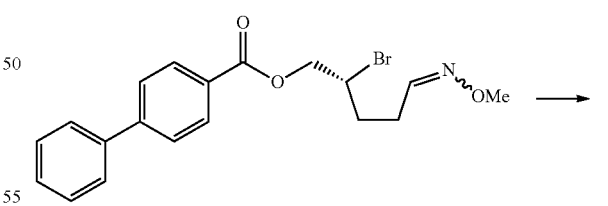

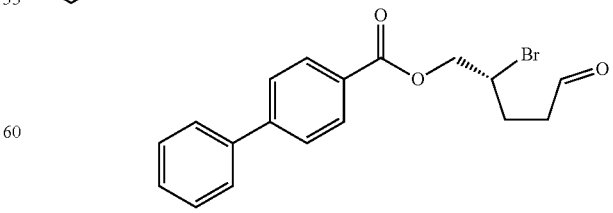

1.83 mL of a 37% formaldehyde aqueous solution and 17 µL of 9% hydrochloric acid were added to a solution of 0.18 g of (2R)-2-bromo-5-(methoxyimino)pentyl 4-phenyl benzoate in 4.6 mL of acetone at room temperature, and the resultant product was stirred at room temperature for 150 minutes. Ethyl acetate and water were added to the reaction mixture, and the organic layer was collected by separation. The organic layer was washed sequentially with water and a saturated sodium chloride aqueous solution, and dried over anhydrous magnesium sulfate. The solvent was distilled off under reduced pressure, and the obtained residue was purified by silica gel column chromatography, whereby 0.15 g of (2R)-2-bromo-5-oxopentyl 4-phenyl benzoate was obtained as a colorless oily material.

$^1$H-NMR (CDCl$_3$) δ value: 9.85(1H,s),8.16-8.09(2H,m), 7.71-7.59(4H,m),7.51-7.37(3H,m),4.68-4.49(2H,m),4.39-4.24(1H,m),2.92-2.70(2H,m),2.48-1.97(2H,m)

Example 16

[A] ((2R)-5-hydroxythiolan-2-yl)methyl benzoate and acetylated product thereof

By reacting (2S)-2-(methanesulfonyloxy)-5-oxopentyl benzoate with hydrate of sodium hydrogen sulfide in the following manner, ((2R)-5-hydroxythiolan-2-yl)methyl benzoate was synthesized.

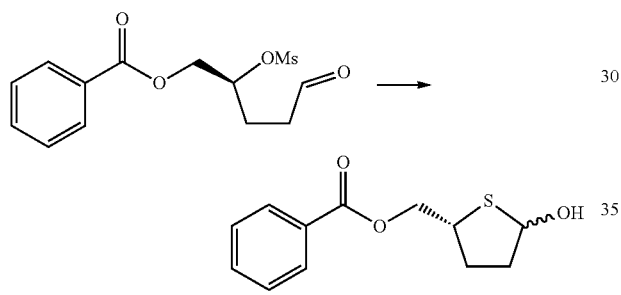

160 mg of hydrate of sodium hydrogen sulfide was added to a solution of 0.3 g of (2S)-2-(methanesulfonyloxy)-5-oxopentyl benzoate in 10 mL of N,N-dimethylformamide at 0° C. to 10° C., and the resultant product was stirred at room temperature for 1 hour. 30 mL of ethyl acetate and a saturated sodium chloride aqueous solution were added to the reaction mixture, and the organic layer was collected by separation. The organic layer was washed with a saturated sodium chloride aqueous solution, and dried over anhydrous magnesium sulfate. The solvent was distilled off under reduced pressure, and the obtained residue was purified by silica gel column chromatography, whereby 0.06 g of ((2R)-5-hydroxythiolan-2-yl)methyl benzoate was obtained as a colorless oily material.

$^1$H-NMR (CDCl$_3$) δ value: 8.08-8.01(2H,m),7.62-7.54 (1H,m),7.48-7.42(2H,m),5.63-5.53(1H,m),4.56(0.53H,dd, J=6.6,11.0 Hz),4.42(0.53H,dd,J=6.9,11.0 Hz),4.30-4.17 (0.94H,m),4.00-3.92(0.47H,m),3.90-3.78(0.53H,m),2.41-1.92(5H,m)

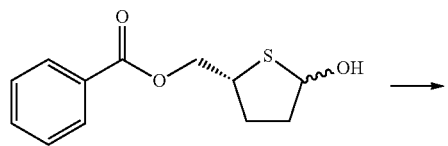

-continued

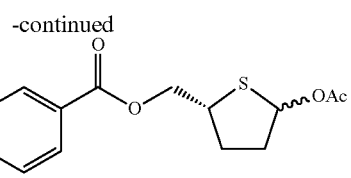

662 μL of acetic anhydride was added to a mixed solution of 0.83 g of ((2R)-5-hydroxythiolan-2-yl)methyl benzoate in 1.13 mL of pyridine and 20 mL of ethyl acetate at 0° C. to 10° C., and the resultant was stirred for 5 minutes. 43 mg of N,N-dimethylaminopyridine was added thereto, and the resultant was stirred at room temperature for 12 hours. Ethyl acetate and water were added to the reaction mixture, and the organic layer was collected by separation. The organic layer was washed with a saturated sodium chloride aqueous solution, and dried over anhydrous magnesium sulfate. The solvent was distilled off under reduced pressure, and the obtained residue was purified by silica gel column chromatography, whereby 0.89 g of ((2R)-5-(acetyloxy)thiolan-2-yl)methyl benzoate was obtained as a colorless oily material.

$^1$H-NMR (CDCl$_3$) δ value: 8.08-8.01(2H,m),7.61-7.53 (1H,m),7.49-7.41(2H,m),6.20-6.14(1H,m),4.56(0.54H,dd, J=6.5,11.0 Hz),4.39-4.18(1.46H,m),3.93-3.76(1H,m),2.41-1.90(7H,m)

[B] Synthesis of Raw Material

Moreover, (2S)-2-(methanesulfonyloxy)-5-oxopentyl benzoate which was a raw material was synthesized through a plurality of steps in the following manner.

(Step 1)

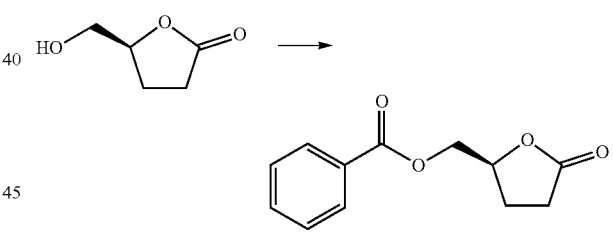

12 mL of benzoyl chloride was added dropwise to a mixed solution of 10 g of (5S)-5-(hydroxymethyl)oxolane-2-one in 100 mL of ethyl acetate and 18 mL of triethylamine at 5° C. to 10° C. in a nitrogen atmosphere, and the resultant product was stirred at room temperature for 60 minutes. Next, 1 g of N,N-dimethylaminopyridine was added thereto, and the resultant was stirred for 60 minutes. After ethyl acetate and water were added thereto, the organic layer was collected by separation, washed with a saturated sodium chloride aqueous solution, and dried over anhydrous magnesium sulfate. The solvent was distilled off under reduced pressure, and the obtained residue was purified by silica gel column chromatography, whereby 19.2 g of ((2S)-5-oxooxolan-2-yl)methyl benzoate was obtained as a white crystal.

$^1$H-NMR (CDCl$_3$) δ value: 8.07-8.01(2H,m),7.63-7.56 (1H,m),7.50-7.43(2H,m),4.93-4.83(1H,m),4.55(1H,dd, J=3.2,12.2 Hz), 4.45(1H,dd,J=5.3,12.2 Hz),2.73-2.07(4H, m)

(Step 2)

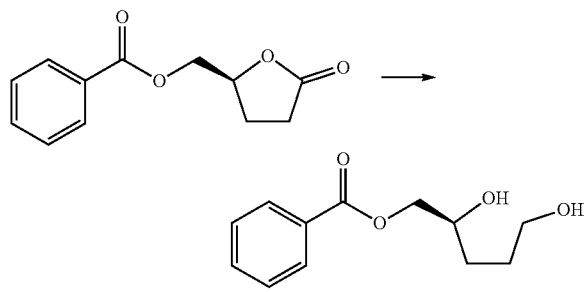

After 3.44 g of sodium tetrahydroborate was added to a mixed solution of 10.0 g of ((2S)-5-oxooxolan-2-yl)methyl benzoate in 50 mL of ethanol and 200 mL of tetrahydrofuran at 0° C. to 10° C. in a nitrogen atmosphere, the resultant product was stirred for 30 minutes, then, a solution of 6.67 g of calcium chloride dihydrate in 50 mL of ethanol was added dropwise thereto, and the resultant product was stirred for 75 minutes. Ice, ammonium chloride, and ethyl acetate were added to the reaction mixture, and the organic layer was collected by separation. The water layer was extracted two times with ethyl acetate, and the collected organic layer was washed with a saturated sodium chloride aqueous solution and dried over anhydrous magnesium sulfate. The solvent was distilled off under reduced pressure, and the obtained residue was purified by silica gel column chromatography, whereby 2.70 g of a mixture (78:22) of (2S)-2,5-dihydroxypentyl benzoate and (2S)-1,5-dihydroxypentan-2-yl benzoate was obtained as a colorless oily material.

¹H-NMR (CDCl₃) δ value: 8.08-8.04(2H,m),7.62-7.55 (1H,m),7.49-7.43(2H,m),5.22(0.22H,ddd,J=3.6,6.1,12.6 Hz),4.40(0.78H,dd,J=3.6,11.4 Hz),4.28(0.78H,dd,J=7.0, 11.4 Hz),4.08-3.99(0.78H,m),3.90-3.67(2.44H,m), 1.92-1.53(4H,m)

(Step 3)

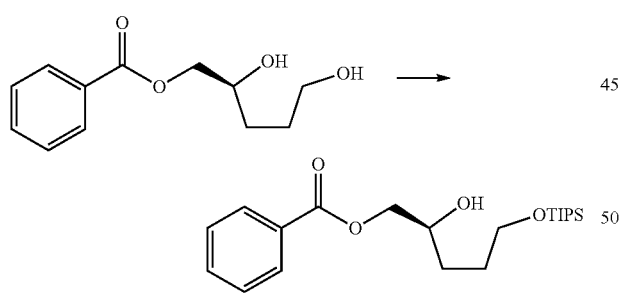

3.35 mL of triisopropylsilyl chloride was added dropwise to a solution of 2.70 g of the mixture (78:28) of (2S)-2,5-dihydroxypentyl benzoate and (2S)-1,5-dihydroxypentan-2-yl benzoate and 1.50 g of imidazole in 30 mL of N,N-dimethylformamide at 5° C. to 10° C. in a nitrogen atmosphere. After the reaction mixture was stirred at room temperature for 16 hours, ethyl acetate and water were added thereto, then, the organic layer was collected by separation, washed sequentially with water and a saturated sodium chloride aqueous solution, and dried over anhydrous magnesium sulfate. The solvent was distilled off under reduced pressure, and the obtained residue was purified by silica gel column chromatography, whereby 3.85 g of (2S)-2-hydroxy-5-((tris(propan-2-yl)silyl)oxy)pentyl benzoate was obtained as a colorless oily material.

¹H-NMR (CDCl₃) δ value: 8.09-8.04(2H,m),7.61-7.54 (1H,m),7.48-7.41(2H,m),4.37(1H,dd,J=4.2,11.3 Hz),4.29 (1H,dd,J=6.3,11.3 Hz),4.08-3.96(1H,m),3.84-3.70(2H,m), 3.16(1H,d,J=4.2 Hz),1.87-1.59(4H,m),1.18-1.01(21H,m)

(Step 4)

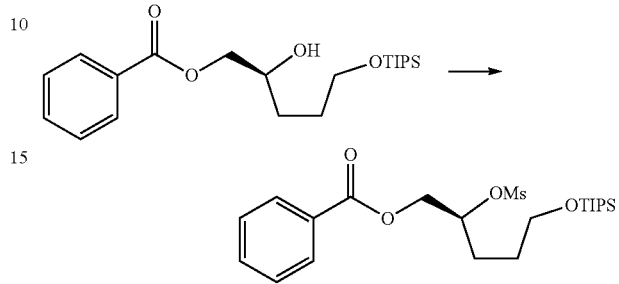

1.24 mL of methanesulfonyl chloride was added dropwise to a solution of 2.98 g of (2S)-2-hydroxy-5-((tris(propan-2-yl)silyl)oxy)pentyl benzoate and 4.5 mL of triethylamine in 60 mL of ethyl acetate at 0° C. to 10° C., and the resultant product was stirred at room temperature for 30 minutes. After ethyl acetate and a saturated sodium chloride aqueous solution were added to the reaction mixture, the organic layer was collected by separation, washed with a saturated sodium chloride aqueous solution, and dried over anhydrous magnesium sulfate. The solvent was distilled off under reduced pressure, whereby 3.41 g of (2S)-2-(methanesulfonyloxy)-5-((tris(propan-2-yl)silyl)oxy)pentyl benzoate was obtained as a colorless oily material.

¹H-NMR (CDCl₃) δ value: 8.10-8.04(2H,m),7.62-7.55 (1H,m),7.49-7.43(2H,m),5.09(1H,ddd,J=3.2,6.9,12.9 Hz), 4.56(1H,dd,J=3.1,12.3 Hz),4.43(1H,dd,J=6.9,12.3 Hz),3.83-3.70(2H,m),3.03(3H,s),2.01-1.63(4H,m),1.15-0.97(21H,m)

(Step 5)

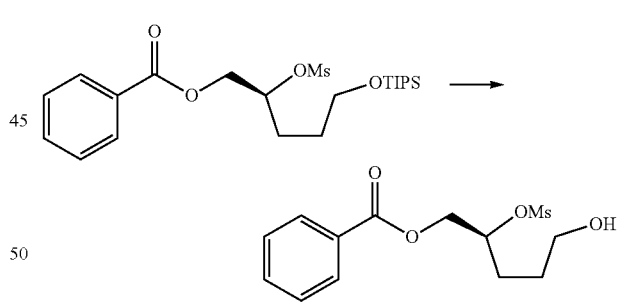

0.70 g of p-toluenesulfonic acid monohydrate was added to a solution of 3.41 g of (2S)-2-(methanesulfonyloxy)-5-((tris(propan-2-yl)silyl)oxy)pentyl benzoate in 40 mL of methanol, and the resultant product was stirred at room temperature for 1 hour. Ethyl acetate and a saturated sodium hydrogen carbonate aqueous solution were added to the reaction mixture. The organic layer was collected by separation, washed with a saturated sodium chloride aqueous solution, and dried over anhydrous magnesium sulfate. The solvent was distilled off under reduced pressure, and the obtained residue was purified by silica gel column chromatography, whereby 1.84 g of (2S)-5-hydroxy-2-(methanesulfonyloxy)pentyl benzoate was obtained as a colorless oily material.

¹H-NMR (CDCl₃) δ value: 8.10-8.04(2H,m),7.63-7.55(1H,m),7.50-7.42(2H,m),5.11(1H,ddd,J=3.1,6.6,13.1 Hz),4.57(1H,dd,J=3.1,12.4 Hz),4.43(1H,dd,J=6.9,12.4 Hz),3.75(1H, br),3.05(3H,s),1.98-1.70(4H,m),1.41(1H, br)

(Step 6)

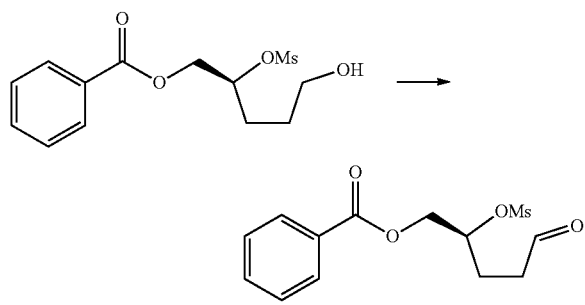

3.9 g of 1,1,1-triacetoxy-1,1-dihydro-1,2-benziodoxol-3(1H)-one (Dess-Martin periodinane) was added to a solution of 1.84 g of (2S)-5-hydroxy-2-(methanesulfonyloxy)pentyl benzoate in 30 mL of dichloromethane, and the resultant product was stirred at room temperature for 1 hour. Ethyl acetate, a saturated sodium hydrogen carbonate aqueous solution, and a sodium thiosulfate aqueous solution were added to the reaction mixture, and the resultant product was stirred at room temperature for 10 minutes. The organic layer was collected by separation, washed sequentially with a sodium thiosulfate aqueous solution and a saturated sodium chloride aqueous solution, and dried over anhydrous magnesium sulfate. The solvent was distilled off under reduced pressure, and the obtained residue was purified by silica gel column chromatography, whereby 1.55 g of (2S)-2-(methanesulfonyloxy)-5-oxopentyl benzoate was obtained as a colorless oily material.

¹H-NMR (CDCl₃) δ value: 9.83(1H,s),8.08-8.03(2H,m),7.64-7.56(1H,m),7.51-7.43(2H,m),5.10-5.02(1H,m),4.55(1H,dd,J=3.3,12.4 Hz),4.43(1H,dd,J=6.6,12.4 Hz),3.04(3H,s),2.82-2.72(2H,m),2.26-1.97(2H,m)

Example 17

[A] ((2R)-5-hydroxythiolan-2-yl)methyl 4-phenyl benzoate and acetylated product thereof By reacting (2S)-2-(methanesulfonyloxy)-5-oxopentyl 4-phenyl benzoate with a sodium hydrogen sulfide aqueous solution in the following manner, ((2R)-5-hydroxythiolan-2-yl)methyl 4-phenyl benzoate was synthesized.

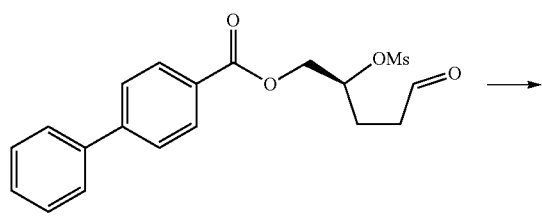

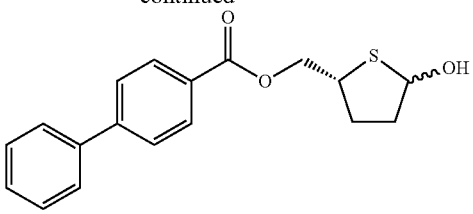

0.4 mL of a 15% sodium hydrogen sulfide aqueous solution was added to a solution of 0.20 g of (2S)-2-(methanesulfonyloxy)-5-oxopentyl 4-phenyl benzoate in 5 mL of N,N-dimethylformamide at 0° C. to 10° C., and the resultant product was stirred at room temperature for 2 hours. Ethyl acetate and a saturated sodium chloride aqueous solution were added to the reaction mixture, and the organic layer was collected by separation. The organic layer was washed with a saturated sodium chloride aqueous solution, and dried over anhydrous magnesium sulfate. The solvent was distilled off under reduced pressure, and the obtained residue was purified by silica gel column chromatography, whereby 0.07 g of ((2R)-5-hydroxythiolan-2-yl)methyl 4-phenyl benzoate was obtained as a colorless oily material.

¹H-NMR (CDCl₃) δ value: 8.14-8.08(2H,m),7.70-7.60(4H,m),7.51-7.36(3H,m),5.64-5.56(1H,m),4.59(0.53H,dd,J=6.6,11.1 Hz),4.44(0.53H,dd,J=6.9,11.1 Hz),4.28(0.47H,dd,J=8.7,11.1 Hz),4.23(0.47H,dd,J=6.6,11.1 Hz), 4.03-3.93(0.47H,m),3.92-3.80(0.53H,m),2.43-1.94(5H,m)

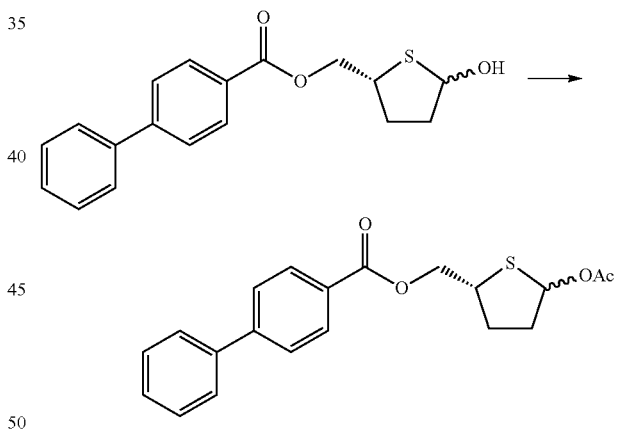

39 μL of acetic anhydride was added to a mixed solution of 65 mg of ((2R)-5-hydroxythiolan-2-yl)methyl 4-phenyl benzoate in 66 μL of pyridine and 5 mL of ethyl acetate at room temperature, and the resultant was stirred for 30 minutes. 3 mg of N,N-dimethylaminopyridine was added thereto, and the resultant product was allowed to stand at room temperature. Ethyl acetate and water were added to the reaction mixture, and the organic layer was collected by separation. The organic layer was washed with a saturated sodium chloride aqueous solution, and dried over anhydrous magnesium sulfate. The solvent was distilled off under reduced pressure, and the obtained residue was purified by silica gel column chromatography, whereby 60 mg of ((2R)-5-(acetyloxy)thiolan-2-yl)methyl 4-phenyl benzoate was obtained as a colorless oily material.

¹H-NMR (CDCl₃) δ value: 8.14-8.07(2H,m),7.70-7.69 (4H,m),7.51-7.36(3H,m),6.22-6.16(1H,m),4.58(0.54H,dd, J=6.6,11.1 Hz),4.41-4.20(1.46H,m),3.94-3.79(1H,m),2.42-1.92(7H,m)

[B] Synthesis of Raw Material

Moreover, (2S)-2-(methanesulfonyloxy)-5-oxopentyl 4-phenyl benzoate which was a raw material was synthesized through a plurality of steps in the following manner.
(Step 1)

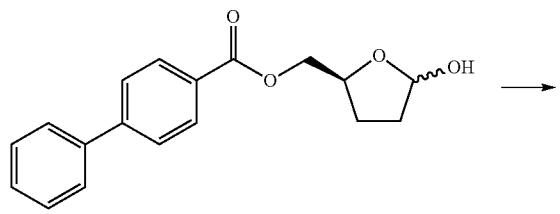

6.24 mL of pyridine, 3.11 g of p-toluenesulfonic acid monohydrate and 1.82 g of O-methylhydroxylamine hydrochloride were added to a solution of 3.61 g of ((2S)-5-hydroxyoxolan-2-yl)methyl 4-phenyl benzoate in 30 mL of methanol, and the resultant product was stirred at room temperature for 2 hours. Ethyl acetate and a saturated sodium chloride aqueous solution were added to the reaction mixture, and the organic layer was collected by separation. The organic layer was washed with a saturated sodium chloride aqueous solution, and dried over anhydrous magnesium sulfate. The solvent was distilled off under reduced pressure, and the obtained residue was washed with ethyl acetate/hexane, whereby 2.5 g of (2S)-2-hydroxy-5-(methoxyimino)pentyl 4-phenyl benzoate was obtained as a white solid.

¹H-NMR (CDCl₃) δ value: 8.15-8.08(2H,m),7.71-7.59 (4H,m),7.52-7.37(3.52H,m),6.74(0.48H,t,J=5.7 Hz),4.46-4.37(1H,m), 4.33-4.24(1H,m),4.10-3.94(1H,m),3.89(1.44H, s),3.83(1.56H,s),2.67-2.37(3H,m),1.87-1.71(2H,m)

(Step 2)

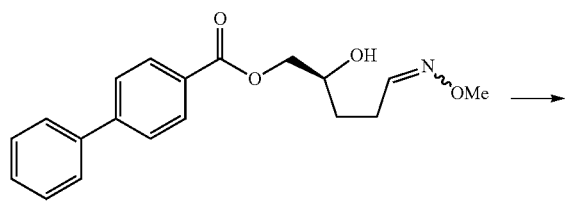

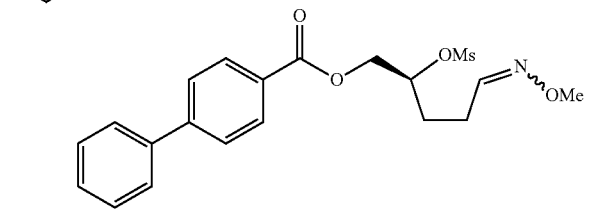

0.46 mL of methanesulfonyl chloride was added dropwise to a mixed solution of 1.0 g of (2S)-2-hydroxy-5-(methoxyimino)pentyl 4-phenyl benzoate in 20 mL of ethyl acetate and 1.67 mL of triethylamine at 0° C. to 10° C., and the resultant product was stirred at room temperature for 100 minutes. Ethyl acetate and water were added to the reaction mixture, and the organic layer was collected by separation. The organic layer was washed sequentially with water and a saturated sodium chloride aqueous solution, and dried over anhydrous magnesium sulfate. The solvent was distilled off under reduced pressure, whereby 1.39 g of (2S)-2-(methanesulfonyloxy)-5-(methoxyimino)pentyl 4-phenyl benzoate was obtained as a colorless oily material.

¹H-NMR (CDCl₃) δ value: 8.17-8.08(2H,m),7.71-7.58 (4H,m),7.50-7.36(3.58H,m),6.72(0.42H,t,J=5.5 Hz),5.15-5.00(1H,m), 4.62-4.41(2H,m),3.88(1.26H,s),3.83(1.74H,s), 3.08(1.74H, 3H),3.07(1.26H,m),2.63-2.37(2H,m),2.11-1.97 (2H,m)

(Step 3)

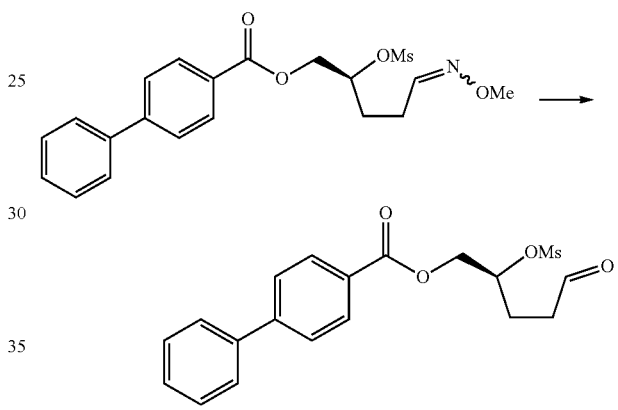

2.4 mL of a 37% formaldehyde aqueous solution and 0.1 mL of 9% hydrochloric acid were added to a solution of 1.39 g of (2S)-2-(methanesulfonyloxy)-5-(methoxyimino)pentyl 4-phenyl benzoate in 15 mL of acetone at room temperature, and the resultant product was stirred at room temperature for 60 minutes. Next, 5 mL of 37% formaldehyde aqueous solution was added thereto, and the resultant product was stirred for 70 minutes. Next, 5 mL of 37% formaldehyde aqueous solution was added thereto, and the resultant product was stirred for 30 minutes. Ethyl acetate and a saturated sodium hydrogen carbonate aqueous solution were added to the reaction mixture, and the organic layer was collected by separation. The organic layer was washed with a saturated sodium chloride aqueous solution, and dried over anhydrous magnesium sulfate. The solvent was distilled off under reduced pressure, and the obtained residue was purified by silica gel column chromatography, whereby 1.13 g of (2S)-2-(methanesulfonyloxy)-5-oxopentyl 4-phenyl benzoate was obtained as a colorless oily material.

¹H-NMR (CDCl₃) δ value: 9.84(1H,s),8.15-8.09(2H,m), 7.72-7.59(4H,m),7.51-7.37(3H,m),5.13-5.03(1H,m),4.57 (1H,dd,J=3.3,12.3 Hz),4.46(1H,dd,J=6.6,12.3 Hz),3.06(3H, s),2.88-2.67(2H,m),2.25-2.00(2H,m)

As apparent from Examples 1 to 17, if, by a reaction of the chain-like compound represented by General Formula (I) of the present invention with a sulfur compound, the sulfur compound is reacted, a thiolane ring is immediately formed. Furthermore, by this reaction, the compound represented by General Formula (II) useful as a thionucleoside synthetic intermediate can be produced with a high yield under mild conditions.

Moreover, by using the compound represented by General Formula (II) as a starting material, it is possible to synthesize thionucleoside expected as a useful physiologically active substance by a method in the art or a method according to the method. Therefore, the production method of the compound represented by General Formula (II) of the present invention and the compound represented by General Formula (II) of the present invention are useful.

Although the present invention has been described with the embodiments thereof, unless otherwise particularly described, the present invention is not intended to be limited in any details of description of the present invention, and it is considered that the present invention must be broadly interpreted without departing from the spirit and the scope of the present invention shown in the appended Claims.

What is claimed is:

1. A production method of a compound represented by the following General Formula (II) through a step of reacting a compound represented by the following General Formula (I) with a sulfur compound, via the compound represented by General Formula (III),

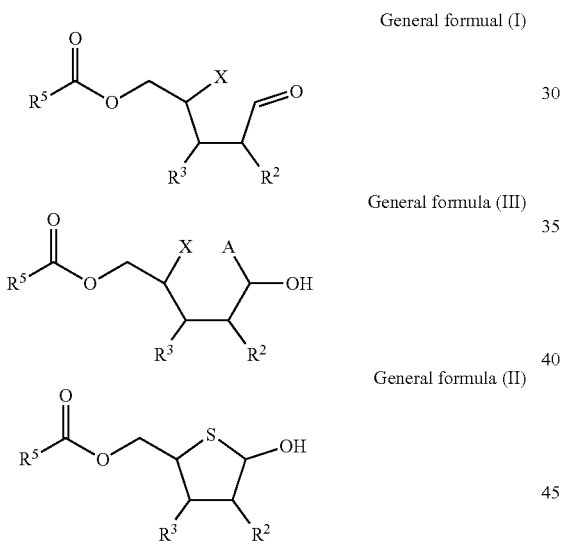

A represents SH or S⁻, wherein, in General Formulas (I) (II), and (III), $R^2$ represents a hydrogen atom, a fluorine atom, an acyloxy group having 1 to 20 carbon atoms, which may have a substituent selected from a halogen atom, an alkyl group, an aryl group, a heterocyclic group, an alkoxy group, an aryloxy group, an alkylthio group, and an arylthio group, an arylmethyloxy group having 7 to 20 carbon atoms, which may have a substituent selected from a halogen atom, an alkyl group, an aryl group, a heterocyclic group, an alkoxy group, an aryloxy group, an alkylthio group, and an arylthio group, an allyloxy group, which may have a substituent selected from a halogen atom, an alkyl group, an aryl group, a heterocyclic group, an alkoxy group, an aryloxy group, an alkylthio group, and an arylthio group, an arylmethyloxycarbonyloxy group having 8 to 21 carbon atoms, which may have a substituent selected from a halogen atom, an alkyl group, an aryl group, a heterocyclic group, an alkoxy group, an aryloxy group, an alkylthio group, and an arylthio group, or an allyloxycarbonyloxy group, which may have a substituent selected from a halogen atom, an alkyl group, an aryl group, a heterocyclic group, an alkoxy group, an aryloxy group, an alkylthio group, and an arylthio group, $R^3$ represents a hydrogen atom or an acyloxy group having 1 to 20 carbon atoms, which may have a substituent selected from a halogen atom, an alkyl group, an aryl group, a heterocyclic group, an alkoxy group, an aryloxy group, an alkylthio group, and an arylthio group, $R^5$ represents an aryl group having 6 to 19 carbon atoms, which may have a substituent selected from a halogen atom, an alkyl group, an aryl group, a heterocyclic group, an alkoxy group, an aryloxy group, an alkylthio group, and an arylthio group, and X represents a halogen atom, an alkylsulfonyloxy group having 1 to 10 carbon atoms, or an arylsulfonyloxy group having 6 to 16 carbon atoms;

wherein, if $R^2$ is the fluorine atom, the acyloxy group, the arylmethyloxy group, the allyloxy group, the arylmethyloxycarbonyloxy group, or the allyloxycarbonyloxy group, $R^3$ is the acyloxy group; and wherein the sulfur compound is hydrogen sulfide or a salt thereof.

2. The production method according to claim 1, wherein the compound represented by General Formula (II) is any one of the following General Formulas (II-1) to (II-14),

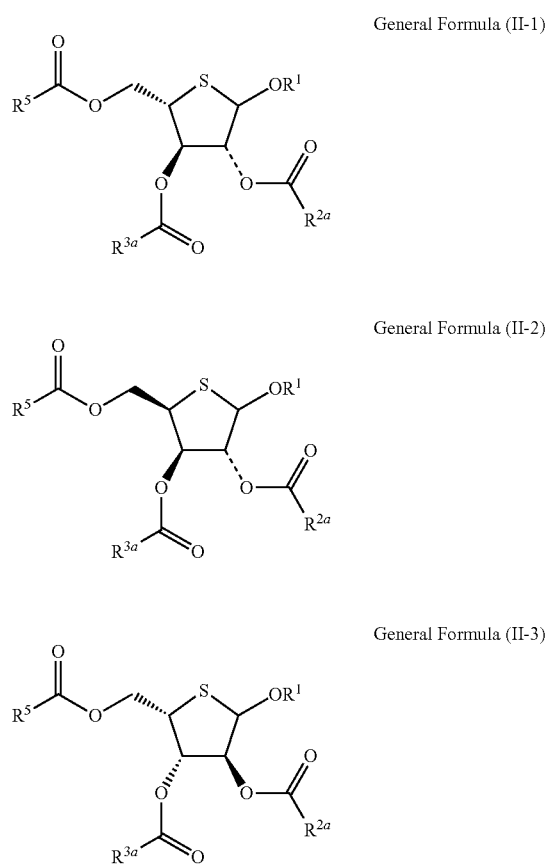

General Formula (II-4)

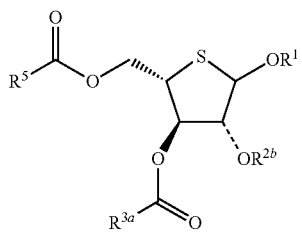

General Formula (II-5)

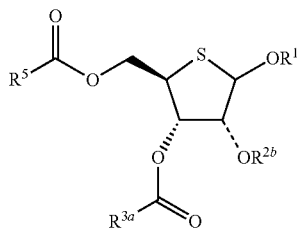

General Formula (II-6)

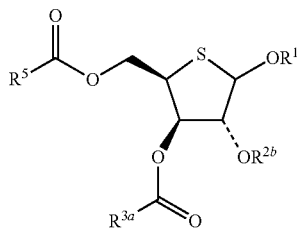

General Formula (II-7)

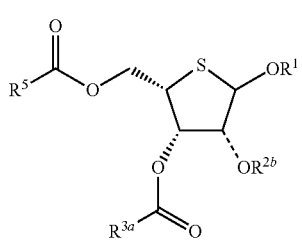

General Formula (II-8)

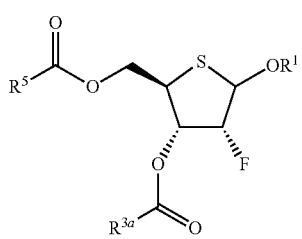

General Formula (II-9)

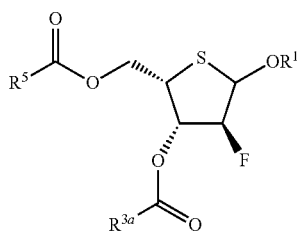

General Formula (II-10)

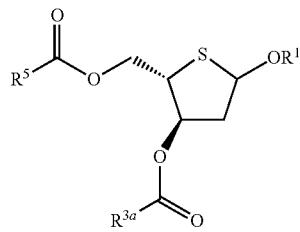

General Formula (II-11)

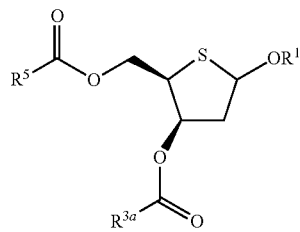

General Formula (II-12)

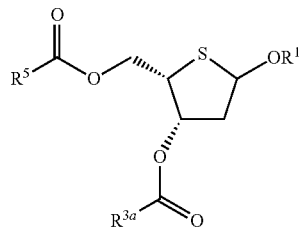

General Formula (II-13)

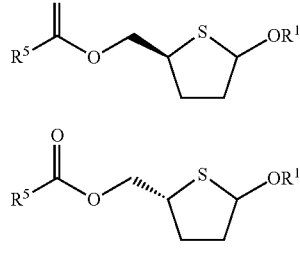

General Formula (II-14)

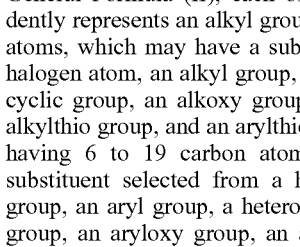

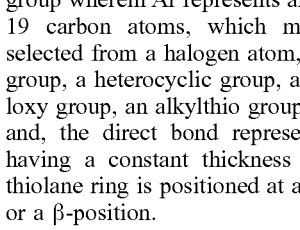

wherein, in General Formulas (II-1) to (II-14), $R^1$ is a hydrogen atom and $R^5$ has the same meaning $R^5$ in General Formula (II), each of $R^{2a}$ and $R^{3a}$ independently represents an alkyl group having 1 to 20 carbon atoms, which may have a substituent selected from a halogen atom, an alkyl group, an aryl group, a heterocyclic group, an alkoxy group, an aryloxy group, an alkylthio group, and an arylthio group or an aryl group having 6 to 19 carbon atoms, which may have a substituent selected from a halogen atom, an alkyl group, an aryl group, a heterocyclic group, an alkoxy group, an aryloxy group, an alkylthio group, and an arylthio group, $R^{2b}$ represents —CH$_2$—Ar, an allyl group, —C(=O)OCH$_2$—Ar, or an allyloxycarbonyl group wherein Ar represents an aryl group having 6 to 19 carbon atoms, which may have a substituent selected from a halogen atom, an alkyl group, an aryl group, a heterocyclic group, an alkoxy group, an aryloxy group, an alkylthio group, and an arylthio group, and, the direct bond represented by a dashed line having a constant thickness which is bonded to a thiolane ring is positioned at any one of an α-position or a β-position.

3. The production method according to claim 1, wherein $R^5$ is an aryl group, and $R^3$ is an arylcarbonyloxy group.

4. The production method according to claim 1,
wherein $R^5$ is a phenyl group, a 4-methylphenyl group, a 4-phenylphenyl group, or a 2-naphthyl group, and $R^3$ is a phenylcarbonyloxy group, a 4-methylphenylcarbonyloxy group, a 4-phenylphenylcarbonyloxy group, or a 2-naphthylcarbonyloxy group.

5. The production method according to claim 1,
wherein, after a compound represented by the following General Formula (IIA) is synthesized in the step of reacting the compound represented by General Formula (I) with a sulfur compound, a compound represented by the following General Formula (IIB) is synthesized in a step of acylating the compound represented by General Formula (IIA),

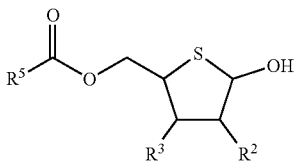

General Formula (IIA)

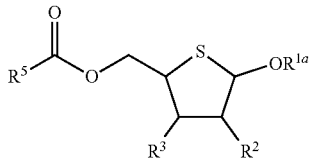

General Formula (IIB)

wherein, in General Formulas (IIA) and (IIB), $R^2$, $R^3$, and $R^5$ have the same meaning as $R^2$, $R^3$, and $R^5$ in General Formula (II), respectively, and $R^{1a}$ represents an acyl group having 1 to 20 carbon atoms, which may have a substituent selected from a halogen atom, an alkyl group, an aryl group, a heterocyclic group, an alkoxy group, an aryloxy group, an alkylthio group, and an arylthio group.

6. The production method according to claim 1,
wherein $R^1$ is an acetyl group or an arylcarbonyl group.

7. The production method according to claim 1,
wherein the sulfur compound is MSH or $M_2S$ in which M is an alkali metal.

8. A compound represented by any one of the following General Formulas (II-4) to (II-7), (II-13) and (II-14),

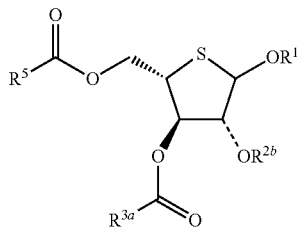

General Formula (II-4)

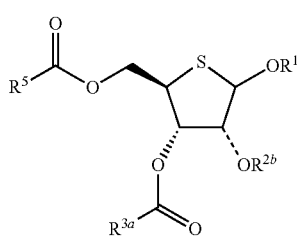

General Formula (II-5)

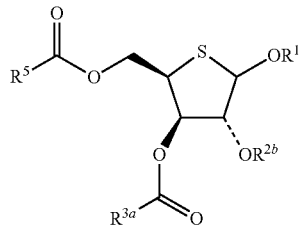

General Formula (II-6)

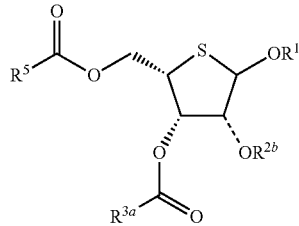

General Formula (II-7)

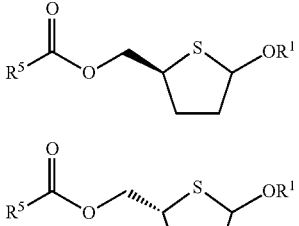

General Formula (II-13)

General Formula (II-14)

wherein, in General Formulas (II-4) to (II-7), (II-13) and (II-14), $R^1$ represents a hydrogen atom or an acyl group having 1 to 20 carbon atoms, which may have a substituent selected from a halogen atom, an alkyl group, an aryl group, a heterocyclic group, an alkoxy group, an aryloxy group, an alkylthio group, and an arylthio group, and $R^{3a}$ represents an aryl group having 6 to 19 carbon atoms, which may have a substituent selected from a halogen atom, an alkyl group, an aryl group, a heterocyclic group, an alkoxy group, an aryloxy group, an alkylthio group, and an arylthio group, and $R^5$ represents an aryl group having 6 to 19 carbon atoms, which may have a substituent selected from a halogen atom, an alkyl group, an aryl group, a heterocyclic group, an alkoxy group, an aryloxy group, an alkylthio group, and an arylthio group, $R^{2b}$ represents —$CH_2$—Ar, an allyl group, —C(=O)O$CH_2$—Ar, or an allyloxycarbonyl group, wherein Ar represents an aryl group having 6 to 19 carbon atoms, which may have a substituent selected from a halogen atom, an alkyl group, an aryl group, a heterocyclic group, an alkoxy group, an aryloxy group, an alkylthio group, and an arylthio group, and the direct bond represented by a dashed line having a constant thickness which is bonded to a thiolane ring is positioned on any one of an α-side or a β-side.

9. The compound according to claim 8,
wherein $R^1$ is a hydrogen atom, an acetyl group, or an arylcarbonyl group, and each of $R^{3a}$ and $R^5$ is independently an aryl group.

10. The compound according to claim 8,
wherein each of $R^{3a}$ and $R^5$ is independently a phenyl group, a 4-methylphenyl group, a 4-phenylphenyl group, or a 2-naphthyl group.

11. A compound represented by any one of the following General Formula (II-6B)(II-13'), and (II-14'),

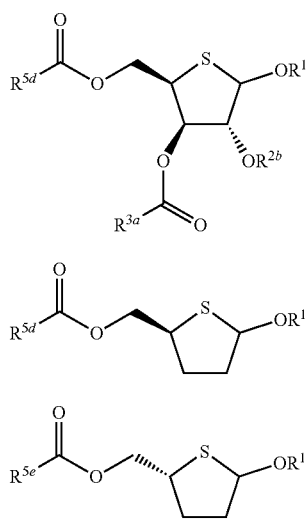

General Formula (II-6B)

General Formula (II-13')

General Formula (II-14')

wherein, in General Formulas (II-6B), (II-13'), and (II-14'), $R^1$ represents a hydrogen atom or an acyl group having 1 to 20 carbon atoms, which may have a substituent selected from a halogen atom, an alkyl group, an aryl group, a heterocyclic group, an alkoxy group, an aryloxy group, an alkylthio group, and an arylthio group, $R^{3a}$ represents an alkyl group having 1 to 20 carbon atoms, which may have a substituent selected from a halogen atom, an alkyl group, an aryl group, a heterocyclic group, an alkoxy group, an aryloxy group, an alkylthio group, and an arylthio group or an aryl group having 6 to 19 carbon atoms, which may have a substituent selected from a halogen atom, an alkyl group, an aryl group, a heterocyclic group, an alkoxy group, an aryloxy group, an alkylthio group, and an arylthio group, $R^{2b}$ represents —$CH_2$—Ar, an allyl group, —C(=O)$OCH_2$—Ar, or an allyloxycarbonyl group, wherein Ar represents an aryl group having 6 to 19 carbon atoms, which may have a substituent selected from a halogen atom, an alkyl group, an aryl group, a heterocyclic group, an alkoxy group, an aryloxy group, an alkylthio group, and an arylthio group, each of $R^5$, $R^{5d}$, and $R^{5e}$ independently represents an aryl group having 6 to 19 carbon atoms, which may have a substituent selected from a halogen atom, an alkyl group, an aryl group, a heterocyclic group, an alkoxy group, an aryloxy group, an alkylthio group, and an arylthio group.

12. The compound according to claim 11, wherein $R^1$ is a hydrogen atom, an acetyl group, a 4-methylbenzoyl group, a 4-phenylbenzoyl group, or a 2-naphthoyl group, each of $R^{3a}$ and $R^5$ is independently a 4-methylphenyl group, a 4-phenylphenyl group, or a 2-naphthyl group, $R^{2b}$ is a phenylmethyl group, and each of $R^{5d}$ and $R^{5e}$ is independently a phenyl group, a 4-methylphenyl group, a 4-phenylphenyl group, or a 2-naphthyl group.

* * * * *